(12) United States Patent
Young et al.

(10) Patent No.: US 6,476,188 B1
(45) Date of Patent: Nov. 5, 2002

(54) CLOCK GENE AND METHODS OF USE THEREOF

(75) Inventors: Michael W. Young, Old Tappan, NJ (US); Brian Kloss; Justin Blau, both of New York, NY (US); Jeffrey Price, Overland Park, KS (US); Joseph S. Takahashi, Wilmette; Phillip L. Lowrey, Evanston, both of IL (US)

(73) Assignees: The Rockefeller University, New York, NY (US); Northwestern University, Evanston, IL (US)

( * ) Notice: Subject to any disclaimer, the term of this patent is extended or adjusted under 35 U.S.C. 154(b) by 0 days.

(21) Appl. No.: 09/553,867

(22) Filed: Apr. 20, 2000

Related U.S. Application Data

(63) Continuation-in-part of application No. 09/335,983, filed on Jun. 18, 1999.
(60) Provisional application No. 60/090,068, filed on Jun. 19, 1998.

(51) Int. Cl.[7] .............................. C07K 7/04; C07K 7/06; C07K 14/435; C07K 14/00
(52) U.S. Cl. ..................... 530/324; 530/350; 530/325; 530/326; 530/327; 530/328; 530/329
(58) Field of Search ............................ 530/350, 324, 530/325, 326, 327, 328, 329

(56) References Cited

U.S. PATENT DOCUMENTS

| | | | |
|---|---|---|---|
| 5,627,064 | A | 5/1997 | Hoekstra |
| 5,874,241 | A | 2/1999 | Takahashi et al. |
| 5,885,831 | A | 3/1999 | Young et al. |
| 6,057,129 | A | 5/2000 | Young et al. |

FOREIGN PATENT DOCUMENTS

| | | |
|---|---|---|
| WO | WO 00/75669 A1 | 12/2000 |

OTHER PUBLICATIONS

Albrecht et al. *Cell*, 91:1055–1064 (1997).
Altschul et al., *J. Mol. Biol.* 215:403–410 (1990).
Antoch et al., *Cell*, 89:65–67 (1997).
Bae et al., *J. Neurosci.*, 20:1746–53 (2000).
Baylies et al., *Nature*, 326:390–392 (1987).
Baylies et al., *Neuron*, 9:575–581 (1992).
Baylies et al. in *Molecular Genetics of Biological Rhythms*, pp. 123–153, M. W. Young, Ed. (Dekker, New York, 1993).
Burbach et al., *Proc. Natl. Acad. Sci. U.S.A.*, 89:8185–8189 (1992).
Cavener, *NAR*, 15:1353–1361 (1987).
Crews et al *Cell*, 52:143–51 (1988).
Crosthwaite et al., *Science*, 276:763–769 (1997).
Curtin et al., *Neuron*, 14:365–372 (1995).
Darlington et al., *Science*, 280:1599–1603 (1998).
Dembinska et al., *J. Biol. Rhythms*, 12:157–172 (1997).
Dunlap, *Annu. Rev. Physiol.*, 55:683–728 (1993).
Dunlap et al., *Cell*, 96:271 (1999).
Edery et al *Proc. Natl. Acad. Sci. U.S.A* 91:2260–4 (1994).
Ewer et al., *J. Neurosci.*, 12:3321–3349 (1992).
Fields et al., *Nature*, 340:245–6 (1989).
Fish et al., *Journ. Biol. Chem*, 270:14875–14883 (1995).
Frisch et al., *Neuron*, 12:555–570 (1994).
Gekakis et al., *Science* 280:1564–1569 (1998).
Gekakis et al., *Science*, 270:811–815 (1995).
Gerhold and Caskey, *BioEssays*, 18:973–81 (1996).
Geysen et al., *J. Mol. Recognition* 1:32–41 (1988).
Giebultowicz and Hege, *Nature*, 386:664 (1997).
Giese et al., *Science*, 279:870–3 (1998).
Hamblen–Coyle et al., *Journal of Insect Behavior* 5:417–446 (1992).
Hanks et al., *Science 241:* 42–54 (1988).
Hao et al., *Mol. Cell. Biol.* 17:3687 (1997).
Hardin, *Molecular and Cellular Biology*, 14(11):7211–7218 (1994).
Hardin et al, *Proc. Natl. Acad. Sci. U.S.A.* 89:11711 (1992).
Hardin et al, *Nature*, 343:536–540 (1990).
Harvey et al., (1997) Drosphilia melanogaster cDNA clone HL01564, Genbank accession number AA567638, GenBank record date Dec. 18, 1997.
Hastings et al., *J. Neurosci.* 19:RC11 (1999).
Helfrich–Forster, *Proc. Natl. Acad. Sci. USA*, 92:612–616 (1995).
Hoffman et al., *Science*, 252:954–958 (1991).
Huang et al., *Science*, 267:1169–1172 (1995).
Hunter–Ensor et al., *Cell*, 84:677–685 (1996).
Ikeda and Nomura, *Biochem. Biophys. Res. Comm.*, 233:258–64 (1997).
Jackson, *Journal of Neurogenetics*, 1:3–15 (1993).
Jackson, in *Molecular Genetics of Biological Rhythms*, pp. 91–121, M. W. Young, Ed. (Dekker, New York, 1993).
James et al., *EMBO J.*, 5:2313–2320 (1986).
Kaneko et al., *Neurosci.*, 17:6745–6760 (1997).
Kelley et al., *Mol. and Cell Bio.*, 7:1545–1548 (1987).
King et al., *Cell*, 89:641–653 (1997).
King and Takahashi, *Annu. Rev. Neurosci.*, 23:713 (2000).
Kloss et al., *Cell*, 94:97–107 (1998).

(List continued on next page.)

Primary Examiner—David Guzo
(74) *Attorney, Agent, or Firm*—Klauber & Jackson; Valeta A. Gregg

(57) ABSTRACT

The present invention discloses the identity of the first enzyme that has been demonstrated to be involved in maintaining circadian rhythms. This enzyme, the Drosophila DOUBLETIME protein is also shown to be an ortholog of human casein kinase-1ε. In addition, a variant of this enzyme is shown to be cause of the hamster tau mutant phenotype. Thus the present invention also relates to variants of DOUBLETIME, and their nucleic acid and amino acid sequences. The present invention further provides methods of using these variants in drug assays and diagnostics.

6 Claims, 32 Drawing Sheets

OTHER PUBLICATIONS

Kongo et al., *Science,* 266:1233–1236 (1994).
Konopka and Benzer, *Proc. Natl. Acad. Sci. U.S.A.,* 68:2112–2116 (1971).
Konopka et al., *J. Neurogenetics,* 7:103–114 (1991).
Kume et al., *Cell,* 98:193–205 (1999).
Kunes et al., *J. Neurosci.,* 13:752–767 (1993).
Lee et al., *Science,* 271:1740–1744 (1996).
Lee et al., *Mol. Cell. Biol.,* 19:5316–25 (1999).
Leloup and Goldbeter, *J. Biol. Rhythms,* 13:70–87 (1998).
Longenecker et al., *J. Mol. Biol.,* 257:618–31 (1996).
Longenecker et al., *Acta Crystallogr.,* D54:473 (1988).
Lowrey et al., *Science,* 288:483–491 (2000).
Malakoff et al., *Science,* 288:943–4 (2000).
Marrus et al., *The EMBO Journal,* 15:6877–6886 (1996).
Millar et al., *Science,* 267:1161–1163 (1995).
Myers et al., *Science,* 271:1736–1740 (1996).
Myers et al., *Nucl. Acids Res.,* 25:4710–4714 (1997).
Myers et al., *Science,* 270:805–808 (1995).
Nambu et al., *Cell,* 67:1157–67 (1991).
Okamura et al., *Science,* 286:2531–2534 (1999).
Peters et al., *Nature,* 401:345 (1999).
Pittendrigh, in *Handbook of Behavioral Neurobiology,* 4, J. Aschoff, Ed., New York: Plenum, 1981, pp. 95–124.
Pittendrigh, *Annu. Rev. Physiol.,* 55:16 (1993).
Price et al., *EMBO J.,* 14:4044–4049 (1995).
Price et al., *Cell,* 94:83 (1998).
Ralph and Menaker, *Science,* 241:1225–1127(1998).
Ralph et al., *Science,* 247:975 (1990).
Rosbash et al., *Cold Spring Harb. Symp. Quant. Biol. J.,* 61:265–278 (1996).
Russell and Barton, *J. Mol. Biol.,* 244:332–350 (1994).
Rutila et al., *Neuron,* 17:921–929 (1996).
Saez and Young, *Neuron,* 17:911–920 (1996).
Sakanaka et al., *Proc. Natl. Acad. Sci. USA,* 96:12548–52 (1999).
Sangoram et al., *Neuron,* 21:1101–13 (1998).
Sehgal et al., *Proc. Natl. Acad. Sci. USA,* 89:1423–1427 (1992).
Sehgal et al., *Science,* 263:1603–1605 (1994).
Sehgal et al., *Science,* 270:808–810(1995).
Shearman et al., *Neuron,* 19:1261–1269 (1997).
Shigeyoshi et al., *Cell,* 91:1043–1053 (1997).
Silver et al., *Nature,* 382:810 (1996).
Siwicki et al., *Neuron* 1:141–50 (1998).
Smith et al., *Science,* 254:1478–1484 (1991).
Sogowa et al., *Proc. Natl. Acad. Sci. USA,* 92:1936–1940 (1995).
Spradling et al., *PNAS, USA,* 92:10824–30 (1995).
Stanewsky et al., *J. Neurosci.,* 17:676–696 (1997).
Sun et al., *Cell* 90:1003–1011 (1997).
Tautz and Pfeifle, *Chromosoma* 98:81–85 (1989).
Tel et al., *Nature,* 389 (1997).
Tosini and Menaker, *Science,* 272:419 (1996).
van der Horst et al., *Nature,* 398:627 (1999).
Vitaterna et al., *PNAS USA,* 96:12114–9 (1999).
Vitaterna et al., *Science,* 264:719–725 (1994).
Vosshall et al., *Science,* 263:1606–1609 (1994).
Vosshall and Young, *Neuron,* 15:345–360 (1995).
Wells and Peitsch, *Journal of Leukocyte Biology,* 61:545–550 (1997).
Welsh et al., *Neuron,* 14:697–706 (1995).
Wheeler et al., *Journal of Biological Rhythms,* 8:67–94 (1993).
Wilsbacher and J.S. Takahashi, *Curr. Opin. Genet. Dev.,* 8:595–602 (1998).
Xu et al., *Proc. Natl. Acad. Sci. USA,* 93:6308–6313 (1996).
Young., *Annu. Rev. Biochem.,* 67:135–52 (1998).
Zeng et al., *Nature,* 380:129–135 (1996).
Zwiebel et al., *Proc. Natl. Acad. Sci. USA,* 88:3882–3886 (1991).
Zylka et al., *Neuron,* 21:1115–22 (1998).

+/+, tau=24.0 hrs $dbt^S$/+, tau=21.5 hrs $dbt^S$/$dbt^S$, tau=18.0 hrs

+/+, tau=23.5 hrs $dbt^L$/+, tau=25.0 hrs $dbt^L$/$dbt^L$, tau=27.0 hrs

FIG. 11A

```
                                                  ATP-binding                                           DBT^S
DBT            start
H. sapiens     M------ELRVGNKYRLGRKIGSGSFGDIYLGTTINFGEEVAIKLECIRTKHPQLHIE  52
A. thaliana    -------ELRV.N.YRLG.......DI..GANIAS........I..CVRTK.....HI..  52
X. laevis      -------DLVI.G.FKLG.......EL..GINVQT........V..SVKTK.....HY..  52
G. gallus      ASSSGSKAEFIV.G.YKLV.......DI..AINITN........V..SQKAR.....LY..  60
S. pombe       ASSSGSKAEFIV.G.YKLV.......DI..AINITN........V..SQKAR.....LY..  60
               A------LDLRI.N.YRIG.......DI..GTNVVS........I..STRAK.....EY..  54
                                                                                    DBT^L
DBT
H. sapiens     SKFYKTMQGGIGIPRIIWCGSEGDYNVMMELLGPSLEDLFNFCSRRFSLKTVLLLADQM  112
A. thaliana    SKF.KMMQ..V.I.SIK.C.A.G...VM.ME..........F.S.KFSL....L....M..  112
X. laevis      SKL.MLLQ..T.V.NLK.Y.V.G...VM.ID..........Y.N.KLSL....M....L..  112
G. gallus      SKL.KILQ..V.I.HIR.Y...K...VL.MD..........F.S.RFTM....M....M..  120
S. pombe       SKL.KILQ..V.I.HIR.Y.Q.K...VL.MD..........F.S.RFTM....M....M..  120
               YRV.RILS..V.I.FVR.F.V.C...AM.MD..........F.N.KFSL....L....L..  114
                                    catalytic
DBT
H. sapiens     ISRIDYIHSRDFIHRDIKPDNFLMGLGKKGNLVYIIDFGLAKKFRDARSLKHIPYRENKN  172
A. thaliana    .S.IEYI.SKN.I....V..............L.KKG.LVYI......A..YRDARTHQ.......N..  172
X. laevis      .N.VEFM.TRG.L....I..............L.RKA.QVYI......G..Y..LQTHR.......N..  172
G. gallus      .S.IEYV.TKN.I....I..............I.RHC.KLFL......A..Y..NRTRQ.......D..  180
S. pombe       .S.IEYV.TKN.I....I..............I.RHC.KLFL......A..Y..NRTRQ.......D..  180
               .S.IEFI.SKS.L....I..............I.KRG.QVNI......A..Y..HKTHL.......N..  174
```

FIG. 11B

```
DBT           LTGTARYASINTHLGIEQSRRDDLESLGYVLMYFNLGALPWQGLKAANKRQKYERISEKK    232
H. sapiens    ..........I.T...I..........L.S......M..NLGS.........AT.R...ER.S...   232
A. thaliana   ..........V.T...V...................L.A......M..LKGS.........GT.K...DR.S...   232
X. laevis     ..........I.A...I...................M.S......M..NRTS.........AT.K...EK.S...   240
G. gallus     ..........I.A...I...................M.S......M..NRTS.........AT.K...EK.S...   240
S. pombe      ..........I.T...I...................L.S......V..CRGS.........TT.K...EK.M...   234

DBT           LSTSIVVLCKGFPSEFVNYLNFCRQMHFDQRPDYCHLRKLFRNLFHRLGFTYDYVFDWNL    292
H. sapiens    MS.PIE...KGY.S...ST.LNFC.SLR.DDK...SY.RQ...N..HRQGFSY..V...NM    292
A. thaliana   VA.PIE...KNQ.S...VS.FRYC.SLR.DDK...SY.KR...D..IREGYQF..V...TV    292
X. laevis     MS.PVE...KGF.A...AM.LNYC.GLR.EEA...MY.RQ...I..RTLNHQY..T...TM    300
G. gallus     MS.PVE...KGF.A...AM.LNYC.GLR.EEA...MY.RQ...I..RTLNHQY..T...TM    300
S. pombe      IS.PTE...RGF.Q...SI.LNYT.SLR.DDK...AY.RK...D..CRQSYEF..M...TL    294

DBT           LKFGGPRNPQAIQQAQDGADGQAGHDAVAAAAVAAAAAASSHQQQHKVNAALGGGGGS    352

DBT           RAQQQLQGGQTLAMLGGNGGGNGSQLIGGNGLNMDDSMAATNSSRPPYDTPERRPSIRMR    412

DBT           QGGGGGGGVGVGMQSGGGGGGVGNAK    440
```

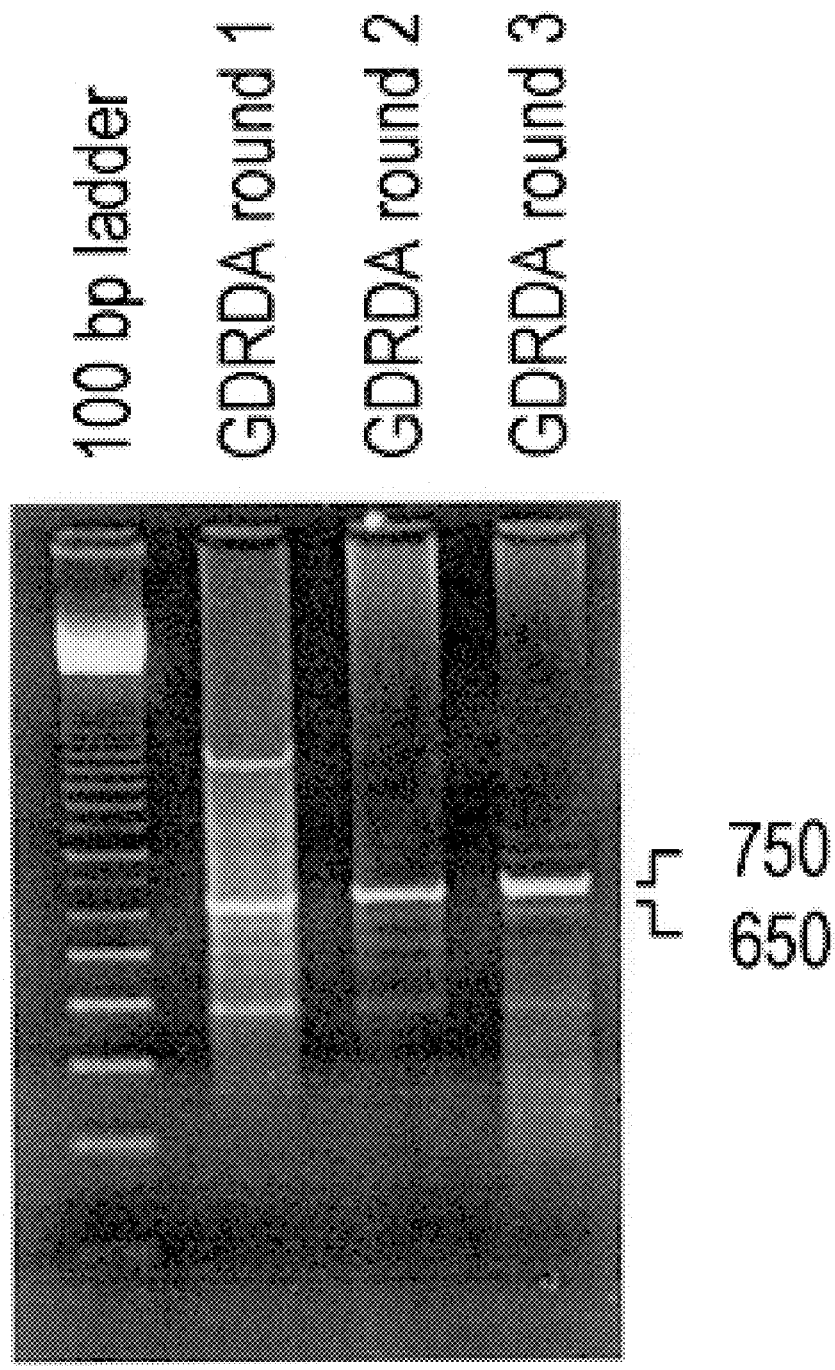

WT tau

FIG. 18A

```
                                                                              dbtˢ
hamster   : MELRVGNKYRLGRKIGSGSFGDIYLGANIASGEEVAIKLECVKTKHEQLH :  50
human     : .E.RV.NKYRL............DI.L.ANIAS........I...CVKTK...H :  50
rat       : .E.RV.NRYRL............DI.L.TDIAA........I...CVKTK...H :  50
fly       : .E.RV.NKYRL............DI.L.TTINT........I...CIRTK...H :  50
Arabidop. : .D.VI.GKFKL............EL.L.INVQT........V...SVKTK...H :  50
yeast     : .D.RV.RKFRI............DL.H.TNLIS........I...SIRSR...D :  50
                                                        II
                                            dbtᴸ
hamster   : IESKFYKMMQGGVGIPSIKWCGAEGDYNVMVMELLGPSLEDLFNFCSRKF : 100
human     : I..KF.KMMQ..V.I.SIK.C.A..D.V..ME................F.S.KF : 100
rat       : I..KI.KMMQ..V.I.TIR.C.A..D.V..ME................F.S.KF : 100
fly       : I..KF.KTMQ..I.I.RII.C.S..D.V..ME................F.S.RF : 100
Arabidop. : Y..KL.MLLQ..T.V.NLK.Y.V..D.V..ID................Y.N.KL : 100
yeast     : Y..RV.RYLS..V.I.FIR.F.R..E.A..ID................Y.H.RF : 100
              III                  IV                      V
                                           catalytic
hamster   : SLKTVLLLADQMISRIEYIHSKNFIHRDVKPDNFLMGLGKKGNLVYIIDF : 150
human     : .L...LL...D.MIS.IEYI.SKN.I......V.........L.KKGNL.YI... : 150
rat       : .L...LL...D.MIS.IEYI.SKN.I......V.........L.KKGNL.YI... : 150
fly       : .L...LL...D.MIS.IDYI.SRD.I......I.........L.KKGNL.YI... : 150
Arabidop. : .L...IM...D.LIN.VEFM.TRG.L......I.........L.RKANQ.YI... : 150
yeast     : .F...IM..L.MFC.IQYI.GRS.I......I.........V.RRGST.HV... : 150
              VIa                            VIb
```

FIG. 18B

```
                    L-9D           ★ tau
                                   ●
hamster   : GLAKKYRDARTHQHIPYRENKNLTGTARYASINTHLGIEQSRRDDLESLG : 200
human     : ..A..Y..ARTHQ.........N..........I..............S.. : 200
rat       : ..A..Y..ARTHQ.........N..........I................ : 200
fly       : ..A..F..ARSLK.........N..........I..............S.. : 200
Arabidop. : ..G..Y..LQTHR.........N..........V..V...........A.. : 200
yeast     : ..S..Y..FNTHR.........S..........V..V..........S.. : 200
                VII                              VIII ★    NLS ★
hamster   : YVLMYFNLGSLPWQGLKAATKRQKYERISEKKMSTPIEVLCKGYPSEFST : 250
human     : ...M..NL.S...........AT.R...E..S...MSTPIEV.KGY.S..ST : 250
rat       : ...M..NL.S...........AT.R...E..S...MSTPIEV.KGY.S..AT : 250
fly       : ...M..NL.A...........AN.R...E..S...LSTSIVV.KGF.S..VN : 250
Arabidop. : ...M..LK.S...........GT.K...D..S...VATPIEV.KNQ.S..VS : 250
yeast     : ...I..CK.S...........TT.K...D..M...LNVSVET.SGL.L..QE : 250
                IX                                   X hamster   : YLNFCRSLRFDDKPDYSYLRQLFRNLFHRQGFSYDYVFDWNMLKFGAARN : 300
human     : .LNF.RSLR..DK...SY.RQ..RN.FHRQGFSY.YV...NM.KFGAARN : 300
rat       : .LNF.RSLR..DK...SY.RQ..RN.FHRQGFSY.YV...NM.KFGASRA : 300
fly       : .LNF.RQMH..QR...CH.RK..RN.FHRLGFTY.YV...NL.KFGGPRN : 300
Arabidop. : .FRY.RSLR..DK...SY.KR..RD.FIREGYQF.YV...TV.KYPQIGS : 300
yeast     : .MAY.KNLK..EK...LF.AR..KD.SIKLEYHN.HL...TM.RYTKAMV : 300
                                    XI
```

FIG. 18C

```
hamster : PEDVDRERREHEREERMGQLRGSATRALPPGPPTGATANRLRSAAEPVAS : 350
human   : ................................................ : 350 hamster : TPASRIQQAGNTSPRAISRADRERKVSMRLHRGAPANVSSSDLTGRQEVS : 400
human   : .......P.................V...................... : 400 hamster : RISASQTSVPFDHLGK : 416
human   : ...P............ : 416
```

CLOCK GENE AND METHODS OF USE THEREOF

CROSS-REFERENCE TO RELATED APPLICATIONS

The present Application is a Continuation-In-Part of copending U.S. Ser. No. 09/335,983 filed Jun. 18, 1999 which is a non-provisional application claiming the priority of copending provisional U.S. Ser. No. 60/090,068 filed Jun. 19, 1998, the disclosure of which are hereby incorporated by reference in their entireties. Applicants claim the benefits of these applications under 35 U.S.C. §§119(e) and 120.

GOVERNMENTAL SUPPORT

The research leading to the present invention was supported, at least in part, by a grant from NIH Grants GM 54339 and NIH MH 56895 and NIMH Grant R37MH39592. Accordingly, the Government may have certain rights in the invention.

FIELD OF THE INVENTION

This invention relates to a protein involved in the nuclear localization of proteins, and more specifically to a protein involved in maintaining circadian rhythms. The invention also relates to mutants of the protein, nucleic acid and amino acid sequences encoding the protein itself, as well as methods of using the protein including in drug assays.

BACKGROUND OF THE INVENTION

Patterns of activity with periodicities of approximately 24 hours are termed circadian rhythms, and are governed by an internal clock that functions autonomously, but can be entrained by environmental cycles of light or temperature. These behaviors can be entrained to a "zeitgeiber" (most commonly light), but are sustained under conditions of constant darkness and temperature, revealing activity of an endogenous biological clock. Circadian rhythms produced in constant darkness, for example, can also be reset by pulses of light. Such light pulses will shift the phase of the clock in different directions (advance or delay) and to varying degrees in a fashion that depends on the time of light exposure [Pittendrigh, in *Handbook of Behavioral Neurobiology*, 4, J. Aschoff, Ed., New York: Plenum, 1981, pp. 95–124].

Circadian rhythms appear to be a universal component of animal behavior [Pittendrigh, C. S., *Proc. Natl. Acad. Sci USA*, 58:1762–1767 (1967); Pittendrigh, C. S., *Neurosciences*, 437–458 (1974)]. Indeed, circadian physiological rhythms are not limited to the animal kingdom, and genetic screens have identified clock genes in Drosophila [Konopka and Benzer, *Proc. Natl. Acad. Sci. USA*, 68:2112–2116 (1971); and Sehgal et al., *Science*, 263:1603–1606 (1994)], Chlamydomonas [Bruce, V. G. *Genetics*, 70:537–548 (1972)], Neurospora [Feldman and Hoyle, *Neurospora crassa Genetics*, 75:605–613 (1973); Crosthwaite et al., *Science*, 276:763–769 (1997)], Cyanobacteria [Kondo et al., *Science*, 266:1233–1236 (1994)], Arabidopsis [Millar et al., *Science*, 267:1161–1163 (1995)], hamster [Ralph and Menaker, *Science*, 241:1225–1127 (1988)], and mouse [Vitaterna et al., *Science*, 264:719–725 (1994)].

Fruit flies show circadian regulation of several behaviors [Pittendrigh in *The Neurosciences Third Study Program*, Chap. 38, F. O. Schmitt and F. G. Worden, Eds. (MIT Press, Cambridge Mass., 1974); Jackson, in *Molecular Genetics of Biological Rhythms*, pp. 91–121, M. W. Young, Ed. (Dekker, New York, 1993)]. When populations of Drosophila are entrained to 12 hours of light followed by 12 hours of darkness (LD 12:12), adults emerge from pupae (eclose) rhythmically, with peak eclosion recurring every morning. The eclosion rhythm persists when the entraining cues are removed and behavior is monitored in constant darkness, thus indicating the existence of an endogenous clock. Adult locomotor activity is also controlled by an endogenous clock and recurs rhythmically with a 24-hour period.

In the fruit fly *Drosophila melanogaster*, two genes are essential components of the circadian clock, period and timeless [Sehgal et al. *Science* 263:1603 (1994)]. Mutations in either of these genes can produce arrhythmicity or change the period of the rhythm by several hours [Konopka and Benzer *Proc. Natl. Acad. Sci. U.S.A.* 68:2112 (1971); Sehgal et al *Science* 263:1603 (1994)]. Molecular studies [Bargiello et al *Proc. Natl. Acad. Sci. U.S.A.* 81:2142 (1984); Reddy et al *Cell* 38:701 (1984); Myers *Science* 270:805 (1995); Hardin et al. *Nature* 343:536 (1990); Sehgal et al., *Science*, 270:808–810 (1995)] have shown that per and tim are transcribed with indistinguishable circadian rhythms that are influenced by an interaction of the TIM and PER proteins [Sehgal et al. *Science* 263:1603 (1994); Gekakiset et al *Science*, 270:811 (1995)]. A physical association of the two proteins appears to be required for accumulation and nuclear localization of PER [Sehgal et al *Science* 263:1603 (1994); Gekakiset et al. (1995); Price et al. *EMBO J.*, 14:4044 (1995)]. It is likely that nuclear localization leads to suppression of per and tim transcription [Hardin et al. *Nature*, 343:536 (1990); Sehgal et al., *Science*, 270:808–810(1995)]. Cycles of gene expression are thought to be sustained by 5 hour differences in the phases of RNA and protein accumulation. The observed delays in PER accumulation may result, in part, from a requirement for TIM to stabilize PER [Sehgal et al *Science* 263:1603 (1994); Sehgal et al.*Science*, 270:808–810(1995); Price et al.*EMBO J.*, 14:4044–4049 (1995)].

More specifically, mutations in the Drosophila period (per) gene, for example, disrupt circadian rhythms of pupal eclosion and adult locomotor behavior [Konopka and Benzer *Proc. Natl. Acad. Sci. U.S.A.* 68:2112 (1971)]. Although per has been cloned and sequenced and its pattern of expression has been analyzed [Baylies et al. in *Molecular Genetics of Biological Rhythms*, pp. 123–153, M. W. Young, Ed. (Dekker, New York, 1993); Rosbash and Hall *Neuron* 3:387 (1989)], the biochemical function of the PER protein is unknown. PER shares some homology with a family of transcription factors [Crews et al *Cell* 52:143 (1988); Nambu et al *Cell* 67:1157 (1991); Reisz-Porszasz et al *Science* 256:1193 (1992); Hoffman et al *Cell* 252:954 (1991); Burbach et al *Proc. Natl. Acad. Sci. U.S.A.* 89:8185 (1992)] that possess a common sequence motif called the PAS domain.

Immunocytochemical experiments demonstrated that PER is a nuclear protein in a variety of Drosophila tissues [Konopka and Benzer *Proc. Natl. Acad. Sci. U.S.A.* 68:2112 (1971); Baylies et al in *Molecular Genetics of Biological Rhythms*, pp. 123–153, M. W. Young, Ed. (Dekker, N.Y., 1993)]. In cells of the adult fly visual and nervous systems, the amount of PER protein fluctuates with a circadian rhythm [Edery et al *Proc. Natl. Acad. Sci. U.S.A* 91:2260 (1994)], the protein is phosphorylated with a circadian rhythm [Edery et al., *Proc. Natl. Acad. Sci. U.S.A* 91:2260 (1994)], and PER is observed in nuclei at night but not late in the day [Siwicki et al *Neuron* 1:141 (1988); Saez and Young *Mol. Cell. Biol.* 8:5378 (1988); Zerr et al *J. Neurosci*

10:2749 (1990)]. The expression of per RNA is also cyclic. However, peak mRNA amounts are present late in the day, and the smallest amounts are present late at night [Konopka and Benzer *Proc. Natl. Acad. Sci. U.S.A.* 68:2112 (1971)]. Three mutant alleles—per$^O$, per$^S$, and per$^L$,—cause arrhythmic behavior or shorten or lengthen periods, respectively [Konopka and Benzer *Proc. Natl. Acad. Sci. U.S.A.* 68:2112 (1971)]. These mutations also produce corresponding changes in the rhythms of per RNA and protein amounts [Edery et al *Proc. Natl. Acad. Sci. U.S.A* 91:2260 (1994); Hardin et al *Nature* 343:536 (1990); *Proc. Natl. Acad. Sci. U.S.A.* 89:11711 (1992); Sehgal et al *Science* 263:1603 (1994)] and PER immunoreactivity in nuclei [Sewicki et al *Neuron* 1:141 (1988); Saez and Young *Mol. Cell. Biol.* 8:5378 (1988); Zerr et al *J. Neurosci.* 10:2749 (1990)]. This suggests a possible role for molecular oscillations of per in the establishment of behavioral rhythms [Hardin et al, *Proc. Natl. Acad. Sci. U.S.A.* 89:11711 (1992)].

Several mutations that affect eclosion and locomotor activity have been isolated in behavioral screens [Jackson, in *Molecular Genetics of Biological Rhythms*, pp. 91–121, M. W. Young, Ed. (Dekker, N.Y., 1993); Konopka and Benzer *Proc. Natl. Acad. Sci. U.S.A.* 68:2112 (1971); Rosbash and Hall *Neuron* 3:387 (1989); Baylies et al in *Molecular Genetics of Biological Rhythms*, pp. 123–153, M. W. Young, Ed. (Dekker, N.Y., 1993); Jackson, *J. Neurogenet* 1:3 (1983); Dushay et al *J. Biol. Rhythms* 4:1 (1989); Dushay et al *Genetics* 125:557 (1990); Konopka et al., *Proc. Natl. Acad. Sci. U.S.A.* 68:2112 (1991)]. The best characterized, and those with the strongest phenotypes, are mutations at the X chromosome-linked period (per) locus [Konopka and Benzer *Proc. Natl. Acad. Sci. U.S.A.* 68:2112 (1971); Rosbash and Hall *Neuron* 3:387 (1989); Baylies et al in *Molecular Genetics of Biological Rhythms*, pp. 123–153, M. W. Young, Ed. (Dekker, N.Y., 1993); Jackson, *J Neurogenet* 1:3 (1983); Dushay et al *J. Biol. Rhythms* 4:1 (1989); Dushay et al *Genetics* 125:557 (1990)]. Missense mutations atper can lengthen or shorten the period of circadian rhythms, whereas null mutations abolish circadian rhythms altogether. The par gene is expressed in many cell types at various stages of development. In most cell types, the period protein (PER) is found in nuclei [James et al *EMBO J.* 5:2313 (1986); Liu et al *Genes Dev.* 2:228 (1988); Saez and Young *Mol. Cell. Biol.* 8, 5378 (1988); Liu et al *J. Neurosci.* 12:2735 (1992) Siwicki et al *Neuron* 1:141 (1988); Zerr et al *J. Neurosci.* 10:2749 (1990); Edery et al *Proc. Natl. Acad. Sci. U.S.A.* 91:2260 (1994)]. A domain within PER is also found in the Drosophila single-minded protein (SIM) and in subunits of the mammalian aryl hydrocarbon receptor [Crews et al *Cell* 52:143 (1988); Hoffman et al *Science* 252:954 (1991); Burbach et al *Proc. Natl. Acad. Sci. U.S.A.* 89:8185 (1992); Reyes et al *Science* 256:1193 (1992)], and this domain (PAS, for PER, ARNT, and SIM) mediates dimerization of PER [Huang et al *Nature* 364:259 (1993)]. The amounts of both PER protein and RNA oscillate with a circadian period, which is affected by the per mutations in the same manner as behavioral rhythms are affected [Siwicki et al *Neuron* 1:141 (1988); Zerr et al *J. Neurosci* 10:2749 (1990) Edery et al *Proc. Natl. Acad. Sci. U.S.A* 91:2260 (1994); Hardin et al *Nature* 343:536 (1990); *Proc. Natl. Acad. Sci. U.S.A.* 89:11711 (1992)]. Given the homologies to sim and the aryl hydrocarbon receptor (which are thought to regulate transcription), the effects of per on behavioral rhythms have been postulated to depend on circadian regulation of gene expression, including that of per itself [Hardin et al, *Nature* 343:536 (1990); Hardin et al, *Proc. Natl. Acad. Sci. U.S.A.* 89:11711 (1992)].

Timeless is a second gene which has been associated with circadian rhythms in Drosophila [U.S. patent application Ser. No. 08/619,198 filed Mar. 21, 1996, hereby incorporated by reference in its entirety]. In the absence of the Timeless protein, TIM, gene products, such as the Period protein, PER, are not stable in the cytoplasm. Upon binding to the Timeless protein, proteins such as PER are stabilized and translocated into the nucleus. Once in the nucleus, the proteins act to inhibit the production of their own RNA. Both the tim and per genes are transcribed cyclically, and this transcription drives behavior. In particular, the gene products are present in the cytoplasm late in the day when a sleeping cycle is induced, while when the gene products are in the nucleus late at night, and a waking cycle follows.

The TIM protein not only acts as a nuclear translocation factor for the PER protein, but the PER protein also serves as a nuclear translocation factor for the TIM protein, thus indicating that PER and TIM act as mutual and reciprocal nuclear translocation factors. The nuclear translocation of the PER-TIM heterodimer is a crucial step in the regulation of both tim DNA and per DNA transcription.

The TIM protein also plays an important role in entraining the circadian rhythm of Drosophila, and by analogy other animals, to environmental cycles of light. This property of the TIM protein is due to its requirement for stabilizing the PER protein; its role in regulating per DNA transcription; and the TIM protein's extreme sensitivity to light. Unlike the PER protein which requires the TIM protein for stability, the stability of the TIM protein is independent of the PER protein.

Our current understanding of the molecular regulation of circadian rhythmicity in Drosophila comes from integrating genetics and molecular biology. Null mutations in either of two genes, period (per) and timeless (tim), abolish behavioral rhythmicity, while alleles encoding proteins with missense mutations have been recovered at both loci and show either short- or long-period behavioral rhythms [Konopka and Benzer, *Proc. Natl. Acad. Sci USA,* 68:2112–2116 (1971); Sehgal et al., *Science,* 263:1603–1606 (1994); Rutila et al., *Neuron,* 17:921–929 (1996)]. The RNA and protein products of the genes oscillate with a circadian rhythm in wild-type flies. These molecular rhythms are abolished by null mutations of either gene, and the periods of all molecular rhythms are correspondingly altered in each long- and short-period mutant indicating a regulatory interaction between these genes (Hardin et al., *Nature,* 343:536–540 (1990); Edery et al., *Proc. Natl. Acad. Sci USA,* 91:2260–2264 (1994); Sehgal et al., *Science,* 263:1603–1606 (1994); Vosshall et al., *Science,* 263:1606–1609 (1994); Seghal et al., *Science,* 270:808–810 (1995); Price et al., *EMBO J.,* 14:4044–4049 (1995); Hunter-Ensor et al., *Cell,* 84:677–685 (1996); Myers et al., *Science,* 271:1736–1740 (1996); Zeng et al., *Nature,* 380:129–135 (1996)].

Production of these molecular cycles appears to depend on the rhythmic formation and nuclear localization of a complex containing the PER and TIM proteins [Seghal et al., *Science,* 270:808–810 (1995); Gekakis et al., *Science,* 270:811–815 (1995); Lee et al., *Science,* 271:1740–1744 (1996); Saez and Young, *Neuron,* 17:911–920 (1996); Saez and Young, *Neuron,* 17:911–920 (1996)]. A physical interaction of PER and TIM is required for nuclear localization of either protein, and nuclear activity of these proteins coordinately regulates per and tim transcription through a negative feedback loop [Sehgal et al., *Science,* 263:1603–1606 (1994); Vosshall et al., *Science,* 263:1606–1609 (1994); Seghal et al., *Science,* 270:808–810

(1995); Gekakis et al., *Science,* 270:811–815 (1995); Hunter-Ensor et al., *Cell,* 84:677–685 (1996); Lee et al., *Science,* 271:1740–1744 (1996); Myers et al., *Science,* 271:1736–1740 (1996); Saez and Young, *Neuron,* 17:911–920 (1996); Zheng et al., *Nature,* 380:129–135 (1996)]. Studies of per$^L$, a mutation that lengthens the period of behavioral rhythms [Konopka and Benzer, *Proc. Natl. Acad. Sci. USA,* 68:2112–2116 (1971)] and delays nuclear localization of PER protein [Curtin et al., *Neuron,* 14:365–372 (1995)], have shown that the PER$^L$ protein has reduced affinity for TIM [Gekakis et al., *Science,* 270:811–815 (1995). This suggests that rates of PER/TIM association influence the period of the molecular cycle in mutant and wild type flies.

Seghal et al., [*Science,* 270:808–810 (1995)] proposed a model for the Drosophila clock in which delayed formation of PER/TIM complexes ensures separate phases of per/tim transcription and nuclear function of the encoded proteins. Recent mathematical treatments of the Drosophila data are consistent with this model [Leloup and Goldbeter, *J. Biol. Rhythms,* 13:70–87 (1998)]. Entrainment of this oscillator is regulated through the TIM protein, which is rapidly eliminated from the nucleus and cytoplasm of pacemaker cells when Drosophila are exposed to daylight [Hunter-Ensor et al., *Cell.,* 84:677–685 (1996); Lee et al., *Science,* 271:1740–1744 (1996); Myers et al., *Science,* 271:1736–1740 (1996); Zheng et al., *Nature,* 380:129–135 (1996)]. Studies of transgenic Drosophila have shown that adult behavioral rhythms can be linked to per and tim expression in a small group of central brain cells, the lateral neurons [Ewer et al., (1992); Frisch et al., *Neuron,* 12:555–570 (1994); Vosshall and Young, *Neuron,* 15:345–360 (1995)]. per and tim are also expressed in larval brain cells that are most likely the larval LNs [Kaneko et al., *Neurosci.,* 17:6745–6760 (1997)], suggesting a basis for larval entrainment to light/dark cycles [Sehgal et al., *Proc. Natl. acad. Sci. USA,* 89:1423–1427 (1992)]. Oscillations of per and tim RNA, and PER and TIM proteins have been found outside of the head in a variety of tissues [Giebultowicz and Hege, *Nature,* 386:664 (1997); Emery et al., *Proc. Natl. Acad. Sci. USA,* 94:4092–4096 (1997); Plautz et al., *Science,* 278:1632–1635 (1997)]. Some of the latter oscillations were observed in vitro with isolated tissues, further indicating a cell autonomous mechanism [Giebultowicz and Hege, *Nature,* 386:664 (1997); Emery et al., *Proc. Natl. Acad. Sci. USA,* 94:4092–4096 (1997); Plautz et al., *Science,* 278:1632–1635 (1997)]. Mammalian homologues of per have recently been identified [Tei et al., *Nature,* 389 (1997); Sun et al., *Cell,* 90:1003–1011 (1997); Shigeyoshi et al., *Cell,* 91:1043–1053 (1997); Albrecht et al., *Cell,* 91:1055–1064 (1997); Shearman et al., *Neuron,* 19:1261–1269 (1997)], suggesting that the molecular basis of circadian rhythms may be conserved from flies to mammals. A related circadian oscillator has also been described at the molecular level in Neurospora through the detailed work of Dunlap and colleagues [reviewed by Dunlap et al., *Annu. Rev. Genet.,* 30:579–601 (1996)].

Although key features of the Drosophila clock have been identified, the involvement of additional, essential factors is suspected from prior work. Since neither PER nor TIM has a recognizable DNA-binding motif, an unidentified transcription factor(s) should mediate repression in response to nuclear PER/TIM complexes [(reviewed by Rosbash et al., *Harb. Symp. Quant. Biol.,* 76:265–278 (1996); Young et al., *Harb. Symp. Quant. Biol.,* 61:279–284 (1996)]. PER fails to accumulate in the absence of TIM even in the presence of high per RNA levels [Vosshall et al., *Neuron,* 15:345–360 (1994); Price et al., *EMBO J.,* 14:4044–4049 (1995)], indicating the existence of an activity that de-stabilizes cytoplasmic PER monomers. Both PER and TIM are phosphorylated with a circadian rhythm [Edery et al., *Proc. Natl. Acad. Sci. USA,* 94:4092–4096 (1994); Zeng et al., *Nature,* 380:129–135, 1996)] indicating unidentified kinases. PER, in particular, becomes progressively phosphorylated over many hours, and the timing of this is changed in period-altering mutants, leading to the suggestion that defined hyperphosphorylated form(s) of PER might signal PER degradation [Edery et al., *Proc. Natl. Acad. Sci. USA,* 94:4092–4096 (1994)].

In summary, circadian rhythms in Drosophila require periodic interaction of the PERIOD (PER) and TIMELESS (TIM) proteins. Physical associations of PER and TIM allow their nuclear translocation, and autoregulation of per and tim transcription through a negative feedback loop. Because PER/TIM heterodimers are only observed when high levels of per and tim RNA have accumulated, self-sustained oscillations are produced in the feedback loop [Gekakis et al., *Science,* 270:811–815 (1995); Hunter-Ensor et al., *Cell,* 84:677–685 (1996); Myers et al., *Science,* 271:1736–1740 (1996); Saez and Young, *Neuron,* 17:911–920 (1996); Sehgal et al., *Science,* 270:808–810 (1995) and Zeng et al., *Nature,* 380:129–135 (1996)]. Although molecular oscillations are maintained in constant darkness for per and tim RNA and for PER and TIM proteins, light can entrain the phases of these rhythms through rapid degradation of the light-sensitive TIM protein [Hunter-Ensor et al., *Cell,* 84:677–685 (1996); Myers et al., *Science,* 271:1736–1740 (1996) and Zeng et al., *Nature,* 380:129–135 (1996)]. Circadian oscillations of PER and TIM phosphorylation have also been described [Edery et al., *PNAS, USA,* 91:2260–2264 (1994) and Zeng et al., *Nature,* 380:129–135 (1996)]. However, prior studies have not demonstrated a function for these modifications. The recent identification of several PER homologues from mammals [Albrecht et al. *Cell,* 91:1055–1064 (1997); Shearman et al., *Neuron,* 19:1261–1269 (1997); Shigeyoshi et al., *Cell,* 19:1043–1053 (1997); Sun et al., *Cell,* 90:10031011 (1997) and Tei et al., *Nature,* 389:512–516 (1997)] suggests that, like many other biological processes, key molecules and mechanisms involved in circadian rhythms may be evolutionarily conserved between flies and mammals. A related mechanism has also been well defined in Neurospora [cf. Crosthwaite et al., *Science,* 276:763–769 (1997); Dunlap, *Ann. Rev. of Gen,* 30:579–601 (1996) and Garceau et al., *Cell,* 89:469–476 (1997)] and additional genes and proteins are known to play roles in the mouse [Antoch et al., (1997); King et al., *Cell,* 89:641–653 (1997) and Vitaterna et al., *Science,* 264:719–725 (1994)] the hamster [Ralph and Menaker, *Science,* 241:1225–1227 (1988)] and Arabidopsis [Millar et al., *Science,* 267:1161–1163 (1995)].

Therefore there is a need to identify other factors involved in circadium rythms. Furthermore, there is a need to use such factors to identify agents that can aid in the regulation of biological clocks, including as an aid in overcoming such maladies as jet lag.

The citation of any reference herein should not be construed as an admission that such reference is available as "Prior Art" to the instant application.

SUMMARY OF THE INVENTION

The present invention discloses a protein DOUBLETIME (DBT), which is involved in circadium rhythms. More particularly, DBT, which is also known as casein kinase-1ε

(CK1ε) is shown herein to play a role in the regulation of the concentration of the important clock gene, Period (PER). The human CK1ε has the nucleic acid sequence of SEQ ID NO:14, and the amino acid sequence of SEQ ID NO:9 [Fish, et al., *J. Biol. Chem.* 270:14875 (1995)]. Other CK1ε's are exemplified in FIG. 18, below.

Therefore the present invention provides isolated nucleic acids and/or recombinant DNA molecules that encode DOUBLETIME (DBT) proteins, variants thereof, and the fragments thereof, including DBT (and DBT variants) chimeric peptides and proteins of the present invention. The present invention further provides the isolated and/or recombinant DBT proteins and fragments thereof including DBT (and DBT variants) chimeric peptides and proteins and DBT. In addition, the present invention provides antibodies to DBT and more specifically antibodies that are specific for the CK1ε variant proteins. Methods of using these nucleic acids, proteins, and antibodies as reagents for drug screening and therapeutics are also provided.

One aspect of the present invention includes a nucleic acid that comprises a nucleotide sequence that encodes DBT or a DBT variant such as the tau CK1ε. In one such embodiment the nucleic acid comprises a nucleotide sequence that encodes a Drosophila DBT. In another embodiment, the nucleic acid comprises a nucleotide sequence that encodes a mammalian DBT. In a specific embodiment of this type the nucleic acid comprises a nucleotide sequence that encodes a tau hamster DBT having the amino acid sequence of SEQ ID NO:18. In a preferred embodiment the nucleic acid encoded a human variant of the DBT that corresponds/is the ortholog for the hamster tau CK1ε.

In a particular embodiment the nucleic acid comprises a nucleotide sequence that encodes a DBT having an amino acid sequence of SEQ ID NO:2. In a preferred embodiment of this type, the nucleic acid comprises the coding sequence of SEQ ID NO:1. In another embodiment the nucleic acid comprises a nucleotide sequence which encodes a DBT and hybridizes to the complementary strand of a nucleotide sequence that encodes a DBT having an amino acid sequence of SEQ ID NO:2. In a related embodiment the nucleic acid comprises a nucleotide sequence that encodes a DBT having an amino acid sequence of SEQ ID NO:2 comprising a conservative substitution. In another embodiment the nucleic acid comprises a nucleotide sequence which encodes a DBT and hybridizes to the complementary strand of a nucleotide sequence that encodes a DBT having an amino acid sequence of SEQ ID NO:2 comprising a conservative substitution.

In another embodiment the nucleic acid comprises a nucleotide sequence that encodes a DBT having an amino acid sequence of SEQ ID NO:16. In a preferred embodiment of this type, the nucleic acid comprises the coding sequence of SEQ ID NO:15. In another embodiment the nucleic acid comprises a nucleotide sequence which encodes a DBT and hybridizes to the complementary strand of a nucleotide sequence that encodes a DBT having an amino acid sequence of SEQ ID NO:16. In a related embodiment the nucleic acid comprises a nucleotide sequence that encodes a DBT having an amino acid sequence of SEQ ID NO:16 comprising a conservative substitution. In another embodiment the nucleic acid comprises a nucleotide sequence which encodes a DBT and hybridizes to the complementary strand of a nucleotide sequence that encodes a DBT having an amino acid sequence of SEQ ID NO:16 comprising a conservative substitution.

In an alternative embodiment the nucleic acid comprises a nucleotide sequence that encodes a DBT variant having an amino acid sequence of SEQ ID NO:3. In another such embodiment the nucleic acid comprises a nucleotide sequence that encodes a DBT variant having an amino acid sequence of SEQ ID NO:3 comprising a conservative substitution. In still another embodiment the nucleic acid comprises a nucleotide sequence that encodes a DBT variant having an amino acid sequence of SEQ ID NO:4. In yet another embodiment the nucleic acid comprises a nucleotide sequence that encodes a DBT variant having an amino acid sequence of SEQ ID NO:4 comprising a conservative substitution. In still another embodiment the nucleic acid comprises a nucleotide sequence that encodes a DBT variant having the amino acid sequence of SEQ ID NO:18. In yet another embodiment the nucleic acid comprises a nucleotide sequence that encodes a DBT variant having an amino acid sequence of SEQ ID NO:18 comprising a conservative substitution.

In addition the present invention provides nucleic acids encoding CK1ε variants as defined below as $dbt^{S\#}$ CK1ε, $dbt^{L\#}$ CK1ε, and tau$^{\#}$ CK1ε, and more specifically as $dbt^{S}$ CK1ε, a $dbt^{L}$ CK1ε, and a tau CK1ε. In addition the present invention provides nucleic acids that encode other variants of CK1ε, in particular, those that have one or more amino acid substitutions in the anion binding motif of the CK1ε, which in the hamster protein corresponds to Arg #178, Gly #215 and Lys #224 of SEQ ID NO:16 (see FIG. 18 below, for the analogous sites in other CK1ε's).

In a related embodiment the present invention provides a nucleic acid that encodes an ATP-binding site of a DBT having an amino acid sequence of SEQ ID NO:6. In a preferred embodiment of this type, the nucleic acid comprises the coding sequence of SEQ ID NO:5. In another embodiment the nucleic acid encodes an ATP-binding site of a DBT having an amino acid sequence of SEQ ID NO:6 comprising a conservative substitution.

In another related embodiment the present invention provides a nucleic acid that comprises a nucleotide sequence that encodes a kinase catalytic domain of a DBT having an amino acid sequence of SEQ ID NO:8. In a preferred embodiment of this type, the nucleic acid comprises the coding sequence of SEQ ID NO:7. In another embodiment the nucleic acid comprises a nucleotide sequence that encodes a kinase catalytic domain of a DBT having an amino acid sequence of SEQ ID NO:8 comprising a conservative substitution.

The present invention further provides a nucleic acid consisting of at least 15, preferably at least 24, more preferably at least 36 consecutive nucleotides of a nucleotide sequence that encodes a DOUBLETIME protein having an amino acid sequence of SEQ ID NO:2. Another such embodiment is a nucleic acid consisting of at least 15, preferably at least 24, more preferably at least 36 consecutive nucleotides of a nucleotide sequence that encodes a DOUBLETIME protein having an amino acid sequence of SEQ ID NO:2 comprising a conservative substitution. In addition, the present invention provides nucleotide probes of at least 18 nucleotides for a nucleotide sequence that encodes a DOUBLETIME protein having an amino acid sequence of SEQ ID NO:2, and nucleotide probes of at least 12, preferably at least 18 and more preferably at least 27 nucleotides that are specific for a CK1ε, variant of the present invention.

All of the nucleic acids of the present invention can further comprise a heterologous nucleotide sequence. Furthermore, all of the nucleic acids of the present invention can be constructed into recombinant DNA molecules. Such recombinant DNA molecules can be operatively linked to an expression control sequence. The expression vectors containing the recombinant DNA molecules of the present invention are also provided by the present invention. In addition methods of expressing the recombinant DNA molecules for making the corresponding recombinant proteins and peptides are also provided. Thus, the recombinant proteins and peptides can be expressed in a cell (either a prokaryotic cell or a eukaryotic cell) containing an expression vector of the present invention by culturing the cell in an appropriate cell culture medium under conditions that provide for expression of the protein by the cell. In one such embodiment, a recombinant DOUBLETIME protein is expressed in a cell containing an expression vector of the present invention by culturing the cell in an appropriate cell culture medium under conditions that provide for expression of the DOUBLETIME protein by the cell. In a preferred embodiment of this type, the method further comprises the step of purifying the recombinant DOUBLETIME. The present invention also includes the recombinant DOUBLETIME proteins (including recombinant CK1ε variants) and peptides made and/or purified by such methods.

Another aspect of the present invention is the protein encoded by a DOUBLETIME gene. In one embodiment the protein is a Drosophila DBT. In another embodiment, the protein is a mammalian DBT. In a preferred embodiment of this type the mammalian DBT is a human DBT. In a specific embodiment of this type the protein is a hamster enzyme. The present invention also provides the dbt$^{S\#}$ CK1ε, dbt$^{L\#}$ CK1ε, and tau$^{\#}$ CK1ε proteins and the unique fragments of these CK1ε variant proteins. In a preferred embodiment of this type the protein is a human variant of the DBT that corresponds/is the ortholog for the hamster tau CK1ε.

In a particular embodiment the DBT has an amino acid sequence of SEQ ID NO:2. In another embodiment the DBT has an amino acid sequence of SEQ ID NO:2 comprising a conservative substitution. In another embodiment the DBT has an amino acid sequence of SEQ ID NO:16. In a related embodiment the DBT has an amino acid sequence of SEQ ID NO:16 comprising a conservative substitution. In a related embodiment the DBT is a DBT variant that has an amino acid sequence of SEQ ID NO:3. In another embodiment the DBT is a DBT variant that has an amino acid sequence of SEQ ID NO:3 comprising a conservative substitution. In still another embodiment the DBT variant has an amino acid sequence of SEQ ID NO:4. In yet another embodiment the DBT variant has an amino acid sequence of SEQ ID NO:4 comprising a conservative substitution. In another embodiment the DBT has an amino acid sequence of SEQ ID NO:18. In a related embodiment the DBT has an amino acid sequence of SEQ ID NO:18 comprising a conservative substitution.

In a related embodiment the present invention provides a protein or peptide comprising an ATP-binding site of a DBT that has an amino acid sequence of SEQ ID NO:6. In another embodiment the protein or peptide comprises an ATP-binding site of a DBT having an amino acid sequence of SEQ ID NO:6 comprising a conservative substitution. In another related embodiment the present invention provides a protein or peptide comprising a kinase catalytic domain of a DBT having an amino acid sequence of SEQ ID NO:8. In another embodiment the protein or peptide comprises a kinase catalytic domain of a DBT that has an amino acid sequence of SEQ ID NO:8 comprising a conservative substitution.

The present invention further provides fragments of the proteins and peptides of the present invention, including proteolytic fragments. In one embodiment the proteolytic fragment comprises at least six amino acids. In a preferred embodiment the proteolytic fragment comprises at least nine amino acids. In a more preferred embodiment the proteolytic fragment comprises at least fifteen amino acids. In one particular embodiment the fragment binds to the period (PER) protein. In another particular embodiment the fragment has protein kinase activity.

The present invention further provides fusion proteins comprising the proteins, peptides and fragments thereof of the present invention. Thus all of the DBTs (and variant DBTs) and fragments thereof of the present invention can be modified, placed in a fusion of chimeric peptide or protein, or labeled e.g., to have an N-terminal FLAG-tag, or a S.Tag. In a particular embodiment a DBT can be modified to contain a marker protein such as green fluorescent protein as described in U.S. Pat. No. 5,625,048 filed Apr. 29, 1997 and WO 97/26333, published Jul. 24, 1997 the disclosures of which each are hereby incorporated by reference herein in their entireties.

Still another aspect of the present invention provides an antibody to a DBT (or variant DBT) or fragment thereof, of the present invention. In a particular embodiment the antibody is specific for the CK1ε variants of the present invention. In one embodiment the antibody of is a polyclonal antibody. In another embodiment the antibody is a monoclonal antibody. In a particular embodiment of this type the monoclonal antibody is a chimeric antibody. The present invention further provides immortal cell lines that produce the monoclonal antibodies of the present invention.

The present invention further provides CK1ε (or CK1ε variant) transgenic, knockin, and knockout animals. These animals can be used as animal models in drug screening assays for drugs that can treat sleep disorders or jet lag. Indeed, all of the CK1ε variants disclosed herein can be used in the transgenic or knockin animals. In a preferred embodiment the transgenic or knockin animal is a mouse. In a particular embodiment the mouse is a tau$^{\#}$ CK1ε knockin mouse. In a preferred embodiment of this type the mouse is a tau CK1ε knockin mouse. In another embodiment the mouse is a dbt$^{S\#}$ CK1ε knockin mouse. In a preferred embodiment of this type the mouse is a dbt$^{S}$ CK1ε knockin mouse. In still another embodiment the mouse is a dbt$^{L\#}$ CK1ε knockin mouse. In a preferred embodiment of this type the mouse is a dbt$^{L}$ CK1ε knockin mouse. The phenotypes of these mice preferably correspond to that found for the prior Drosophila and hamster variants.

The cells from the knockin and transgenic animals of the present invention and cells that are constructed to contain a variant CK1ε are also part of the present invention. These cells can also be used in the drug assays described below.

Another aspect of the present invention provides methods for detecting the presence or activity of the DBTs of the present invention. One such embodiment comprises contacting a biological sample from an organism in which the presence or activity of the DBT is suspected with a binding partner for the DBT under conditions that allow binding of the DBT to the binding partner to occur, and then detecting whether the binding has occurred between the DBT and the binding partner in the sample. Detection of such binding indicates that the DBT is present in the sample.

A related aspect of the present invention includes methods for detecting a casein kinase1ε (CK1ε) variant in a mammal. In a particular embodiment of this type the mammal has a sleep or related disorder. Preferably the mammal is a human. One method comprises obtaining a biological sample from the mammal and assaying the biological sample for the presence of a CK1εvariant. In another embodiment the biological sample is assayed for the presence of a nucleic acid encoding the CK1 variant. Preferably the CK1ε variant is a CK1ε polymorphism. In one particular embodiment the CK1ε variant is a dbt$^{S\#}$ CK1ε. In a preferred embodiment of this type the CK1ε variant is a dbt$^S$ CK1ε. In another particular embodiment the CK1ε variant is a dbt$^{L\#}$ CK1ε. In a preferred embodiment of this type the CK1ε variant is a dbt$^L$ CK1ε. In yet another particular embodiment the CK1ε variant is a tau$^\#$ CK1ε. In a preferred embodiment of this type the CK1ε variant is a tau CK1ε.

In a particular embodiment the biological sample is assayed by being contacted with a probe that specifically binds to the nucleic acid that encodes the CK1ε variant under conditions that allow the binding of the probe to the nucleic acid. The assaying can either be performed in vitro, after making a cell extract or in situ using FISH for example. In a particular embodiment of this type the probe is a nucleotide probe, and preferably the assaying is performed by hybridizing a labeled probe to the nucleic acid encoding the CK1ε variant that is present in the biological sample. In another embodiment the probe is a primer, and the assaying includes performing PCR on the nucleic acid encoding the CK1ε variant that is present in the biological sample. Alternatively, a probe can specifically bind to the CK1ε variant present in the biological sample. In one such embodiment the probe is an antibody. In this case the antibody can either be detected directly or indirectly. In any case, the binding of the probe to the CK1ε variant or the nucleic acid that encodes it, facilitates the detection of the CK1ε variant in the biological sample. Alternatively, a CK1ε variant can be detected through determining its enzymatic activity.

Once a CK1ε variant is detected the nucleotide sequence of the nucleic acid encoding the CK1ε variant can be determined. The isolated nucleic acid is also part of the present invention. In a particular embodiment the method can further comprise constructing a recombinant DNA that encodes the coding region of the nucleic acid. In addition, the recombinant DNA can be placed into an expression vector and expressed to make the corresponding recombinant protein. The isolated recombinant protein is also part of the present invention. The recombinant protein can also be assayed for its kinase and/or binding activity towards one or more variants of PER.

Still another aspect of the present invention includes methods of identifying an agent that modulates the interaction between a PER protein and a DBT protein. One such method comprises contacting the PER protein with the DBT protein in the presence of the agent under conditions in which the DBT protein binds the PER protein in the absence of the agent. The binding of the PER protein and the DBT protein is then measured. An agent that modulates the interaction between the PER protein and the DBT protein is identified when the binding of the PER protein with the DBT protein is different in the presence of the agent than in its absence. An agent that modulates the PER protein-DBT protein interaction by enhancing the binding is identified as an agonist. On the other hand, an agent that modulates the PER protein-DBT protein interaction by diminishing the binding is identified as an antagonist. In a preferred embodiment the DBT protein is human casein kinase Iε.

In a particular embodiment, the step of determining the binding of the PER protein and the DBT protein includes determining the dissociation constant between the PER protein and the DBT protein. In another embodiment, an active fragment of the PER protein is used in place of the PER protein. In this case the active fragment of the PER protein minimally retains its DBT protein binding capacity. In a related embodiment, an active fragment of the DBT protein is used in place of the DBT protein. In this case the active fragment of the DBT protein minimally retains its PER protein binding capacity. In still another embodiment, an active fragment of the PER protein is used in place of the PER protein and an active fragment of the DBT protein is used in place of the DBT protein. Again, the active fragment of the PER protein minimally retains its DBT protein binding capacity, whereas the active fragment of the DBT protein minimally retains its PER protein binding capacity.

A related aspect of the present invention includes a method of identifying an agent that modulates the phosphorylation of a PER protein by a DBT. One such embodiment comprises contacting the PER protein with the DBT protein in the presence of the agent under conditions in which the DBT protein phosphorylates the PER protein in the absence of the agent. The phosphorylation of the PER protein is then measured (either directly or indirectly). An agent that modulates the phosphorylation of the the PER protein by the DBT protein is identified when the phosphorylation of the PER protein is different in the presence of the agent than in its absence. An agent that modulates the DBT-dependent phosphorylation of the PER protein by enhancing the phosphorylation is identified as an agonist. On the other hand, an agent that modulates the DBT-dependent phosphorylation of the PER protein by diminishing the phosphorylation is identified as an antagonist. In a preferred embodiment the DBT protein is human casein kinase Iε.

In a particular embodiment, an active fragment of the PER protein is used in place of the PER protein. In this case the active fragment of the PER protein minimally retains its phosphorylation site, but preferably also retains its DBT protein binding capacity. In a related embodiment, an active fragment of the DBT protein is used in place of the DBT protein. In this case the active fragment of the DBT protein minimally retains its kinase activity but preferably also retains its PER protein binding capacity. In still another embodiment, an active fragment of the PER protein is used in place of the PER protein and an active fragment of the DBT protein is used in place of the DBT protein. Again, the active fragment of the PER protein minimally retains its phosphorylation site, but preferably also retains its DBT protein binding capacity, whereas the active fragment of the DBT protein minimally minimally retains its kinase activity but preferably also retains its PER protein binding capacity.

Such assays can be performed in vitro or in situ (for example in cells as in the cis-trans assays as described below). In one such in situ assay, the proteins or active fragments thereof are contacted in the cell by expressing the corresponding nucleic acids that encode the CK1ε and PER in the cell. In addition, any of the CK1ε variants of the present invention can be used in place of the wild type CK1ε in the assays. Additional assays are also exemplified in Example 3, below.

The present invention also provides methods of using the transgenic and knockin animals of the present invention in drug assays and screens. More specifically, nucleic acids that express the various CK1ε variants can be used to construct knockin mice which express the corresponding CK1ε variant. In a particular embodiment the knockin mouse encodes a dbt$^{S\#}$ CK1ε. In another embodiment the knockin mouse encodes a dbt$^{L\#}$ CK1ε. In yet another embodiment the knockin mouse encodes a tau$^\#$ CK1ε. The knockin mice can then be used in in vivo drug assays. Similarly cells obtained from the knockin mice and cells constructed to comprise a CK1ε variant can also be employed in such assays.

In a particular embodiment an agent is administered to a CK1ε variant knockin mouse having a specific phenotype due to the expression of the CK1ε variant. The effect of the agent on the phenotype is then determined. An agent that modifies the specific phenotype is then selected. Agents can thus be identified which either extend or contract the animal's period of rhythm. In one embodiment the knockin mouse has a shorter period of rhythm, e.g., a dbt$^S$ CK1ε, or a tau CK1ε, whereas in another embodiment the knockin mouse has a longer period of rhythm, e.g., the dbt$^L$ CK1ε.

Alternatively, the agents can be administered to the knockin or transgenic animal but the assay can be performed in situ or in vitro. Since CK1ε is known to be a kinase, its relative activity is readily measured (see Examples below). Furthermore, since PER is a disclosed substrate for CK1ε, binding assays (including affinity kinase assays, see Example 3) with PER can also be performed. In addition, when the drug assay is performed in vivo, assays that measure locomotor activity (as described in Example 3) can be employed.

Yet another aspect of the present invention comprises methods of identifying the nucleotide and amino acid sequences of homologues to the Drosophila doubletime gene. Once the coding region of the nucleotide sequence is identified, the corresponding amino acid sequence can be readily determined using the genetic code, preferably with the aid of a computer. Preferably the full-length nucleotide sequence of the coding region of a homologue to the Drosophila doubletime gene is identified. Recombinant DNA molecules and the recombinant DBT proteins obtained by these methods are also part of the present invention.

One method of identifying a nucleotide sequence of the coding region of a homologue to the Drosophila doubletime gene comprises comparing SEQ ID NO:2 with the amino acid sequences encoded by nucleic acids that are obtained from a library of nucleic acids containing partial nucleotide sequences of the coding regions from non-Drosophila genes. Preferably this determination is aided by computer analysis. A nucleic acid containing a partial nucleotide sequence of a coding region from a non-Drosophila gene that is highly homologous to SEQ ID NO:2 can then be selected. Methods of ascertaining which nucleic acid and amino acid sequences are highly homologous are described below.

The full-length sequence of the coding region of the non-Drosophila gene is preferably determined. The sequence is identified as being that of the homologue to the Drosophila doubletime gene when it is highly homologous to SEQ ID NO:2 as discussed below. In a preferred embodiment this method further comprises determining whether the nucleotide sequence that contains a coding region for an amino acid sequence that is highly homologous to SEQ ID NO:2 is also expressed in the corresponding suprachiasmatic nucleus (SCN), i.e., if the putative homologue is a mouse homologue, the SCN of a mouse is tested [Sun et al., *Cell* 90:1003–1011 (1997)]. When the nucleotide sequence is expressed in the SCN, it is identified as the nucleotide sequence of the coding region of the homologue to the Drosophila doubletime gene. One means of determining whether the nucleotide sequence is expressed in the SCN is through the use of a labeled nucleotide probe for the nucleotide sequence that contains the coding region for an amino acid sequence that is highly homologous to SEQ ID NO:2. The labeled nucleotide probe can then be hybridized with a sample containing nucleic acids that are expressed in the SCN under stringent conditions. If hybridization is detected, the sequence is identified as being that of the homologue to the Drosophila doubletime gene. Similarly, a PCR primer can be used to aid in the confirmation of the identification of a nucleotide sequence of the coding region of the homologue to the Drosophila doubletime gene In a particular embodiment of the method, determining the full-length sequence of the coding region is performed by sequencing the insert of a plasmid which contains a nucleic acid encoding an amino acid sequence that is highly homologous with SEQ ID NO:2. In this case, the insert comprises the nucleic acid. In another embodiment, the full-length sequence is determined by PCR.

A related embodiment includes a method of identifying the full-length nucleotide sequence of the coding region of a homologue to the Drosophila doubletime gene that comprises determining the percent homology of SEQ ID NO:2 to amino acid sequences encoded by nucleotide sequences from a library of nucleotide sequences for non-Drosophila genes and then selecting a nucleotide sequence that contains a coding region for an amino acid sequence that is highly homologous to SEQ ID NO:2. The full-length nucleotide sequence of the coding region for the amino acid sequence is determined and the full-length nucleotide sequence of the coding region of the homologue to the Drosophila doubletime gene is identified. This method can also comprise determining whether the nucleotide sequence is expressed in the suprachiasmatic nucleus (SCN). When the nucleotide sequence is expressed in the SCN, it is identified as the nucleotide sequence of the coding region of the homologue to the Drosophila doubletime gene.

In another embodiment, the method can further comprise constructing a recombinant DNA that contains the coding region. In one such embodiment a recombinant DBT protein is made by expressing the recombinant DNA. In a preferred embodiment of this type an activity of the recombinant Drosophila DBT is assayed. In one such embodiment, the activity assayed is the ability of the recombinant protein to bind to PER. In another such embodiment the activity assayed is the ability of the recombinant protein to act as a protein kinase. In yet another such embodiment the activity assayed is the ability of the recombinant protein to phosphorylate PER. The sequence is identified as being that of the homologue to the Drosophila doubletime gene when the recombinant protein has the activity of the Drosophila DBT.

In addition the present invention provides test kits for demonstrating the presence or absence of a DBT or a DBT variant in a cellular sample. One such kit comprises a predetermined amount of a binding partner of the protein or the nucleic acid that encodes the DBT or DBT variant. Preferably the binding partner is detectably labeled. A preferred kit further comprises a predetermined amount of the DBT and/or DBT variant to be used as a standard. A kit of the present invention can also provide a protocol for using the kit.

The present invention also provides methods of preventing and/or treating disorders of a circadian rhythm which include depression, narcolepsy and jet lag. Such methods rely on temporary antagonisms to transiently inhibit the natural clock, and then supplying agonists to subsequently reset it e.g., for the treatment of jet lag. One such embodiment comprises administering to an animal a therapeutically effective amount of a DBT. Another such embodiment comprises administering to an animal a therapeutically effective amount of an agent capable of promoting the production and/or activity of a DBT. Yet another such embodiment comprises a mixtures of such agents. Still another embodiment comprises administering to an animal a therapeutically effective amount of an agent capable of inhibiting the activity of the DBT.

Accordingly, it is a principal object of the present invention to provide DBTs in purified form that exhibit activities associated with circadium rhythms.

It is a further object of the present invention to provide antibodies to the DBTs, and methods for their preparation, including by recombinant means.

It is a still further object of the present invention to provide nucleic acids encoding DBTs.

It is a further object of the present invention to provide a method for detecting the presence of the DBT in mammals.

It is a further object of the present invention to provide a method and associated assay system for screening substances such as drugs, agents and the like, that are potentially effective in either mimicking the activity or combating the adverse effects of the DBTs in mammals.

It is a still further object of the present invention to provide a method for the treatment of mammals to control depression, jet lag and/or narcolepsy.

It is a still further object of the present invention to provide pharmaceutical compositions for use in therapeutic methods which comprise or are based upon DBT or upon agents or drugs that control the production, or that mimic or antagonize the activities of the DBT.

It is a still further object of the present invention to provide a method of obtaining a human homologue to the Drosophila DBT.

It is a still further object of the present invention to provide Drosophila expressing mutant (variant) forms of DBT.

It is a still further object of the present invention to provide transgenic or knockin animals that express mutant (variant) forms of DBT.

These and other aspects of the present invention will be better appreciated by reference to the following drawings and Detailed Description.

BRIEF DESCRIPTION OF THE DRAWINGS

FIG. 3C shows the side by side analysis of PER proteins at ZT22, ZT0 and CT2 from $dbt^S$, wild type and $dbt^L$ and demonstrates that, relative to wild type, PER phosphorylation is advanced in $dbt^S$ and delayed in $dbt^L$. Note that three times as much total protein was used in the $dbt^S$ lanes in this panel.

FIG. 4C shows the high magnification of 1vLNs which shows TIM protein in wild type (left), $per^o$ (center), and $per^o$; $dbt^P$ (right) strains at ZT22. TIM is nuclear in wild type, but forms cytoplasmic rings in $per^o$, and $per^o$; $dbt^P$.

In FIG. 5A larvae were entrained as in FIG. 4, and PER protein detected as described in Experimental Procedures, Example 1, below. Arrowheads indicate 1vLNs. PER protein oscillates in wild type (WT) 1vLNs, with staining only at ZT1 and CT1. PER is detectable in $dbt^P$ 1vLNs at all 4 time points shown, as well as strongly in other cell clusters. Western blot of extracts from 10 larval brains for $per^o$, wild type, and $dbt^P$ larvae at ZT12 and ZT24 (ZT24 coincides with peak PER accumulation in wild type), run alongside 2 mg protein from wild-type adult heads from either ZT14 or ZT2 (FIG. 5B). The asterisk marks a cross-reacting band that serves as a loading control, confirming that PER accumulates to higher levels in $dbt^P$ than in wild-type or $per^o$. PER is difficult to detect in wild type brain extracts, but a clear PER signal distinguishes wild type from the per$^o$ control. FIG. 5C shows RNase protection of per, tim and rp49 RNA from 10 mg wild-type (left) or dbt$^P$ (right) larval brain RNA at ZT14–16 (predicted peak for per RNA expression in wild type). Relative to rp49, per and tim levels are similar in wild type and dbt$^P$. FIG. 5D displays whole brains of wild-type (left) and dbt$^P$ larvae (center) at ZT1 stained with anti-PER, and SG3 (right) stained with anti-β-gal antibodies. The PER-SG3 pattern is very similar to PER in dbt$^P$, indicating that the pattern of PER protein seen in dbt$^P$ larval brains reflects the normal activity of the per promoter. Brain hemispheres from wild type (left) or dbt$^P$ larvae (right) raised in constant light from embryogenesis onwards and stained for PER show that PER accumulates to high levels in 1vLNs and many additional cells of dbt$^P$, but is not detected in wild type (FIG. 5E).

FIG. 6A shows that in dbt$^P$ mutants, loss of DBT activity results in increased stability of monomeric PER proteins. In constant darkness, high titers of stable PER promote constitutive nuclear translocation of PER/TIM heterodimers. An equilibrium is established in which constitutive production of nuclear PER/TIM dimers is balanced with constitutively low levels of expression of per and tim RNA. High stability of PER in dbt$^P$ leads to a pool of nuclear PER monomers as TIM turns over in nuclei. In wild type Drosophila, DBT activity promotes instability of PER monomers (FIG. 6B). PER proteins are stabilized only when physically associated with TIM. The DBT-conferred instability delays the appearance of PER/TIM complexes, and therefore promotes separate phases of per and tim transcription and PER/TIM complex formation and function.

FIG. 9A shows the total RNA that was isolated from pupae of each of the revertant lines described in Table 4 and dbt mRNA was detected by RNAse protection analysis. Because levels of the dbt transcript do not appear to oscillate (see FIG. 8), pupae from each revertant line were collected without first entraining developing flies to a light:dark cycle. dbt mRNA is weakly detected in homozygous dbt$^P$ pupae and in two incomplete revertants (VIII and IX), high levels of expression are restored in all seven complete phenotypic revertants (see text). Revertant VII was sampled twice. FIG. 9B shows the relative levels of dbt mRNA in (FIG. 9A) which were determined by normalizing to tubulin mRNA levels in each line. The revertant line in which the highest levels of dbt mRNA were detected (line VII) was set to one. Level of dbt mRNA in dbt$^P$ homozygous pupae is ~10% of that detected in line VII. In all of the homozygous viable, behaviorally rhythmic revertant lines, the dbt transcript is detected at 75% or more of the levels detected in revertant line VII.

FIG. 11 shows the dbt gene encodes a casein kinase I family member that is altered in dbt$^S$ and dbt$^L$ mutants. The conceptual translation of the open reading frame of the dbt gene is shown. The predicted protein is 440 amino acids in length with a molecular mass of 48 kDa. PROSITE [Bairoch, *Nucleic Acids Research* 19 *Suppl.*: 2241–2245 (1991)] searches have identified an ATP-binding site between amino acids 15–38 and a Serine/Threonine kinase catalytic domain between amino acids 124–136. Both of these domains are indicated. Sequencing of genomic DNA isolated from the dbt$^S$ and dbt$^L$ lines, as well as the parental line used for EMS mutagenesis identified single nucleotide changes, which result in amino acid changes, in each mutant. The dbt$^S$ mutation changes Proline to Serine at amino acid 47 and the dbt$^L$ mutation changes Methionine to Isoleucine at amino acid 80. An alignment of the kinase domains between DBT and casein kinase I family members from five different species is shown. BLAST [Altschul et al. (1990)] searches reveal that DBT is most closely related to human casein kinase Iε, being 86% identical at the amino acid level over the length of the kinase domain. Gaps in sequence are indicated by dashes. Amino acids which are identical to DBT in every species are indicated with a dot. Sequence identity between DBT and other kinases begins with the initiator Methonine and is shaded. Significant homology to other kinases ends with amino acid 292. The names, accession numbers and SEQ ID NOs: of the kinases used for sequence alignment are as follows: *H. sapiens* (human casein kinase Iε, L37043; SEQ ID NO:9), *A. thaliana* (dual specificity kinase, U48779; SEQ ID NO: 10), *X. laevis* (casein kinase Ia, Y08817, SEQ ID NO: 11), *G. gallus* (casein kinase Ia S, U80822, SEQ ID NO: 12) and *S. pombe* (hhpI protein kinase, yeast casein kinaseI homologue, X78871, U10863, SEQ ID NO: 13). [The nucleotide sequence that naturally encodes the human homolog of doubletime is SEQ ID NO: 14]. The nucleotide and amino acid sequences of the dbt open reading frame have been deposited to GenBank and have been assigned accession number .

FIG. 12A shows Canton S flies that were entrained to a 12:12 LD cycle and collected at four hour intervals over three days. Heads were separated from bodies of flies collected at each time point and total head RNA was isolated from each sample. per, tim and dbt mRNAs were detected by RNAse protection analysis. FIG. 12B shows per, tim and dbt mRNA levels that were normalized to tubulin mRNA levels at each time point and the relative levels of each transcript plotted against time. The time point with the highest levels of each transcript was set to 100%. While both the per and tim mRNAs display an approximately 10-fold circadian oscillation in their levels, levels of the dbt transcript remain essentially unchanged over three days.

FIG. 13A shows (Left) Coomassie-stained, SDS-PAGE of GST and GST-PER fusions proteins after binding of $^{35}$S-labeled DBT proteins. The staining confirms that similar amounts of GST and GST-PER fusion proteins were used in the assay. Arrow indicates BSA present in all the washes. (Right) GST alone and the indicated GST-PER fusions were used to bind in vitro translated, $^{35}$S-labeled DBT protein. Labeled DBT proteins that bound to the indicated GST-PER fusions were visualized by SDS-PAGE and autoradiography. DBT binds to the first 365 aa of PER, but does not bind to aa 530–640 of PER or to GST alone. FIG. 13B shows the co-immunoporecipitation of PER and a GFP-DBT fusion protein in S2 Drosophila cells. FIG. 13C shows proteins from S2 cells, or from S2 cells transfected with hs-per and hs-gfp-dbt, hs-gfp-dbt alone, or hs-per alone were immunoprecipitated with anti-GFP antibodies, separated by SDS-PAGE, transferred to nitrocellulose and co-immunoprecipitated PER was detected by Western analysis. For hs-gfp-dbt, GFP was fused to the amino terminus of DBT.

FIG. 15A depicts a diagram of the Syrian hamster cross used to map the tau mutation. FIG. 15B depicts the representative locomotor activity records of the three circadian phenotypes observed among the F$_2$ hamster progeny. Records are double-plotted so that 48 hours are shown for each horizontal trace. Dark regions represent activity. For the first 7 days, animals were housed in a cycle of 14 hours light, 10 hours dark (LD14:10), noted by the bar above each record. Animals were transferred to constant darkness (DD) for a total of three weeks beginning on day 8 (indicated by a line in the right margin). The top record is that of a wild-type animal with a period of 24 hours. The middle record is that of an animal heterozygous for the tau mutation with a period of 22 hours. The bottom record represents a homozygous tau animal with a period of 20 hours. FIG. 15C shows the distribution of period among 237 F$_2$ offspring tested for circadian phenotype. The Mendelian 1:2:1 ratio of wild-type (n=50) : heterozygous tau (n=131): homozygous tau (n=56), indicative of semidominance, is evident. Further details are disclosed in the Materials and Methods section in Example 3, below.

FIGS. 16A–16C show the results of the products from genetically directed representational difference analysis (GDRDA). FIG. 16A shows the ethidium bromide staining of products from three rounds of GDRDA. The two products (650 and 750 bp) from round three that exhibited linkage to the tau mutation are indicated. FIGS. 16B and 16C depict the Southern hybridization analysis of DNA from the 30 F$_2$ animals comprising the tester and driver pools for GDRDA analysis and the parental animals. A 750 bp product is evident in the M70 parental animal and in all tester animals. A product of about 3 kb is present in the homozygous tau parental animal and in all driver animals. A triangle marks the single animal in which a recombination event occurred. Driver, tester and parental animals are indicated (numbers identify individual progeny). Further details are disclosed in the Materials and Methods section in Example 3, below.

Figure 17A:
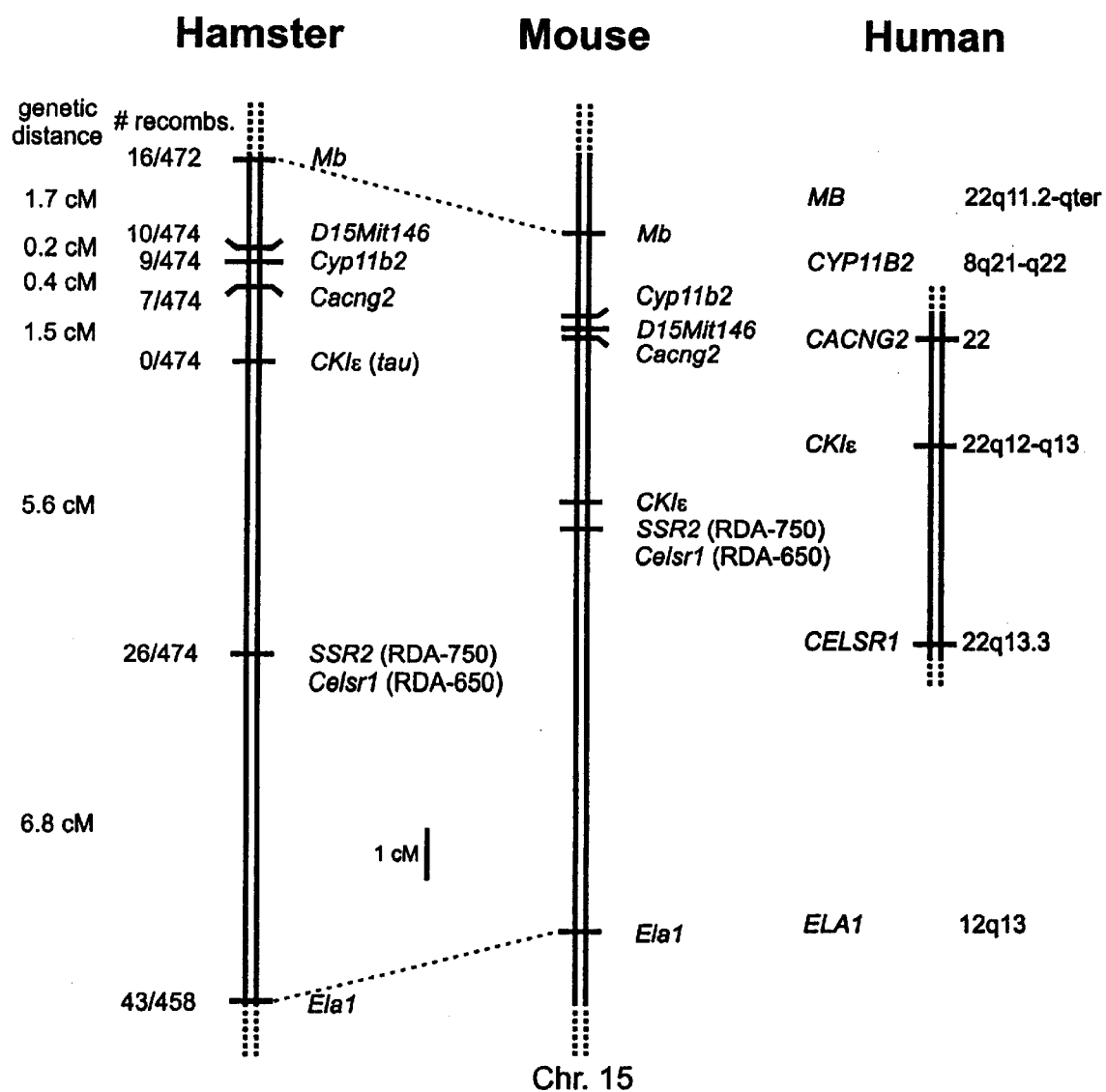
FIGS. 17A–17C show the genetic map of the Syrian hamster tau locus (FIG. 17A), and the electropherogram of sequence around the tau mutation region from wild-type (WT) (FIG. 17B) and the tau homozygous mutant (FIG. 17C) CK1ε cDNA. Regions of conserved synteny in mouse and human are shown (FIG. 17A). The position of the tau locus (CK1ε) relative to seven other loci is indicated. A search was carried out to identify polymorphisms in hamster orthologs of genes that map to the region of conserved synteny in mice or humans; genes for which 5'- and 3'-untranslated and intronic sequences exist in the GenBank database. The genes indicated are as follows: myoglobin (Mb); aldosterone synthase (Cyp11b2); calcium channel, voltage-dependent, gamma subunit 2 (Cacng2, stargazer); casein kinase Iε (CK1ε; tau); cadherin EGF LAG seven-pass G-type receptor (Celsr1); elastase (Ela1). A single mouse SSLP marker, D15Mit146, was mapped in hamster. The mouse SSLP marker, D15Mit146, was used to amplify a hamster polymorphism of approximately 200 bp in tau homozygous animals and approximately 205 bp in wild-type homozygotes. Products were separated on 7% denaturing PAGE gels using protocols modified from Dietrich et al. [*Genetics* 131:423 (1992)]. The two hamster GDRDA markers, RDA-650 and RDA-750 (SSR2), are indicated. The genetic distance between each locus in hamster is given in centimorgans (cM). In addition, the number of recombinants out of the total number of meiotic events tested in hamster is shown. In mouse, the locus amplified by the SSR2 hamster primers has been designated D15Nwu1 in the Mouse Genome Database (MGD).
Figure 17B:
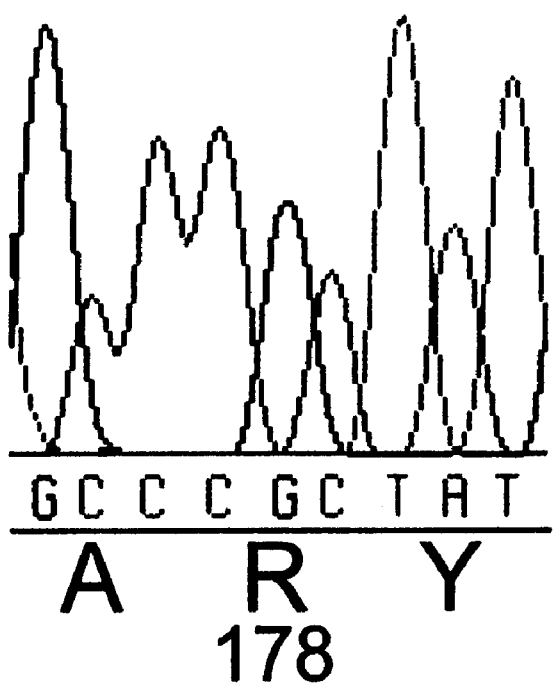
Figure 17C:
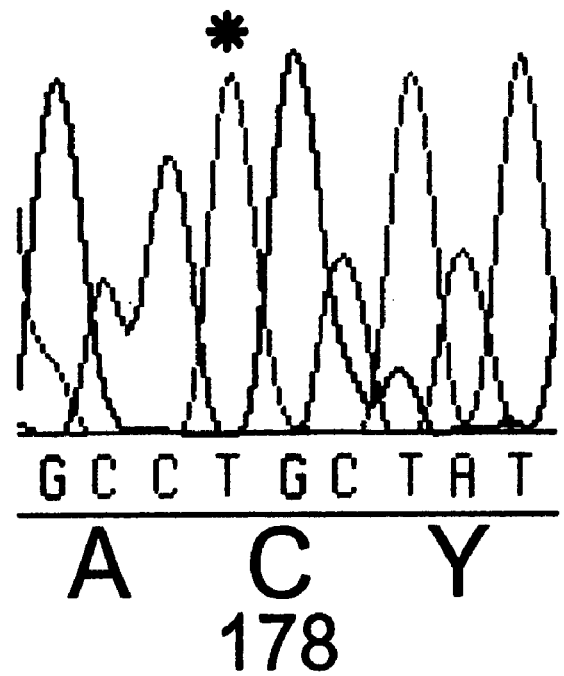

FIGS. 17B–17C depict electropherograms of the sequence around the tau mutation region. An asterisk denotes the point mutation (C→T transition) in the tau cDNA sequence. Amino acid residues are listed under their corresponding nucleotide codons. The point mutation in the tau cDNA sequence gives rise to an amino acid substitution at residue #178 of the protein sequence. Arg #178 in the wild-type protein is substituted by cysteine in the tau mutant protein. Further details are disclosed in the Materials and Methods section in Example 3, below.

FIG. 18 shows the alignment of casein kinase I isoforms from various species. Dots indicate identities. Filled circles mark the kinase domain. Kinase subdomains are bounded by the "|" symbol and are numbered with Roman numerals according to convention [Hanks and Hunter, *FASEB J.* 9:576 (1995)]. Shaded residues indicate the catalytic loop, the L-9D loop and the putative nuclear localization signal (NLS). The ★ symbol marks each of the three residues (Arg #178, Gly #215, Lys #224) that form the anion binding motif. Putative autophosphorylation sites on the carboxyl-terminal tail are indicated by the ♦ symbol [Gietzen and Virshup, *J. Biol. Chem.* 274:32063 (1999)]. Drosophila double-time short and long period mutation sites and the hamster tau mutation site are boxed and labeled [Price et al., *Cell* 94:83 (1998); B. Kloss et al., *Cell* 94:97 (1998): Examples 1 and 2, below]. The amino acid sequences of all proteins except hamster and human CK1ε are omitted following residue #300 because of reduced homology thereafter. Names and GenBank accession numbers for the kinase sequences shown are as follows: *Mesocricetus auratus* CK1ε; *Homo sapiens* CK1ε (L37043, SEQ ID NO:16); *Rattus norvegicus* CK1ε (L07578, SEQ ID NO:19); *Drosophila melanogaster* double-time (AF055583, SEQ ID NO:2); *Arabidopsis thaliana* dual specificity kinase (U48779,SEQ ID NO:10); *Saccharomyces cerevisiae* HRR25 (M68605, SEQ ID NO:13); *H. sapiens* (human casein kinase Iε, L37043; SEQ ID NO:9).

Figure 19A:
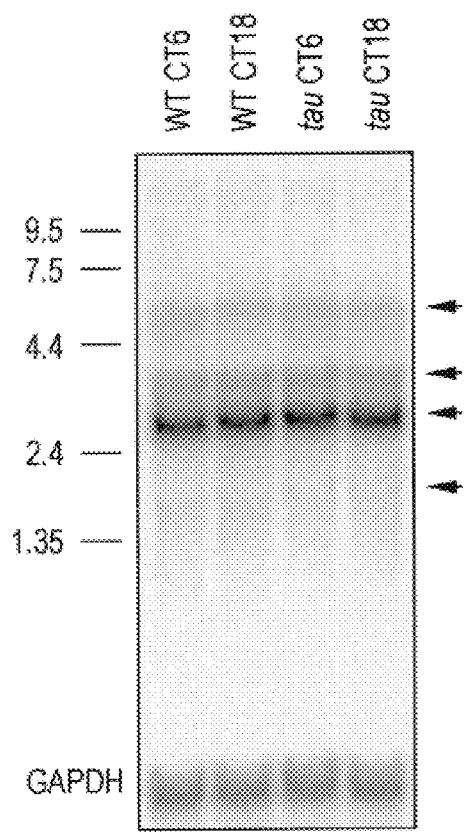
Figure 19B:
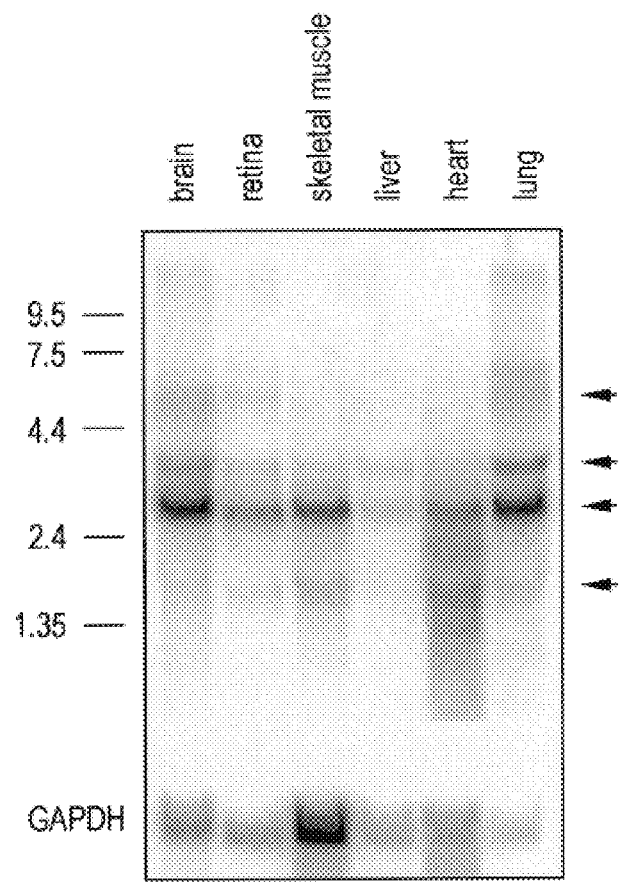
Figure 19C:
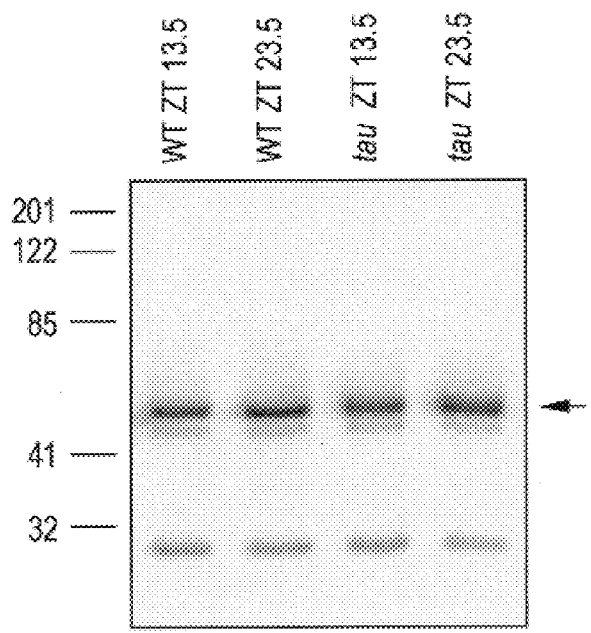

FIGS. 19A–19C depict the Northern analysis of total RNA and corresponding immunoblot prepared from wild-type and homozygous tau hamsters. The hamsters were sacrificed at CT6 and CT18 and tissues (heart, liver, lung, skeletal muscle, retina, brain) were removed and frozen as described in Example 3, below. FIG. 19A depicts the Northern analysis of total RNA prepared from brains of wild-type and homozygous tau hamsters collected at the two circadian times, CT6 and CT18. A major transcript of 2.7 kb and minor transcripts of 1.6, 3.5 and 5.9 kb are indicated by triangles. The blot was normalized by hybridization with probe to mouse GAPDH. No circadian oscillation in CK1ε transcript is evident. In addition, there is no obvious difference in transcript size or abundance between wild-type and homozygous tau animals. FIG. 19B shows the Northern analysis of total RNA from wild-type hamster brain, retina, heart, liver, lung and skeletal muscle tissue. RNA was transferred to nylon membrane and hybridized with probe to full-length hamster CK1ε cDNA as described in Example 3, below. A major transcript of 2.7 kb and minor transcripts of 1.6, 3.7 and 5.9 kb are indicated by triangles. The blot was normalized by hybridization with a probe to hamster GAPDH. The pattern of CK1ε expression in hamster is similar to that reported for human [Fish, et al., *J. Biol. Chem.* 270:14875 (1995)]. FIG. 19C is an immunoblot of wild-type and tau hamster hypothalamic tissue extracts. For this experiment, a human CK1ε-specific antibody (Transduction Laboratories, #C40520) was used to probe the tissue blots. A strong signal is evident at ~48 kDa (triangle), the reported size of human CK1ε [Fish et al., *J. Biol. Chem.* 270:14875 (1995)]. Further details are disclosed in the Materials and Methods section in Example 3, below.

Figure 20A:
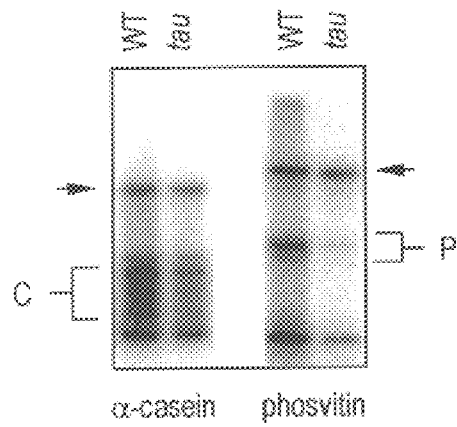

FIGS. 20A–20E show the results of in vitro kinase assays using recombinant homozygous wild-type and tau mutant CK1ε protein in the presence and absence of the protein substrates α-casein and phosvitin. FIG. 20A shows an exposed film of a 12% SDS gel in which $^{32}$P-labeled proteins can be visualized. This gel contains the reaction products of the in vitro incubation of α-casein or phosvitin with [γ-$^{32}$P]ATP and the recombinant homozygous wild-type and tau mutant CK1ε kinases. "C" and "P" denote the α-casein and phosvitin phosphorylation products respectively, whereas, the triangles denote the kinase autophosphorylation products. The wild-type CK1ε kinase produces an 8-fold and 4-fold greater signal intensity, for phosvitin and α-casein respectively, relative to that produced by the tau enzyme. Thus, a clear decrease in the kinase activity due to the tau mutation is evident for both of the protein substrates. These results are representative of 5 independent experiments.

Figure 20D:
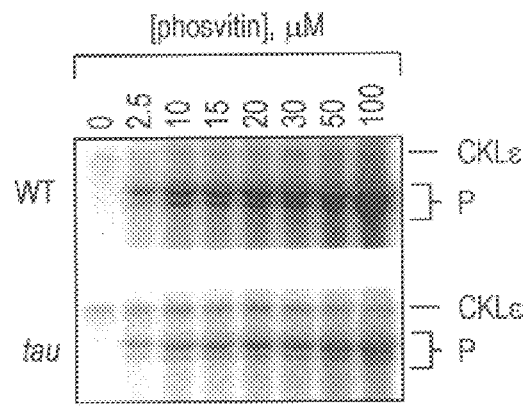
Figure 20B:
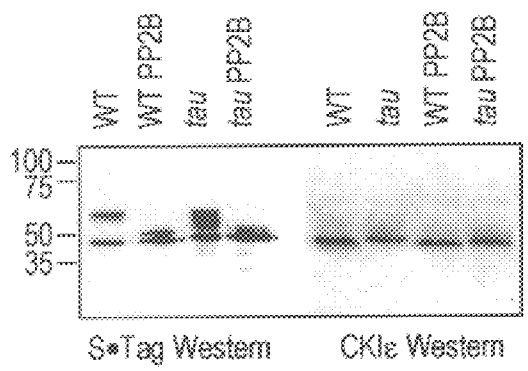

FIG. 20B shows the Western blot analysis of homozygous wild-type and tau mutant recombinant CK1ε enzymes that were allowed to undergo autophosphorylation in the absence of a protein substrate. Following the assay, half of the product was treated with protein phosphatase 2B (PP2B). Blots were incubated with antibody to the S•Tag sequence at the N-terminus of the recombinant protein, see Example 3 below, and an antibody to the C-terminus of human CK1ε. S•Tag antibody results are shown on the left half of FIG. 20A and CK1ε-specific antibody results are shown on the right half of FIG. 20A. A clear difference in mobility for wild-type and tau mutant species identified by the S•Tag antibody is evident. Two products are present in the untreated wild-type sample, while at least three are present in the untreated tau sample. PP2B treatment causes the slower migrating bands to shift lower so that an identical migration pattern is seen between wild-type and tau proteins indicating that PP2B dephosphorylates both enzymes. The antibody to the C-terminus of human CK1ε recognizes only the unphosphorylated form of the kinase in both recombinant samples. These results are representative of 3 independent experiments.

Figure 20E:
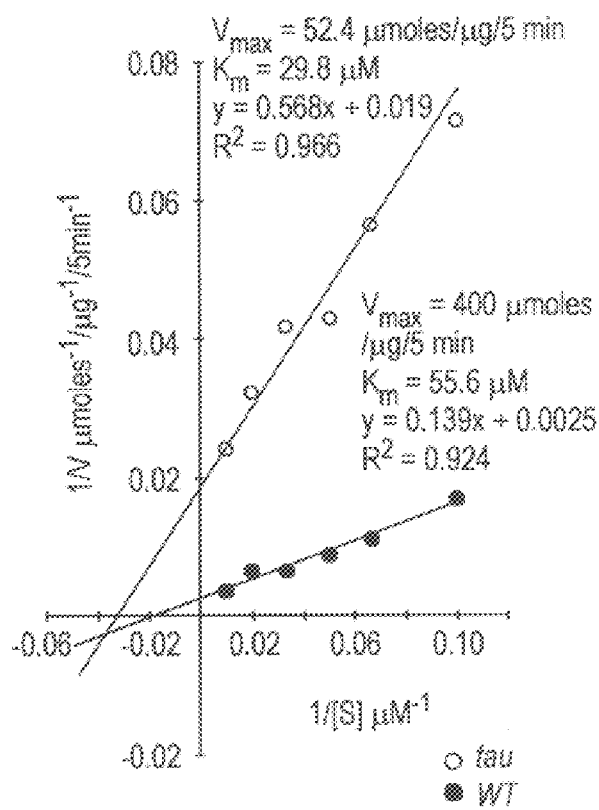
Figure 20C:
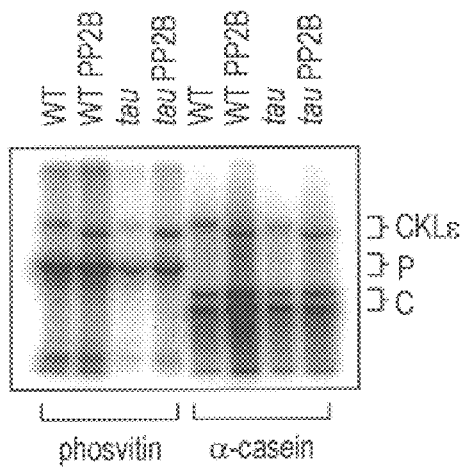

FIG. 20C shows the results of an in vitro kinase assays in which the homozygous wild-type and tau mutant recombinant CK1ε. were permitted to undergo autophosphorylation prior to their incubation with the protein substrates α-casein and phosvitin. Again "C" and "P" denote the α-casein and phosvitin phosphorylation products, respectively. Thus the enzymes were incubated alone in a kinase reaction (as described in Example 3) prior to the addition of substrates to allow autophosphorylation to occur. α-casein and phosvitin were used as the protein substrates. Half of each reaction was then treated with PP2B. PP2B treatment results in an increase in kinase activity in both recombinant enzymes, yet tau activity remains lower relative to wild-type. A clear difference in autophosphorylation signal is evident in PP2B-treated samples compared to untreated reactions. The results here are representative of 3 independent experiments.

FIG. 20D shows the results of kinetic analyses of homozygous wild-type and tau mutant CK1ε recombinant protein. Kinase reactions for kinetic analyses were performed as described above (and in Example 3, below) except that substrate concentrations were varied in a total reaction volume of 50 μl with 80 ng of recombinant enzyme. Time course experiments showed that the kinase assay was linear for up to 20 minutes. A 5 minute incubation time was used for the kinetic analyses. Phosvitin substrate concentrations were as follows: 0, 2.5, 10, 15, 20, 30, 50, and 100 $\mu$M. Duplicate reactions were performed for each concentration. Products were separated on 12% SDS-PAGE gels. Gels were dried before detecting signal with a Storm Phosphorimager (Molecular Dynamics) and by exposure of X-OMAT AR film at −80° C. $^{32}$P incorporation was quantified by excising the phosvitin phosphorylation bands from the dried gels and counting gel pieces using liquid scintillation methods. In vitro kinase assays were performed by varying phosvitin substrate concentration as indicated. The autophosphorylation signal is indicated and phosphorylated phosvitin is denoted by the letter P. These results are representative of 2 independent experiments, each performed in duplicate.

FIG. 20E shows a Lineweaver-Burke (double-reciprocal) plot of the kinetic results. Each point represents the average of duplicate samples. For the wild-type enzyme, the $K_m$ is 55.6 $\mu$M and the $V_{max}$ is 400 $\mu$moles/$\mu$g/5 minutes. Homozygous tau mutant CK1$\epsilon$ has a $K_m$ of 29.8 $\mu$M and a $V_{max}$ of 52.5 $\mu$moles/$\mu$g/5 minutes. Further details are disclosed in the Materials and Methods section in Example 3, below.

Figure 21A:
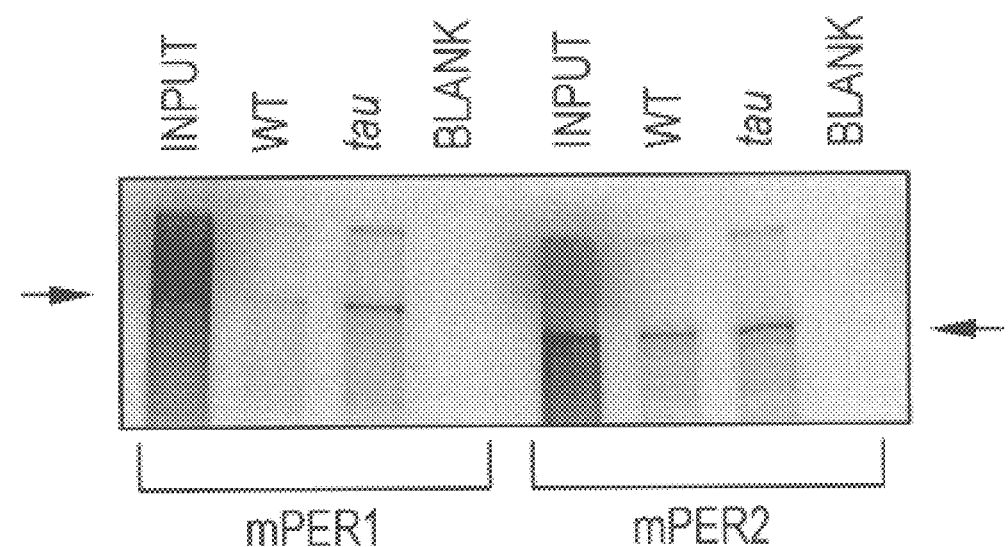
Figure 21B:
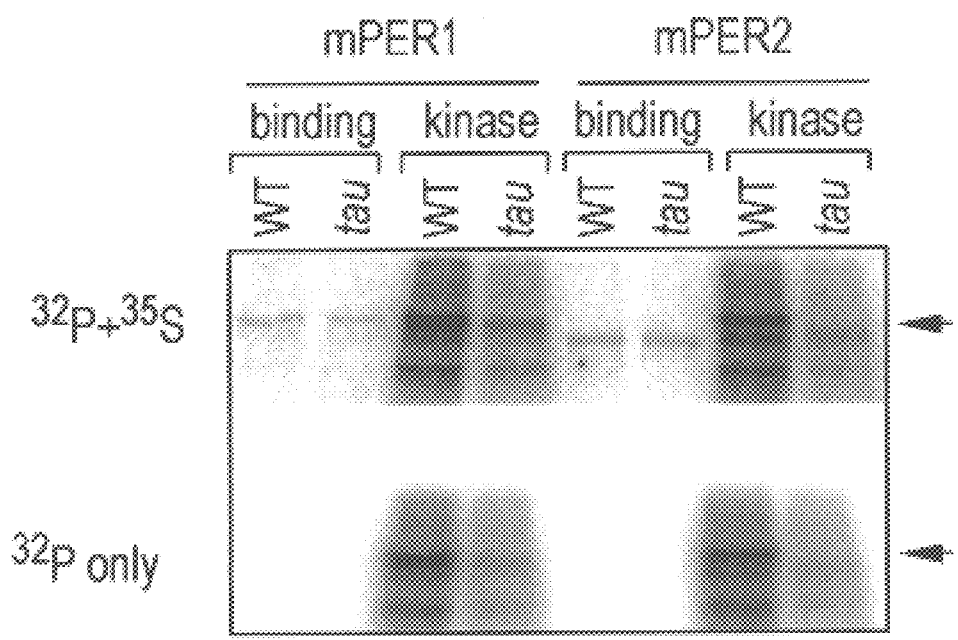

FIGS. 21A and 21B show that hamster CK1$\epsilon$ interacts with the mouse PERIOD1 (mPER1) and PERIOD2 (mPER2) proteins in vitro. For binding assays, mPER1 and mPER2 were synthesized from cDNAs cloned in plasmids by coupled in vitro transcription/translation reactions using $^{35}$S-methionine. Recombinant CK1$\epsilon$ was purified from *E. coli* by capture on S-agarose beads as described in Example 3, below. Beads containing wild-type or tau mutant enzyme were then incubated with in vitro-translated, $^{35}$S-methionine-labeled substrate (mPER1 or mPER2). In FIG. 21A INPUT denotes in vitro-translated product alone. BLANK indicates S-agarose beads mixed with in vitro-translated substrate. From the results it is clear that recombinant wild-type and tau mutant CK1$\epsilon$ bind both mPER proteins. Beads alone do not bind the mPER product as judged by the BLANK lanes. In FIG. 21B binding and affinity kinase reactions (as described in the Material and Methods of Example 3, below) are indicated for both substrates. Affinity kinase assays were performed by mixing 20 $\mu$l of an in vitro translation reaction containing $^{35}$S-methionine-labeled mPER1 or nPER2 with 20 $\mu$l S-protein agarose-bound recombinant CK1$\epsilon$ (either the tau mutant or the wild-type CK1$\epsilon$) and washed extensively. Half of the bound beads were then added to a kinase reaction as described above and in Example 3 below, but without c-casein or phosvitin, and incubated at 37° C. for 5 minutes. 2× loading buffer was then added to the affinity and kinase reactions which were then boiled for 2 minutes prior to gel loading. Reactions were separated on 12% SDS-PAGE gels, dried and exposed to phosphor screens. Following exposure to detect both the $^{35}$S and $^{32}$P signals, dried gels were covered with two layers of exposed X-OMAT film to block the $^{35}$S signal. As demonstrated in previous experiments with other substrates, the tau mutant enzyme exhibits attenuated kinase activity both with mPER1 and mPER2 as substrate. PER signal is indicated by filled triangles.

Figure 22A:
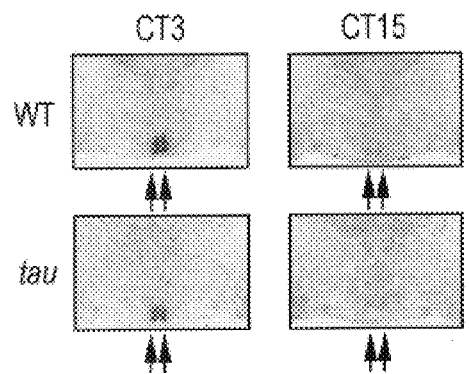
Figure 22B:
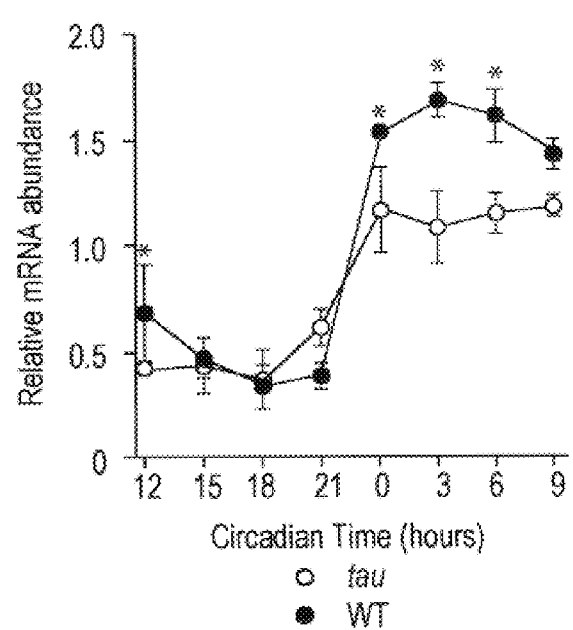
Figure 22C:
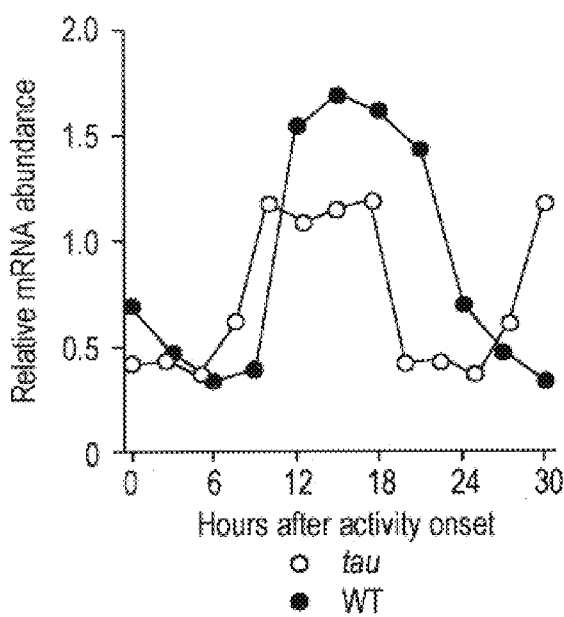

FIGS. 22A–22C shows the effect of the tau mutation on hamster Per1 gene expression in the suprachiasmatic nucleus. Example sections showing hamster Per1 in situ hybridization signals in the SCN region are depicted in FIG. 22A (see Example 3, below for details).

Arrows indicate the position of the SCN. Peak levels of hamster Per1 mRNA can be seen at CT3 as compared to basal levels seen at CT15. FIG. 22B shows the circadian rhythm of hamster Per1 mRNA expression in the SCN. Samples were collected every 3 circadian hours following seven days in constant darkness. Onset of locomotor activity for each hamster (which is considered CT12 by convention) was used to determine the circadian phase of the sample. Thus, for the tau mutant hamsters, which have an average period length of 20 hours, samples were collected approximately every 2.5 hours. In situ hybridization Per1 signal was quantified as described previously [Sangoram et al., *Neuron* 21:1101 (1998) which is hereby incorporated by reference in its entirety]. Data are plotted relative to the 24-hour average for the wild-type animals. Two way analysis of variance was significant for circadian time (F-ratio=30.5, $p<10^{-6}$, df=7), genotype (F-ratio=12.2, p=0.0015, df=1) and their interaction (F-ratio=2.52, p=0.036, df=7). FIG. 22C shows the in situ results plotted in real time. From this graph it is evident that hamster Per1 mRNA levels rise about 2 hours earlier and decline about 4 hours earlier in homozygous tau animals relative to wild-type animals. Points from 0–9 hours after activity onset were re-plotted to better represent the differences between tau and wild-type animals.

Figure 23A:
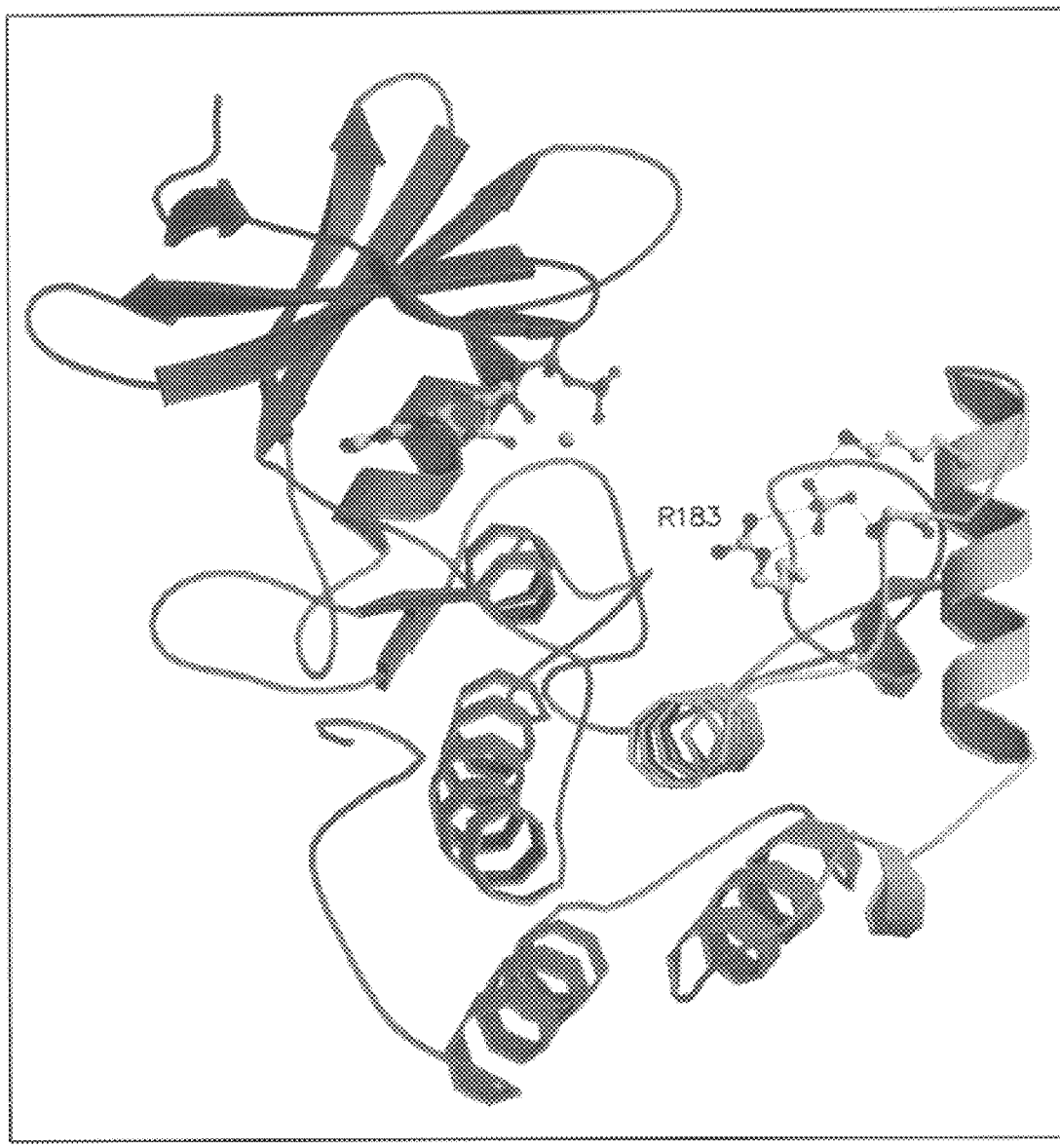
Figure 23B:
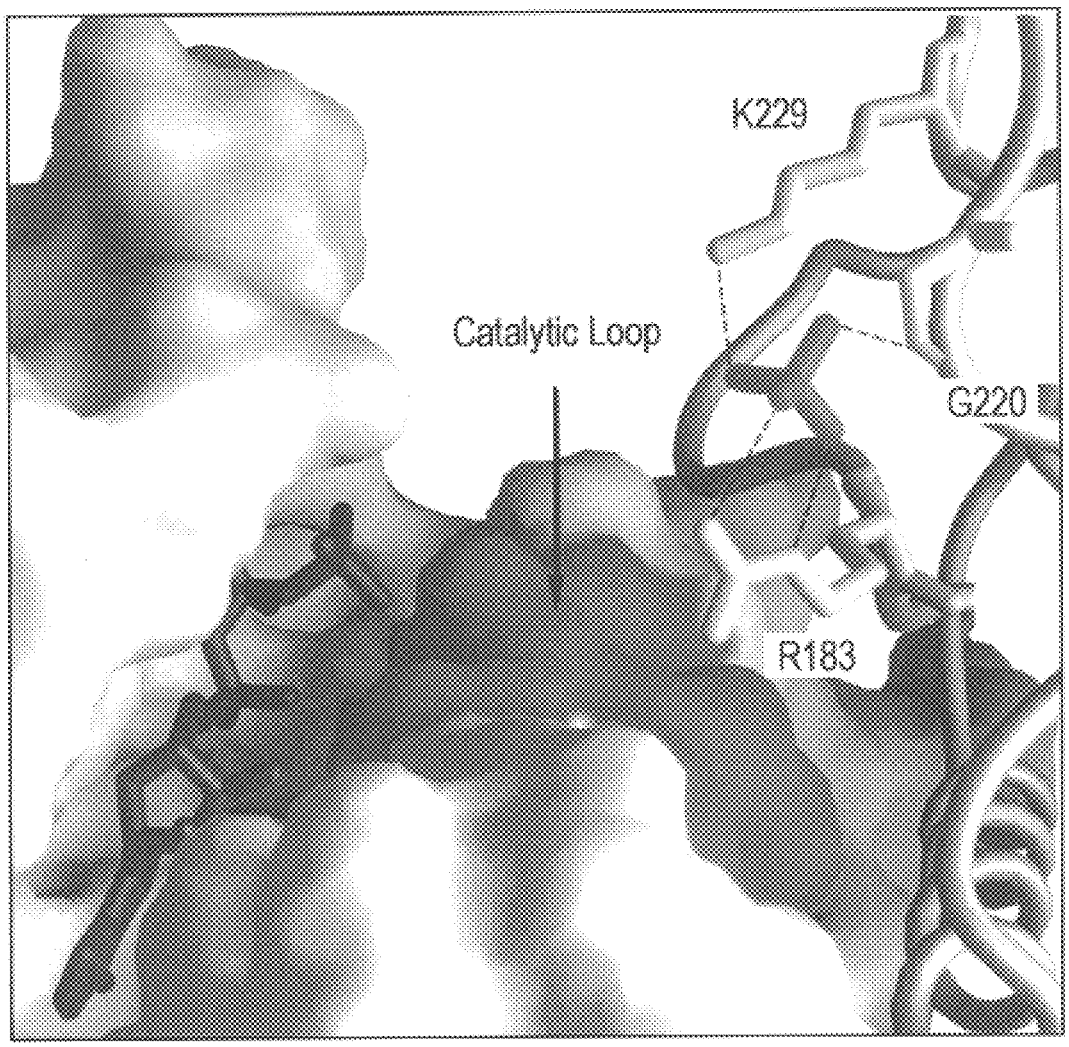

FIGS. 23A–23B show ribbon diagrams of the three-dimensional structure of CK1$\epsilon$. FIG. 23A illustrates the site of the tau mutation. The ribbon diagram and the catalytic surface model of CK1$\epsilon$ were created using coordinates from the published crystallographic data of *Schizosaccharotnyces pombe* casein kinase-1 [Xu et al., *EMBO J.* 14:1015 (1995)]. The modeling program, MOLSCRIPT, was used to create the ribbon diagram [Kraulis, *J. Appl. Cryst.* 24:946 (1991)]. The catalytic surface model was created with the program, GRASP [Nicholls et al., *Proteins* 11:281 (1991)]. In yeast, residues forming the anion binding motif, Arg #183, Gly #220 and Lys #229, correspond to hamster CK1$\epsilon$ residues, Arg #178, Gly #215 and Lys #224, respectively (see FIG. 18). The published 3-dimensional structure of *S. pombe* Cki1 is used here to illustrate the location of the hamster tau mutation. ATP is shown bound in the catalytic cleft. A sulfate ion is shown bound by hydrogen bonds within the anion binding pocket formed by the side chains of three residues (Arg #183, Gly #220 and Lys #229). The corresponding residues in hamster CK1$\epsilon$ are Arg #178, Gly #215 and Lys #224 (see FIG. 18). Arg #178 is replaced by cysteine in the tau mutant enzyme. The model of the CK1$\epsilon$ catalytic surface is shown in FIG. 23B. Again, coordinates from *S. pombe* Cki1 are used to model the analogous region in hamster CK1$\epsilon$. ATP is shown bound in the catalytic cleft (left). The three residues forming the anion binding site are shown binding a sulfate ion (right). Shaded in red is the catalytic loop which corresponds to residues 128–133 (DVKPDN) in hamster CK1$\epsilon$ (see FIG. 18).

Figure 24:
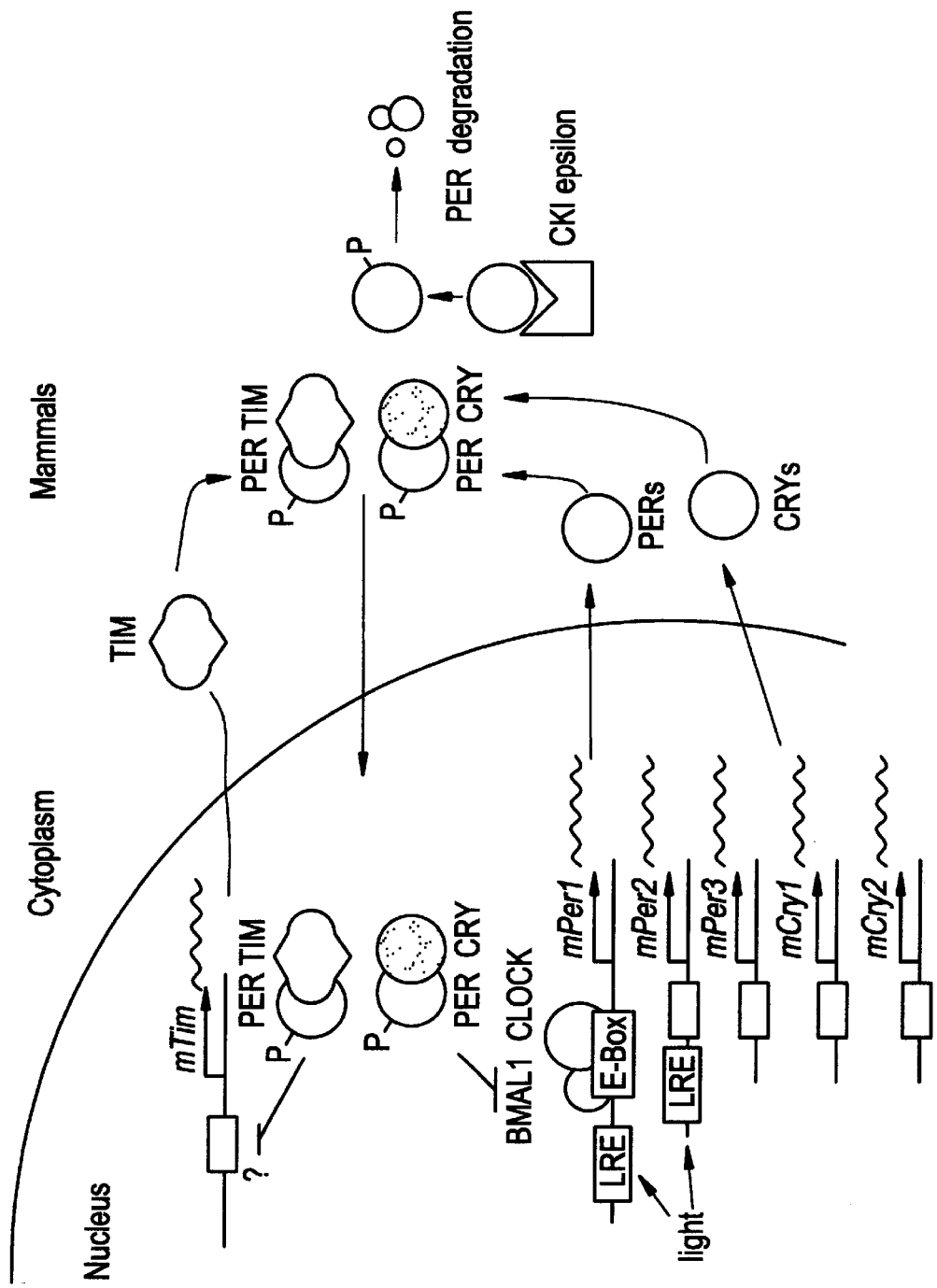

FIG. 24 depicts a model for the role of CK1$\epsilon$ in the mammalian circadian system. Represented are the interactions among various components of the autoregulatory feedback loop. Evidence disclosed herein indicates that the tau mutation results in a CK1$\epsilon$ form that shows reduced kinase activity. LRE, light-responsive element. Blank boxes indicate presumed E-box elements.

DETAILED DESCRIPTION OF THE INVENTION

The present invention provides the identification and genetic characterization of the clock gene double-time (dbt), a new gene required for circadian rhythms in Drosophila. Isolated alleles that either shorten or lengthen the periods of behavioral and molecular rhythms are also disclosed. A strongly hypomorphic dbt allele that is associated with pupal lethality, and blocks circadian oscillations of per and tim gene products in larvae has been isolated. dbt is therefore shown to be a central clock component alongside per and tim. dbt period-altering alleles alter the kinetics of PER phosphorylation and degradation. The hypomorphic allele produces unusually high levels of PER proteins that are hypophosphorylated. Thus, DBT is involved in the regulation of PER concentration in the cell.

$dbt^S$ and $dbt^L$, mutations (variants) which confer short- and long-period mutant phenotypes respectively, are produced by amino acid changes in highly conserved regions of the predicted kinase domain. $dbt^P$ mutants, which fail to show circadian rhythms of per and tim expression and produce unusually high levels of hypo-phosphorylated PER protein, produce very low levels of dbt mRNA. In wild type adult fly heads, dbt mRNA appears to be expressed in the same cell types as are per and tim. Furthermore, the present invention shows that DBT is capable of binding to PER in vitro and in cultured Drosophila cells, indicating that a physical association of PER and DBT regulates PER phosphorylation and accumulation in vivo. Two features of dbt distinguish it from other genes involved in circadian rhythms of Drosophila: First, levels of its transcript show no evident oscillation. Second, hypomorphic mutations of dbt are lethal during pupal development, suggesting that DBT may have other important roles beyond that in circadian rhythms.

In addition, the present invention shows that DBT is most closely related to human casein kinase Iϵ, thereby providing strong evidence that human casein kinase Iϵ is the Drosophila DBT ortholog. This aspect of the present invention therefore allows the novel use of the human casein kinase Iϵ for the development of new assays and pharmaceuticals based on its role as a human DOUBLETIME protein. More particularly, such assays can lead to the identification of agents that act as either agonists or antagonists of the DBT-dependent phosphorylation of PER.

Furthermore, as disclosed herein, the tau locus that had been identified in Syrian hamsters, encodes casein kinase I epsilon (CK1ϵ) which is indeed the DOUBLETIME protein. Heretofore, it was only known that the tau mutation was a semidominant autosomal allele that dramatically shortened the period length of circadian rhythms in Syrian hamsters. However, as demonstrated herein, tau is an allele of hamster CK1ϵ (or DOUBLETIME). The identification as disclosed herein was achieved using genetically directed representational difference analysis (GDRDA) to define a region of conserved synteny in hamsters with both the mouse and human genomes. In vitro expression and functional studies for both the wild-type and tau CK1ϵ enzyme reveal striking differences in maximal enzyme velocity ($V_{max}$) and autophosphorylation state. In addition, it is demonstrated herein that CK1ϵ can interact with mammalian PERIOD proteins and that the tau mutant enzyme phosphorylates the mammalian PERIOD proteins at a slower catalytic rate than does the wild-type enzyme.

Therefore, if appearing herein, the following terms shall have the definitions set out below As used herein "DOUBLETIME" and "DBT" and "CK1ϵ" are interchangeable names for an enzyme that can bind the clock protein PER and possesses protein kinase activity. As disclosed herein, Drosophila DBT has an amino acid sequence of SEQ ID NO:2. The natural nucleic acid sequence encoding Drosophila DBT consists of the coding region of SEQ ID NO:1. The human CK1ϵ protein is the human DOUBLETIME and has the amino acid sequence of SEQ ID NO:9. The natural nucleic acid sequence encoding human CK1ϵ consists of the coding region of SEQ ID NO:14. As disclosed herein, the tau locus of the Syrian hamster encodes DOUBLETIME. The "tau" CK1ϵ is a CK1ϵ variant as defined in Example 3.

As used herein a "tau# CK1ϵ" is a CK1ϵ variant that has had the arginine that corresponds to the hamster CK1ϵ amino acid residue, Arg #178 replaced/substituted by another amino acid. Preferably the substitute amino acid is an uncharged amino acid. More preferably, the substitute amino acid is a cysteine (the tau CK1ϵ). The precise location of the substitution is shown in FIG. 18 for a representative number of CK1ϵ's including for the human CK1ϵ.

As used herein a "$dbt^{S\#}$ CK1ϵ" is a CK1ϵ variant that has had the proline that corresponds to the Drosophila CK1ϵ amino acid residue, Pro #47 replaced/substituted by another amino acid. Preferably the substitute amino acid is an uncharged amino acid. More preferably, the substitute amino acid is a serine (the $dbt^S$ CK1ϵ). The precise location of the substitution is shown in FIG. 18 for a representative number of CK1ϵ's including for the human CK1ϵ.

As used herein a "$dbt^{L\text{™}}$ CK1ϵ" is a CK1ϵ variant that has had the methionine that corresponds to the Drosophila CK1ϵ amino acid residue, Met #80 replaced/substituted by another amino acid. Preferably the substitute amino acid is an uncharged amino acid. More preferably the substitute amino acid is a hydrophobic amino acid. Most preferably, the substitute amino acid is an isoleucine (the $dbt^L$ CK1ϵ). The precise location of the substitution is shown in FIG. 18 for a representative number of CK1ϵ's including for the human CK1ϵ.

As used herein the term "approximately" is used to signify that a value is within ten percent of the indicated value i.e., a protein containing "approximately" 450 amino acid residues can contain between 405 and 495 amino acid residues.

As used herein the term "binds to" is meant to include all such specific interactions that result in two or more molecules showing a preference for one another relative to some third molecule. This includes processes such as covalent, ionic, hydrophobic and hydrogen bonding but does not include non-specific associations such as solvent preferences.

A "vector" is a replicon, such as a plasmid, phage or cosmid, to which another DNA segment may be attached so as to bring about the replication of the attached segment. A "replicon" is any genetic element (e.g., plasmid, chromosome, virus) that functions as an autonomous unit of DNA replication in vivo, i.e., capable of replication under its own control.

A "cassette" refers to a segment of DNA that can be inserted into a vector at specific restriction sites. The segment of DNA encodes a polypeptide of interest, and the cassette and restriction sites are designed to ensure insertion of the cassette in the proper reading frame for transcription and translation.

A cell has been "transfected" by exogenous or heterologous DNA when such DNA has been introduced inside the cell. A cell has been "transduced" by exogenous or heterologous DNA when the exogenous or heterologous DNA is introduced by a viral vector.

A "heterologous nucleotide sequence" as used herein is a nucleotide sequence that is added to a nucleotide sequence of the present invention by recombinant methods to form a nucleic acid which is not naturally formed in nature. Such nucleic acids can encode chimeric and/or fusion proteins. Thus the heterologous nucleotide sequence can encode peptides and/or proteins which contain regulatory and/or structural properties. In another such embodiment the heterologous nucleotide can encode a protein or peptide that functions as a means of detecting the protein or peptide encoded by the nucleotide sequence of the present invention after the recombinant nucleic acid is expressed. In still another embodiment the heterologous nucleotide can function as a means of detecting a nucleotide sequence of the present invention. A heterologous nucleotide sequence can comprise non-coding sequences including restriction sites, regulatory sites, promoters and the like.

A "heterologous" region of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. Another example of a heterologous coding sequence is a construct where the coding sequence itself is not found in nature (e.g., a cDNA where the genomic coding sequence contains introns, or synthetic sequences having codons different than the negative gene). Allelic variations or naturally-occurring mutational events do not give rise to a heterologous region of DNA as defined herein.

A "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules (e.g., restriction fragments), plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA). A "recombinant DNA molecule" is a DNA molecule that has undergone a molecula biological manipulation.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., supra). The conditions of temperature and ionic strength determine the "stringency" of the hybridization. For preliminary screening for homologous nucleic acids, low stringency hybridization conditions, corresponding to a $T_m$ of 55°, can be used, e.g., 5×SSC, 0.1% SDS, 0.25% milk, and no formamide; or 30% formamide, 5×SSC, 0.5% SDS). Moderate stringency hybridization conditions correspond to a higher $T_m$, e.g., 40% formamide, with 5× or 6×SSC. High stringency hybridization conditions correspond to the highest $T_m$, e.g., 50% formamide, 5× or 6×SSC. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_m$ have been derived (see Sambrook et al., supra, 9.50–10.51). For hybridization with shorter nucleic acids, i.e., oligonucleotides, the position of mismatches becomes more important, and the length of the oligonucleotide determines its specificity (see Sambrook et al., supra, 11.7–11.8). Preferably a minimum length for a hybridizable nucleic acid is at least about 12 nucleotides; preferably at least about 18 nucleotides; and more preferably the length is at least about 27 nucleotides; and most preferably at least about 36 nucleotides.

In a specific embodiment, the term "standard hybridization conditions" refers to a $T_m$ of 55° C., and utilizes conditions as set forth above e.g., 5×SSC. In a preferred embodiment, the $T_m$ is 60° C.; in a more preferred embodiment, the $T_m$ is 65° C.

"Homologous recombination" refers to the insertion of a foreign DNA sequence of a vector in a chromosome. Preferably, the vector targets a specific chromosomal site for homologous recombination. For specific homologous recombination, the vector will contain sufficiently long regions of homology to sequences of the chromosome to allow complementary binding and incorporation of the vector into the chromosome. Longer regions of homology, and greater degrees of sequence similarity, may increase the efficiency of homologous recombination.

A DNA "coding sequence" is a double-stranded DNA sequence which is transcribed and translated into a polypeptide in a cell in vitro or in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. If the coding sequence is intended for expression in a eukaryotic cell, a polyadenylation signal and transcription termination sequence will usually be located 3' to the coding sequence.

"Transcriptional and translational control sequences" are DNA regulatory sequences, such as promoters, enhancers, terminators, and the like, that provide for the expression of a coding sequence in a host cell. In eukaryotic cells, polyadenylation signals are control sequences.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase.

A coding sequence is "under the control" of transcriptional and translational control sequences in a cell when RNA polymerase transcribes the coding sequence into mRNA, which is then trans-RNA spliced and translated into the protein encoded by the coding sequence.

A "signal sequence" is included at the beginning of the coding sequence of a protein to be expressed on the surface of a cell. This sequence encodes a signal peptide, N-terminal to the mature polypeptide, that directs the host cell to translocate the polypeptide. The term "translocation signal sequence" is used herein to refer to this sort of signal sequence. Translocation signal sequences can be found associated with a variety of proteins native to eukaryotes and prokaryotes, and are often functional in both types of organisms.

As used herein, the term "sequence homology" in all its grammatical forms refers to the relationship between proteins that possess a "common evolutionary origin," including proteins from superfamilies (e.g., the immunoglobulin superfamily) and homologous proteins from different species (e.g., myosin light chain, etc.) (Reeck et al., 1987, Cell 50:667).

As used herein, the terms "homologue", "homolog" and "ortholog" are used interchangeably and refer to the relationship between proteins that have a common evolutionary origin and differ because they originate from different species. For example, Drosophila xanthine dehydrogenase is a homologue/orthog of human xanthine dehydrogenase.

The term "sequence similarity" in all its grammatical forms refers to the degree of identity or correspondence between nucleic acid or amino acid sequences of proteins that do not share a common evolutionary origin (see Reeck et al., supra). However, in common usage and in the instant application, the term "homologous," when modified with an adverb such as "highly," may refer to sequence similarity and not necessarily a common evolutionary origin.

In a specific embodiment, two highly homologous DNA sequences can be identified by the homology of the amino acids they encode. Such comparison of the sequences can be performed using standard software available in sequence data banks. Alternatively, two highly homologous DNA sequences can be identified by Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra.

As used herein a nucleic acid sequence is 100% "homologous" to a second nucleic acid sequence if the two nucleic acid sequences are identical. Accordingly, a nucleic acid sequence is 50% "homologous" to a second nucleic acid sequence if 50% of the two nucleic acid sequences are identical.

As used herein an amino acid sequence is 100% "homologous" to a second amino acid sequence if the two amino acid sequences differ only by neutral or conservative substitutions as defined below, or preferably if the two amino acid sequences are identical. Accordingly, an amino acid sequence is 50% "homologous" to a second amino acid sequence if 50% of the two amino acid sequences differ by only neutral or conservative amino acid substitutions, or preferably 50% of the two amino acid sequences are identical. Since amino acids 1–292 of SEQ ID NO:2 contain a relatively conserved putative protein kinase domain, a "highly homologous" sequence as used herein which corresponds to amino acids 1–292 of SEQ ID NO:2 would be at least about 75%, and preferably at least about 85%, and more preferably at least 90% homologous to amino acids 1–292 of SEQ ID NO:2. For the remainder of the DBT amino acid sequence, i.e., amino acids 293–440 of SEQ ID NO:2, a highly homologous amino acid sequence is at least about 20% homologous with the corresponding portion of SEQ ID NO:2. In a preferred embodiment a highly homologous amino acid sequence is at least about 30% homologous with the corresponding portion of SEQ ID NO:2. In a more preferred embodiment a highly homologous amino acid sequence is at least about 40% homologous with a corresponding portion of SEQ ID NO:2. The amount of homology required for nucleic acids that contain amino acid sequences corresponding to portions of both the kinase and/or non-kinase domains can be determined accordingly. A full-length amino acid sequence that is highly homologous to SEQ ID NO:2 is at least about 55% homologous to SEQ ID NO:2. [In this case 66% of the sequence (contained by amino acids 1–292) is at least 75% homologous, whereas 34% of the sequence (amino acids 293–440) is at least about 20% homologous, or 0.75*0.66+0.34*0.20=~55% homologous.] This calculation is partially based on the finding that the mouse and human PER homologue is about 35% homologous to the Drosophila PER protein [Sun et al., Cell, 90:1003–1011 (1997)]. Such homologous sequences can be identified by alignment using, for example, the GCG (Genetics Computer Group, Program Manual for the GCG Package, Version 7, Madison, Wis.) pileup program using the default parameters. Alternatively, the commercially available MEGALIGN program within the LASERGENE sequence analysis software package from DNASTAR, Inc, can also be used (see below).

The term "corresponding to" is used herein to refer similar or homologous sequences, whether the exact position is identical or different from the molecule to which the similarity or homology is measured. Thus, the term "corresponding to" refers to the sequence similarity, and not the numbering of the amino acid residues or nucleotide bases.

DBTs: Proteins and Polypeptides

The present invention provides isolated DBTs and active fragments thereof. DBT is the third Drosophila gene to be isolated that has an essential role in circadian rhythms. DBT has been shown to be capable of binding to PER in vitro and in Drosophila cells. DBT is a kinase that is required for wild type patterns of PER phosphorylation and for adult viability. Sequence analyses indicate that DBT is a structural homologue/ortholog of human casein kinase Iε, with 86% of the amino acids comprising the putative kinase domain of Drosophila DBT being identical to those comprising the kinase domain of human casein kinase Iε. PER proteins are hypo-phosphorylated in dbt$^P$ mutants, and the timing of PER phosphorylation appears to be altered in dbt$^L$ and dbt$^S$ mutants [Example 1, below] indicating that a kinase activity supplied by DBT is required for normal PER phosphorylation in vivo. PER and DBT also physically associate in vitro and in cultured Drosophila cells, and in addition, the formation of a PER/DBT complex leads to DBT-dependent phosphorylation of PER in vitro. DBT is the first Drosophila clock protein to have a structure that indicates a recognizeable biochemical function. Although strong evidence for involvement of protein phosphorylation in circadian rhythmicity has been reported in several organisms DBT is the first specific kinase to be isolated which regulates circadian rhythmicity.

In one embodiment the DBT is a mammalian protein, preferably a human protein. In another embodiment the DBT is a protein encoded by a nucleotide sequence that is hybridizable with the coding sequence of SEQ ID NO:1 under standard, or preferably stringent conditions. In still another embodiment the DBT is encoded by a nucleotide sequence having the coding sequence of SEQ ID NO:1. In yet another embodiment the DBT has an amino acid sequence of SEQ ID NO:2 comprising one or more conservative substitutions. The DBTS of the present invention may be used in assays to identify novel drugs, and the like, and in protein structure and mechanistic studies.

Modified DBTs: The present invention also provides modified DBTs and DBTs that are tagged proteins, labeled proteins, fusion proteins and the like. Such DBTs may be used for example as antigens or for marker purposes. In a particular embodiment of this type, the fusion protein comprises an DBT protein or active fragment thereof having an amino acid sequence of SEQ ID NO:2 or SEQ ID NO:2 comprising a conservative substitution. Such DBTs preferably retain their protein kinase activity and bind PER. One particular use of the DBT fusion proteins of the present invention is for the production of the DBT-antibodies of the present invention.

A DBT fusion protein comprises at least a portion of a non-DBT protein joined via a peptide bond to at least a portion of an DBT polypeptide. In preferred embodiments the portion of the DBT is functional. The non-DBT sequences can be amino- or carboxy-terminal to the DBT sequences. More preferably, for stable expression of a DBT fusion protein, the portion of the non-DBT fusion protein is joined via a peptide bond to the amino terminus of the DBT protein. A recombinant DNA molecule encoding such a fusion protein comprises a sequence encoding at least a portion of a non-DBT protein joined in-frame to the DBT coding sequence, and preferably encodes a cleavage site for a specific protease, e.g., thrombin or Factor Xa, preferably at the DBT-non-DBT juncture. In a specific embodiment, the fusion protein is expressed in *Escherichia coli*. Such a fusion protein can be used to isolate the DBTs of the present invention, through the use of an affinity column which is specific for the protein fused to the DBT. The purified DBT may then be released from the fusion protein through the use of a proteolytic enzyme and the cleavage site such as has been referred to above.

In one such embodiment, a chimeric DBT can be prepared, e.g., a glutathione-S-transferase (GST) fusion protein, a maltose-binding (MBP) protein fusion protein, or a poly-histidine-tagged fusion protein, for expression in a eukaryotic cell. Expression of a DBT as a fusion protein can facilitate stable expression, or allow for purification based on the properties of the fusion partner. For example, GST binds glutathione conjugated to a solid support matrix, MBP binds to a maltose matrix, and poly-histidine chelates to a Ni-chelation support matrix. The fusion protein can be eluted from the specific matrix with appropriate buffers, or by treating with a protease specific for a cleavage site usually engineered between the DBT and the fusion partner (e.g., GST, MBP, or poly-His) as described above. Alternatively the chimeric DBT protein may contain the green fluorescent protein, and be used to determine the intracellular localization of the DBT in the cell.

Genes Encoding DBTs

The present invention contemplates isolation of a gene encoding a DBT of the present invention, including a full length, or naturally occurring form of DBT, and antigenic fragments thereof from any animal, particularly mammalian, and more particularly human, source. Such nucleic acids may be used for designing primers for RT-PCR, and for making probes that are useful for determining the expression of DBT messenger RNA in tissues and tumors. Similarly such nucleic acids can be used to determine the expression of DBT messenger RNA in normal tissues and tumors by Northern Blot analysis, RNA protection assays and the like. As used herein, the term "gene" refers to an assembly of nucleotides that encode a polypeptide, and includes cDNA and genomic DNA nucleic acids. Therefore, the present invention provides the primary structure of a gene encoding a.

In accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook et al., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization* [B. D. Hames & S. J. Higgins eds. (1985)]; *Transcription And Translation* [B. D. Hames & S. J. Higgins, eds. (1984)]; *Animal Cell Culture* [R. I. Freshney, ed. (1986)]; *Immobilized Cells And Enzymes* [IRL Press, (1986)]; B. Perbal, *A Practical Guide To Molecular Cloning* (1984); F. M. Ausubel et al. (eds.), *Current Protocols in Molecular Biology*, John Wiley & Sons, Inc. (1994).

A gene encoding DBT, whether genomic DNA or cDNA, can be isolated from any source, particularly from a human cDNA or genomic library. In view and in conjunction with the present teachings, methods well known in the art, as described above can be used for obtaining DBT genes from any source (see, e.g., Sambrook et al., 1989, supra).

Accordingly, any animal cell or transformed animal cell line potentially can serve as the nucleic acid source for the molecular cloning of a DBT gene. The DNA may be obtained by standard procedures known in the art from cloned DNA (e.g., a DNA "library"), and preferably is obtained from a cDNA library prepared from tissues with high level expression of the protein, by chemical synthesis, by cDNA cloning, or by the cloning of genomic DNA, or fragments thereof, purified from the desired cell (See, for example, Sambrook et al., 1989, supra; Glover, D. M. (ed.), 1985, DNA Cloning: A Practical Approach, MRL Press, Ltd., Oxford, U.K. Vol. I, II). Clones derived from genomic DNA may contain regulatory and intron DNA regions in addition to coding regions; clones derived from cDNA will not contain intron sequences. Whatever the source, the gene should be molecularly cloned into a suitable vector for propagation of the gene.

In the molecular cloning of the gene from genomic DNA, DNA fragments are generated, some of which will encode the desired gene. The DNA may be cleaved at specific sites using various restriction enzymes. Alternatively, one may use DNAse in the presence of manganese to fragment the DNA, or the DNA can be physically sheared, as for example, by sonication. The linear DNA fragments can then be separated according to size by standard techniques, including but not limited to, agarose and polyacrylamide gel electrophoresis and column chromatography.

Once the DNA fragments are generated, identification of the specific DNA fragment containing the desired DBT gene may be accomplished in a number of ways. For example, the generated DNA fragments may be screened by nucleic acid hybridization to a labeled probe of the present invention (Benton and Davis, 1977, Science 196:180; Grunstein and Hogness, 1975, Proc. Natl. Acad. Sci. U.S.A. 72:3961). For example, a set of oligonucleotides corresponding to the sequence information provided by the present invention can be prepared and used as probes for DNA encoding DBT (e.g., in combination with a poly-T primer for RT-PCR). Preferably, a probe is selected that is highly unique to DBT of the invention. Those DNA fragments with substantial homology to the probe will hybridize. As noted above, the greater the degree of homology, the more stringent hybridization conditions can be used.

Further selection can be carried out on the basis of the properties of the gene, e.g., if the gene encodes a protein product having the isoelectric, electrophoretic, amino acid composition, or partial amino acid sequence of the DBT as disclosed herein. Thus, the presence of the gene may be detected by assays based on the physical, chemical, or immunological properties of its expressed product. For example, cDNA clones, or DNA clones which hybrid-select the proper mRNAs, can be selected which produce a protein that, e.g., has similar or identical electrophoretic migration, isoelectric focusing or non-equilibrium pH gel electrophoresis behavior, proteolytic digestion maps, or antigenic properties as known for DBT.

A DBT gene of the invention can also be identified by mRNA selection, i.e., by nucleic acid hybridization followed by in vitro translation. In this procedure, nucleotide fragments are used to isolate complementary mRNAs by hybridization. Such DNA fragments may represent available, purified DBT DNA, or may be synthetic oligonucleotides designed from the partial amino acid sequence information. Immunoprecipitation analysis or functional assays (e.g., nucleoside transport activity) of the in vitro translation products of the products of the isolated mRNAs identifies the mRNA and, therefore, the complementary DNA fragments, that contain the desired sequences. In addition, specific mRNAs may be selected by adsorption of polysomes isolated from cells to immobilized antibodies specifically directed against DBT.

A radiolabeled DBT cDNA can be synthesized using the selected mRNA (from the adsorbed polysomes) as a template. The radiolabeled mRNA or cDNA may then be used as a probe to identify homologous DBT DNA fragments from among other genomic DNA fragments.

The present invention also relates to cloning vectors containing genes encoding analogs and derivatives of DBT of the invention, that have the same or homologous functional activity as DBT, and in particular homologue thereof from other species. The production and use of derivatives and analogs related to DBT are within the scope of the present invention. In a specific embodiment, the derivative or analog is functionally active, i.e., capable of phosphorylating PER.

DBT derivatives can be made by altering encoding nucleic acid sequences by substitutions, additions or deletions that provide for functionally equivalent molecules. Preferably, derivatives are made that have enhanced or increased functional activity or greater specificity.

Due to the degeneracy of nucleotide coding sequences, other DNA sequences which encode substantially the same amino acid sequence as a DBT gene may be used in the practice of the present invention. These include but are not limited to allelic genes, homologous genes from other species, and nucleotide sequences comprising all or portions of DBT genes which are altered by the substitution of different codons that encode the same amino acid residue within the sequence, thus producing a silent change. Likewise, the DBT derivatives of the invention include, but are not limited to, those containing, as a primary amino acid sequence, all or part of the amino acid sequence of a DBT protein including altered sequences in which functionally equivalent amino acid residues are substituted for residues within the sequence resulting in a conservative amino acid substitution. Such alterations define the term "a conservative substitution" as used herein. For example, one or more amino acid residues within the sequence can be substituted by another amino acid of a similar polarity, which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. Amino acids containing aromatic ring structures are phenylalanine, tryptophan, and tyrosine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Such alterations will not be expected to affect apparent molecular weight as determined by polyacrylamide gel electrophoresis, or isoelectric point.

Particularly preferred conservative substitutions are:
Lys for Arg and vice versa such that a positive charge may be maintained;
Glu for Asp and vice versa such that a negative charge may be maintained;
Ser for Thr such that a free —OH can be maintained; and
Gln for Asn such that a free $NH_2$ can be maintained.

Amino acid substitutions may also be introduced to substitute an amino acid with a particularly preferable property. For example, a Cys may be introduced at a potential site for disulfide bridges with another Cys. Pro may be introduced because of its particularly planar structure, which induces β-turns in the protein's structure.

The genes encoding DBT derivatives and analogs of the invention can be produced by various methods known in the art. The manipulations which result in their production can occur at the gene or protein level. For example, the cloned DBT gene sequence can be modified by any of numerous strategies known in the art (Sambrook et al., 1989, supra). The sequence can be cleaved at appropriate sites with restriction endonuclease(s), followed by further enzymatic modification if desired, isolated, and ligated in vitro. In the production of the gene encoding a derivative or analog of DBT, care should be taken to ensure that the modified gene remains within the same translational reading frame as the DBT gene, uninterrupted by translational stop signals, in the gene region where the desired activity is encoded.

Additionally, the DBT-encoding nucleic acid sequence can be mutated in vitro or in vivo, to create and/or destroy translation, initiation, and/or termination sequences, or to create variations in coding regions and/or form new restriction endonuclease sites or destroy preexisting ones, to facilitate further in vitro modification. Preferably, such mutations enhance the functional activity of the mutated DBT gene product. Any technique for mutagenesis known in the art can be used, including but not limited to, in vitro site-directed mutagenesis (Hutchinson, C., et al., 1978, J. Biol. Chem. 253:6551; Zoller and Smith, 1984, DNA 3:479–488; Oliphant et al., 1986, Gene 44:177; Hutchinson et al., 1986, Proc. Natl. Acad. Sci. U.S.A. 83:710), use of TAB® linkers (Pharmacia), etc. PCR techniques are preferred for site directed mutagenesis (see Higuchi, 1989, "Using PCR to Engineer DNA", in *PCR Technology: Principles and Applications for DNA Amplification*, H. Erlich, ed., Stockton Press, Chapter 6, pp. 61–70).

The identified and isolated gene can then be inserted into an appropriate cloning vector. A large number of vector-host systems known in the art may be used. Possible vectors include, but are not limited to, plasmids or modified viruses, but the vector system must be compatible with the host cell used. Examples of vectors include, but are not limited to, *E. coli,* bacteriophages such as lambda derivatives, or plasmids such as pBR322 derivatives or pUC plasmid derivatives, e.g., pGEX vectors, pmal-c, pFLAG, etc. The insertion into a cloning vector can, for example, be accomplished by ligating the DNA fragment into a cloning vector which has complementary cohesive termini. However, if the complementary restriction sites used to fragment the DNA are not present in the cloning vector, the ends of the DNA molecules may be enzymatically modified. Alternatively, any site desired may be produced by ligating nucleotide sequences (linkers) onto the DNA termini; these ligated linkers may comprise specific chemically synthesized oligonucleotides encoding restriction endonuclease recognition sequences. Recombinant molecules can be introduced into host cells via transduction, transformation, transfection, infection, electroporation, etc., so that many copies of the gene sequence are generated. Preferably, the cloned gene is contained on a shuttle vector plasmid, which provides for expansion in a cloning cell, e.g., *E. coli,* and facile purification for subsequent insertion into an appropriate expression cell line, if such is desired. For example, a shuttle vector, which is a vector that can replicate in more than one type of organism, can be prepared for replication in both *E. coli* and *Saccharomyces cerevisiae* by linking sequences from an *E. coli* plasmid with sequences from the yeast 2 μ plasmid.

In an alternative method, the desired gene may be identified and isolated after insertion into a suitable cloning vector in a "shot gun" approach. Enrichment for the desired gene, for example, by size fractionation, can be done before insertion into the cloning vector.

The nucleotide sequence of the Drosophila doubletime, SEQ ID NO:1 or more preferably the amino acid sequence of SEQ ID NO:2, can also be used to search for highly homologous genes from other species, including humans using computer data bases containing partial nucleic acid sequences. Human ESTs, for example, can be searched. The Drosophila doubletime amino acid sequence, for example, can be compared with computer translated human EST sequences, e.g., in GenBank, using GCG software and the blast search program for example. Matches with highly homologous EST sequences can then be obtained.

The matched EST can then be fully sequenced. One such example is outlined here, though many equivalent systems and variations are known and practiced in the art. DNA sequencing reactions can be assembled on a Beckman Biomek robotic system using standard dye-terminator chemistry, Taq polymerase and thermal cycling conditions described by the vendor (Perking Elmer/Applied Biosystems Division (PE/AB)). Preferably sequencing is performed multiple times to insure accuracy. Reaction products can be resolved on PE/ABD model 373 and 377 automated DNA sequencers. Contig assembly can be performed using any number of programs (e.g., Gap4) and a consensus sequence can be further analyzed using the GCG suite of applications. The resulting sequence can then be used in place of, and/or in conjunction with SEQ ID NO:1 to identify other ESTs which contain coding regions of the human homologue to DBT.

Plasmids containing the matched ESTs can be digested with restriction enzymes in order to release the cDNA inserts. If the plasmid does not contain the full length homologue the digests can be purified, e.g., run on an agarose gel and the bands corresponding to the inserts can be cut from the gel and purified (Quiagen Gel Extraction kit). Such purified inserts are likely to contain overlapping regions which can be combined as templates of a PCR reaction using primers which are preferably located outside of the human DBT open reading frame. The PCR reaction can be performed using ELONGASE (and its standard amplification system) supplied by Gibco-BRL, Gaithersburg, Md., under the following standard conditions: 5 minutes at 94° C.; followed by 25 cycles of: 30 seconds at 94° C., 30 seconds at 50° C., and 3.5 minutes at 72° C.; followed by 10 minutes at 72° C. Amplification should yield the expected product which can be ligated into a vector and used to transform an *E coli* derivative via TA cloning (Invitrogen) for example. The resulting full-length human DBT can be placed into an expression vector and the expressed recombinant DBT can then be assayed for kinase activity and PER binding activity.

Alternatively, plasmids containing matched EST homologue fragments can be used to transform competent bacteria (e.g, from Gibco BRL, Gaithersburg Md.). Bacteria can be streaked, then grown up overnight. Plasmid preps can be performed (e.g., Quiagen Corp, Santa Clarita Calif.) and the plasmids can be digested by simultaneous restriction digest. Products of the digest can be separated by size on an agarose gel, for example, and purified. The corresponding bands cut from these gels can be ligated to form a fulllength dbt cDNA and used to transform competent bacteria (DHFalpha) and the resulting plasmid can be purified.

In addition, polymorphisms, particularly human polymorphisms can be identified. Such polymorphisms can be identified using biological samples (e.g., a blood sample) from an animal subject, preferably a human subject. Tests that identify a polymorphism (such as a single nucleotide polymorphism, SNP) can be used in the diagnosis of a biochemical basis for a sleep disorder, etc., for example. Such a diagnosis can lead a skilled health practitioner to the optimal treatment of the disorder.

In one such embodiment, a nucleic acid that naturally encodes CK1ε can be cut into small overlapping pieces (e.g., 15–50 nucleotides long) and placed on a chip in a microarray. Within the microarray, a single nucleotide of the nucleic acid fragment can be systematically substituted by the three possible alternative nucleotides. In this manner all possible single nucleotide variations can be constructed. The microarray would then contain a family of nucleic acid fragments that have been systematically constructed to contain single nucleotide substitutions. An extract of the blood sample, for example, that contains the nucleic acids of the animal subject, could then be prepared. A control sample can be used for the standard "wild-type" hybridization pattern (which can be visualized by any number of methods including using fluorescent tags). The hybridization pattern of the test sample can then be compared with the standard. A blood sample that varies in its hybridization pattern is selected as having a polymorphism. The sequence difference between CK1ε from the test sample and the wild-type can then be determined.

The CK1ε from the test sample can also be isolated and/or fully sequenced. Alternatively, a polymorphism can be identified as described in Example 3.

In a particular embodiment a recombinant DNA is prepared that has the nucleic acid sequence of the test sample CK1ε polymorphism. The recombinant DNA can be expressed and purified. The purified CK1ε polymorphism (enzyme variant) can then be studied as a recombinant enzyme in in vitro assays as disclosed in the Examples below. The recombinant DNA can also be used to construct a transgenic or knockin animal that contains that particular CK1ε variant. In either case, the CK1ε variant could be used in drug screens, exemplified below.

Expression of DBTs

The present invention provides for expressing the nucleic acids which encode the DBTs fragments thereof, derivatives or analog thereof, or a functionally active derivative, including a chimeric protein, thereof, that has been inserted into an appropriate expression vector, i.e., a vector which contains the necessary elements for the transcription and translation of the inserted protein-coding sequence. Such elements are termed herein a "promoter." Thus, the nucleic acid encoding a DBT of the invention is operationally associated with a promoter in an expression vector of the invention. Both cDNA and genomic sequences can be cloned and expressed under control of such regulatory sequences. An expression vector also preferably includes a replication origin. One particular use for such expression vectors is to express a DBT in large quantities that can be used for functional and structural studies of the purified protein kinase. The necessary transcriptional and translational signals can be provided on a recombinant expression vector, or they may be supplied by the native gene encoding DBT and/or its flanking regions.

Potential chimeric partners for the DBT of the present invention include green fluorescent protein which may be useful in monitoring the cellular localization of the DBT.

Potential host-vector systems include but are not limited to mammalian cell systems, infected with virus (e.g., vaccinia virus, adenovirus, etc.); insect cell systems infected with virus (e.g., baculovirus); microorganisms such as yeast containing yeast vectors; or bacteria transformed with bacteriophage, DNA, plasmid DNA, or cosmid DNA. The expression elements of vectors vary in their strengths and specificities. Depending on the host-vector system utilized, any one of a number of suitable transcription and translation elements may be used.

A recombinant DBT protein of the invention, or functional fragment, derivative, chimeric construct, or analog thereof, may be expressed chromosomally, after integration of the coding sequence by recombination. In this regard, any of a number of amplification systems may be used to achieve high levels of stable gene expression (See Sambrook et al., 1989, supra). The cell containing the recombinant vector comprising the nucleic acid encoding DBT is cultured in an appropriate cell culture medium under conditions that provide for expression of DBT by the cell.

Any of the methods previously described for the insertion of DNA fragments into a cloning vector may be used to construct expression vectors containing a gene consisting of appropriate transcriptional/translational control signals and the protein coding sequences. These methods may include in vitro recombinant DNA and synthetic techniques and in vivo recombination (genetic recombination).

Expression of DBT may be controlled by any promoter/ enhancer element known in the art, but these regulatory elements must be functional in the host selected for expression. Promoters which may be used to control DBT gene expression include, the SV40 early promoter region (Benoist and Chambon, 1981, Nature 290:304–310), the promoter contained in the 3' long terminal repeat of Rous sarcoma virus (Yamamoto, et al, 1980, Cell 22:787–797), the herpes thymidine kinase promoter (Wagner et al., 1981, Proc. Natl. Acad. Sci. U.S.A. 78.1441–1445), the regulatory sequences of the metallothionein gene (Brinster et al., 1982, Nature 296:39–42); prokaryotic expression vectors such as the β-lactamase promoter (Villa-Kamaroff, et al., 1978, Proc. Natl. Acad. Sci. U.S.A. 75:3727–3731), or the tac promoter (DeBoer, et al., 1983, Proc. Natl. Acad. Sci. U.S.A. 80:21–25); see also "Useful proteins from recombinant bacteria" in Scientific American, 1980, 242:74–94; promoter elements from yeast or other fungi such as the Gal 4 promoter, the ADC (alcohol dehydrogenase) promoter, PGK (phosphoglycerol kinase) promoter, alkaline phosphatase promoter; and the animal transcriptional control regions, which exhibit tissue specificity and have been utilized in transgenic animals: elastase I gene control region which is active in pancreatic acinar cells (Swift et al., 1984, Cell 38:639–646; Ornitz et al., 1986, Cold Spring Harbor Symp. Quant. Biol. 50:399–409; MacDonald, 1987, Hepatology 7:425–515); insulin gene control region which is active in pancreatic beta cells (Hanahan, 1985, Nature 315:115–122), immunoglobulin gene control region which is active in lymphoid cells (Grosschedl et al., 1984, Cell 38:647–658; Adames et al., 1985, Nature 318:533–538; Alexander et al., 1987, Mol. Cell. Biol. 7:1436–1444), mouse mammary tumor virus control region which is active in testicular, breast, lymphoid and mast cells (Leder et al., 1986, Cell 45:485–495), albumin gene control region which is active in liver (Pinkert et al., 1987, Genes and Devel. 1:268–276), alpha-fetoprotein gene control region which is active in liver (Krumlauf et al., 1985, Mol. Cell. Biol. 5:1639–1648; Hammer et al., 1987, Science 235:53–58), alpha 1-antitrypsin gene control region which is active in the liver (Kelsey et al., 1987, Genes and Devel. 1:161–171), beta-globin gene control region which is active in myeloid cells (Mogram et al., 1985, Nature 315:338–340; Kollias et al., 1986, Cell 46:89–94), myelin basic protein gene control region which is active in oligodendrocyte cells in the brain (Readhead et al., 1987, Cell 48:703–712), myosin light chain-2 gene control region which is active in skeletal muscle (Sani, 1985, Nature 314:283–286), and gonadotropic releasing hormone gene control region which is active in the hypothalamus (Mason et al., 1986, Science 234:1372–1378).

Expression vectors containing a nucleic acid encoding a DBT of the invention can be identified by four general approaches: (a) PCR amplification of the desired plasmid DNA or specific mRNA, (b) nucleic acid hybridization, (c) presence or absence of selection marker gene functions, and (d) expression of inserted sequences. In the first approach, the nucleic acids can be amplified by PCR to provide for detection of the amplified product. In the second approach, the presence of a foreign gene inserted in an expression vector can be detected by nucleic acid hybridization using probes comprising sequences that are homologous to an inserted marker gene. In the third approach, the recombinant vector/host system can be identified and selected based upon the presence or absence of certain "selection marker" gene functions (e.g., β-galactosidase activity, thymidine kinase activity, resistance to antibiotics, transformation phenotype, occlusion body formation in baculovirus, etc.) caused by the insertion of foreign genes in the vector. In another example, if the nucleic acid encoding DBT is inserted within the "selection marker" gene sequence of the vector, recombinants containing the DBT insert can be identified by the absence of the DBT gene function. In the fourth approach, recombinant expression vectors can be identified by assaying for the activity, biochemical, or immunological characteristics of the gene product expressed by the recombinant, provided that the expressed protein assumes a functionally active conformation. For example, the protein kinase activity of DBT can be tested.

A wide variety of host/expression vector combinations may be employed in expressing the DNA sequences of this invention. Useful expression vectors, for example, may consist of segments of chromosomal, non-chromosomal and synthetic DNA sequences. Suitable vectors include derivatives of SV40 and known bacterial plasmids, e.g., E. coli plasmids col E1, pCR1, pBR322, pMal-C2, pET, pGEX (Smith et al., 1988, Gene 67:31–40), pMB9 and their derivatives, plasmids such as RP4; phage DNAS, e.g., the numerous derivatives of phage λ, e.g., NM989, and other phage DNA, e.g., M13 and filamentous single stranded phage DNA; yeast plasmids such as the 2μ plasmid or derivatives thereof; vectors useful in eukaryotic cells, such as vectors useful in insect or mammalian cells; vectors derived from combinations of plasmids and phage DNAs, such as plasmids that have been modified to employ phage DNA or other expression control sequences; and the like.

For example, in a baculovirus expression systems, both non-fusion transfer vectors, such as but not limited to pVL941 (BamH1 cloning site; Summers), pVL1393 (BamH1, SmaI, XbaI, EcoR1, NotI, XmaIII, BglII, and PstI cloning site; Invitrogen), pVL1392 (BglII, PstI, NotI, XmaIII, EcoRI, XbaI, SmaI, and BamH1 cloning site; Summers and Invitrogen), and pBlueBacIII (BamH1, BglII, PstI, NcoI, and HindIII cloning site, with blue/white recombinant screening possible; Invitrogen), and fusion transfer vectors, such as but not limited to pAc700 (BamH1 and KpnI cloning site, in which the BamH1 recognition site begins with the initiation codon; Summers), pAc701 and pAc702 (same as pAc700, with different reading frames), pAc360 (BamH1 cloning site 36 base pairs downstream of a polyhedrin initiation codon; Invitrogen(195)), and pBlueBacHisA, B, C (three different reading frames, with BamH1, BglII, PstI, NcoI, and HindIII cloning site, an N-terminal peptide for ProBond purification, and blue/white recombinant screening of plaques; Invitrogen (220)) can be used.

Mammalian expression vectors contemplated for use in the invention include vectors with inducible promoters, such as the dihydrofolate reductase (DHFR) promoter, e.g., any expression vector with a DHFR expression vector, or a DHFR/methotrexate co-amplification vector, such as pED (PstI, SalI, SbaI, SmaI, and EcoRI cloning site, with the vector expressing both the cloned gene and DHFR; see Kaufman, Current Protocols in Molecular Biology, 16.12 (1991). Alternatively, a glutamine synthetase/methionine sulfoximine co-amplification vector, such as pEE14 (HindIII, XbaI, SmaI, SbaI, EcoRI, and Bc/I cloning site, in which the vector expresses glutamine synthase and the cloned gene; Celltech). In another embodiment, a vector that directs episomal expression under control of Epstein Barr Virus (EBV) can be used, such as pREP4 (BamH1, SfiI, XhoI, NotI, NheI, HindIII, NheI, PvuII, and KpnI cloning site, constitutive RSV-LTR promoter, hygromycin selectable marker; Invitrogen), pCEP4 (BamH1, SfiI, XhoI, NotI, NheI, HindIII, NheI, PvuII, and KpnI cloning site, constitutive hCMV immediate early gene, hygromycin selectable marker; Invitrogen), pMEP4 (KpnI, PvuI, NheI, HindIII, NotI, XhoI, SfiI, BamH1 cloning site, inducible methallothionein IIa gene promoter, hygromycin selectable marker: Invitrogen), pREP8 (BamH1, XhoI, NotI, HindIII, NheI, and KpnI cloning site, RSV-LTR promoter, histidinol selectable marker; Invitrogen), pREP9 (KpnI, NheI, HindIII, NotI, XhoI, SfiI, and BamHI cloning site, RSV-LTR promoter, G418 selectable marker; Invitrogen), and pEB-VHis (RSV-LTR promoter, hygromycin selectable marker, N-terminal peptide purifiable via ProBond resin and cleaved by enterokinase; Invitrogen). Selectable mammalian expression vectors for use in the invention include pRc/CMV (HindIII, BstXI, NotI, SbaI, and ApaI cloning site, G418 selection; Invitrogen), pRc/RSV (HindIII, SpeI, BstXI, NotI, XbaI cloning site, G418 selection; Invitrogen), and others. Vaccinia virus mammalian expression vectors (see, Kaufman, 1991, supra) for use according to the invention include but are not limited to pSC11 (SmaI cloning site, TK- and β-gal selection), pMJ601 (SalI, SmaI, AflI, NarI, BspMII, BamHI, ApaI, NheI, SacII, KpnI, and HindIII cloning site; TK- and β-gal selection), and pTKgptF1S (EcoRI, PstI, SalI, AccI, HindII, SbaI, BamHI, and Hpa cloning site, TK or XPRT selection).

Yeast expression systems can also be used according to the invention to express the DBT protein. For example, the non-fusion pYES2 vector (XbaI, SphI, ShoI, NotI, GstXI, EcoRI, BstXI, BamH1, SacI, Kpn1, and HindIII cloning sit; Invitrogen) or the fusion pYESHisA, B, C (XbaI, SphI, ShoI, NotI, BstXI, EcoRI, BamH1, SacI, KpnI, and HindIII cloning site, N-terminal peptide purified with ProBond resin and cleaved with enterokinase; Invitrogen), to mention just two, can be employed according to the invention.

Once a particular recombinant DNA molecule is identified and isolated, several methods known in the art may be used to propagate it. Once a suitable host system and growth conditions are established, recombinant expression vectors can be propagated and prepared in quantity. As previously explained, the expression vectors which can be used include, but are not limited to, the following vectors or their derivatives: human or animal viruses such as vaccinia virus or adenovirus; insect viruses such as baculovirus; yeast vectors; bacteriophage vectors (e.g., lambda), and plasmid and cosmid DNA vectors, to name but a few.

In addition, a host cell strain may be chosen which modulates the expression of the inserted sequences, or modifies and processes the gene product in the specific fashion desired. Different host cells have characteristic and specific mechanisms for the translational and post-translational processing and modification (e.g., glycosylation, cleavage [e.g., of signal sequence]) of proteins. Appropriate cell lines or host systems can be chosen to ensure the desired modification and processing of the foreign protein expressed. For example, expression in a bacterial system can be used to produce an nonglycosylated core protein product. However, DBT expressed in bacteria may not be properly folded. Expression in yeast can produce a glycosylated product. Expression in eukaryotic cells can increase the likelihood of "native" glycosylation and folding of a heterologous protein. Moreover, expression in mammalian cells can provide a tool for reconstituting, or constituting, DBT activity. Furthermore, different vector/host expression systems may affect processing reactions, such as proteolytic cleavages, to a different extent.

Vectors are introduced into the desired host cells by methods known in the art, e.g., transfection, transduction, electroporation, microinjection, cell fusion, DEAE dextran, calcium phosphate precipitation, lipofection (lysosome fusion), use of a gene gun, or a DNA vector transporter (see, e.g., Wu et al., 1992, J. Biol. Chem. 267:963–967; Wu and Wu, 1988, J. Biol. Chem. 263:14621–14624; Hartmut et al., Canadian Patent Application No. 2,012,311, filed Mar. 15, 1990).

The present invention also provides cell lines made from cells transfected or transduced with the DBTs of the present invention. In preferred embodiments of this type the cells are Drosophila cells. In another embodiment the cells are mammalian cells.

General Protein Purification Procedures

The initial step for purifying the DBTs of the present invention, active fragments thereof, and related tagged or fusion proteins can consist of lysing the cells containing the DBTs. Cell lysis can be achieved by a number of methods including through the use of a physical means such as a French press, a sonicator, or a blender; or through chemical means including enzymatic extractions (with for example, lysozyme or pancreatin), and/or organic extractions or solubilizations with detergents, such as sodium dodecyl sulfate (SDS), Triton X-100, nonidet P-40 (NP-40), digoxin, sodium deoxycholate, and the like, including mixtures thereof, or through a combination of chemical and physical means. For example, solubilization can be enhanced by sonication of the suspension. Subsequent steps of purification include salting in or salting out, such as in ammonium sulfate fractionations; solvent exclusion fractionations, e.g., an ethanol precipitation; detergent extractions to free the membrane bound DBTs of the present invention using such detergents as Triton X-100, Tween-20 etc.; or high salt extractions. Solubilization of proteins may also be achieved using aprotic solvents such as dimethyl sulfoxide and hexamethylphosphoramide. In addition, high speed ultracentrifugation may be used either alone or in conjunction with other extraction techniques.

Generally good secondary isolation or purification steps include solid phase absorption using calcium phosphate gel or hydroxyapatite; or solid phase binding. Solid phase binding may be performed through ionic bonding, with either an anion exchanger, such as diethylaminoethyl (DEAE), or diethyl [2-hydroxypropyl] aminoethyl (QAE) SEPHADEX or cellulose; or with a cation exchanger such as carboxymethyl (CM) or sulfopropyl (SP) SEPHADEX or cellulose. Alternative means of solid phase binding includes the exploitation of hydrophobic interactions e.g., the using of a solid support such as PHENYLSEPHAROSE and a high salt buffer; affinity-binding, using, e.g., placing a nucleoside or nucleoside analog on to an activated support; immuno-binding, using e.g., an antibody to a DBT of the present invention bound to an activated support; as well as other solid phase supports including those that contain specific dyes or lectins etc. A further solid phase support technique that is often used at the end of the purification procedure relies on size exclusion, such as SEPHADEX and SEPHAROSE gels, or pressurized or centrifugal membrane techniques, using size exclusion membrane filters.

Solid phase support separations are ggenerally performed batch-wise with low-speed centrifugations or by column chromatography. High performance liquid chromatography (HPLC), including such related techniques as FPLC, is presently the most common means of performing liquid chromatography. Size exclusion techniques may also be accomplished with the aid of low speed centrifugation.

In addition size permeation techniques such as gel electrophoretic techniques may be employed. These techniques are generally performed in tubes, slabs or by capillary electrophoresis.

Almost all steps involving protein purification employ a buffered solution. Unless otherwise specified, generally 25–100 mM concentrations are used. Low concentration buffers generally infer 5–25 mM concentrations. High concentration buffers generally infer concentrations of the buffering agent of between 0.1–2M concentrations. Typical buffers can be purchased from most biochemical catalogues and include the classical buffers such as Tris, pyrophosphate, monophosphate and diphosphate. The Good buffers [Good, et al., *Biochemistry*, 5:467 (1966); Good et al. *Meth. Enzymol.*, 24: Part B, 53 (1972); and Fergunson, et. al *Anal. Biochem.* 104:300,(1980)] such as Mes, Hepes, Mops, tricine and Ches.

Materials to perform all of these techniques are available from a variety of sources such as Sigma Chemical Company in St. Louis, Mo.

Alignment Programs

DNA and protein sequence alignments can be created using the MEGALIGN program (for ALIGN in older versions) within the LASERGENE sequence analysis software package from DNASTAR, Inc. (See *User's Guide for LASERGENE for the Macintosh,* especially Pages 119–120). The alignments of the DNA sequence for the present invention is performed by the method of Wilbur-Lipman [Wilbur and Lipman, *Proc. Natl. Acad. Sci.* USA 80: 726–730 (1983)] using the default parameters:

(i) K-tuple=3; (ii) Gap Penalty=3; and (iii) Window=20

The alignments of the amino acid sequence for the present invention is performed by the method of Lipman-Pearson [Lipman, and Pearson. *Science* 227:1435–1441 (1985)] using the default parameters:

(i) K-tuple=2; (ii) Gap Penalty=4; and (iii) Gap Length Penalty=12

The LASERGENE manual defines the following terms as:

(1) K-tuple: A K-tuple, or word, is the number of residues compared to each other at a time.

A K-tuple of 1 provides a more exhaustive search but takes longer. A higher K-tuple value finds fewer but longer matching regions. A lower K-tuple value finds shorter matching regions.

(2) Gap penalty: For each gap introduced in the alignment, the MEGALIGN deducts a penalty from the score. A higher gap penalty suppresses gapping, a lower value promotes it.

(3) Gap length penalty: MEGALIGN also assesses penalties based on the length of the gap. The more residues the gap spans, the greater the penalty. These penalties are deducted from the overall score of the alignment.

(4) Window: Window determines over how long a range MEGALIGN searches for all possible k-tuples. MAGALIGN first finds a dominant region of similarity. It then uses this region as its starting point and extends diagonally until it reaches the end of the window.

Antibodies to DBTs

According to the invention, a DBT obtained from a natural source or produced recombinantly or by chemical synthesis, and fragments or other derivatives or analogs thereof, including fusion proteins, may be used as an immunogen to generate antibodies that recognize the DBT polypeptide. In a particular embodiment, the antibodies recognize a specific CK1ε variant, e.g., a human ortholog of the hamster tau mutant. The antibodies of the present invention include but are not limited to polyclonal, monoclonal, chimeric, humanized, single chain, Fab fragments, and an Fab expression library. The anti-DBT antibodies of the invention may be cross reactive, e.g., they may recognize a DBT from different species. Polyclonal antibodies have greater likelihood of cross reactivity.

Alternatively, an antibody of the invention may be specific for a single form of the DBT, such as Drosophila DBT.

Various procedures known in the art may be used for the production of polyclonal antibodies to a DBT of the present invention or derivative or analog thereof. For the production of antibody, various host animals can be immunized by injection with a DBT or a derivative (e.g., fragment or fusion protein) thereof, including but not limited to rabbits, mice, rats, sheep, goats, etc. In one embodiment, a DBT or fragment thereof can be conjugated to an immunogenic carrier, e.g., bovine serum albumin (BSA) or keyhole limpet hemocyanin (KLH). Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*.

For preparation of monoclonal antibodies directed toward a DBT of the present invention, or fragment, analog, or derivative thereof, any technique that provides for the production of antibody molecules by continuous cell lines in culture may be used. These include but are not limited to the hybridoma technique originally developed by Kohler and Milstein [*Nature* 256:495–497 (1975)], as well as the trioma technique, the human B-cell hybridoma technique [Kozbor et al., *Immunology Today* 4:72 1983); Cote et al., *Proc. Natl. Acad. Sci. U.S.A.* 80:2026–2030 (1983)], and the EBV-hybridoma technique to produce human monoclonal antibodies [Cole et al., in *Monoclonal Antibodies and Cancer Therapy*, Alan R. Liss, Inc., pp. 77–96 (1985)]. In an additional embodiment of the invention, monoclonal antibodies can be produced in germ-free animals utilizing recent technology [PCT/US90/02545]. In fact, according to the invention, techniques developed for the production of "chimeric antibodies" [Morrison et al., *J. Bacteriol.* 159:870 (1984); Neuberger et al., *Nature* 312:604–608 (1984); Takeda et al., *Nature* 314:452–454 (1985)] by splicing the genes from a Drosophila antibody molecule specific for a DBT, for example, together with genes from a human antibody molecule of appropriate biological activity can be used; such antibodies are within the scope of this invention. Such human or humanized chimeric antibodies are preferred for use in therapy of human diseases or disorders (described infra), since the human or humanized antibodies are much less likely than xenogenic antibodies to induce an immune response, in particular an allergic response, themselves.

According to the invention, techniques described for the production of single chain antibodies [U.S. Pat. Nos. 5,476,786 and 5,132,405 to Huston; U.S. Pat. No. 4,946,778] can be adapted to produce DBT-specific single chain antibodies. An additional embodiment of the invention utilizes the techniques described for the construction of Fab expression libraries [Huse et al., *Science* 246:1275–1281 (1989)] to allow rapid and easy identification of monoclonal Fab fragments with the desired specificity for a DBT or its derivatives, or analogs.

Antibody fragments which contain the idiotype of the antibody molecule can be generated by known techniques. For example, such fragments include but are not limited to: the $F(ab')_2$ fragment which can be produced by pepsin digestion of the antibody molecule; the Fab' fragments which can be generated by reducing the disulfide bridges of the $F(ab')_2$ fragment, and the Fab fragments which can be generated by treating the antibody molecule with papain and a reducing agent.

In the production of antibodies, screening for the desired antibody can be accomplished by techniques known in the art, e.g., radioimmunoassay, ELISA (enzyme-linked immunosorbant assay), "sandwich" immunoassays, immunoradiometric assays, gel diffusion precipitin reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. For example, to select antibodies which recognize a specific epitope of a DBT, for example the kinase catalytic site, one may assay generated hybridomas for a product which binds to a DBT fragment containing such an epitope. For selection of an antibody specific to a DBT from a particular species of animal, one can select on the basis of positive binding with a DBT expressed by or isolated from cells of that species of animal.

The foregoing antibodies can be used in methods known in the art relating to the localization and activity of the DBT, e.g., for Western blotting, imaging DBT in situ, measuring levels thereof in appropriate physiological samples, etc. using any of the detection techniques mentioned above or known in the art. More particularly, the antibodies of the present invention can be used in flow cytometry studies, in immunohistochemical staining, and in immunoprecipitation which serves to aid the determination of the level of expression of a DBT in a tumor or normal cell or tissue.

In a specific embodiment, antibodies that agonize or antagonize the activity of a DBT can be generated. Such antibodies can be tested using the assays described herein.

Assays for Identifying Agonists and Antagonists of DOUBLETIME

Identification of the Drosophila DOUBLETIME protein provides a basis for screening for drugs capable of specific interaction with the functionally relevant aspects of the protein. Moreover, the identification of the DOUBLETIME protein as the Drosophila ortholog of human CK1ε, the elucidation of the role of CK1ε in circadian rhythms, and the discovery that the phenotype of the mutant tau hamster is due to a CK1ε variant, (all of which is disclosed herein), permits CK1ε to be employed in specific drug assays useful for identifying agents that can effect circadian phenotypes e.g., for sleep disorders and/or jet lag and/or other physiological and metabolic processes under circadian regulation.

Thus, the present invention describes a method for expressing and purifying recombinant mammalian CK1ε proteins (and related variants) on affinity beads for use as a functional screen for inhibitors and activators of the enzyme. The use of both normal and mutant (variant) mammalian CK1ε expressed as recombinant proteins, allows their relative casein kinase activity to be determined as well as the identification of compounds that regulate the role of these enzymes in the circadian clock of animals. Since different variants (mutant alleles) of CK1ε can either shorten or lengthen the circadian period in animals, such agents can be tested in vitro for their effect on the individual variants. In this manner compounds that shorten or lengthen the circadian period can be identified. Appropriate biochemical assays are exemplified in the Examples below.

Compounds that are selected can then be tested in animals to see if they effect the circadian rhythms in vivo. These compounds could also be tested and then selected using an animal model that exhibits either advanced or delayed phase shifts in its circadian rhythm. For example, the tau hamster can be used as the animal model. More preferably, transgenic and/or knockin animals that have been constructed to express a variant CK1ε can also be used to confirm and extend these results. In a particular embodiment the animal model is a "knockin" mouse. More particularly, the hamster "tau" mutation as described below, can be produced in a knockin or transgenic animal such as a mouse. For example, a mouse comprising the mouse ortholog of $dbt^S$ CK1ε and/or the mouse ortholog of $dbt^L$ CK1ε and/or the mouse ortholog of $dbt^P$ CK1ε described in Examples 1 and 2 may also be used in the assay. The present invention also envisions making other animal models in which the amino acid residues that correspond to Gly #215 and Lys #224 of the hamster (see FIG. 18) are substituted for. In addition, the use of both single allele and double allele variants are envisioned by the present invention.

In a particular embodiment, a compound could be tested in two or more transgenic or knockin animals each comprising one of these CK1ε variants. Additional transgenic or knockin animals could be prepared using other CK1ε variants (either naturally occurring or constructed via site direct mutagenesis or analogous methods). In any case, a spectrum of transgenic or knockin animals provides an array of animal models to test and validate potential drugs involved in circadian phenotypes e.g., sleep disorders and/or jet lag and/or other physiological and metabolic processes under circadian regulation. In a particular embodiment, a drug first identified in an in vitro assay is next tested in the in vivo assay.

For example, an agonist or antagonist can be identified that stimulate or inhibit the kinase activity of the DOUBLETIME protein. Since DOUBLETIME plays an important role regarding the stabilization of PER and therefore, the regulation of the biological clocks dependent on PER such agonists or antagonists can be used in treating disorders related to these biological clocks. Indeed, as described below, particular assays can be designed to identify drugs that particularly modulate the interaction between the PER protein and the DBT protein [including the human casein kinase Iε (CK1ε) protein]. In addition, the present invention envisions the use of alternative assays that can aid in distinguishing antagonists or agonists of the interaction of the DBT protein, e.g., CK1ε, with the PER protein in order to limit undesirable side effects on alternative biologically important substrates by such agents.

Accordingly, in addition to rational design of compounds that bind to DOUBLETIME, the present invention contemplates an alternative method for identifying specific agents that bind to DOUBLETIME using the various screening assays known in the art. Thus any screening technique known in the art can be used to screen for agonists or antagonists to the DOUBLETIME protein and/or its interaction with the PER protein including those performed using high throughput techniques and biological chip technology such as exemplified in U.S. Pat. No. 5,874,219, Issued Feb. 23, 1999, the disclosure of which is hereby incorporated by reference in its entirety. Such compounds can then be employed in specific assays to test their effect on CK1ε-dependent PER phosphorylation in vitro and/or in vivo. The present invention further contemplates screens for small molecule ligands or ligand analogs and mimics, as well as screens for natural ligands that bind to and antagonize DOUBLETIME in vivo.

Knowledge of the primary sequence of a factor of the present invention, see above, e.g., the DOUBLETIME protein (CK1ε), and the similarity of that sequence with proteins of known function, can provide an initial clue as to the agonists or antagonists of the protein. Identification and screening of antagonists is further facilitated by determining structural features of the DOUBLETIME protein, e.g., using X-ray crystallography, neutron diffraction, nuclear magnetic resonance spectrometry, and other techniques for structure determination. In particular the structure of the related yeast *Schizosaccharomyces pombe* enzyme Cki1 has been disclosed and a particular compound, N-(2-aminoethyl)-5-chloroisoquinolone-8-sulfonamide (CK17) has been identified as an inhibitor of Cki1 from the yeast *Schizosaccharomyces pombe* [Xu et al.*Proc. Natl. Acad. Sci. USA* 93:6308–6313 (1996)]. Therefore, this compound can be a starting point for rational drug design. The use of such a compound and corresponding techniques provide for the rational design or identification of potential agonists and antagonists.

Another approach uses recombinant bacteriophage to produce large libraries. Using the "phage method" [Scott and Smith, 1990, *Science* 249:386–390 (1990); Cwirla, et al., *Proc. Natl. Acad. Sci.*, 87:6378–6382 (1990); Devlin et al., *Science*, 249:404–406 (1990)], very large libraries can be constructed ($10^6$–$10^8$ chemical entities). A second approach uses primarily chemical methods, of which the Geysen method [Geysen et al., *Molecular Immunology* 23:709–715 (1986); Geysen et al. *J. Immunologic Method* 102:259–274 (1987)] and the method of Fodor et al. [*Science* 251:767–773 (1991)] are examples. Furka et al. [14*th International Congress of Biochemistry, Volume 5*, Abstract FR:013 (1988); Furka, *Int. J. Peptide Protein Res.* 37:487–493 (1991)], Houghton [U.S. Pat. No. 4,631,211, issued December 1986] and Rutter et al. [U.S. Pat. No. 5,010,175, issued Apr. 23, 1991] describe methods to produce a mixture of peptides that can be tested as agonists or antagonists.

The screening can be performed directly using peptides corresponding to the kinase catalytic domain of DBT. Alternatively, chimeric proteins, which contain the kinase catalytic domain of DBT may be used, as such proteins will contain one element under investigation.

Screening can be performed with recombinant cells that express the DOUBLETIME protein, or alternatively, using purified enzyme, and/or specific structural/functional domains of the DOUBLETIME protein e.g., produced recombinantly, as described above. For example, a labeled CK1ε can be used to screen libraries, as described in the foregoing references for small molecules that will modulate the kinase activity of the CK1ε, and more particularly the kinase activity towards PER.

The effective peptide(s) can be synthesized in large quantities for use in in vivo models and eventually in humans to modulate CK1ε. It should be emphasized that synthetic peptide production is relatively non-labor intensive, easily manufactured, quality controlled and thus, large quantities of the desired product can be produced quite cheaply. Similar combinations of mass produced synthetic peptides have recently been used with great success [Patarroyo, *Vaccine* 10:175–178 (1990)].

In addition, a potential drug, e.g., a modulating agent, can be obtained from a commercially available chemical library such as is available from most large chemical companies including Merck, Glaxo Welcome, Bristol Meyers. Squib, Monsanto/Searle, Eli Lilly, Novartis, and Pharmacia UpJohn. In another aspect, synthetic libraries [Needels et al., Proc. Natl. Acad. Sci. USA 90:10700–4 (1993); Ohlmeyer et al., Proc. Natl. Acad. Sci. USA 90:10922–10926 (1993); Lam et al., International Patent Publication No. WO 92/00252; Kocis et al., International Patent Publication No. WO 9428028, each of which is incorporated herein by reference in its entirety], and the like can be used to screen for modulators and/or binding partners of the DOUBLE-TIME protein.

The reagents that contain the DOUBLETIME protein or fragments thereof can be labeled for use in the screening assays. In one embodiment, the compound may be directly labeled including as part of a fusion protein, e.g., with green fluorescent protein. In another embodiment, a labeled secondary reagent may be used to detect binding of the compound to a solid phase support containing a binding molecule of interest. Binding may be detected by in situ formation of a chromophore by an enzyme label. Suitable enzymes include, but are not limited to, alkaline phosphatase and horseradish peroxidase. Other labels for use in the invention include colored latex beads, magnetic beads, fluorescent labels (e.g., fluorescein isothiocyanate (FITC), phycoerythrin (PE), Texas red (TR), rhodamine, Lucifer Yellow, AMCA blue, free or chelated lanthanide series salts, especially $Eu^{3+}$, to name a few fluorophores), chemiluminescent molecules, radio-isotopes, or magnetic resonance imaging labels.

As mentioned above, an important aspect of the present invention is the recognition of casein kinase I$\epsilon$ as a human homologue of DBT. Therefore, the present invention provides assays that can be used to identify agents/compounds that (i) bind to a mammalian PER protein (of which three are currently known) and affect the physical association between the PER protein and human CK1$\epsilon$ and/or (ii) affect the kinase activity of human CK1$\epsilon$ towards the PER protein substrate. Agents are selected that alter the binding constant of the physical association and/or the quantity or quality of phosphorylation of the PER protein by the CK1$\epsilon$ protein. Such assays can also be performed with active fragments of the PER protein and/or active fragments CK1$\epsilon$ protein. In this case an active fragment of the PER protein would minimally retain its CK1$\epsilon$ protein binding capacity and/or its phosphorylation site whereas the active fragment of the CK1$\epsilon$ protein would minimally retain its PER protein binding capacity and/or its kinase activity. Of course, the CK1$\epsilon$ protein, the PER protein and their corresponding active fragments could also be part of fusion proteins and peptides as described above.

In a particular embodiment, a chemical agent might be initially selected by its ability to bind to a PER protein or its ability to bind to a DBT, such as human CK1$\epsilon$. This agent then can be subsequently tested to determine if it is a modulator of the physical association of PER with CK1$\epsilon$ in vitro and/or in a cultured cell expression assay. An agent that is selected as such a modulator is identified as an agonist if it increases the physical association between PER and CK1$\epsilon$ whereas a modulator is identified as an antagonist if it decreases the physical association. As discussed above, such binding agents could be small peptides or non-protein chemical agents.

An assay useful and contemplated in accordance with the present invention is known as a "cis/trans" assay. Briefly, this assay employs one or more constructs, which encode: a Per, Tim and DOUBLETIME (including the human CK1$\epsilon$) and a reporter gene that is under the control of the activated transcription factors e.g. the Tim-Per dimer. The contruct(s) are transfected into an appropriate cell line (preferably a mammalian cell line) and the expression of the reporter (such as luciferase, or green fluorescent protein) can be monitored. This assay may be performed to identify antagonists and agonists to the DOUBLETIME protein. For example, if it is desired to evaluate a compound as an agonist for the DOUBLETIME protein, a constuct is used that possesses a promoter linked to the reporter gene (e.g., luciferase) in which a response element is inserted that is ultimately under the control of the PER-Tim dimer (e.g., a response element for the per and/or tim genes). The resulting signal (chemiluminescence in this example) is then measured (photometrically in this example), and dose response curves are obtained and compared to those in which the agonist is not included in the assay. Since the DOUBLETIME protein serves to destabilize Per, and therefore inhibit the negative effect that Per has on its own transcription, an agonist for the DOUBLETIME protein should cause an increase in the transcription of a reporter gene that is ultimately under the control of the PER-Tim dimer. Protocols somewhat analogous to the one presented above can be found U.S. Pat. No. 4,981,784 and PCT International Publication No. WO 88/03168, for which purpose the artisan is referred. Additional assays that can be used to test potential agents/drugs can be readily adapted from the assays described below in the Examples and above in the Brief Description of the Drawings.

Kits

The present invention provides test kits for demonstrating the presence or absence of a DBT protein or nucleic acid encoding a DBT in a cellular sample. One such kit comprises a predetermined amount of a binding partner of the protein or nucleic acid. Preferably the binding partner is detectably labeled (such as a labeled antibody or nucleic acid probe). A preferred embodiment further comprises a predetermined amount of the DBT protein or nucleic acid encoding a DBT to be used as a standard. A kit of the present invention preferably also provides a protocol for using the kit.

The present invention further provides kits that can be used to identify agents/compounds that (i) bind to a mammalian PER protein (of which three are currently known) and affect the physical association between the PER protein and a DBT, such as human CK1$\epsilon$ and/or (ii) affect the kinase activity of the DBT (e.g., human CK1$\epsilon$) towards the PER protein substrate. One such kit comprises a predetermined amount of a DBT (e.g., human CK1$\epsilon$) or an active fragment thereof, and a predetermined amount of a PER protein or an active fragment thereof. As above, an active fragment of the PER protein would minimally retain its DBT protein binding capacity and/or its phosphorylation site, whereas the active fragment of the DBT protein would minimally retain its PER protein binding capacity and/or its kinase activity. Of course, the DBT protein, the PER protein and their corresponding active fragments could also be part of fusion proteins and peptides as described above. Preferably either the DBT protein or the PER protein are detectably labeled (e.g., as part of a fusion protein). Either the DBT protein or the PER protein can also be on a solid support. This kit preferably also provides a protocol for using the kit.

Labels

Suitable labels include enzymes and proteins such as green fluorescent protein, fluorophores (e.g., fluorescene isothiocyanate (FITC), phycoerythrin (PE), Texas red (TR), rhodamine, free or chelated lanthanide series salts, especially $Eu^{3+}$, to name a few fluorophores), chromophores, radioisotopes, chelating agents, dyes, colloidal gold, latex particles, ligands (e.g., biotin), and chemiluminescent agents. When a control marker is employed, the same or different labels may be used for the receptor and control marker.

In the instance where a radioactive label, such as the isotopes $^3H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$ are used, known currently available procedures may be utilized. In the instance where the label is an enzyme, detection may be accomplished by any of the presently utilized colorimetric, spectrophotometric, fluorospectrophotometric, amperometric or gasometric techniques known in the art.

Direct labels are one example of labels which can be used according to the present invention. A direct label has been defined as an entity, which in its natural state, is readily visible, either to the naked eye, or with the aid of an optical filter and/or applied stimulation, e.g. U.V. light to promote fluorescence. Among examples of colored labels, which can be used according to the present invention, include metallic sol particles, for example, gold sol particles such as those described by Leuvering (U.S. Pat. No. 4,313,734); dye sole particles such as described by Gribnau et al. (U.S. Pat. No. 4,373,932) and May et al. (WO 88/08534); dyed latex such as described by May, supra, Snyder (EP-A 0 280 559 and 0 281 327); or dyes encapsulated in liposomes as described by Campbell et al. (U.S. Pat. No. 4,703,017). Other direct labels include a radionucleotide, a fluorescent moiety or a luminescent moiety. In addition to these direct labelling devices, indirect labels comprising enzymes can also be used according to the present invention. Various types of enzyme linked immunoassays are well known in the art, for example, alkaline phosphatase and horseradish peroxidase, lysozyme, glucose-6-phosphate dehydrogenase, lactate dehydrogenase, urease, these and others have been discussed in detail by Eva Engvall in Enzyme Immunoassay ELISA and EMIT in *Methods in Enzymology*, 70. 419–439, 1980 and in U.S. Pat. No. 4,857,453.

Suitable enzymes include, but are not limited to, alkaline phosphatase and horseradish peroxidase.

Other labels for use in the invention include magnetic beads or magnetic resonance imaging labels.

In another embodiment, a phosphorylation site can be created on an antibody of the invention for labeling with $^{32}P$, e.g., as described in European Patent No. 0372707 (application No. 89311108.8) by Sidney Pestka, or U.S. Pat. No. 5,459,240, issued Oct. 17, 1995 to Foxwell et al.

Proteins, including the DBTs of the present invention and antibodies thereto, can be labeled by metabolic labeling. Metabolic labeling occurs during in vitro incubation of the cells that express the protein in the presence of culture medium supplemented with a metabolic label, such as [$^{35}S$]-methionine or [$^{32}P$]-orthophosphate. In addition to metabolic (or biosynthetic) labeling with [$^{35}S$]-methionine, the invention further contemplates labeling with [$^{14}C$]-amino acids and [$^3H$]-amino acids (with the tritium substituted at non-labile positions).

Solid Supports

A solid phase support for use in the present invention will be inert to the reaction conditions for binding. A solid phase support for use in the present invention must have reactive groups in order to attach a binding partner, such as an oligonucleotide encoding a DBT, a DBT, or an antibody to a DBT, or for attaching a linker or handle which can serve as the initial binding point for any of the foregoing. In another embodiment, the solid phase support may be a useful chromatographic support, such as the carbohydrate polymers SEPHAROSE, SEPHADEX, and agarose. As used herein, a solid phase support is not limited to a specific type of support. Rather a large number of supports are available and are known to any person having skill in the art. Solid phase supports include silica gels, resins, derivatized plastic films, glass beads, cotton, plastic beads, alumina gels, magnetic beads, membranes (including but not limited to nitrocellulose, cellulose, nylon, and glass wool), plastic and glass dishes or wells, etc. For example, solid phase supports used for peptide or oligonucleotide synthesis can be used, such as polystyrene resin (e.g., PAM-resin obtained from Bachem Inc., Peninsula Laboratories, etc.), POLYHIPE® resin (obtained from Aminotech, Canada), polyamide resin (obtained from Peninsula Laboratories), polystyrene resin grafted with polyethylene glycol (TentaGel®, Rapp Polymere, Tubingen, Germany) or polydimethylacrylamide resin (obtained from Milligen/Biosearch, California). In synthesis of oligonucleotides, a silica based solid phase support may be preferred. Silica based solid phase supports are commercially available (e.g., from Peninsula Laboratories, Inc.; and Applied Biosystems, Inc.).

Antisense, Gene Targeting and Ribozymes

The functional activity of a DOUBLETIME protein can be evaluated with transgenic or knockin animals. Therefore, the present invention also provides transgenic, knockin, and knockout animals. In one embodiment of this type the knockin animal is a mouse. In another embodiment the animal is a kockout mouse. One embodiment comprises a disruption in an endogenous allele encoding CK1ε, which prevents the expression of functional CK1ε from that individual allele. In another embodiment, the disruption is in both endogenous alleles that encode CK1ε, preventing the knockout animal from expressing functional endogenous CK1ε. Although a transgenic/knockin/knockout mouse is preferred other rodents such as rats and rabbits, or mammals such as pigs, goats, sheep, and monkeys can also be used.

Though Drosophila and hamster are exemplified, other species including mice with altered dbt alleles (variants) are also part of the present invention. Altering a single allele may be preferable in certain instances since in Drosophila such a single alteration appears to be dominant, and disruption of both alleles of dbt appeared to be lethal in Drosophila.

The present invention also includes non-human transgenic or knockin animals that comprise cells that express a CK1ε variant of the present invention. For example, a rat comprising the rat ortholog of $dbt^S$ CK1ε and/or the rat ortholog of $dbt^L$ CK1ε and/or the rat ortholog of $dbt^P$ CK1ε described in Examples 1 and 2 may also be used in the assay. The present invention also envisions making other animal models in which the amino acid residues that correspond to Gly #215 and Lys #224 of the hamster (see FIG. 18) are substituted for. Such transgenic or knockin animals can be used for identifying and testing drugs that can be useful in the regulation of circadian rhythms, e.g., to treat sleep disorders. Thus the transgenic, knockin, and knockout animals of the present invention can be used in drug screens and the like.

The CK1ε gene can be used in complementation studies employing transgenic mice. Transgenic vectors, including viral vectors, or cosmid clones (or phage clones) corresponding to the wild type locus of candidate gene, can be constructed using the isolated CK1ε gene. Cosmids may be introduced into transgenic mice using published procedures [Jaenisch, *Science*, 240:1468–1474 (1988)]. In a particular embodiment, a mouse ortholog of the tau CK1ε, or a mouse ortholog of one or more of the Drosophila dbt mutants can be placed into a transgenic or knockin mouse and compared with a wild-type mouse. Alternatively, a transgenic or knockin mouse comprising the mouse ortholog of the tau CK1ε can be compared with a mouse comprising the mouse ortholog of $dbt^S$ CK1ε and/or the mouse ortholog of dbtL CK1ε and/or the mouse ortholog of $dbt^P$ CK1ε as described in Examples 1 and 2. Similarly, transgenic or knockin animals other than mice may also be generated and used.

A transgenic or knockin animal can thus be prepared that expresses a recombinant CK1ε (or a CK1ε variant such as a polymorphism as described below) or a fragment thereof. In a particular embodiment, the transgenic or knockin animal expresses a CK1ε variant. Such transgenic animals can be obtained through gene therapy techniques described above or by microinjection of a nucleic acid [such as a bacterial artificial chromosome (BAC) that encodes a CK1ε variant] for example, into an embryonic stem cell or an animal zygote. Microinjection of BACs has been shown to be successful in a number of animals including rats, rabbits, pigs, goats, sheep, and cows [in *Transgenic Animals Generation and Use* ed., L. M. Houdebine, Harwood Academic Publishers, The Netherlands (1997)]. Methods of constructing BACs [or other DNAs such as bacteriophage P1 derived artificial chromosomes (PACs)] that encode specific nucleic acids through homologous recombination have recently been described in great detail [Heintz et al, PCT/US98/12966, (1998) the contents of which are hereby incorporated by reference in its entirety]. Alternatively, a yeast artificial chromosome (YAC) that encodes a CK1ε variant for example, can be used. In a preferred embodiment the transgenic animal is a mouse.

Alternatively, an animal model can be prepared in which expression of the CK1ε gene is disrupted. Gene expression is disrupted, according to the invention, when no functional protein is expressed. One standard method to evaluate the phenotypic effect of a gene product is to employ knock-out technology to delete a gene as described in U.S. Pat. No. 5,464,764, Issued Nov. 7, 1995; and U.S. Pat. No. 5,777,195, Issued Jul. 7, 1998 (both of which are hereby incorporated by reference herein in their entireties.)

In yet another aspect of the invention a knockin animal is made. A knockin animal is prepared in an analogous manner as a knockout animal except a variant/modified exon or gene is substituted for the exon or gene of interest through homologous recombination rather than disrupting the gene. Knockins and transgenic animals can be prepared with CK1ε variants including the $tau^\#$ CK1ε, $dbt^{L\#}$ CK1ε, and $dbt^{S\#}$ CK1ε as defined above.

A gene-targeting strategy can be used that utilizes a replacement vector containing a particular point mutation and a neo gene flanked by loxP sites to construct the Arg178Cys (tau) mutation in mice. This procedure is known as the Pointlox procedure [Giese et al. *Science* 279:870–873 (1998)].

The point mutation is introduced by polymerase chain reaction (PCR) mutagenesis into a restriction enzyme fragment containing the exon encoding Arg#178. The restriction fragment of the wild-type genomic clone is then substituted with the mutagenized restriction fragment. A PGKneo cassette flanked by loxP sites is inserted into an adjacent restriction site. After transfection of embryonic stem cells and selection with G418, targeted clones are identified by Southern (DNA) blot analyses. Because the PGKneo cassette could interfere with the expression of neighboring genes, it is removed by transient transfection with pBS185, a plasmid containing Cre recombinase DNA. Chimeras, generated by injection of targeted ES cells into blastocysts, are mated with C57BL/6J mice, and crosses of F1 heterozygotes yield a Mendelian distribution of F2 offspring. The mutants (knockins) are identified by PCR.

PCR primers are designed around the CK1ε point mutation in tau homozygous animals such that a product of approximately 160 basepairs is amplified:
F 5'-GATAACTTTCTCATGGGCTTGG-3(SEQ ID NO:34),
R 5'-GGGTGTTGATGGAGGCATAG-3' (SEQ ID NO:35)

PCR products are digested for 2 hours at 60° C. directly in PCR reaction buffer without purification, using the restriction enzyme BstAPI (New England Biolabs). The point mutation in mutant (knockin) animals results in the creation of a BstAPI restriction site.

The present invention also extends to the preparation of antisense nucleotides and ribozymes that may be used to interfere with the expression of the dbt gene. This approach utilizes antisense nucleic acid and ribozymes to block translation of a specific mRNA, either by masking that mRNA with an antisense nucleic acid or cleaving it with a ribozyme.

Antisense nucleic acids are DNA or RNA molecules that are complementary to at least a portion of a specific mRNA molecule [See Weintraub, *Sci. Amer.* 262:40–46 (1990); Marcus-Sekura, *Nucl. Acid Res,* 15: 5749–5763 (1987); Marcus-Sekura *Anal.Biochem.*, 172:289–295 (1988); Brysch et al., *Cell Mol. Neurobiol.*, 14:557–568 (1994)]. Preferably, the antisense molecule employed is complementary to a substantial portion of the mRNA. In the cell, the antisense molecule hybridizes to that mRNA, forming a double stranded molecule. The cell does not translate an mRNA in this double-stranded form. Therefore, antisense nucleic acids interfere with the expression of mRNA into protein. Preferably a DNA antisense nucleic acid is employed since such an RNA/DNA duplex is a preferred substrate for RNase H. Oligomers of greater than about fifteen nucleotides and molecules that hybridize to the AUG initiation codon will be particularly efficient. Antisense methods have been used to inhibit the expression of many genes in vitro [Marcus-Sekura, *Anal.Biochem.*, 172:289–295 (1988); Hambor et al., *Proc. Natl. Acad. Sci. U.S.A.* 85:4010–4014 (1988)] and in situ [Arima et al., *Antisense Nucl. Acid Drug Dev.* 8:319–327 (1998); Hou et al., *Antisense Nucl. Acid Drug Dev.* 8:295–308 (1998)].

Ribozymes are RNA molecules possessing the ability to specifically cleave other single stranded RNA molecules in a manner somewhat analogous to DNA restriction endonucleases. Ribozymes were discovered from the observation that certain mRNAs have the ability to excise their own introns. By modifying the nucleotide sequence of these ribozymes, researchers have been able to engineer molecules that recognize specific nucleotide sequences in an RNA molecule and cleave it [Cech, *JAMA*, 260:3030–3034 (1988); Cech, *Biochem. Intl*, 18:7–14 (1989)]. Because they are sequence-specific, only mRNAs with particular sequences are inactivated.

Investigators have identified two types of ribozymes, Tetrahymena-type and "hammerhead"-type [Haselhoff and Gerlach, *Nature* 334:585–591 (1988)]. Tetrahymena-type ribozymes recognize four-base sequences, while "hammerhead"-type recognize eleven- to eighteen-base sequences. The longer the recognition sequence, the more likely it is to occur exclusively in the target mRNA species. Therefore, hammerhead-type ribozymes are preferable to Tetrahymena-type ribozymes for inactivating a specific mRNA species, and eighteen base recognition sequences are preferable to shorter recognition sequences.

The DNA sequences of DOUBLETIME described herein may thus be used to prepare antisense molecules against, and ribozymes that cleave mRNAs encoding the DOUBLE-TIME protein.

Gene Therapy and Transgenic Vectors

In one embodiment, a gene encoding a DOUBLETIME protein is introduced in vivo in a viral vector. Such vectors include an attenuated or defective DNA virus, such as but not limited to herpes simplex virus (HSV), papillomavirus, Epstein Barr virus (EBV), adenovirus, adeno-associated virus (AAV), or a defective retrovirus such as HIV. Defective viruses, which entirely or almost entirely lack viral genes, are preferred. Defective virus is not infective after introduction into a cell. Use of defective viral vectors allows for administration to cells in a specific, localized area, without concern that the vector can infect other cells. Thus, any tissue can be specifically targeted. Examples of particular vectors include, but are not limited to, a defective herpes virus 1 (HSV1) vector [Kaplitt et al., *Molec. Cell. Neurosci.* 2:320–330 (1991)], an attenuated adenovirus vector, such as the vector described by Stratford-Perricaudet et al. [*J. Clin. Invest.* 90:626–630 (1992)], and a defective adeno-associated virus vector [Samulski et al., *J. Virol.* 61:3096–3101 (1987); Samulski et al., *J. Virol.* 63:3822–3828 (1989)].

For in vitro administration, an appropriate immunosuppressive treatment may be employed in conjunction with the viral vector, e.g., adenovirus vector, to avoid immuno-deactivation of the viral vector and transfected cells. For example, immunosuppressive cytokines, such as interleukin-12 (IL-12), interferon-γ (IFN-γ), or anti-CD4 antibody, can be administered to block humoral or cellular immune responses to the viral vectors [see, e.g., Wilson, *Nature Medicine* 1:887–889 (1995)]. In addition, it is advantageous to employ a viral vector that is engineered to express a minimal number of antigens.

In another embodiment the gene can be introduced in a retroviral vector, e.g., as described in Anderson et al., U.S. Pat. No. 5,399,346; Mann et al., 1983, Cell 33:153; Temin et al., U.S. Pat. No. 4,650,764; Temin et al., U.S. Pat. No. 4,980,289; Markowitz et al., 1988, J. Virol. 62:1120; Temin et al., U.S. Pat. No. 5,124,263; International Patent Publication No. WO 95/07358, published Mar. 16, 1995, by Dougherty et al.; and Kuo et al., 1993, Blood 82:845.

Targeted gene delivery is described in International Patent Publication WO 95/28494, published October 1995.

Alternatively, the vector can be introduced in vivo by lipofection. For the past decade, there has been increasing use of liposomes for encapsulation and transfection of nucleic acids in vitro. Synthetic cationic lipids designed to limit the difficulties and dangers encountered with liposome mediated transfection can be used to prepare liposomes for in vivo transfection of a gene encoding a marker [Felgner, et. al., *Proc. Natl. Acad. Sci. U.S.A.* 84:7413–7417 (1987); see Mackey, et al., *Proc. Natl. Acad. Sci. U.S.A.* 85:8027–8031 (1988)]. The use of cationic lipids may promote encapsulation of negatively charged nucleic acids, and also promote fusion with negatively charged cell membranes [Felgner and Ringold, *Science* 337:387–388 (1989)]. The use of lipofection to introduce exogenous genes into the specific organs in vivo has certain practical advantages. Molecular targeting of liposomes to specific cells represents one area of benefit. It is clear that directing transfection to particular cell types would be particularly advantageous in a tissue with cellular heterogeneity, such as pancreas, liver, kidney, and the brain. Lipids may be chemically coupled to other molecules for the purpose of targeting [see Mackey, et. al., supra]. Targeted peptides, e.g., hormones or neurotransmitters, and proteins such as antibodies, or non-peptide molecules could be coupled to liposomes chemically.

It is also possible to introduce the vector in vivo as a naked DNA plasmid. Naked DNA vectors for gene therapy can be introduced into the desired host cells by methods known in the art, e.g., transfection, electroporation, microinjection, transduction, cell fusion, DEAE dextran, calcium phosphate precipitation, use of a gene gun, or use of a DNA vector transporter [see, e.g., Wu et al., *J. Biol. Chem.* 267:963–967 (1992); Wu and Wu, *J. Biol. Chem.* 263:14621–14624 (1988); Hartmut et al., Canadian Patent Application No. 2,012,311, filed March 15, 1990].

Administration

The nucleic acids encoding DBT (including human CK1ε) and fragments thereof, and the proteins and fragments encoded thereby, can be used to promote desired effects on circadian rhythms or related disorders. Thus such factors can be used in the treatment of numerous sleep-related disorders, including depression, narcolepsy, shift work, psychological disturbances associated with sleep disorder, and other mental disorders linked to the sleep-wake cycle. These proteins and nucleic acids can also be used in the treatment of jet lag. Similarly, the therapeutic administration of agents exhibiting mimicry or antagonism to a DBT such as the human CK1ε kinase, or antagonism to DBT binding activity toward PER, or antagonism to DBT kinase activity toward PER can also be used for the treatments of the conditions outlined above.

Thus, in instances where it is desired to reduce or inhibit the transcription of per or tim, an appropriate inhibitor of DBT could be introduced to stabilize PER and thereby aid in the inhibition of per and tim transcription.

DBT or a binding partner or agents exhibiting mimicry or are agonist or antagonists of DBT or control over its production, may be prepared in pharmaceutical compositions, with a suitable carrier and at a strength effective for administration by various means to a patient experiencing an adverse medical condition associated with PER or TIM. A variety of administrative techniques may be utilized, among them parenteral techniques such as subcutaneous, intravenous and intraperitoneal injections, catheterizations and the like. The precise doses used should be based upon the recommendations and prescription of a qualified physician or veterinarian.

Also, antibodies including both polyclonal and monoclonal antibodies, and drugs that modulate the production or activity of the DBT may possess certain diagnostic applications and may for example, be utilized for the purpose of detecting and/or measuring conditions such as to classify groups of individuals with sleep-related disorders, in order to better treat the disorders. For example, antibodies directed against a DBT, e.g., human CK1ε and/or PER can be used to aid in the diagnosing of the effects and/or in the evaluation of the therapies described above that are aimed at disturbing the normal interaction and inter-related functions of CK1ε and PER proteins.

A DBT (such as human CK1ε) may be used to produce both polyclonal and monoclonal antibodies in a variety of cellular media, by known techniques such as the hybridoma technique utilizing, for example, fused mouse spleen lymphocytes and myeloma cells. Likewise, small molecules that mimic or antagonize the activity(ies) of DBT may be identified (see above) or synthesized, and may be used in diagnostic and/or therapeutic protocols.

The present invention further contemplates therapeutic compositions useful in practicing the therapeutic methods of this invention. A subject therapeutic composition includes, in admixture, a pharmaceutically acceptable excipient (carrier) and DBT (such as human CK1ε), a polypeptide analog thereof or fragment thereof, as described herein as an active ingredient. In a preferred embodiment, the composition comprises an antigen capable of modulating the specific binding of DBT within a target cell.

The preparation of therapeutic compositions which contain polypeptides, analogs or active fragments as active ingredients is well understood in the art. Typically, such compositions are prepared as injectables, either as liquid solutions or suspensions, however, solid forms suitable for solution in, or suspension in, liquid prior to injection can also be prepared. The preparation can also be emulsified. The active therapeutic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the composition can contain minor amounts of auxiliary substances such as wetting or emulsifying agents, pH buffering agents which enhance the effectiveness of the active ingredient.

A polypeptide, analog or active fragment can be formulated into the therapeutic composition as neutralized pharmaceutically acceptable salt forms. Pharmaceutically acceptable salts include the acid addition salts (formed with the free amino groups of the polypeptide or antibody molecule) and which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropyl amine, trimethylamine, 2-ethylamino ethanol, histidine, procaine, and the like.

The therapeutic polypeptide-, analog- or active fragment-containing compositions are may be administered intravenously, as by injection of a unit dose, for example. The term "unit dose" when used in reference to a therapeutic composition of the present invention refers to physically discrete units suitable as unitary dosage for humans, each unit containing a predetermined quantity of active material calculated to produce the desired therapeutic effect in association with the required diluent; i.e., carrier, or vehicle.

A subject in whom administration of the agent is an effective therapeutic regimen is preferably a human, but can be any animal, preferably a mammal. Thus, as can be readily appreciated by one of ordinary skill in the art, the methods and pharmaceutical compositions of the present invention are particularly suited to administration to any animal, particularly a mammal, and including, but by no means limited to, domestic animals, such as feline or canine subjects, farm animals, such as but not limited to bovine, equine, caprine, ovine, and porcine subjects, wild animals (whether in the wild or in a zoological garden), research animals, or for veterinary medical use.

The present invention may be better understood by reference to the following non-limiting Examples, which are provided as exemplary of the invention. The following examples are presented in order to more fully illustrate the preferred embodiments of the invention. They should in no way be construed, however, as limiting the broad scope of the invention.

EXAMPLES

Example 1

DOUBLE-TIME is a New Dropsophila Clock Gene that Regulates Period Protien Accumulation

Introduction

Three alleles of a new Drosophila clock gene, double-time (dbt) have been isolated. Short ($dbt^S$) and long-period ($dbt^L$) mutants alter both behavioral rhythmicity and the molecular oscillations of the protein products of the two previously identified clock genes, period and timeless. This indicates that dbt encodes a central clock component. A third allele, $dbt^P$, is associated with pupal lethality and eliminates circadian cycling ofper and tim gene products in larvae. In $dbt^P$ mutants, PERIOD (PER) protein constitutively accumulates to very high levels, is no longer dependent on TIM for its accumulation and remains hypo-phosphorylated. Evidence is presented for altered PER stability in $dbt^S$ and $dbt^L$ mutants. The results presented herein are consistent with the normal function of DOUBLETIME protein (DBT) being to reduce the stability and thus the level of accumulation of monomeric PER proteins. This would promote a delay between per/tim transcription and PER/TIM complex function, which is essential for molecular rhythmicity.

Experimental Procedures

Mutagenesis and Genetic Crosses: cn bw males were mutagenized with EMS (denoted by *) as described [Lewis and Bacher, Dros. Inf. Serv. 43:193 (1968)] and mated to virgin females. Two cross strategies were employed. Strategy I generated lines with isogenous second chromosomes, while strategy II allowed the $F_1$ generation to be screened for dominant or semidominant mutations on the second or third chromosome.

Strategy I
1) cn bw*/cn bw* males X CyO/Sco virgins
2) cn bw*/(CyO or Sco) single $F_1$ male X CyO/Sco virgins
3) cn bw*/CyO $F_2$males X cn bw*/CyO $F_2$ females
4) Screen cn bw*/cn bw* males in locomotor assays.

Strategy II
1) cn bw*/cn bw* males X TM3, Ser/Sb virgins
2) assay locomotor activity of male progeny, and if aberrant phenotype is displayed, cross cn bw*/+; */Sb single $F_1$ male X TM3, Ser/Sb and Sp/SM5 virgins
3) rescreen locomotor activity of male progeny, and if aberrant phenotype is reproduced, establish lines with isogenous second or third chromosomes:
  a) (cn bw* or +)/+; */TM3, Ser $F_2$ males X TM3, Ser/Sb virgins
  b) cn bw*/SM5; +/Sb males X SpISM5 virgins Locomotor Assays and Eclosion Assays: Flies were first entrained to 12 hr of light followed by 12 hrs of darkness at 25° C. (LD), and then transferred to constant darkness at 25° C. for the DD assays. Monitoring and analysis of locomotor activity of individual flies, and chi-square periodogram analysis, was as described previously [Sehgal et al., *Proc. Natl. Acad. Sci. USA*, 89:1423–1427 (1992)].

For eclosion assays, populations of flies with the indicated genotypes were reared in pint-size plastic bottles and entrained in LD. They were then transferred to DD, and emerging adults collected and counted every two hours. Bottles in DD were handled under a darkroom red light (15 W bulb, Kodak GBX-2 filter), the wavelength of which has no effect on Drosophila circadian rhythms.

Recombination and Complementation Tests: Flies from the $dbt^S$ lines were crossed to several different lines containing multiple mutations on their third chromosomes. Heterozygous females containing a third chromosome from the $dbt^S$ line and a third chromosome with these other mutations ($dbt^S$/multiple mutations) were mated to males from a third chromosome balancer stock (TM3,Sb Ser/D), so that individual recombinant chromosomes could be recovered in male progeny which also carried the balancer chromosome (TM3,Sb Ser/recombinant chromosome). Lines were established from each individual male (TM3,Sb Ser/recombinant male X TM3,Sb Ser/D virgins), and multiple individuals from each line were scored for the presence or absence of all the mutations, including $dbt^S$ (which by definition leads to short-period locomotor activity).

For the deficiency analysis, flies from the $dbt^S$ and $dbt^L$ stocks were crossed to the following stocks obtained from the Drosophila Stock Center (Bloomington, Ind.): Df(3R) XTA1 (96A 17-21;96D 1-2), Df(3R)T1-I (97B;97E), Df(3R) T1-X (97B;97D1-2), Df(3)3450 (98E3;99A6-8), Df(3R) X3F (99D1-2;99E1), Df(3R)awdKRB (100C;100D), Df(3) T1-P (97A;98A1-2), Df(3R)ro80b (97D1;97D13), Df(3R) tll-g(99F1-2;100B5).

The duplication employed came from Df(3R)R133, B(S)/TM3; Dp(3;1)124P. A recombinant chromosome was produced in which the mutation bv (distal to 100B5) was linked to $dbt^S$ (see recombination test 3, table 2). This chromosome was introduced into a line in which the X chromosome was either normal or contained a duplication [Dp(3: 1)124P] of the right tip of the third chromosome (includes 99E to 100F). The presence of the duplication was detected by absence of the bv mutant phenotype (short bristles), since the duplication contains a wild-type copy of the bv gene that rescues the phenotype.

Larval culture: Larvae were entrained for at least 3 days before an experiment in a standard 12 h:12 hr light:dark cycle at 25° C.

Immunocytochemistry: Larval brains were processed for immunocytochemistry using a modified protocol of Kunes et al. [ *J. Neurosci.*, 13:752–767 (1993)]. Brains were dissected from entrained wandering third instar larvae, treated with 1 mg/ml Sigma blend collagenase in PBS with 50 mM $CaCl_2$ for 15 min at room temperature, and then fixed for 30 min in 4% paraformaldehyde in PBS. Including a collagenase pre-treatment gave a stronger signal for TIM than omitting it—therefore TIM is not light-sensitive in the short time before fixing. Brains were permeabilized and rinsed in PBS, 1% Triton for 2 periods of 20 min, and then blocked in PBS, 0.5% Triton (PBT) with 10% heat inactivated goat serum for 1 hr or longer. Primary antibodies were incubated overnight at 4° C. in blocking solution. Anti-TIM 316, anti-PER [Stanewsky et al., *J. Neurosci.*, 17:676–696 (1997)], and anti-lacZ (Promega) were used at dilutions of 1:1500, 1:16,000 and 1:1,000 respectively. PER and TIM antisera were pre-absorbed against $per^o$ or $tim^{01}$ embryos, and neither antibody gave significant staining on the relevant control (respectively $per^o$ or $tim^{01}$ larval brains). The rest of the procedure was carried out at room temperature according to standard procedures. The results shown are representatives of at least 20 larvae analyzed for each time shown in independent experiments, which all had results consistent with one another.

In situ hybridization: In situ hybridizations were performed essentially as described in Tautz and Pfeifle [*Chromosoma* 98:81–85 (1989)] except that proteinase K was used at 5 mg/ml. The TIM probe was synthesized from pSK-TIM2 [Myers et al., *Nucl. Acids Res.*, 25:4710–1714 (1997)] using DIG RNA labeling mix (Boehringer Mannheim) according to manufacturer's instructions.

RNase protection: 100 larval brains were dissected in PBS, placed into RNAzol (TelTest), frozen on dry ice, thawed and RNA isolated according to the manufacturer's instructions. 10 mg RNA (approximately 50 brains) were used for one lane of an experiment. RNase protections used the Ambion RPAII kit according to manufacturer's instructions. The per $^{32}$P-labeled riboprobe protects nucleotides 1426–1749 of the per cDNA; the tim probe was as in Myers et al. [*Nucl. Acids Res.*, 25:4710–1714 (1997)]; and the rp49 probe protects nucleotides 323–381 of the rp49 cDNA. per and tim probes were synthesized with only radioactive UTP, while synthesis of the rp49 probe included 5 mM non-radioactive UTP.

Western blotting: For adult head Western blots, extracts were made as in Edery et al, [*Proc. Natl. Acad. Sci. USA*, 91:2260–2264 (1994)], and 100 mg protein loaded per lane. For larval brain extracts, 10 larval brains were dissected in PBS, frozen, boiled in 30 ml 1.1×SDS loading buffer, spun and the supermatant loaded on a gel. All samples were run on 5.7% (75:1) SDS-polyacylamide gels [Edery et al., *Proc. Natl. Acad. Sci. USA*, 91:2260–2264 (1994)]. They were transferred with either a semi-dry or wet transfer apparatus according to manufacturer's instructions (Bio-Rad). Blots were incubated overnight at 4° C. with either anti-PER [Stanewsky et al., *J. Neurosci*, 17:676–696 )1997)] or anti-TIM [Myers et al., *Nucl. Acids Res.*, 25:4710–1714 (1997) at dilutions of 1:10,000 or 1:2,000 respectively. For washes, secondary antibody incubation, and ECL (Amersham), we followed standard procedures.

Results double-time is a New Gene that Alters the Period of Locomotor Activity Rhythms of Drosophila: Ethyl methane sulfonate (EMS) mutagenesis was used to induce new clock mutations affecting the period length of locomotor activity rhythms in homozygous or heterozygous flies (Experimental Procedures). Screening of heterozygous phenotypes was performed because all known clock mutations that affect period length in Drosophila, Neurospora, Arabidopsis, mice, and hamsters, are semi-dominant [reviewed by Dunlap, *Genet*, 30:579–601 (1996)].

The locomotor activity of individual flies, each bearing heterozygous or homozygous mutagenized chromosomes, was monitored under constant darkness (DD), to reveal free-running period length (Experimental Procedures, above). From a screen of ~15,000 second and third chromosomes, three lines were recovered carrying long-period alleles of timeless. Two additional lines were isolated that contained mutations in a new clock gene, which is named doubletime (dbt), because the first mutant allele to be isolated ($dbt^S$) dramatically shortens the behavioral period (described below). The second dbt allele ($dbt^L$) lengthens the period.

TABLE 1

Locomoter Activity of dbt Flies in DD

| genotype | tau ± SEM | (#AR/n) |
|---|---|---|
| dbt$^S$ | 18.0 ± 0.1 | (4/24) |
| dbt$^S$/+ | 21.8 ± 0.2 | (0/10) |
| +/+ | 23.8 ± 0.1 | (0/9) |
| dbt$^L$ | 26.8 ± 0.1 | (0/19) |
| dbt$^L$/+ | 24.9 ± 0.1 | (1/17) |
| +/+ | 23.6 ± 0.1 | (0/15) |

The average period (tau) of each genotype is indicated. The dbt/+ and +/+ genotypes in each group came from the progeny of a cross between dbt/+ parents. #AR/n, number of arrhythmic flies/total number of flies assayed.

Figure 1A:
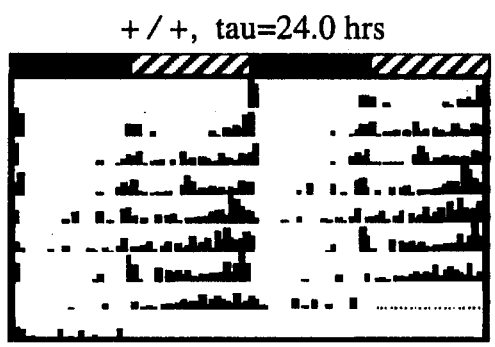
FIGS. 1A–1F show that $dbt^S$ shortens and $dbt^L$ lengthens periods of locomotor activity. Representative locomotor records of single flies of wild type (+/+) in FIG. 1A; $dbt^S$/+ in FIG. 1B; $dbt^S/dbt^S$ in FIG. 1C; wild type in FIG. 1D; $dbt^L$/+ in FIG. 1E; and $dbt^L/dbt^L$ in DD in FIG. 1F. Adult flies were entrained in a 12 hr light: 12 hr dark cycle for more than 3 days, and then locomotor activity was monitored in constant darkness. The phase of the previous light:dark regime is indicated at the top of each record with the hatched boxes indicating the time of the photophase. Horizontal lines are 48 hour intervals and activity is denoted by filled bars, with level of activity indicated by height of each bar. The record for each 24 hour period composing the right half of each line is plotted again on the left half of the line underneath for visual continuity. The period of the rhythm, calculated by chi-square periodogram analysis, and the genotype of each fly are indicated on top of the records. Records in each column are from sibling flies. Activity events occur later on successive days in records with long periods, while they occur earlier on successive days in records with short periods. Note that both $dbt^L$ and $dbt^S$ are semidominant.
Figure 1B:
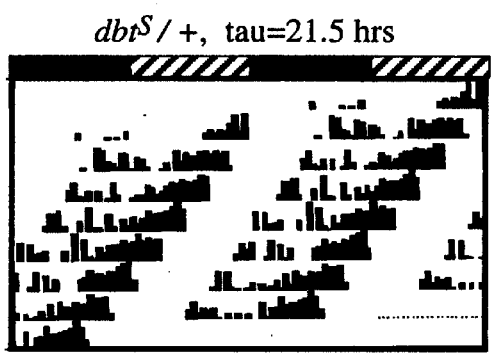
Figure 1C:
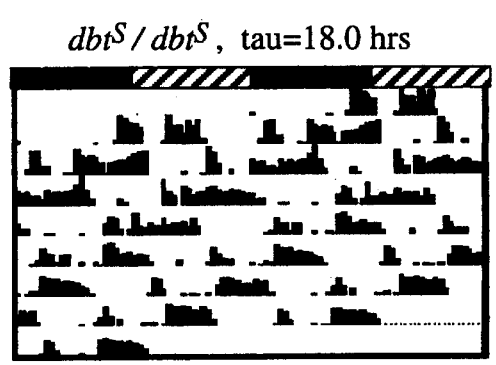
Figure 1D:
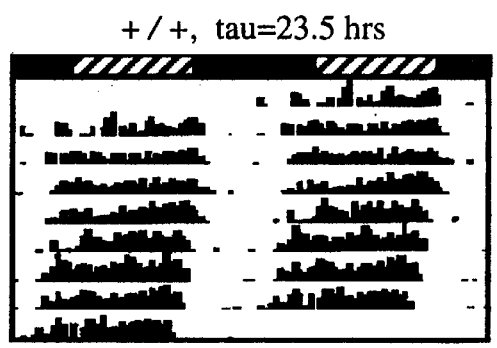
Figure 1E:
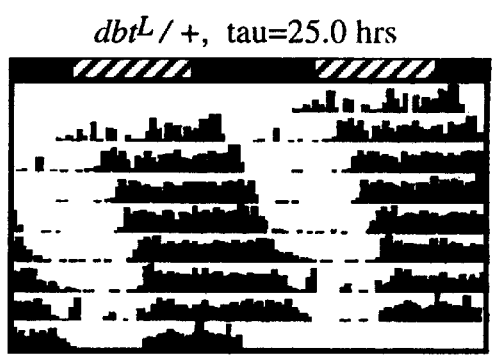
Figure 1F:
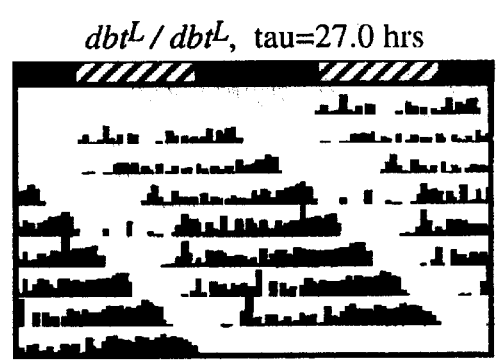

Flies that are heterozygous for the dbt$^S$ mutation (dbt$^S$/+) produce locomotor rhythms with an average period of 21.8 hrs in DD (FIG. 1B and Table 1), while homozygous flies (dbt$^S$/dbt$^S$) produce locomotor rhythms with an average period of 18.0 hrs (FIG. 1C and Table 1). Flies that are heterozygous for the dbt$^L$ mutation (dbt$^L$/+) produce locomotor rhythms with an average period of 24.9 hr (FIG. 1E and Table 1), while homozygous flies (dbt$^L$/dbt$^L$) produce locomotor rhythms with 26.8 hr periods (FIG. 1F and Table 1). Because dbt$^S$/+ and dbt$^L$/+ flies have shorter and longer periods, respectively, than wild type controls, but not as short or long as homozygous mutant flies, dbt$^S$ and dbt$^L$ are semi-dominant. Homozygous dbt$^S$ and dbt$^L$ flies can be entrained by an imposed 12 hr light: 12 hr dark cycle (LD 12:12) since they exhibit 24 hr periodicity under such conditions. Analysis of several hundred locomotor activity records from homozygous dbt$^S$ and dbt$^L$ flies indicated complete penetrance of the mutant phenotypes.

The dbt$^S$ mutant was also tested for aberrant circadian rhythms of eclosion (emergence of the adult fly from the pupal case) to determine whether dbt mutations affect this phenotype as previously observed for per and tim [Konopka and Benzer, et al., *Proc. Natl. Acad. Sci. USA*, 68:2112–2116 (1971); Sehgal et al., *Science,* 263:1603–1606 (1994)]

Figure 2:
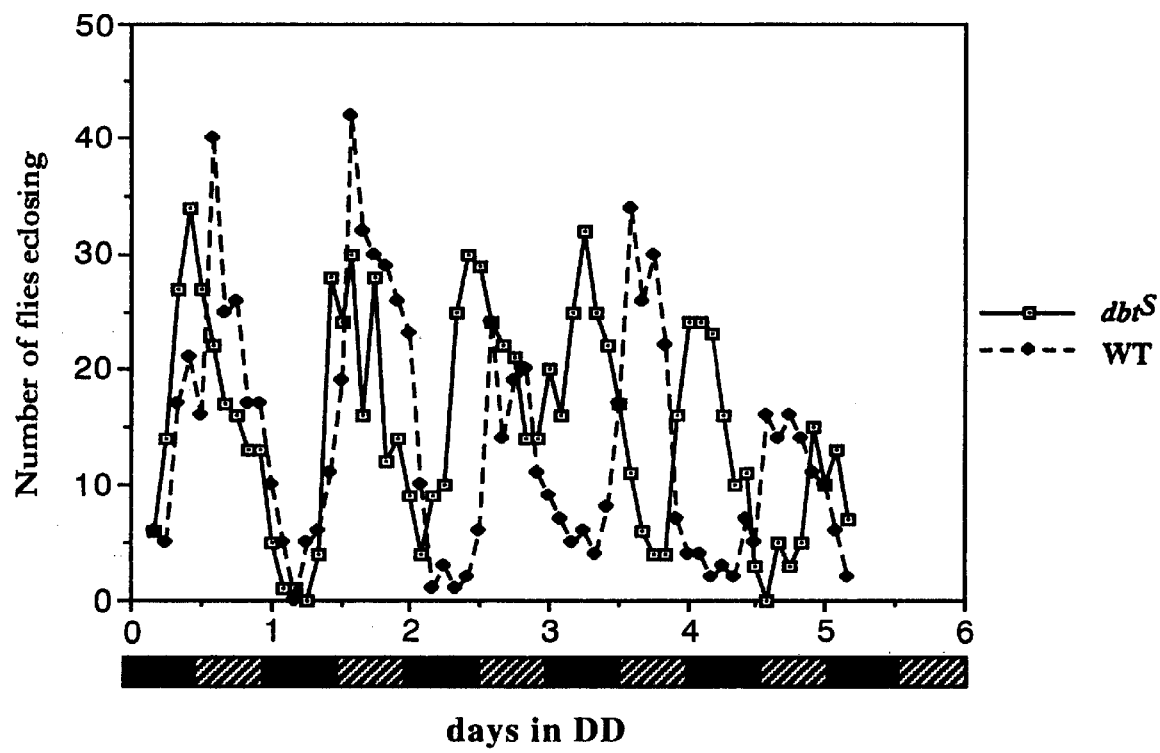
FIG. 2 shows the circadian rhythm of eclosion has a shorter period in $dbt^S$ flies than in wild type flies. Bottles of wild type (wt) and $dbt^S$ flies were maintained in LD 12hr: 12 hr for 10 days at 25° C. At the end of the final 12 hr period of light (day 0 on the plot), the bottles were cleared of adult flies and transferred to constant darkness (DD). Newly emerged adults were cleared and counted every 2 hours. A Kodak safelight with a 15 W bulb and a GBX-2 filter, which blocks wavelengths less than 600 nm, was used to collect the flies. The phase of the previous light:dark regime is indicated at the bottom, with the hatched boxes indicating the time of the photophase.

Although eclosion occurs only once in the lifetime of an individual fly, it occurs repeatedly and rhythmically in a population of flies of diverse ages. In DD, the period of the dbt$^S$ eclosion rhythm was shorter than the rhythm of the wild type population. Peaks of eclosion occurred progressively earlier in dbt$^S$ as compared to wild type over the 5 day interval tested (FIG. 2). The parallel effects of the dbt$^S$ mutation on two behavioral outputs of the Drosophila circadian clock are consistent with an effect on the central pacemaker mechanism rather than on a specific output pathway. In this regard, the effects of dbt mutations on rhythmicity are comparable to those of period and timeless mutations (see also below).

Genetic Tests Co-Localize the dbt$^S$ and dbt$^L$ Mutations to the Right Arm of the Third Chromosome: Flies from the dbt$^S$ stock were crossed to Drosophila stocks containing multiple third chromosome mutations and individual recombinant F$_2$ progeny used to establish lines. Locomotor activity rhythms were analyzed for several representatives from each recombinant line to verify the presence or absence of the dbt$^S$ mutation. These recombination tests placed the dbt$^S$ mutation near the tip of the right arm of chromosome 3 between claret (ca) and brevis (bv), and closely linked to loboid (ld) (Table 2).

TABLE 2

Recombination Analysis of dbt$^S$

| Parental Chromosome | Recombinant Chromosome | Frequency |
|---|---|---|
| (ru$^-$h$^-$th$^-$st$^-$cu$^-$sr$^-$) e$^-$ca$^-$dbt$^+$ | e$^-$ca$^-$dbt$^S$ | 0/38 |
| (ru$^+$h$^+$th$^+$st$^+$cu$^+$sr$^+$) e$^-$ca$^+$dbt$^S$ | e$^+$ca$^-$dbt$^S$ | 0/38 |
| | e$^+$ca$^-$dbt$^+$ | 2/38 |
| | e$^-$ca+dbt$^+$ | 0/38 |
| | e$^-$ca+dbt$^S$ | 6/38 |
| | e$^+$ca$^-$dbt$^+$ | 6/38 |
| (h$^-$th$^-$st$^-$cu$^-$sr$^-$) e$^-$[lb$^+$, dbt$^S$] | e$^-$[ld$^+$, dbt$^+$] | 0/50 |
| (h$^+$th$^+$st$^+$cu$^+$sr$^-$) e$^+$[ld$^-$, dbt$^+$] | e$^+$[ld$^+$, dbt$^+$] | 0/50 |
| | e$^+$[ld$^-$, dbt$^S$] | 0/50 |
| | e$^-$[ld$^-$, dbt$^S$] | 0/50 |
| | e$^-$[ld$^-$, dbt$^+$] | 12/50 |
| | e$^+$[ld$^-$, dbt$^S$] | 4/50 |
| ca$^-$dbt$^+$bv$^-$ | ca$^-$dbt$^S$bv$^+$ | 2/93 |
| ca$^+$dbt$^S$bv$^+$ | ca$^-$dbt$^+$bv$^+$ | 0/93 |
| | ca$^+$dbt$^+$bv$^-$ | 2/93 |
| | ca$^+$dbt$^S$bv$^-$ | 1/93 |
| | ca$^-$dbt$^+$bv$^+$ | 0/93 |
| | ca$^+$dbt$^S$bv$^-$ | 0/93 |

Flies with the indicated parental chromosomes were mated, and F$_1$ heterozygous females were mated to males with the TM3 balancer. Single F$_2$ male progeny with TM3 were mated to TM3 females to establish a line. The dbt allele of each line was scored by locomotor assays of multiple individuals in DD, while the other markers were scored visually in homozygous flies. Recombination events between the markers in parentheses () are not tabulated here.

dbt$^S$ and dbt$^L$ were also genetically localized by complementation analyses with a series of deficiencies affecting the right arm of chromosome 3 (see Experimental Procedures, above, for a complete list of the deficiencies tested). One deficiency, Df(3R)tll-g, produced flies with 19.1 hr locomotor rhythms in dbt$^S$ /Df heterozygotes, and 27.2 hr rhythms in dbt$^L$/Df heterozygotes (Table 3). Df(3R)tll-g/+ heterozygotes produced flies with wild type periods (~24 hr). These results argue that this deficiency lacks the wild-type allele of dbt. The deficiency is missing polytene chromosomal region 99E–F to 100B, which is distal to ca. The results are consistent with the recombination analysis of dbt$^S$.

Figure 3A:
FIGS. 3A–3C shows the timing of PER and TIM oscillations are altered in $dbt^S$ and $dbt^L$ adult heads. Western blot analysis of TIM (FIG. 3A) and PER (FIG. 3B) from $dbt^S$ (top), wild-type, wt, (middle) and $dbt^L$ (bottom) fly head extracts during one day of LD, and two days of DD. The times of collection are indicated above the blots. Total protein levels in all lanes of a panel were judged to be similar by comparing a slower running cross-reacting band. Note the successive phase changes in DD for $dbt^S$ and $dbt^L$ respectively.

Duplication analysis was also performed. dbt$^S$/dbt$^S$ flies carrying Dp(3;1)124P, which includes chromosomal region 99E–100F, produced locomotor activity rhythms with a period of 21.2 hr (Table 3; Experimental Procedures, above). Hence, dbt is contained within the duplicated region. The duplication had no significant effect on the period of the rhythm of wild type flies indicating that an essentially wild type rhythm is obtained with 1, 2 or 3 doses of wild type dbt.

dbt$^S$ and dbt$^L$ Alter the Periods of PER and TIM Protein Oscillations. To investigate whether dbt period-altering alleles change the molecular oscillation of known clock components, PER and TIM protein time-courses were looked at on Western blots. One day of LD, and two days of DD were assayed for wild type, dbt$^S$ and dbt$^L$ genotypes (FIG. 3). Overall, the levels of expression of both PER and TIM are not grossly altered. However, in LD, both proteins oscillate with a slight phase advance in dbt$^S$ and phase delay in dbt$^L$. In DD, the protein levels oscillate with a period length corresponding to the locomotor activity rhythms of the mutants. Hence, mutations at dbt that change behavioral rhythms also change molecular oscillations of PER and TIM.

Figure 3B:
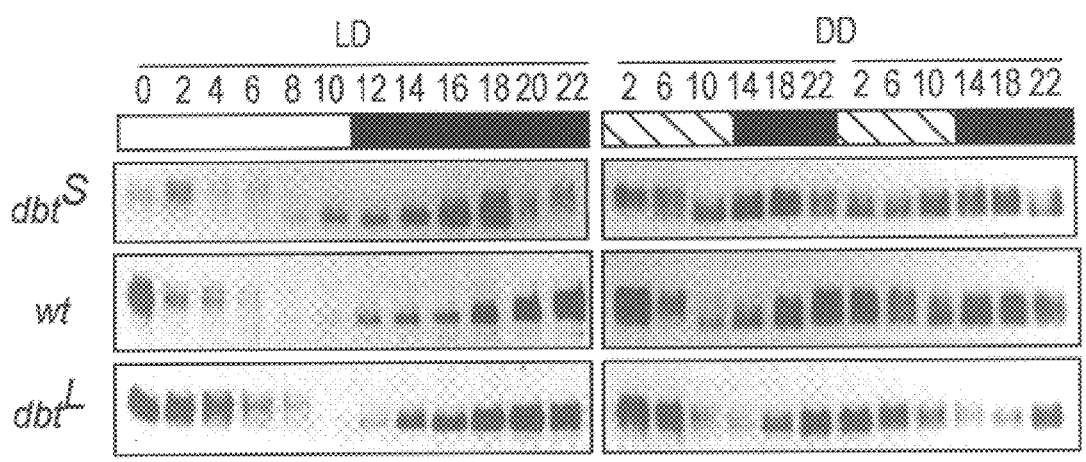
Figure 3C:
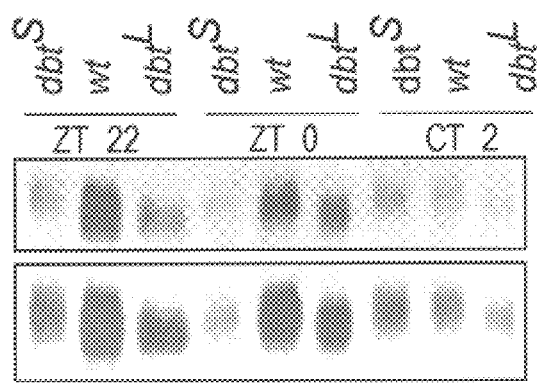

A closer inspection of dbt$^S$ reveals that both PER and TIM disappear prematurely in an LD cycle. Forms of PER with lowest electrophoretic mobility, which have been associated with highest levels of PER phosphorylation [Edery et al., *Proc. Natl. Sci. Acad. USA,* 91:2260–2264 (1994)], appear earlier than in wild type (FIG. 3C). In contrast, in dbt$^L$, both PER and TIM are detectable for an extended period of time in DD (see LD to DD transition, FIG. 3A–3B), and the appearance of low mobility forms of PER is delayed (FIG. 3C). In contrast to wild type flies, persistence of PER in the absence of TIM after lights-on in an LD cycle in $dbt^L$ are detected(FIG. 3B). This effect suggests unusual persistence of monomeric PER proteins after TIM is eliminated by light. The higher level of PER from ZT2–6 (ZT, zeitgeiber time, indicates time in LD cycles) is not simply due to increased PER levels in $dbt^L$, since a side by side comparison of PER proteins in wild type and $dbt^L$ at ZT0 shows roughly equal amounts of PER (FIG. 3C). Thus, there seems to be an increase in PER stability in $dbt^L$. Conversely, $dbt^S$ may cause premature degradation of both PER and TIM.

Isolation of a P Elenzent Insertion in the dbt Locus: Drosophila strains containing single P element insertions on the right arm of the third chromosome were screened for failure to complement the original $dbt^S$ mutation. One strain, referred to hereafter as $dbt^P$, behaved like the Df(3R)tll-g deficiency. $dbt^S/dbt^P$ flies produced locomotor activity rhythms with a period of 19 hr, while $dbt^P/+$ flies had wild-type periods (23.8 hrs; Table 3). Similarly, $dbt^L/dbt^P$ flies had locomotor activity rhythms of 26.6 hrs, similar to those obtained in $dbt^L$/Df(3R)tll-g flies (Table 3). The P element is therefore likely to result in a large reduction, or even absence, of dbt gene products (demonstrated in Example 2, below). The finding that $dbt^P$ fails to complement both $dbt^S$ and $dbt^L$, indicates that the latter mutations affect the same gene, a conclusion that has been confirmed by molecular studies described in Example 2.

TABLE 3

Complementation of Analysis of dbt

| genotype | tau ± SEM | (#AR/n) |
|---|---|---|
| $dbt^S$/Df(3R)tllG | 19.1 ± 0.04 | (1/25) |
| $dbt^S$/TM6B | 21.7 ± 0.1 | (1/11) |
| Df(3R)tllG/TM3 | 24.8 ± 0.2 | (3/5) |
| $dbt^S$/$dbt^P$ | 19.0 ± 0.1 | (1/11) |
| $dbt^S$/TM3 | 21.8 ± 0.3 | (1/4) |
| $dbt^P$/TM3 | 23.8 ± 0.1 | (0/4) |
| Dp(3;1)124P; $dbt^S$/$dbt^S$ | 21.2 ± 0.1 | (1/7) |
| $dbt^S$/$dbt^S$ | 18.4 ± 0.1 | (3/10) |
| Dp(3;1)124P; $dbt^S$/$dbt^+$ | 22.5 ± 0.2 | (0/5) |
| $dbt^S$/$dbt^+$ | 22.4 ± 0.1 | (0/4) |
| $dbt^L$/Df(3R)tllG | 27.2 ± 0.1 | (0/16) |
| $dbt^L$/TM3 | 25.1 ± 0.1 | (1/14) |
| Df(3R)tllG/TM3 | 24.7 ± 0.3 | (1/6) |
| $dbt^L$/$dbt^P$ | 26.6 ± 0.1 | (0/15) |
| $dbt^L$/TM3 | 25.0 ± 0.1 | (0/14) |
| $dbt^P$/TM3 | 24.4 ± 0.3 | (0/8) |
| $dbt^S$/TM3 | 21.5 ± 0.1 | (0/19) |
| $dbt^L$/$dbt^S$ | 22.9 ± 0.1 | (0/15) |
| $dbt^L$/TM3 | 24.9 ± 0.1 | (0/13) |
| $dbt^P$/Df(3R)tllG | † | |

Lines with the three alleles of dbt ($dbt^S$, $dbt^L$, and $dbt^P$) were crossed to each other and to lines containing Df(3R)tllG or DP(3;1)124P, and progeny with the indicated genotypes were tested in locomotor assays in DD. The average period (tau) of each genotype is indicated. Genotypes in each group came from the same cross. #AR/n, number of arrhythmic flies/total number of flies assayed. † indicates no progeny survived to adulthood.

Recessive lethality is associated with the $dbt^P$ strain, as no adults of the genotype $dbt^P$/$dbt^P$ or Df(3R)tll-g/$dbt^P$ have been recovered (Table 3). A strain, $dbt^P$/TM6, that produces homozygous larvae and pupae distinguishable from their heterozygous siblings by virtue of the dominant marker Tubby (on TM6), was constructed. Most third-instar homozygous $dbt^P$ larvae pupate, but die later in pupal development. Proof that dbt function is required for both viability and circadian rhythmicity has come from reversion studies of $dbt^P$ (Example 2, below).

Using Third Larval Instar Brain Clock Cells to Analyze $dbt^P$: The strongly hypomorphic allele, $dbt^P$ was hypothesized to show the most dramatic effects on clock gene cycling. Although $dbt^P$ embryos take longer to develop into third instar larvae than do their heterozygous siblings, the foraging motility of these larvae and their touch sensitivity appear normal. In the analyses below, only clearly motile larvae were used.

Behavioral studies have demonstrated that a circadian clock is active in Drosophila larvae [Sehgal et al., *Proc. Natl. Acad. Sci. USA*, 89:1423–1427 (1992)]. It has recently been shown that a specific group of central brain cells is likely to compose the larval pacemaker [Kaneko et al., *Neurosci*, 17:6745–6760 (1997)]. In each hemisphere of the third instar larval brain, four to five cells co-express PER and TIM with circadian oscillations that are in phase with the oscillations of these proteins in adult pacemaker cells (LNs) (FIGS. 4A and 5A) [Kaneko et al., *J. Neurosci.*, 17:6745–6760 (1997]. The only detectable staining in the hemispheres of the larval brain for pigment-dispersing hormone (PDH), a marker for adult lateral neurons [Helfrich-Forster, *Proc. Natl. Acad. Sci. USA*, 92:612–616 (1995)], is found in the axons of these PER-TIM expressing cells [Kaneko et al., *J. Neurosci.*, 17:6745–6760 (1997)]. Therefore, the PER-TIM-PDH co-expressing larval brain cells can be considered larval lateral neurons (IvLNs). In $per^0$ larvae, TIM is constitutively cytoplasmic in IvLNs (FIG. 4C), and in $tim^{01}$ larvae, PER is undetectable in these cells by immunocytochemistry. Both of these mutant phenotypes are characteristics of adult clock cells [Vosshall et al., *Neuron*, 15:345–360 (1994); Myers et al., *Science*, 271:1736–1740 (1996)]. PER and TIM oscillations can also be seen in two groups of cells at the anterior of the third instar larval brain, but in one of these groups, the oscillations are out of phase with the 1vLNs [Kaneko et al., *J Neurosci.*, 17:6745–6760 (1997)]; {FIGS. 4A and 4B), and may be regulated by activity of the 1vLNs [Kaneko et al., *J Neurosci.*, 17:6745–6760 (1997)]. These oscillations are not as robust as in the 1vLNs.

The 1vLNs were initially examined to see if they were still present in $dbt^P$ larvae. In a total of 13 $dbt^P$ larval brains (25 hemispheres) in either LD or DD, PDH staining was detected in the cytoplasm of precisely 4 cells in each hemisphere, as seen for wild-type larvae [Kaneko et al., *J. Neurosci.*, 17:6745–6760 (1997)]. The axons of these $dbt^P$ 1vLNs fasciculate and head to the anterior of the brain as in wild type. However, dbtp 1vLNs are found slightly more peripherally than in wild-type, as seen in the staining patterns of PER and TIM in FIGS. 4A, 4B, 5A and 5E.

Figure 4A:
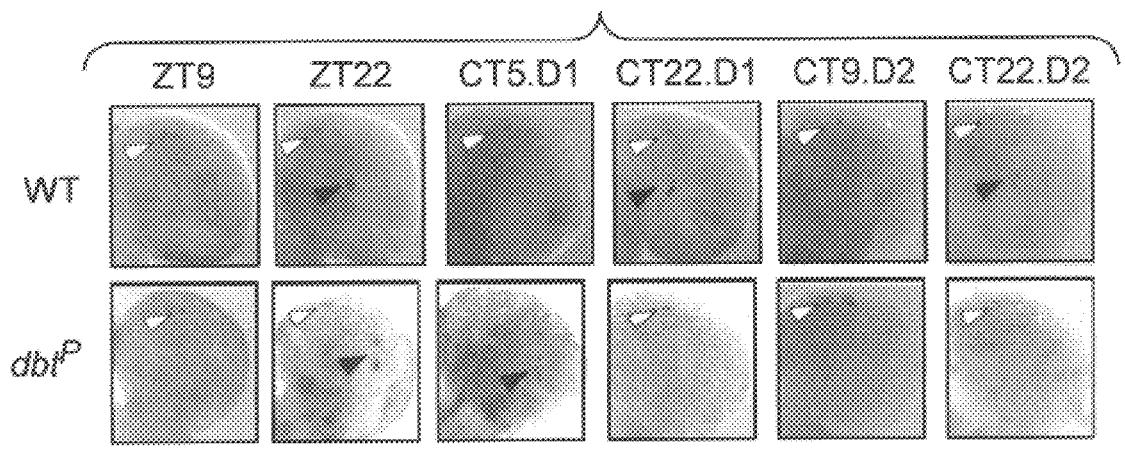
FIGS. 4A–4C shows the Circadian oscillations of tim RNA and protein are blocked in $dbt^P$ third instar larval brains. Larvae were entrained for at least 3 days in standard LD cycles, with some transferred to DD for either one (D1) or two (D2) further days. Larval brains were isolated at the times shown (ZT and CT indicate time in LD and DD cycles respectively), and processed for either TIM protein (A, C), or tim RNA (B) as described (see Experimental Procedures in Example 1, below). Representative single hemispheres are shown in FIG. 4A and 4B. Closed arrowheads indicate 1vLNs, and open arrowheads indicate out of phase cells (see text of Example 1). Wild type brains (WT, top panels in FIG. 4A and 4B) show oscillations of TIM protein and tim RNA in 1vLNs in both LD and DD cycles. In contrast, 1vLNs of $dbt^P$ brains (bottom panels in FIG. 4A and 4B) show oscillations of TIM protein and tim RNA only in LD. On transfer to DD, TIM protein and tim RNA persist weakly in 1vLNs at CT5 or CT2 respectively, and are subsequently not detected. TIM protein and tim RNA levels oscillate in out of phase cells in wild type, albeit more weakly than in 1vLNs, whereas significant oscillations are not seen in these cells in $dbt^P$. TIM protein is detected in $dbt^P$ brain hemispheres in the out of phase cells at CT5, but in the panel shown, visualization required a slightly different optical plane. The 1vLNs in $dbt^P$ are found more peripherally than in wild type, as seen for PDH expression (see text, Example 1).

Regulation of TIM's Light-Sensitivity and Nuclear Localization are not Affected by $dbt^P$: In an LD cycle, TIM oscillates in the 1vLNs in both wild-type and $dbt^P$ larvae, and is detected only during the dark phase of the cycle (FIG. 4A compare ZT9 and 22). Therefore, the light sensitivity of TIM in 1vLNs is not affected in a strongly hypomorphic dbt background. In contrast to wild type, TIM can be detected in the out of phase cells in $dbt^P$ larvae at both day and night time-points, indicating that $dbt^P$ blocks molecular cycling in these cells, and, as previously shown by [Kaneko et al., *J. Neurosci.*, 17:6745–6760 (1997)], that TIM fails to show light sensitivity in the out of phase cells. TIM accumulation was also examined in $per^0$ and $per^0$; $dbt^P$ larvae. TIM accumulated at night in the cytoplasm of 1vLNs in both strains in contrast to the predominantly nuclear localization observed in wild-type (FIG. 4C). A similar cytoplasmic accumulation of TIM is observed in the photoreceptors and LNs of adult $per^0$ Drosophila [Myers et al., *Science*, 271:1736–1740 (1996)]. Therefore dbt has no role in retaining TIM in the cytoplasm in the absence of PER [Myers et al., *Science*, 271:1736–1740 (1996); Saez and Young, *Neuron*, 17:911–920 (1996)].

Oscillations of TIM Protein and tim RNA Cease in $dbt^P$ Larval Brains in Constant Darkness: When wild-type larvae are transferred to constant darkness, TIM continues to oscillate robustly with only night time TIM accumulation in the 1vLNs, and subjective day time TIM accumulation in the out of phase brain cells (FIG. 4A; Kaneko et al., *J. Neurosci.*, 17:6745–6760 (1997)]. In contrast, in $dbt^P$ larvae transferred to DD, TIM is weakly detected in 1vLNs in the first subjective morning at CT5 (CT, circadian time, indicates time in DD), disappears by CT10 and is undetectable thereafter in the 1vLNs (FIG. 4A). TIM is detected in $dbt^P$ in the out of phase larval brain cells in DD as in LD. The staining in these cells serves not only as a positive control for the procedure, but also indicates that in DD, $dbt^P$ blocks molecular cycling in both the 1vLNs and in the out of phase brain cells. For the 1vLNs, the differential effects of $dbt^P$ on TIM in LD and DD shown in FIG. 4A are not due to selecting larvae from slightly different developmental stages since identical results were derived from larvae that had been synchronized developmentally.

Figure 4B:
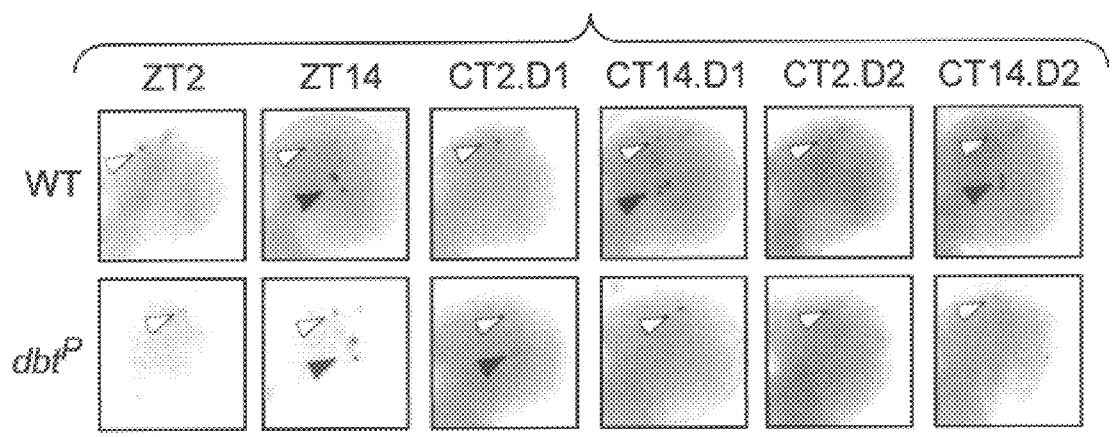
Figure 4C:
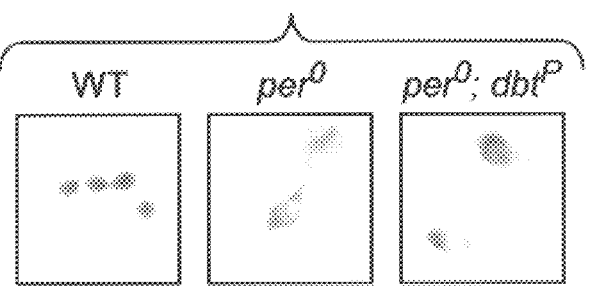

In wild-type larvae, tim RNA, as detected by in situ hybridization with an antisense tim probe, shows robust oscillations in the 1vLNs both in LD and in DD (FIG. 4B). Cycling is also seen for tim RNA in the out of phase brain cells, with the expected phase difference (FIG. 4B). tim RNA levels oscillate in the 1vLNs of $dbt^P$ mutants in an LD cycle (FIG. 4B), indicating that PER/TIM complexes can still negatively regulate tim gene expression in $dbt^P$ larvae, and that this regulation can be blocked by light-dependent degradation of TIM. When $dbt^P$ larvae are transferred to DD, tim RNA is weakly detected in 1vLNs on the first subjective morning (CT2), but is undetectable thereafter in these cells (FIG. 4B). In DD and LD, tim RNA is detected in the out of phase brain cells of $dbt^P$ larvae. Thus the effects of the $dbt^P$ mutation on levels of TIM protein (FIG. 4A) probably reflect more direct effects of $dbt^P$ on tim RNA levels (FIG. 4B).

Figure 5A:
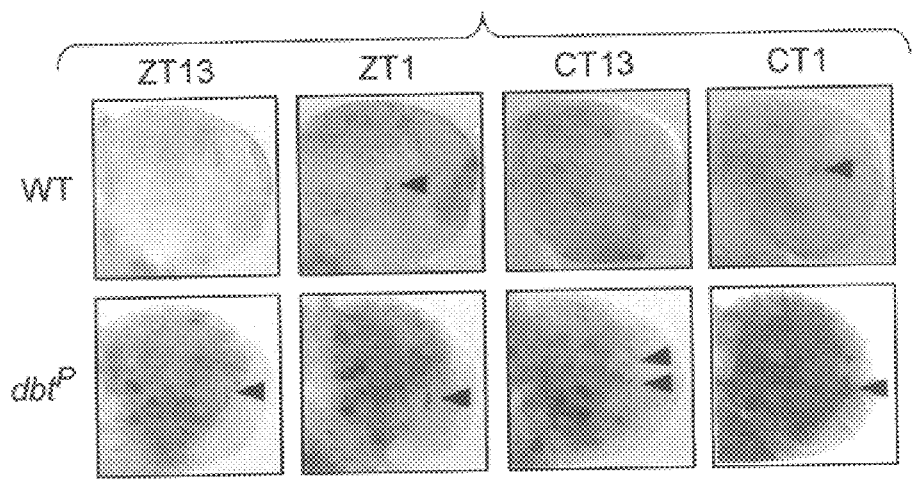
FIGS. 5A–5E show that PER accumulates to unusually high levels in $dbt^P$ third instar larval brains.
Figure 5B:
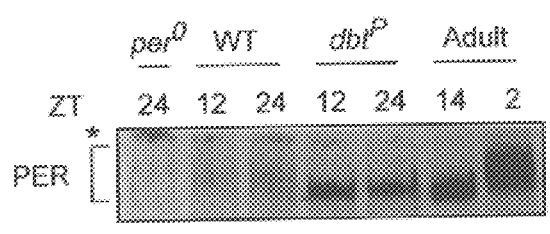

PER is Constitutively Expressed at High Levels in $dbt^P$ Larval Brains: PER protein levels oscillate in the 1vLNs of wild-type larvae in LD cycles and in DD, with detectable protein at ZT1 or CT1, but not at ZT13 or CT13 [(FIG. 5A; Kaneko et al., *J. Neurosci.*, 17:6745–6760 (1997)]. PER proteins produced by $dbt^P$ larvae show three significant differences from wild-type (FIG. 5A). First, PER is detectable at ZT13 and CT13 in the 1vLNs of $dbt^P$ larvae. Second, the intensity of staining in the 1vLNs is stronger in $dbt^P$ than in wild-type larvae (samples shown were processed identically on the same day). Third, the pattern of expression in $dbt^P$ is widened to include regions of the brain not significantly stained in a wild-type background (seen most clearly in FIG. 5D). The elevated level of PER in $dbt^P$ was confirmed by Western blotting using extracts from dissected larval brains collected in LD (FIG. 5B). The latter results show that PER protein accumulation is dramatically increased by the $dbt^P$ mutation (compare $dbt^P$ to wild-type larvae, where PER is difficult to detect, FIG. 5B), and the high levels of accumulated PER protein do not show significant differences between ZT12 and ZT24 (FIG. 5B) in LD cycles in $dbt^P$. In addition, the electrophoretic mobility of PER proteins is relatively high and uniform in $dbt^P$ larvae, in contrast to the broad spectrum of lower PER protein mobilities observed in wild type larvae and adult heads (FIG. 5B). As the spectrum of protein mobilities in wild type Drosophila reflect PER protein phosphorylation [Edery et al., *Proc. Natl. Acad. Sci. USA*, 91:2260–2264 (1994)], the results suggest that PER is hypo-phosphorylated in $dbt^P$ mutants.

Figure 5C:
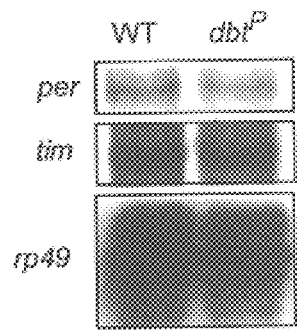

To determine whether the high levels of PER protein found by Western blotting of dissected $dbt^P$ larval brains reflected altered per RNA levels, RNase protection was used to detect per RNA in these tissues at ZT14–16 (time of expected peak per RNA accumulation in wild type Drosophila). The results in FIG. 5C show that per RNA is expressed at similar levels in wild-type and $dbt^P$ larval brains. Thus, the aberrant accumulation of PER proteins in $dbt^P$ mutants does not reflect increased per transcription or per RNA stability, but must be downstream of these events.

Figure 5D:
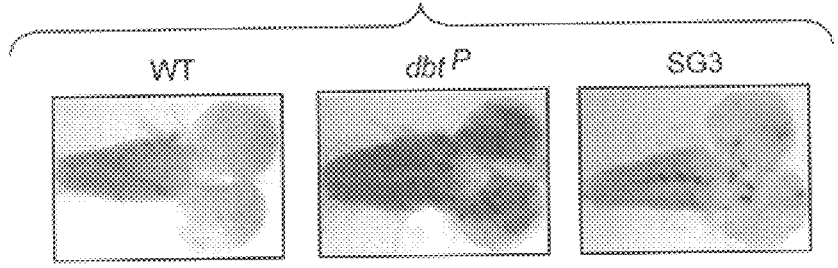

The pattern of PER expression in $dbt^P$ is similar to a PER-β-galactosidase fusion protein, PER-SG, expressed from the per promoter (FIG. 5D). In adults, per-SG RNA oscillates, but PER-SG protein does not. In fact, the PER-SG protein accumulates over progressive cycles, suggesting that it is a stable protein [Vosshall et al., *Science*, 263:1606–1609 (1994); Dembinska et al., *J. Biol.*, 12:157–172 (1997)]. PER-SG, detected with an antibody against β-galactosidase, is expressed in larvae in the 1vLNs and other cell clusters in the brain hemispheres, as well as cells adjacent and close to the ventral ganglion midline (FIG. 5D; Kaneko et al., *J. Neurosci.*, 17:6745–6760 (1997)]. The presence of the non-cycling PER-SG fusion protein therefore marks cells in which the per promoter is active, or has been active, during development. Comparable patterns were seen with two independently constructed SG lines [Kaneko et al., *J. Neurosci.*, 17:6745–6760 (1997)]. PER in wild type larvae has also been detected at very low levels in these cells [Kaneko et al., *J. Neurosci.*, 17:6745–6760 (1997)]. Thus, the pattern of staining of PERseen in $dbt^P$ reflects a normal spatial expression of per, but this pattern is only easily visible with a stable fusion protein or in a $dbt^P$ background.

Figure 5E:
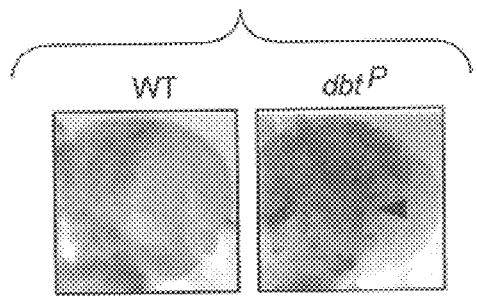

PER is Stable in $dbt^P$ Larvae in Constant Light: PER is detected at high levels in $dbt^P$ larval brains in DD as in LD (FIG. 5A). The persistence of PER proteins in 1vLNs in DD is presumably occurring in the presence of very low levels of the TIM protein which, as indicated above, fall below immunocytochemical detection in these cells in DD (FIG. 4A). In $dbt^+$ larvae and adults, PER accumulation is suppressed in the absence of TIM [Vosshall et al., *Science*, 263:1606–1609 (1994); Price et al., *EMBO J.*, 14:4044–4049 (1995)]. It therefore seemed likely that PER in $dbt^P$ had become less dependent on TIM for its accumulation than in wild-type, especially since PER is detectable in brain cells where TIM is not detected in wild type or $dbt^P$ larvae (FIGS. 4A, 5D) [Kaneko et al., *J. Neurosci.*, 17:6745–6760 (1997)]. This possibility would have been ideally tested using $tim^{01}$; $dbt^P$ larvae. However, it has not been possible to obtain third instar larvae from two different $tim^{01}$; $dbt^P$/TM6 lines. This may indicate a shift in the lethal phase of $dbt^P$ by the $tim^{01}$ mutation. An alternative to $tim^{01}$ was possible as constant light (LL) in a wild-type background produces a $tim^{01}$ phenocopy through light-dependent degradation of TIM [Hunter-Ensor et al., *Cell*, 84:677–685 (1996); Lee et al., *Science*, 271:1740–1744 (1996); Myers et al., *Scinece*, 271:1736–1740 (1996); Zeng et al., *Nature*, 380:129–135 (1996)]. FIG. 5E shows that in wild type larvae, PER accumulation is suppressed in response to LL as previously seen for adults. In contrast, in $dbt^P$ larvae raised in LL, PER continues to be strongly detected in the 1vLNs and the other PER-expressing cells (FIG. 5E). The persistence of PER in DD and LL indicates that PER proteins can accumulate in $dbt^P$ mutants even with very low levels of TIM.

Discussion doubletime Encodes a Central Clock Component: A new Drosophila clock gene, double-time, has been isolated by screening for circadian rhythm mutants. The short-period and long-period alleles alter behavioral rhythms and the timing of molecular oscillations of products of the two previously identified clock genes, per and tim. A third allele, $dbt^P$, is arrhythmic since it stops circadian oscillations of PER and TIM in third instar larvae. $dbt^P$ behaves as a strong hypomorph or null allele in complementation tests with $dbt^S$ and $dbt^L$. Since dbt mutations alter both behavior and clock gene cycling, it can be concluded that dbt encodes a central clock component as opposed to part of an output pathway.

The Role of dbt in the Clock: tim RNA and protein cycle in LD, and TIM remains cytoplasmic in $per^0$; $dbt^P$ indicating that at least some regulatory features of the Drosophila clock are unaffected in $dbt^P$ mutants. In contrast, PER is constitutively expressed at very high levels in LD and DD cycles, with increased levels also seen in new regions of the larval brain. These observations, and the finding that increased PER accumulation is not due to increased per RNA production, suggest that dbt affects circadian rhythmicity through PER protein. Altered patterns of tim RNA and TIM protein accumulation in $dbt^P$ are presumably secondary effects derived from the substantially increased accumulation of PER.

dbt Appears to Affect Stability of the PER Protein: The high levels of PER observed in $dbt^P$ are due either to: (i) increased per RNA translation; or (ii) increased PER stability. Altered patterns of PER degradation in $dbt^S$ and $dbt^L$ mutants could also reflect changes in either translational control or stability: PER in $dbt^S$ starts to accumulate 2 hours before wild type, but most PER disappears at least 6 hours before loss of the wild type protein (FIG. 3B). This is consistent with decreased stability of PER in $dbt^S$ mutants, although the possibility that in $dbt^S$, per RNA available at ZT20 is translated significantly less efficiently than at other times of day cannot be completely ruled out. In wild type flies, light degrades TIM which promotes elimination of PER. However, in $dbt^L$ mutants, PER remains for about 4 hours longer than in wild-type. Since these are times of day when little per RNA is present, the results suggest that the $dbt^L$ mutation reduces the rate of PER degradation. The low electrophoretic mobility observed for PER in $dbt^L$ mutants collected from ZT2 to ZT6 indicates hyperphosphorylation of the persistent PER proteins, which also suggests that these proteins were translated many hours earlier [Edery et al., *Proc. Natl. Acad. Sci. USA*, 91:2260–2264 (1994)]. The delayed degradation of PER in $dbt^L$ is not simply a consequence of lengthening the period of the rhythm, because in $per^L$ mutants, which have a period two hours longer than $dbt^L$ [Konopka and Benzer, *Proc. Natl. Acad. Sci. USA*, 68:2112–2116 (1971)], 'KMPER is degraded with kinetics more comparable to wild type [Rutila et al., *Neuron*, 17:921–929 (1996)]. It has been suggested that hyperphosphorylation of PER may signal nuclear degradation of this protein in wild type flies [Edery et al., *Proc. Natl. Acad. Sci. USA*, 91:2260–2264 (1994)]. Consistent with this proposal hyperphosphorylated forms of PER appear prematurely in $dbt^S$ mutants, and with a delay in $dbt^L$ mutants (FIG. 3C).

The electrophoretic mobility of PER in $dbt^P$ mutants differs significantly from wild-type: its migration in relation to PER proteins formed in wild type larval brains and in adult heads suggests that it is constitutively hypophosphorylated (FIG. 5B). Since a substantial portion of the PER accumulating in $dbt^P$ larval brains is derived from non-clock cells, the possibility that PER is more highly phosphorylated in 1vLNs cannot be ruled out, but slower-migrating PER proteins have never been observed in $dbt^P$ mutants despite high protein levels. dbt mutants appear to affect PER stability and circadian rhythmicity by altering PER phosphorylation. This is also consistent with the results of dbt sequence analysis, which has shown that the DBT protein is very closely related to human casein kinase Iε (Example 2, below). Therefore, the most likely role for DBT in the Drosophila clock is as a mediator of post-translational modification that determines PER stability.

PER in $dbt^P$ behaves much like the PER-β-galactosidase fusion protein, PER-SG, in wild type flies. PER-SG is expressed widely in the larval brain, and is detectable at high levels in adults even in the absence of TIM [Vosshall et al., *Neuron J.*, 263:345–360 (1994)] as well as in constant light in adults and larvae. In adults, per-SG RNA cycles, but the protein does not, indicating that PER-SG is either more stable than PER or its translation is much more efficient. Adding an additional 231 amino acids of PER to PER-SG to make the fusion protein PER-BG results in cycling of this larger fusion protein [Dembinska et al., *J. Biol. Rhythms*, 12:157–172 (1997)]. Since cycling was correlated with a change in protein structure, it was suggested that the SG-BG region confers protein instability [Dembinska. et al., *J. Biol. Rhythms*, 12:157–172 (1997)]. PER-SG is not phosphorylated in a circadian manner, whereas PER-BG is, [Dembinska. et al., *J. Biol. Rhythms*, 12:157–172 (1997)] showing that a defined segment of PER may be involved in both phosphorylation and stability, and that a possible link exists between the two events. The parallels between PER in $dbt^P$ larvae and PER-SG are very striking. Neither protein cycles, both accumulate to high levels with a similar expression pattern in larvae, and phosphorylation is affected for both proteins. If the 231 amino acid difference between PER-SG and PER-BG indeed confers instability, one interpretation of our data is that DBT works through this region of PER.

Determination of where DBT Acts in the Cell: In $tim^{01}$ mutants, which block PER nuclear translocation, PER is unstable [Vosshall et al., *Science*, 263:1606–1609 (1994); Price et al., *EMBO J.*, 14:4044–4049 (1995)], indicating the presence of a cytoplasmic activity that destabilizes PER monomers. In wild type adults, constant light suppresses TIM, which subsequently results in very low levels of PER [Price et al., *EMBO J.*, 14:4044–4049 (1995)], and the same result is seen in wild-type third instar larvae raised in constant light (FIG. 5E). However, in $dbt^P$ mutants, similar high levels of PER accumulate in LD, DD and LL. Since the $dbt^P$ allele allows comparable PER accumulation with either high or low levels of TIM, we conclude that $dbt^P$ allows TIM-independent PER accumulation, and that DBT is a component of the cytoplasmic activity that destabilizes PER monomers in wild type and $tim^{01}$ flies. Consistent with this conclusion, predominantly cytoplasmic accumulation for the expanded PER pattern in $dbt^P$ larval brains was observed. tim does not appear to be expressed in this expanded pattern in wild type larvae [Kaneko et al., *J. Neurosci.*, 17:6745–6760 (1997)], so expanded accumulation of PER monomers in $dbt^P$, but not wild type, larval brains indicates novel cytoplasmic stability for PER in the mutant.

There is also evidence that DBT influences stability of nuclear PER proteins. PER is detected immunocytochemically in nuclei of $dbt^S$ and $dbt^L$ 1vLNs prior to its disappearance, suggesting that the differing kinetics of PER degradation in wild type, $dbt^S$ and $dbt^L$, reflect different rates of PER elimination from the nucleus. Increased nuclear stability of PER monomers is also apparent from our analyses of $dbt^P$ 1vLNs: PER is lost from wild type, but persists in $dbt^P$ nuclei after exposure to light has removed most TIM proteins (FIGS. 5A and 5E). Thus, dbt may affect the stability of both cytoplasmic and nuclear PER monomers. This does not mean that DBT must function in both subcellular compartments, since a post-translational modification generated in the cytoplasm could have delayed effects in the nucleus.

Figure 6A:
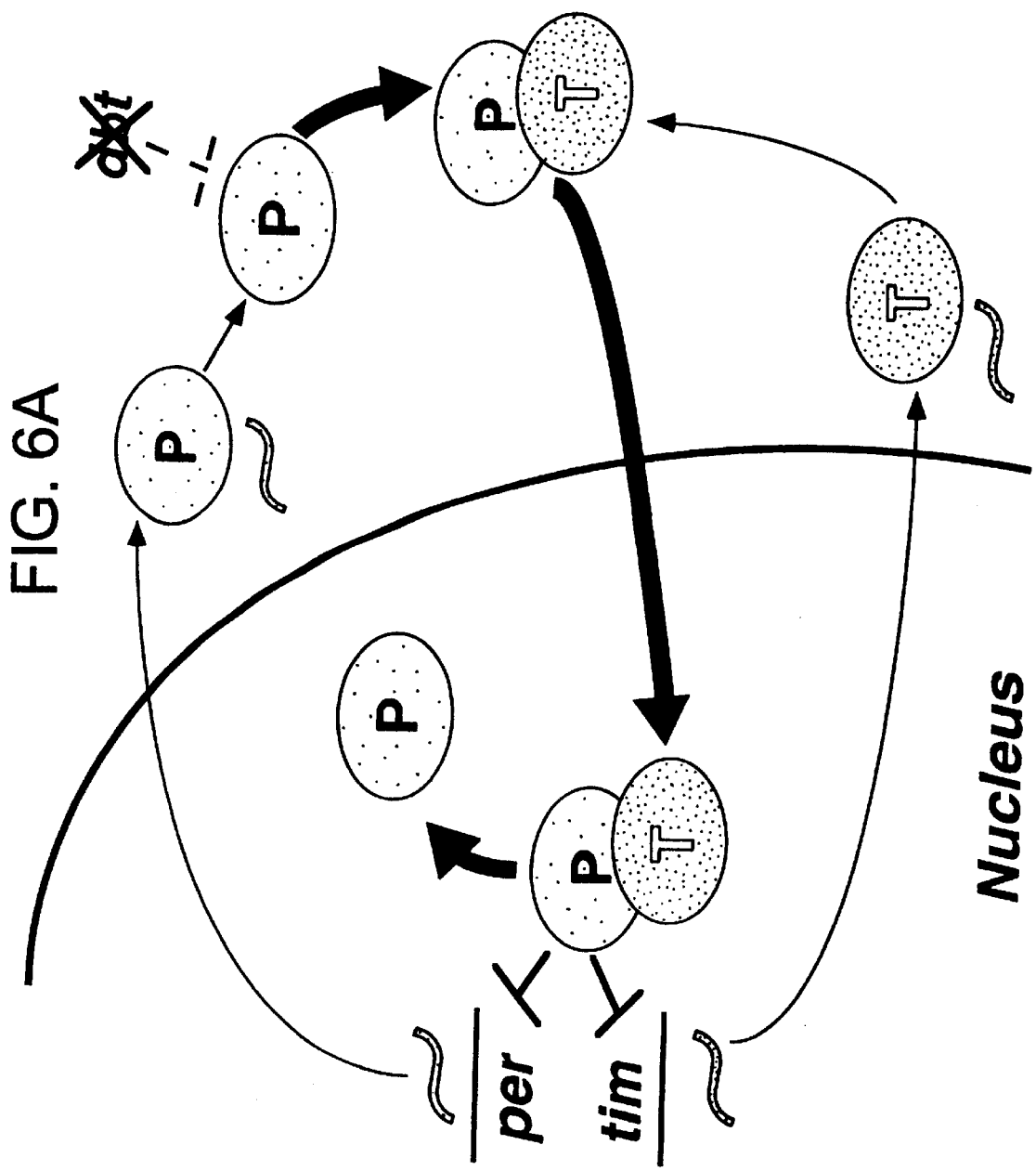
FIGS. 6A–6B show a model depicting influence of dbt on circadian rhythms through altered stability of PER.
Figure 6B:
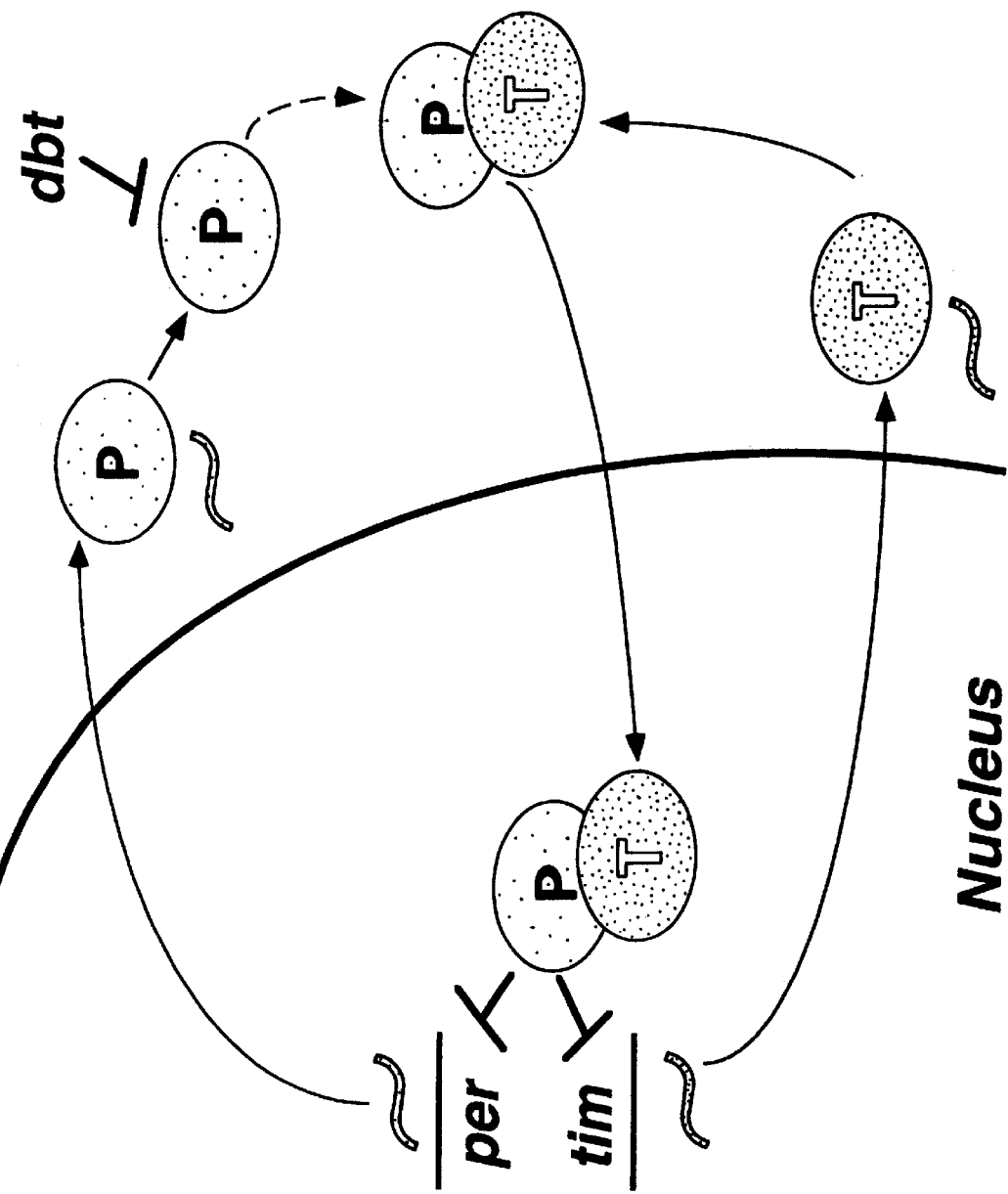

A Basis for Light-Driven Molecular Cycles in $dbt^P$ Mutants: If PER is constitutively expressed in the nuclei of 1vLNs in $dbt^P$, why are tim RNA oscillations seen in LD cycles, but not in DD? Prior work has indicated that suppression of per and tim RNA levels requires activity of a PER/TIM complex (reviewed in [Rosbash et al., Harb. Symp. Quant. Biol. J., 61:265–278 (1996); Young et al., Harb. Symp. Quant. Biol., 61:279–284 (1996)]. Because light eliminates TIM proteins, LD cycles will periodically eliminate PER/TIM complexes, but generate a large pool of long-lived, monomeric PER proteins in $dbt^P$ mutants. The latter proteins are predicted to have little or no influence on per and tim transcription. One interpretation of the present results is that in DD, $dbt^P$ mutants produce a low level of tim transcription that is maintained by constitutive formation, nuclear translocation, and nuclear activity of PER/TIM complexes. In wild type Drosophila, PER's cytoplasmic instability allows high levels of per and tim RNA to accumulate prior to formation of PER/TIM complexes, promoting oscillations of RNA and protein accumulation. Stable accumulation of PER monomers in $dbt^P$ mutants should allow an equilibrium to be established in DD in which constitutive transfer of PER/TIM complexes to nuclei produces two effects: (i) low levels of RNA expression and (ii) a sizeable pool of PER monomers that are evidently much more stable than TIM (FIGS. 4A and 5A). Although, neither tim RNA nor protein were detected in $dbt^P$ in DD immunocytochemically, this probably reflects how even a very low level of TIM (which is stable in the absence of light) is sufficient to maintain continuous nuclear entry of PER/TIM complexes when PER proteins are stabilized (further evidence is discussed below). An important difference between wild-type and $dbt^P$ Drosophila is that most PER monomers are degraded with only a small fraction of the proteins escaping to form PER/TIM complexes in wild type flies, whereas stable PER proteins in $dbt^P$ mutants now bind TIM without temporal constraints. This interpretation is summarized in FIG. 6.

In constant light, PER translocation to the nucleus is seen in the IvLNs, but this probably reflects that light is less effective at removing TIM than the $tim^{01}$ mutation, and that increased tim transcription during the period of lights-on can offset some light-induced TIM depletion (FIG. 4B). The results also indicate that a very low level of residual TIM protein can translocate highly stabilized PER to the nucleus. A precedent for nuclear translocation of PER in constant light exists with the PER-β-gal fusion protein, PER-SG, which is stable cytoplasmically in $tim^0$, but can be found in the nucleus in $tim^+$ LNs and photoreceptors in constant light.

EXAMPLE 2

The Drosophila Clock Gene Double-Time Encodes a Protein Closely Related to Human Casein Kinase Iε

Introduction

In Example 1, above, the isolation of mutant alleles of a new clock gene, double-time (dbt) was described. Two of these mutations either shorten ($dbt^S$) or lengthen ($dbt^L$) the period of the behavioral rhythm, and each mutation has period-altering effects on molecular oscillations of PER and TIM that are correlated with the mutant behavioral rhythms. A third, P-element-induced mutation ($dbt^P$), is associated with pupal lethality, but blocks circadian molecular rhythms of per and tim gene products in pacemaker cells of the larval brain.

Therefore dbt is an essential component of the Drosophila clock [Example 1, above]. In both short- and long-period dbt mutants, the kinetics of PER protein phosphorylation and degradation are altered, and $dbt^P$ mutants constitutively produce unusually high levels of a hypophosphorylated PER protein. In contrast to wild type larvae, PER protein accumulation in $dbt^P$ larvae is not dependent on accumulation of TIM. All of these observations suggested that DBT regulates circadian rhythmicity through effects on stability of monomeric PER proteins [Example 1, above] The finding that both PER phosphorylation and stability are simultaneously affected in all three dbt alleles suggests that dbt might alter PER stability through effects on phosphorylation.

In this example, both the clock and lethal phenotypes of $dbt^P$ are shown to be capable of being reverted by excision of the associated P-element, and that the affected gene encodes a protein closely related to human casein kinase Iε. $dbt^P$ suppresses transcription of the locus, and transcription is restored following P-element excision. $dbt^S$ isand $dbt^L$ are caused by single amino acid substitutions in highly conserved residues of the predicted kinase domain of the protein. dbt is expressed in the same regions of the adult Drosophila brain as per and tim, but, in contrast to per and tim, dbt RNA levels do not appear to oscillate. DBT protein is shown to interact with PER both in vitro and in Drosophila cells. These studies establish dbt as the first vital gene to be associated with circadian rhythmicity in any organism, and indicate a role for the predicted kinase in phosphorylation and regulated accumulation of PER in wild type flies.

Experimental Procedures

Genomic and cDNA Library Screening: Drosophila genomic library in Lambda FIX II vector is from Stratagene. Directionally cloned Drosophila adult head cDNA library has been described previously [Hamilton et al., NAR, 19:1951–1952 (1991); Palazzolo et al., Gene, 88:25–36 (1990)]. Directionally cloned Drosophila embryonic and pupal cDNA libraries were prepared using the ZAP cDNA synthesis kit and the Uni-ZAP XR cloning kit (both from Stratagene) and were generously provided by Simon Kidd. Molecular techniques were performed using standard protocols [Ausubel et al., in Current Protocols in Molecular Biology, edited by K. Janssen: John Wiley & Sons, Inc. (1995); and Sambrook et al., Molecular Cloning: A Laboratory Manual: Cold Spring Harbor Laboratory Press. (1989)].

Genomic DNA flanking the P element insertion site was isolated by plasmid rescue [Pirrotta, In Drosophila: A Practical Approach, edited by D. B. Roberts. (Oxford: IRL Press Limited) 1986)]. DNA fragments to be used as template for probe preparation were purified using QIAquick gel extraction kit (Qiagen). $^{32}$P labeled probes were prepared by random priming of gel purified DNA fragments using a 10×hexanucleotide mix (Boehringer Mannheim) according to the manufacturer's recommendations. Hybridizations were performed in 50% formamide, 6×SSPE, 5×Denhardt's, 1% SDS and 0.1 mg/ml salmon sperm DNA at 42° C. for at least 16 hours. Membranes were washed twice in 2×SSC/0.1% SDS at room temperature and twice in 0.2×SSC/0.1% SDS at 65° C. before being exposed to film at −80° C. with an intensifying screen.

Southern Hybridization: Isolation of genomic DNA from adult flies was performed as described [Jowett, In Drosophila: A Practical Approach, edited by D. B. Roberts. (Oxford: IRL Press Limited), (1986)]. $^{32}$P labeled probes were prepared by random priming as described above. Hybridizations were perfomed for at least 16 hours at 42° C. in 20 ml hybridization buffer (50% formamide, 2×SSPE, 1% SDS, 0.5×Denhardt's, 10% w/v dextran sulphate and 0.5 mg/ml salmon sperm DNA). Probes were removed by two washes in boiling 0.1×SSC/0.5% SDS and the stripped membranes were exposed to film to confirm that the hybridized probe had been completely removed before re-probing.

RNA Isolation and Analysis: Total RNA from pupae, adult heads or adult bodies was isolated using RNAzol B (Tel-Test). Poly A+ mRNA was isolated using the Oligotex mRNA isolation kit (Qiagen). For Northern analysis, RNA was separated by denaturing agarose gel electrophoresis and transferred to membranes as described [Fourney et al., Focus, 10:5–7 (1988)]. $^{32}$P labeled probes were prepared as described above. Hybridizations were carried out for at least 16 hours at 42° C. in 20 ml hybridization buffer (50% formamide, 2×SSPE, 1% SDS, 2×Denhardt's, 10% w/v dextran sulphate and 0.5 mg/ml salmon sperm DNA). Probes were removed as described above.

Ribonuclease (RNAse) protection analysis was performed using 20 mg total RNA from each time point. Therper [Sehgal et al., Science, 263:1603–1606 (1994)], tini and tubulin [Sehgal et al., Sciencie, 270:808–810 (1995)] riboprobes have been described previously. The dbt riboprobe template was prepared by subcloning a fragment from the dbt cDNA corresponding to nucleotides 1583–2090 into pBSIISK- (Stratagene). This was linearized with Earl and transcribed with T3 RNA polymerase to generate an antisense riboprobe 294 nucleotides in length and which produces a protected fragment of 270 nucleotides. Hybridizations and RNAse digestions were performed using the RPA II kit (Ambion), according to the manufacturer's recommendations. Protected fragments were separated on 5% acrylamide/8M Urea gels and visualized by autoradiography. Quantitation of protected fragments was performed with a Molecular Dynamics phosphorimager, with levels of per, tim and dbt mRNA normalized to tubulin at each time point.

DNA Sequencing: Genomic DNA from dbt$^S$, dbt$^L$ and the cn bw parental line used for mutagenesis (see Example 1, above) was isolated as described above. Genomic DNA from each line was used as template for PCR amplification of the dbt gene with AmpliTaq DNA Polymerase (Perkin Elmer). An aliquot of each reaction was used as template for re-amplification. PCR products were separated by agarose gel electrophoresis and purified as described above. 100–200 ng of each gel purified PCR product was used as template for sequencing with the AmpliCycle Sequencing Kit (Perkin Elmer) according to the manufacturer's recommendations. Complete sequencing of cDNA and genomic clones was performed using the AmpliCycle Sequencing Kit, or by the Taq FS dye terminator cycle sequencing method using a Perkin Elmer/Applied Biosystems Model 377 DNA Sequencer (Protein/DNA Technology Center, Rockefeller University).

In Situ Hybridization to Adult Head Sections: 12 mm frozen sections of adult Drosophila heads were cut as in Amrein and Axel [Amrein and Axel, Cell 88: 459–69 (1997)]. In situ hybridization was performed as described in Schaeren-Wiemers and Gerfin-Moser [Schaeren-Wiemers and Gerfin-Moser, Histochemistry, 100:431–40 (1993)] except that per and tim antisense DIG RNA probes derived from full-length cDNAs were hydrolyzed prior to use, and all the hybridization and washes were performed at 55° C. The dbt probe was the same as used in RNAse protection experiments.

Protein Interaction Studies: GST fusion proteins were constructed and expressed as described [Saez and Young, Neuron, 17:911–920 (1996)]. In vitro translation of DBT proteins, and interaction studies with GST-PER fusion proteins in vitro and GFP-DBT fusion proteins in S2 cultured Drosophila cells were performed as described [Saez and Young, Neuron, 17:911–920 (1996)].

Results

Analysis of the Region Surrounding the dbt$^P$ Insertion Site: As described in greater detail in Example 1, above, short and long period alleles of a novel circadian rhythm gene, double-time (db$^S$ and dbt$^L$, respectively) have been isolated from a genetic screen for locomotor rhythm mutations. A chromosome deficiency, Df(3R)tll-g, and a P-element-induced mutation (dbt$^P$), both of which fail to complement the dbt$^S$ and dbt$^L$ mutations, have been identified as well. Given the similar behavioral phenotype of Df(3R)tll-g/dbt$^S$ and dbt$^P$/dbt$^S$ flies [Example 1, above], dbt$^P$ is most likely a null or strong hypomorphic allele. As dbt$^P$ failed to complement the Df(3R)tll-g, dbt$^S$ and dbt$^L$ mutations [Example 1, above], it provided a basis for molecular cloning of the dbt locus.

Figure 7:
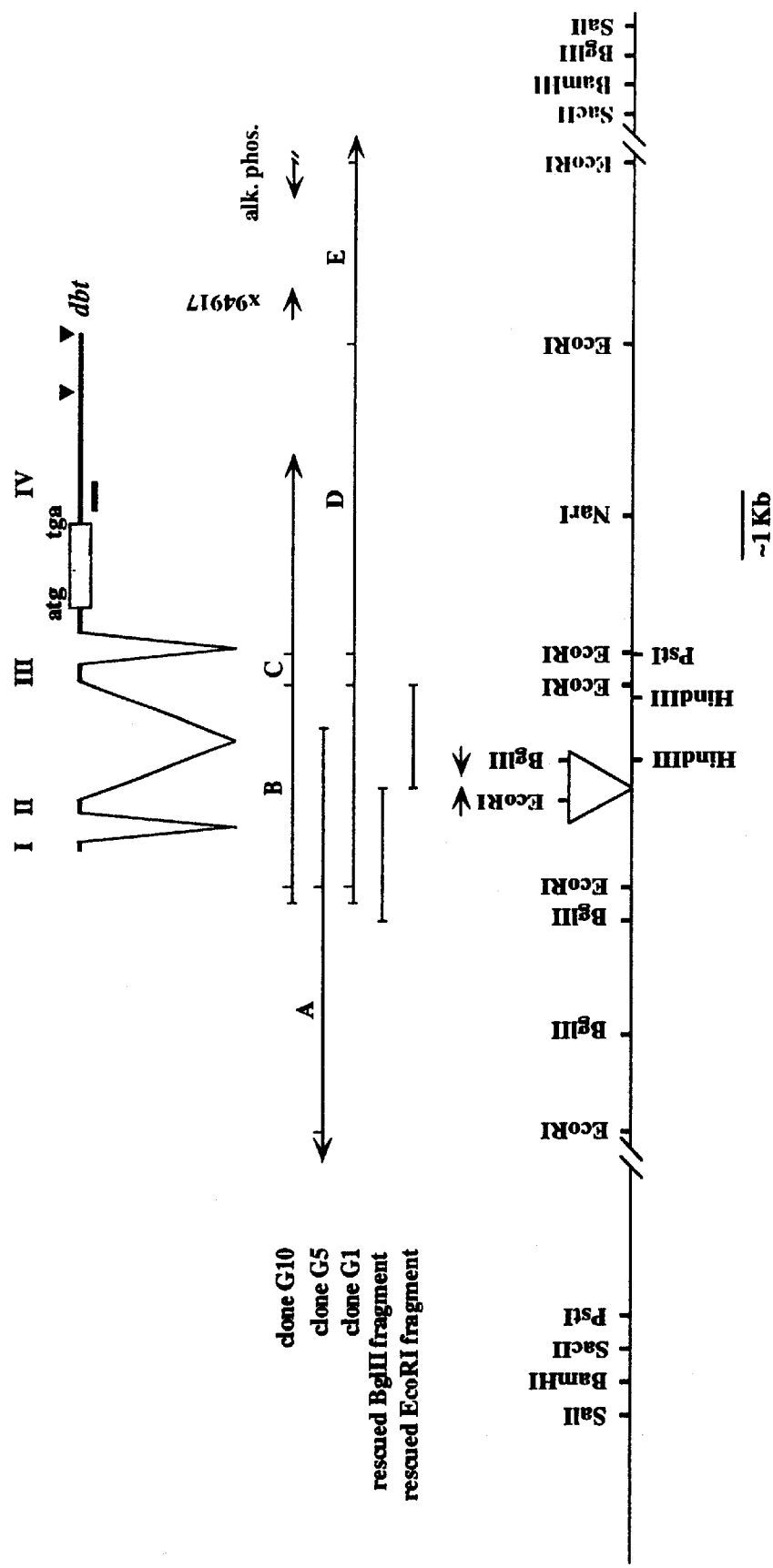
FIG. 7 shows a map of the region surrounding the P element insertion site of dbt$^P$. The map was created following Southern hybridization of genomic DNA isolated from dbt$^P$ and dbt$^{Pex}$ lines, as well as analysis of restriction digests of the genomic DNA clones. Restriction sites far to the right or left of the P element insertion were identified, but were not resolved well enough to accurately determine their distance from the the P element. Regions of genomic DNA recovered by plasmid rescue are indicated. The relative sizes and orientations of genomic clones 1, 5 and 10 are shown. Arrows on the ends of genomic clones indicate that those ends were not precisely defined. A–E, fragments resulting from EcoRI digestion of the three genomic DNA clones. Positions and orientations of a 1.9 kb alkaline phosphatase gene (accession number X98402), and a previously described 0.9 kb transcript of unknown function (accession number X94917) are indicated (see text in Example 2). The dbt transcription unit is comprised of four exons with the open reading frame (shaded rectangle) residing entirely within exon IV. The P element insertion is within the intron separating exons II and III. The black bar beneath the dbt transcript indicates the location of the fragment used to synthesize antisense riboprobes for RNAse protection analysis and in situ hybridization. Filled triangles identify to the locations of two potential polyadenylation signals (see text in Example 2).

Genomic DNA fragments flanking the P element insertion site were obtained by plasmid rescue [Pirrotta, In Drosophila: A Practical Approach, edited by D. B. Roberts. (Oxford: IRL Press Limited) (1986)], and these fragments (rescued BglII- and EcoRI fragments, FIG. 7) were then used as probes to screen a Drosophila genomic DNA library. Three genomic DNA fragments (clones G1, G5 and G10, FIG. 1), each between 8 and 12 kilobases (kb) in length, were recovered and mapped by restriction analysis. FIG. 7 shows a restriction map of the region surrounding the P element insertion site. Five smaller genomic DNA fragments, resulting from EcoRi digestion of the genomic clones, were isolated and subcloned (fragments A–E, FIG. 1). Together, these five non-overlapping fragments represent approximately 16 kb of genomic DNA surrounding the P element insertion site.

Since P elements tend to insert near the transcription start site of the affected gene [Kelley et al., Mol. and Cell Bio., 7:1545–1548 (1987); Spradling et al., PNAS, USA, 92:10824–10830 (1995)], it was predicted that the P element insertion site would be close to the transcribed region of the dbt gene. To determine the number of transcription units in the cloned genomic region, the five EcoRI fragments were used as probes for Northern analysis of poly A+ RNA isolated from heads and bodies of wild type flies. While no transcribed regions within EcoRI fragments A or B were detected, three transcripts, approximately 1.1, 2.05 and 3.2 kb in length, were detected by this method with probes corresponding to fragments D and E.

Since all of the transcribed regions surrounding the P element insertion site appeared to include sequences located within EcoRi fragments D and E, these two genomic DNA fragments were selected as probes to screen Drosophila embryonic, pupal, and adult head cDNA libraries. In addition, genomic sequence from both ends of each of the EcoRI fragments was obtained. Conceptual translation of these genomic sequences revealed the presence of a gene encoding a previously described alkaline phosphatase [GenBank accession NO: X98402] within EcoRI fragment E (FIG. 7). The complete cDNA for the alkaline phosphatase gene is 1867 nucleotides in length [GenBank accession NO:X98402] and presumably corresponds to the 2.05 kb transcript observed by Northern analysis. The P-element insertion site maps ~9 kb downstream of this gene. Three cDNA clones were isolated from the embryonic library, and partial sequencing of these cDNAs revealed that all were part of the same transcript. Following a search of DNA and protein sequence databases [Altschul et al., *J. Mol. Biol.* 215: 403–410 (1990)], it was determined that this gene had been previously isolated as part of a GAL4 enhancer trap screen. The complete cDNA is 907 bp in length and presumably corresponds to the 1.1 kb transcript detected by Northern analysis. Comparison of this cDNA sequence to genomic sequence obtained from EcoRi fragment E demonstrated that this gene is located ~7 kb downstream of the P element insertion in $dbt^P$ (FIG. 1, transcript x94917).

The pupal and head cDNA libraries yielded a total of eight cDNA clones. Partial sequencing of each cDNA revealed that all were derived from the same transcript and demonstrated that the 3' end of this gene spanned the EcoRI site separating the D and E fragments used as probes (FIG. 7). These cDNAs also included 5' sequences from EcoRI fragment C, and fragment B, which contains the P-element insertion site. This gene was likely to correspond to dbt, and (as shown below), to encode the 3.2 kb transcript found by Northern analysis.

Figure 8:
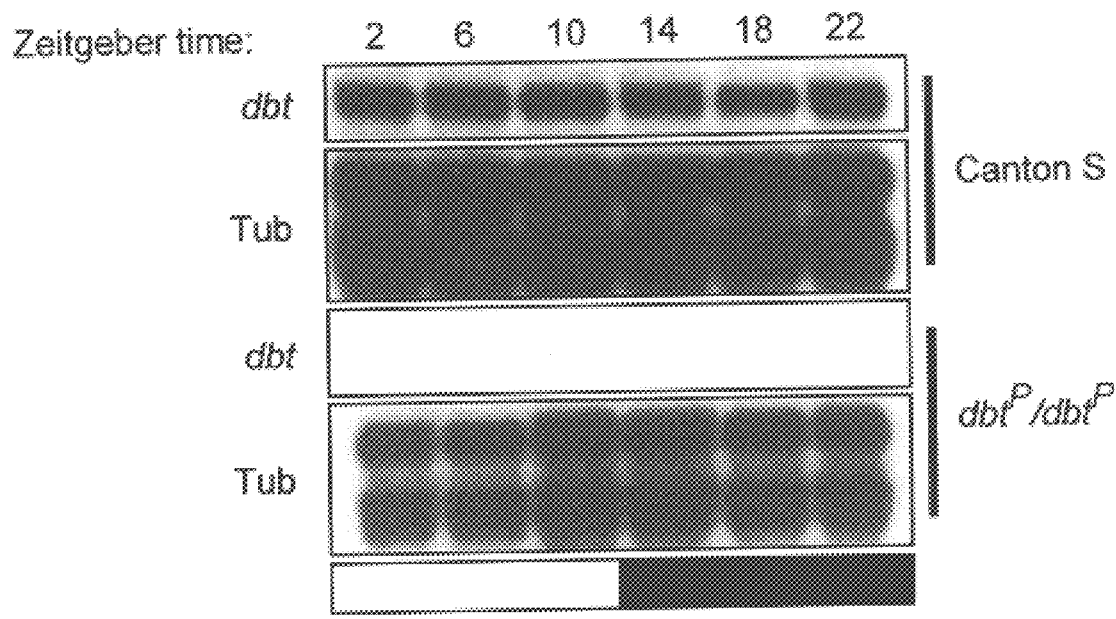
FIG. 8 shows the mRNA levels of the candidate dbt gene are significantly reduced in homozygous P element containing lines. Canton S and dbt$^P$/TM6Tb flies were transferred to fresh bottles and allowed to lay for 1–2 days. Adult flies were removed and bottles were placed in incubators to entrain developing flies to LD12:12. As Drosophila began to pupate, wild type, or Tb$^+$ (dbt$^P$ homozygous) pupae were collected at four hour intervals for one day. Total RNA was isolated from whole pupae of each genotype at each time point, and candidate dbt mRNA detected by RNAse protection analysis using a $^{32}$P labeled antisense riboprobe (see FIG. 7). Protected fragments were resolved by denaturing polyacrylamide gel electrophoresis and visualized by autoradiography. While the dbt transcript is readily detected at each time point in Canton S pupae, it is barely detected in dbt$^P$ homozygous pupae. Tubulin served as an internal control to confirm that intact total RNA had been isolated and quantitation of dbt mRNA levels was normalized to tubulin mRNA levels at each time point.

Molecular and Behavioral Analyses of $dbt^P$ and its Revertants: Because mid- to late stage $dbt^P$ pupae do not survive, $dbt^P$ homozygotes were recovered as viable early pupae from balanced $dbt^P$TM6, Tubby stocks as previously described [Example 1, above]. In order to measure the relative levels of the candidate RNA in mutant and wild type pupae, $dbt^P$ and wild type pupae were collected at four hour intervals over one day of LD, and total RNA prepared for each time point. The cDNA sequence (described below) was used to generate an antisense riboprobe for RNAse protection studies. A protected fragment of the expected size was detected in total RNA isolated from wild type pupae at all timepoints, but the same protected fragment is detected at no more than 10–20% of the wild type level in the $dbt^P$ samples (FIG. 8). A similar result was obtained on comparing RNA from mutant and wild type third instar larvae. Thus, the P-element strongly reduces the level of the candidate RNA, but not control RNA species (FIG. 8), further indicating an association between the dbt mutant phenotypes and changes in this transcription unit.

Several revertant lines were produced and subsequently examined, to determine if viability, normal locomotor rhythms, and putative dbt RNA expression were restored in lines from which the P-element had been excised. Seven of nine P-element revertants produced were viable as homozygotes and showed normal locomotor activity rhythms. Two lines failed to fully revert the rhythm phenotype, and one of these also did not revert lethality (VIII and IX, Table 4). To determine whether the collection of revertants restored normal levels of the candidate dbt MRNA as well, RNA was derived from homozygous, $dbt^P$ revertant pupae as described above. Since no oscillation in the putative dbt transcript was previously observed in $dbt^P$ pupae (FIG. 8), pupae were not first entrained to a light:dark cycle prior to collection.

Figure 9A:
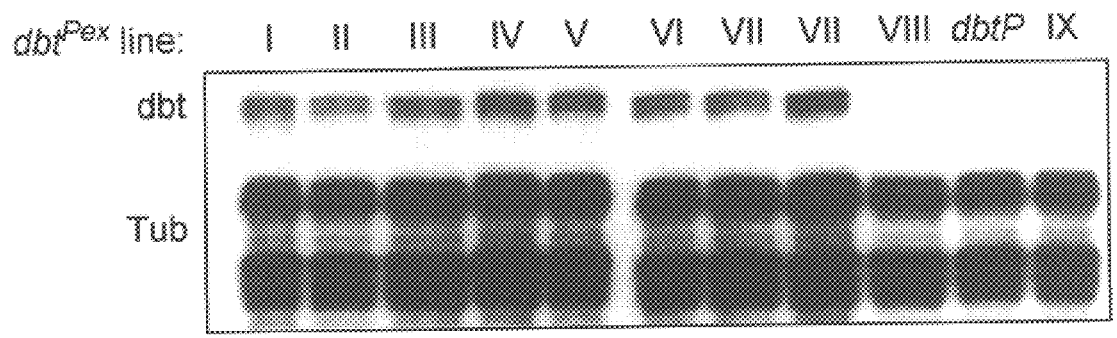
FIGS. 9A–9B show the loss of the P element restores expression of the dbt gene.
Figure 9B:
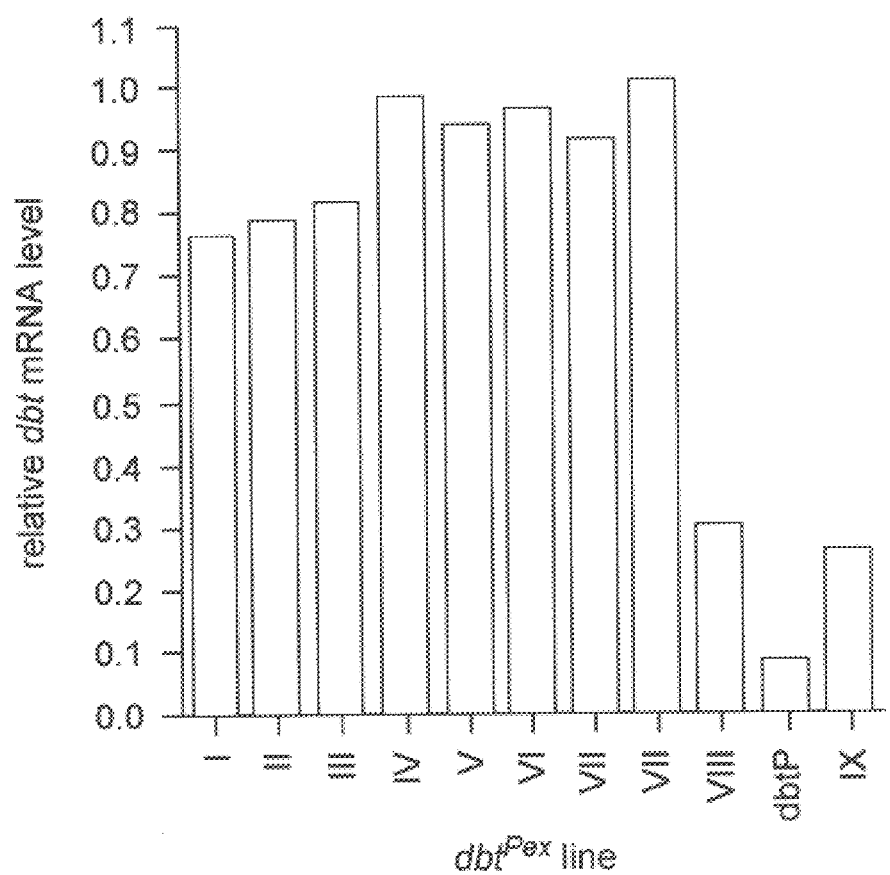

The seven revertants that restored both viability and rhythmicity expressed approximately 8–10 times as much of the putative dbt RNA as the parental $dbt^P$ mutant line (FIG. 9), confirming that the P element insertion disrupts the normal expression of the candidate dbt gene. The two lines showing incomplete reversion of the dbt phenotypes continued to produce low to intermediate levels of the putative dbt RNA (FIG. 9). Molecular studies to be presented elsewhere indicate that the incomplete revertants VIII and IX have obtained additional sequence changes affecting this transcription unit in conjunction with the P-element excision. Together the revertant data strongly indicate that the P-element is the cause of both pupal lethality and aberrant circadian rhythmicty, and that the affected transcript is a product of the dbt locus.

TABLE 4

| $dbt^{Pex}$-Line | $dbt^{Pex}/dbf$ | | $dbt^{Pex}/dbt^S$ | |
| --- | --- | --- | --- | --- |
| | tau ± SEM | (#AR/n) | tau ± SEM | (#AR/n) |
| I | 24.2 ± 0.2 | (2/8) | 22.1 ± 0.1 | (0/5) |
| II | 24.01 ± 0.1 | (0/10) | 22.0 ± 0.0 | (0/5) |
| III | 24.1 ± 0.2 | (3/8) | 22.0 ± 0.4 | (1/5) |
| IV | 23.8 ± 0.2 | (5/13) | 21.7 ± 0.2 | (1/9) |
| V | 23.7 ± 0.3 | (0/5) | 21.8 ± 0.2 | (0/5) |
| VI | 24.5 ± 0.5 | (6/8) | 21.9 ± 0.1 | (0/5) |
| VII | 23.8 ± 0.6 | (4/7) | 29.1 ± 0.1 | (0/5) |
| VIII | L | | 19.0 ± 0.1 | (2/12) |
| $dbt^P$ | L | | 19.0 ± 0.1 | (0/18) |
| IX | 26.5 ± 0.3 | (17/27) | 20.5 ± 0.1 | (3/24) |

Loss of the P element restores viability and reverts the behavioral phenotype of $dbt^P$. Excision of lines ($dbt^{Pex}$), in which the third chromosome was generated from $dbt^P$ by apparent excision of the P element (loss of orange eye color), were crossed to a dbt line (the original $dbt^P$ of Df(3R) tll-g), and to $dbt^S$. The average periods (tau) of locomotor activity in the transheterozygous progeny were assayed in DD. #AR/n, number of arrhythmic flies/total number assay; L, a lethal genotype; $dbt^P$, a line which resulted from the same series of genetic crosses as the others, but in which the orange eye color was not lost.

Figure 10:
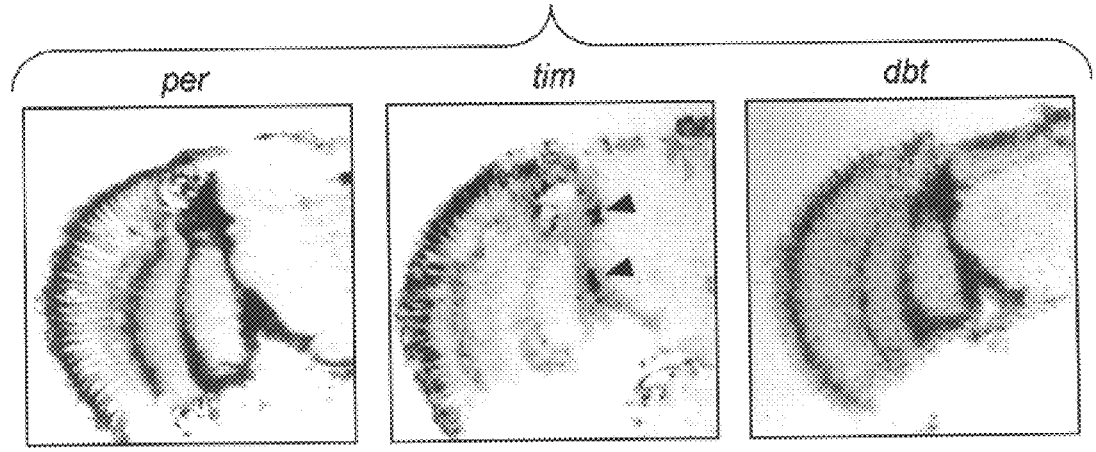
FIG. 10 shows that per, tim and dbt mRNAs are co-localized in adult heads. In situ hybridization of antisense digoxigenin RNA probes for per, tim and dbt to sections of Canton S adult heads at ZT12. Only half of each head section is shown. Expression of all three transcripts is detected in the photoreceptor cells. per and dbt transcripts are expressed in a broad region between the optic lobes and central brain, whereas tim is expressed discretely in lateral neuron pacemaker cells (indicated by arrowheads).

In situ Hybridization Analysis of dbt mRNA: In order to test whether dbt is expressed in clock cells in the brain, in situ hybridizations to adult head sections with per, tim and dbt antisense RNAs were performed. The results in FIG. 10 indicate that all three genes are expressed in photoreceptor cells composing the eyes. tim shows a discrete pattern in brain, and is expressed at highest levels in the lateral neurons [LNs; Ewer et al., *J. Neurosci.*, 12:3321–3349 (1992); Frisch et al., *Neuron,* 12:555–570 (1994) and Vosshall and Young, *Neuron,* 15:345–360 (1995)]. per and dbt are expressed in a wider region between the optic lobe and the central brain, which includes the LNs. The pattern of per RNA expression seen here is identical to the anti-β-galactosidase staining previously seen in a per promoter b-galactosidase transgenic line [Vosshall and Young, *Neuron,* 15:345–360 (1995)], and the pattern of tim staining is the same as that observed with anti-TIM antibody [Myers et al., *Science,* 271:1736–1740 (1996)]. Therefore, per and dbt appear to be expressed in the same cells in the brain, which include the tim-expressing cells. Interestingly, the RNA signals for all three genes are located predominantly at the periphery of the nucleus in the photoreceptors, although the significance of this is not yet clear.

Sequence Analysis of dbt and the $dbt^S$ and $dbt^L$ Mutations: Each of the eight putative dbt cDNA clones was completely sequenced. The most complete of these (~3.0 kb, clone P12) contained an open reading frame of 1320 bp flanked by 5' and 3' untranslated sequences. In vitro transcription and translation of P12 demonstrated that this clone encodes a protein of ~46 kDa, as determined by SDS-PAGE (discussed further below). The sequence of the P12 open reading predicts a 440 aa protein with a molecular mass of 48 kDa.

Oligonucleotide primers flanking the predicted open reading frame were synthesized and used for PCR amplification of the dbt gene from genomic DNA isolated from the dbt$^S$ and dbt$^L$ mutant lines, as well as from the parental line used for chemical mutagenesis. Comparison of genomic DNA sequence obtained from each line revealed a single nucleotide change from the corresponding parental DNA for each mutant, providing perhaps the strongest evidence that the gene isolated is dbt. Each point mutation results in an amino acid change with Pro$^{47}$→Ser in dbt$^S$ flies and Met$^{80}$→Ile in dbt$^L$ (FIG. 11).

BLAST [Altschul et al., *J. Mol. Biol.* 215:403–410 (1990)] searches conducted with the dbt DNA sequence revealed that DBT is closely related to a family of previously identified protein kinases. The most closely related kinase is the epsilon isoform of human casein kinase I [Fish et al., *Journ.BiolChlem*, 270:14875–14883 (1995)]. dbt is 75% (719/947) identical at the nucleotide level and 86% (260/301) identical at the amino acid level to the kinase domain of human casein kinase IE, suggesting that DBT is a structural homologue of this enzyme. FIG. 11 shows an alignment of the amino acid sequences of casein kinase I family members from diverse species. Because the DBT amino acid sequence identity with casein kinase I family members begins at the initiator methionine, and the sequence surrounding the predicted AUG start codon precisely matches the consensus sequence for a Drosophila translation start site [Cavener, *NAR*, 15:1353–1361 (1987)], it is believed that the Met$^1$ in FIG. 11 is the authentic translation initiation site. Note that the amino acid changes in the dbt$^S$ and dbt$^L$ mutants occur at positions which are highly conserved between organisms. Although no specific function has been attributed to these regions [Hanks et al., *Science* 241: 42–54 (1988)], they are probably required for normal DBT function.

The nucleotide sequences of all eight cDNAs, were compared to the wild type sequence of the genomic region surrounding the P element insertion site. Alignment of the cDNA and genomic sequences demonstrates that the dbt transcript is encoded by four exons and that the predicted open reading frame resides within a single exon (FIG. 7). Two potential polyadenylation signals have been identified, which could produce transcripts of approximately 3.2 and 4.0 kb. Most of the cDNAs terminate after the first putative poly A addition signal. The P element insertion is located within the intron separating exons II and III (FIG. 7), providing further support for identification of the gene as dbt.

Figure 12A:
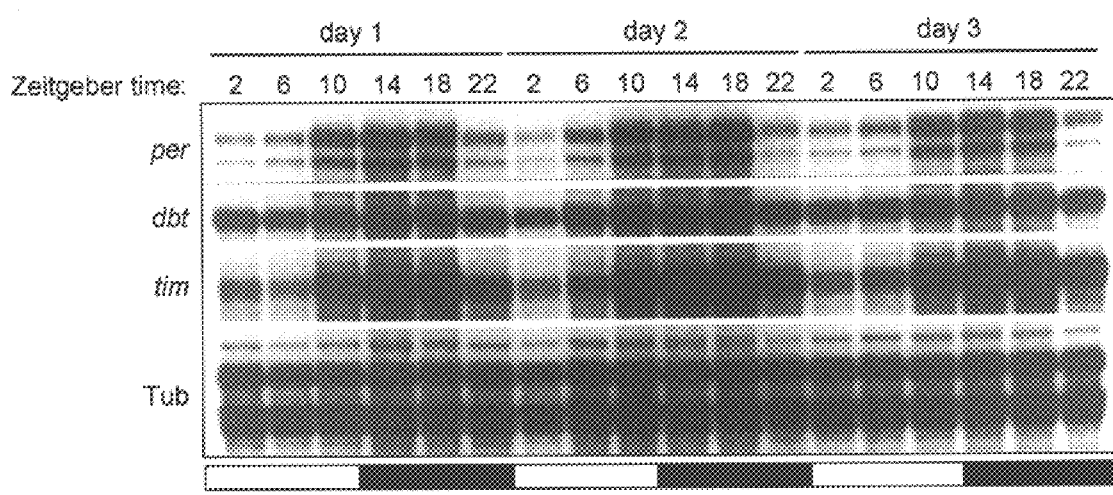
FIGS. 12A–12B show that the levels of the dbt transcript in adult heads do not appear to oscillate.
Figure 12B:
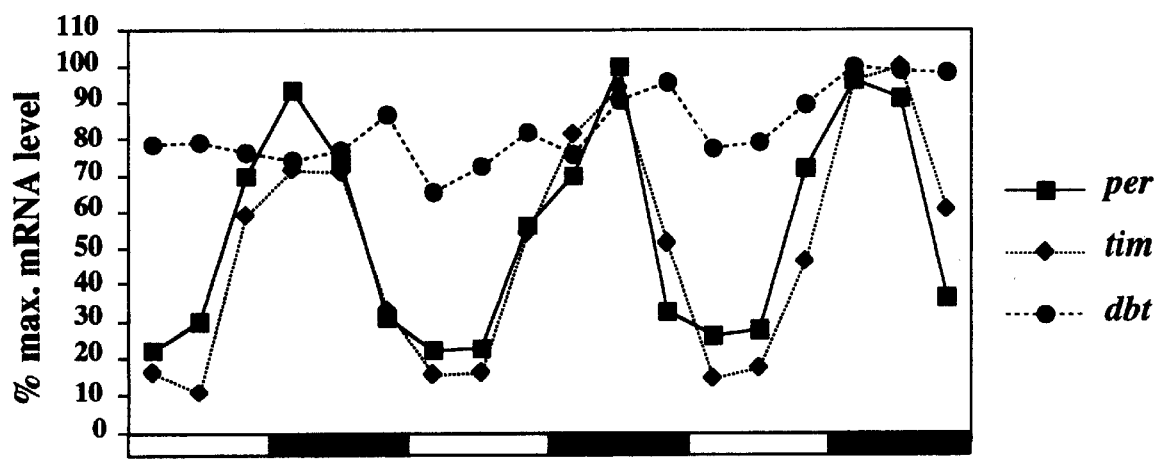

Analysis of dbt RNA levels in Wild type Flies at Different Times of Day: Because mRNA levels of the two previously identified Drosophila clock genes, per and tim, have been shown to oscillate with a 24 hour period in heads of adult wild type flies [Hardin et al., *Nature*, 343:536–540 (1990) and Sehgal et al., *Science*, 270:808–810 (1995)], it was of interest to determine whether levels of dbt mRNA oscillate as well. Although analysis of wild type pupae had already suggested that the abundance of dbt RNA remains essentially constant throughout the day and night, these measurements represent RNA levels found in whole pupae. Oscillations in the levels of the per and tim transcripts are considered to be such a central feature of a normally functioning clock, that it was necessary to repeat this analysis under conditions where per and titn oscillations could be robustly observed (i.e. in adult fly heads). Wild type flies were entrained to a 12:12 LD cycle and flies were collected at four hour intervals for three days. Heads were isolated from the flies collected at each time point and used to prepare total RNA. RNAse protection analyses demonstrated that while per and tim mRNA levels display strong (approximately 10-fold) circadian oscillations, levels of dbt mRNA remain essentially constant (FIG. 12). Therefore, there are two unique features of dbt that distinguish it from per and tim: (a) Strong hypomorphic mutations of this gene are homozygous lethal, and (b) levels of the dbt transcript apparently do not oscillate.

DBT and PER Proteins Physically Interact In Vitro and in Cultured Drosophila Cells: Because DBT and PER appear to be expressed in the same cells in the Drosophila brain and eyes, and patterns of PER phosphorylation and accumulation are altered in dbt mutants, it was asked whether functional interactions between PER and DBT might include a physical association of these proteins. Two independent methods were employed to test and confirm such a physical interaction: in vitro binding studies, and co-immunoprecipitation of DBT and PER from cultured Drosophila cells (S2) programmed to express both proteins.

Figure 13A:
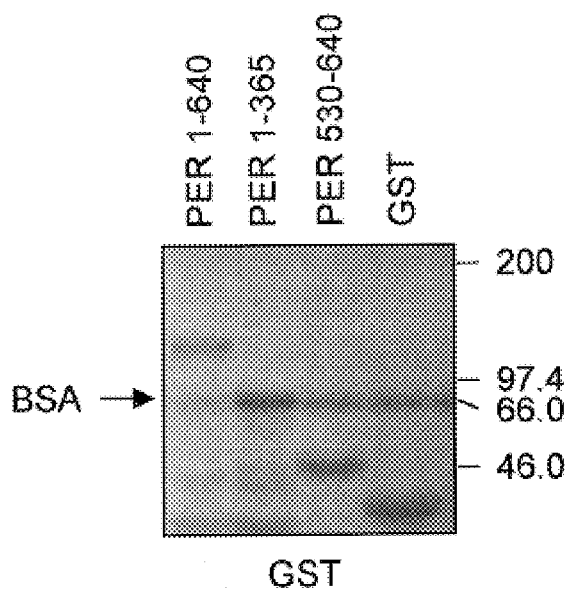
FIGS. 13A–13C show DBT and PER physically interact in vitro and in cultured Drosophila cells.

In vitro translation of DBT from dbt cDNA P12 showed that this cDNA encoded a protein of ~46 kDa as predicted from sequence analysis (FIG. 13A, input). GST (Glutathione-S-transferase) fusions, involving varying segments of PER, were tested for evidence of affinity for this DBT protein. The GST-PER fusions were immobilized on gluthatione agarose beads and subsequently incubated with in vitro translated, $^{35}$S-labeled DBT. After extensive washing to remove nonspecifically bound proteins, SDS-PAGE analysis of labeled DBT proteins bound to the beads showed that DBT binds to PER 1–640 and PER 1–365, but the protein does not bind to PER 530–640 or GST alone. These results show that DBT and PER can physically associate in vitro, and that DBT interacts directly with an N-terminal region of PER.

Figure 13B:
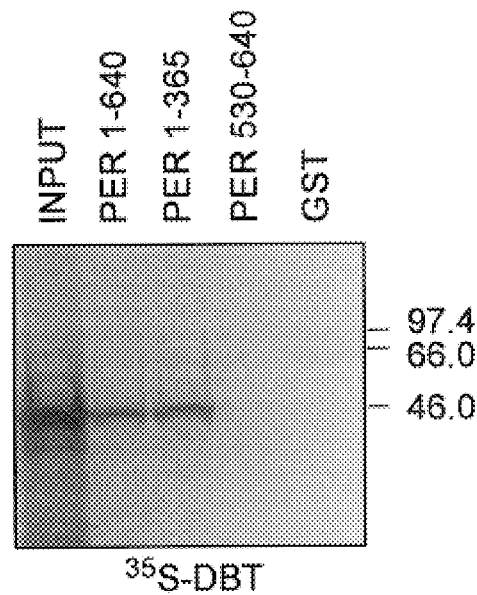

In order to confirm that such a physical interaction between DBT and PER can take place in Drosophila cells, immunoprecipitations were performed using extracts from four groups of S2 cells, one expressing only a Green Fluorescent Protein (GFP)-DBT fusion, a second co-expressing PER and GFP-DBT, a third producing PER alone, and a fourth expressing neither protein. FIG. 13B shows that when the cell extracts were immunoprecipitated with anti-GFP antibodies, PER-DBT complexes are only detected in cells co-expressing PER and GFP-DBT proteins. The results indicate that PER and DBT are present in a complex when expressed in the same Drosophila cell.

Discussion

The cloning of the dbt gene is reported. This is the third Drosophila gene to be isolated that has an essential role in circadian rhythms. Several lines of evidence were presented to show that the gene cloned is dbt: (a) The P-element insertion associated with dbt$^P$ resides within an intron of the dbt gene and causes a strong reduction in dbt RNA levels. (b) Viability, behavioral rhythmicity, and dbt mRNA levels are restored following simple excision of the P-element associated with dbt$^P$. (c) The dbt$^S$ and dbt$^L$ phenotypes are each associated with single nucleotide mutations, that result in amino acid changes, in the dbt gene. (d) The dbt transcript is detected in the same cell types as are per and tim. (e) DBT has been shown to be capable of binding to PER in vitro and in Drosophila cells.

dbt encodes a kinase that is required for wild type patterns of PER phosphorylation and for adult viability: Sequence analyses indicate that dbt is a structural homologue of human casein kinase Iε, with 86% of the amino acids composing DBT identical to those composing the kinase domain of human casein kinase Iε. PER proteins are hypophosphorylated in dbt$^P$ mutants, and the timing of PER phosphorylation appears to be altered in dbt$^L$ and dbt$^S$ mutants [Example 1, above] suggesting that a kinase activity supplied by DBT is required for normal PER phosphorylation in vivo. In this study it is shown that PER and DBT will physically associate in vitro and in cultured Drosophila cells, and in addition, the formation of a PER/DBT complex leads to DBT-dependent phosphorylation of PER in vitro. DBT is the first Drosophila clock protein to have a structure that indicates a recognizeable biochemical function. Although strong evidence for involvement of protein phosphorylation in circadian rhythmicity has been reported in several organisms [Edery et al., PNAS USA, 91:2260–2264 (1994); Garceau et al., Cell, 89:469–476 (1997); Price et al., EMBO J., 14:4044–4049 (1995); Roberts et al., Res., 504:211–215 (1989); Schulz et al., Cronobiol.1 Intern., 2:223–233 (1985) and Zwartjes and Eskin, J. Neurobiol, 21:376–383 (1989)], this is the first evidence linking a specific kinase to regulation of circadian rhythmicity.

Levels of dbt mRNA show no evident circadian oscillation, so in pacemaker cells, DBT activity may be constitutive. dbt is also the first clock gene to be described in any organism that is essential for viability. The lethality of dbt$^P$ homozygotes is not due to over-accumulation of PER because per$^o$; dbt$^P$ doubly homozygous mutants are inviable [Example 1, above]. Thus, the pupal lethality of dbt$^P$ mutants suggests that vital proteins require DBT activity for their phosphorylation.

Figure 14:
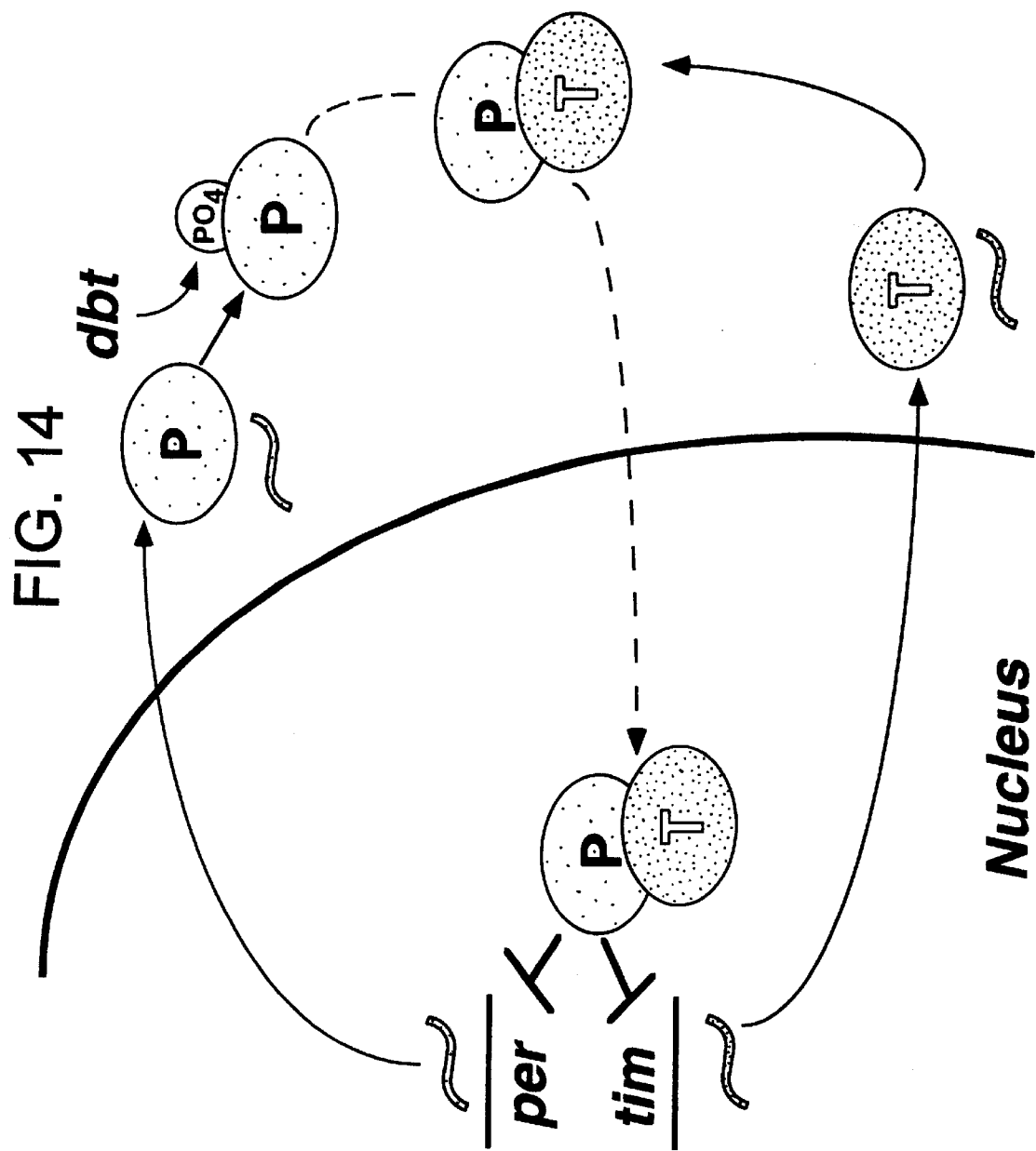
FIG. 14 shows a model depicting regulation of PER phosphorylation and stability by dbt in wild type flies. In the model, dbt function promotes phosphorylation of cytoplasmic PER monomers. Once modified, PER proteins turn over rapidly. Physical association of PER and TIM stabilizes PER either because residual, un-phosphorylated PER proteins are incorporated into PER/TIM dimers and these are no longer subject to modification by DBT, or phosphorylated PER proteins are stabilized by association with TIM. The latter alternative is consistent with Example 1, below because monomeric PER proteins also stably accumulate in nuclei in dbt$^P$ mutants, but not in wild type Drosophila. The model indicates that instability of phosphorylated PER monomers delays PER/TIM heterodimerization (dashed arrow) until per and tim RNA levels are high. Thus, phosphorylation promotes a delay between phases of per/tim transcription and PER/TIM complex function, which establishes molecular oscillations of RNA and protein.

A model for DBT function in a PER/TIM oscillator: FIG. 14 presents a model for the role of DBT in the regulation of circadian rhythms. As DBT and PER physically associate, as hypo-phosphorylated PER proteins accumulate to high levels in dbt$^P$ mutants [Example 1, above], and because PER proteins appear to be unstable in the cytoplasm of pacemaker cells in the absence of TIM in vivo [Dembinska et al., J. of Bio. Rhythms., 12:157–172 (1997); Price et al., EMBO J., 14:4044–4049 (1995) and Vosshall et al., Science, 263:1606–1609 (1994), Example 1, above], PER/DBT complexes appear to promote PER phosphorylation(s) that, in turn, destabilizes cytoplasmic PER monomers (FIG. 14). This is further supported by the finding that, in dbtp larval brains, PER accumulates cytoplasmically in many new cells in the apparent absence of TIM [Kaneko et al., (1997); Example 1, above]. DBT activity thus serves to retard accumulation of PER/TIM complexes in wild type Drosophila, by keeping PER levels low at times of increasing per/tim transcription. As seen with dbt$^P$ mutants, stable PER accumulation favors continuous rather than periodic nuclear transport of PER/TIM complexes, resulting in a feedback loop at equilibrium, rather than a molecular oscillator.

Edery et al. [Edery et al., PNAS USA, 91:2260–2264 (1994)] have shown that PER is phosphorylated over many hours, and that the most highly phosphorylated forms of the protein occur at times of night when PER proteins are predominantly nuclear. This suggests that DBT may act in both the cytoplasm and the nucleus, or that additional kinases continue to phosphorylate PER in the nucleus. The present finding that dbt$^P$ mutants accumulate high levels of nuclear PER, and that dbt$^L$ mutants show delayed degradation of hyper-phosphorylated, monomeric forms of PER [Example 1, above], suggests that DBT activity can influence stability of nuclear PER proteins after they have dissociated from TIM. However, this could be due to the production of a phosphorylated form of PER by cytoplasmic DBT, with subsequent transfer of phosphorylated PER to nuclei as a PER/TIM complex. It is not yet known whether all monomeric PER proteins are phosphorylated in response to DBT, so that PER/TIM complexes stabilize previously phosphorylated PER proteins, or whether only PER proteins that have escaped phosphorylation as a monomer contribute to PER/TIM complexes (see also FIG. 14, legend).

Why dbt$^S$ and dbt$^L$ mutations are semi-dominant: The amino acids affected in DBT$^S$ and DBT$^L$ are highly conserved in the catalytic domains of other casein kinase I family members (FIG. 11). Thus, DBT$^S$ and DBT$^L$ may have altered kinase activities. However, changes in enzyme activity are not easily linked to the semi-dominant rhythm phenotypes produced by these mutations; studies of flies carrying 1 to 3 copies of the wild type gene have indicated that period length is relatively insensitive to dbt gene dosage [Example 1, above].

Figure 13C:
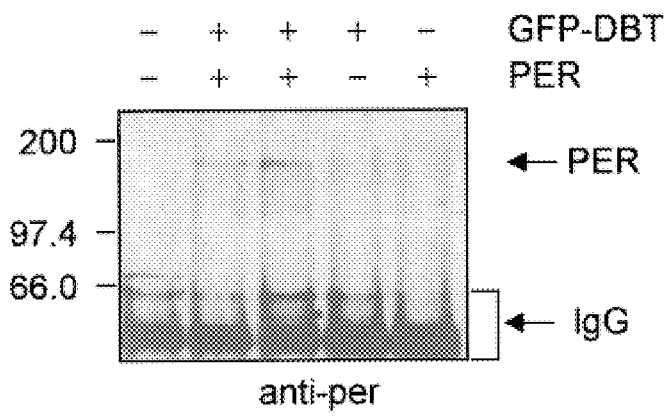

Although the basis for dbt$^S$ and db$^L$ semi-dominance is unknown, one possibility is that semi-dominance reflects a stable stoichiometric interaction between PER and DBT in vivo, as the two proteins have been shown to physically interact in vitro and in cultured Drosophila cells (FIG. 13). For example, in dbt$^S$/dbt$^+$ flies, there might be distinct pools of PER-one complexed to wild type DBT and one to DBT$^S$. PER complexed to DBT$^S$ should be prematurely degraded as in dbr$^S$ homozygotes [Example 1, above]. In db$^L$/dbt$^+$ flies, degradation should be delayed for PER/DBT$^L$ complexes as in dbt$^L$ homozygotes [Example 1, above].

It is possible that alterations in protein affinities have occurred for mutant DBT and wild type PER proteins. If DBT$^S$, for example, were to interact more strongly with PER than wild type DBT, degradation might be enhanced in dbt$^S$/dbt$^+$ in comparison to wild type. However, even if changes in PER/DBT affinity were associated with the mutants, there would still be a requirement for functionally distinct pools of PER/DBT complexes, as outlined above, to produce the observed molecular and behavioral mutant phenotypes. Differences in the stability of wild type, DBT$^L$ and DBT$^S$ proteins cannot be ruled out in the absence of an antibody, but once again this seems unlikely given the dosage insensitivity of wild type DBT.

Structural homologues of two Drosophila clock genes are now recognized in mammals: per homologues have recently been identified in mice and humans, and cycling patterns of per expression in the suprachiasmatic nucleus (SCN), the mouse pacemaker, suggest a role in the regulation of mammalian circadian rhythms as in Drosophila [Albrecht et al., Cell, 91:1055–1064 (1997); Shearman et al., Neuron, 19:1261–1269 (1997); Shigeyoshi et al., Cell, 91:1043–1053 (1997); Sun et al., Cell, 90:1003–1011 (1997) and Tei et al., Nature, 389:512–516 (1997)]. As the protein encoded by dbt is the drosophila ortholog of human casein kinase 1ε, it is likely that a specific DBT homologue is expressed in cells composing the SCN, and that such a kinase similarly regulates the phosphorylation and stability of PER to control mammalian circadian rhythms.

Example 3

Positional Syntenic Cloning and Functional Characterization of the Mammalian Circadian Mutation, tau Summary CK1ε is a critical component of the circadian clock in mammals. Using a positional syntenic cloning approach, it is demonstrated that the hamster tau mutation is an allele of CK1ε. Indeed, disclosed herein is the molecular cloning of the first single-gene circadian mutation to be discovered in mammals: the hamster tau mutation. Biochemical analyses reveal a striking difference in the maximal enzyme velocity and autophosphorylation state of the mutant tau CK1ε relative to the corresponding wild-type enzyme. CK1ε is also shown to interact with and phosphorylate the mammalian PERIOD proteins. Because Per1 gene expression is altered in tau mutants, CK1ε must play a significant role in delaying the negative feedback signal within the transcription-translation-based autoregulatory loop that composes the core of the circadian mechanism (see FIG. 24). A mechanism that explains why the tau mutation leads to the observed aberrant circadian phenotype in mutant animals is provided. In addition, of the nine genes now identified with circadian function in mammals, CK1ε is unique as it is the only enzyme. As such, CK1ε makes an excellent target for discovery of pharmaceutical compounds influencing circadian rhythms, sleep, jet lag, as well as other physiological and metabolic processes under circadian regulation.

Introduction

Daily rhythms in biochemical, physiological and behavioral processes are regulated by biological clocks [*Handbook of Behavioral Neurobiology: Biological Rhythms*, J. Aschoff, Plenum Press, New York, (1981); Pittendrigh, *Annu. Rev. Physiol.* 55:16 (1993)]. Under natural conditions, the endogenous circadian rhythms that are generated by these clocks are synchronized or entrained to the 24-hour cycles of the external world via time cues such as the daily light/dark cycle [Pittendrigh, *Annu. Rev. Physiol.* 55:16 (1993)]. In mammals the hypothalamic suprachiasmatic nucleus (SCN) contains a circadian pacemaker that drives virtually all daily physiological and behavioral rhythms expressed by the organism [*Suprachiasmatic Nucleus:The Mind's Clock*, Klein, et al., Oxford University Press, New York, (1991)]. The SCN are both necessary and sufficient for the generation of circadian behavioral rhythms [Ralph, et al., *Science* 247:975 (1990)]. Recent work has shown that individual SCN neurons are cell autonomous circadian oscillators [Welsh et al., *Neuron* 14:697 (1995); Liu et al., *Cell* 91:855 (1997); Herzog et al., *Nature Neurosci.* 1:708 (1998)]. Thus, even in mammals, the primary focus on the mechanism of circadian rhythms can be reduced to the cellular level.

Over the past decade, and with a quickening pace during the last three years, major components constituting the core molecular elements of circadian clocks have been identified. While these clocks are found in organisms as divergent as cyanobacteria, plants, fruit flies, and mammals, there is an extraordinary degree of evolutionary conservation of the underlying generative molecular mechanisms [Kondo and Ishiura, *Bioessays* 22:10 (2000); Johnson and Golden, *Annu. Rev. Microbiol.* 53:389 (1999); Anderson and Kay, *Adv. Genet.* 35:1 (1997); Young, *Annu. Rev. Biochem.* 67:135 (1998); Dunlap, *Cell* 96:271 (1999); Wilsbacher and J. S. Takahashi, *Curr. Opin. Genet. Dev.* 8:595 (1998); King and Takahashi, *Annu. Rev. Neurosci.* 23:713 (2000)]. Studies in Drosophila and Neurospora have emphasized the importance of an autoregulatory transcription/translation-based feedback loop as the basis of rhythm generation [Young, *Annu. Rev. Biochem.* 67:135 (1998); Dunlap, *Cell* 96:271 (1999); Siwicki, et al., *Neuron* 1:141 (1988); Hardin, et al., *Nature* 343: 536 (1990); Rosbash, *Curr. Opin. Genet. Dev.* 5:662 (1995); Hall, *J. Neurogenet.* 12:115 (1998)]. Subsequent work in prokaryotic, invertebrate and mammalian systems has both extended and unified this finding around a general autoregulatory feedback model.

Perhaps nowhere has progress in the field of circadian biology been more rapid than in our recent understanding of the mammalian circadian system. Despite numerous efforts over more than a decade to identify mammalian orthologs of circadian genes cloned in lower organisms, most notably period per) and timeless (tim) in Drosophila, the molecular components of the mammalian clock remained elusive [Takahashi, *Annu. Rev. Neurosci.* 18:531 (1995)]. Just three years ago, however, the first mammalian circadian gene, Clock, was cloned and characterized in mouse [Vitaterna, et al., *Science* 264: 719 (1994); King, et al., *Cell* 89:641 (1997); Antoch, et al., *Cell* 89:655 (1997)]. The Clock gene encodes a novel member of the basic helix-loop-helix (bHLH) PER-ARNT-SIM (PAS) family of transcription factors. In rapid succession over the next few months, three mouse Period orthologs denoted mPer1 [Sun et al., *Cell* 90:1003 (1997); Tei et al., *Nature* 389:512 (1997)] mPer2 [Shearman et al., *Neuron* 19: 1261 (1997); Albrecht et al., *Cell* 91:1055 (1997); Takumi et al., *Genes Cells* 3:167 (1998)] and mPer3 [Zylka et al., *Neuron* 20:1103 (1998); Takumi et al., *EMBO J.* 17:4753 (1998)], as well as a Timeless (mTim) ortholog were cloned (Sangoram et al., *Neuron* 21:1101 (1998); U.S. application Ser. No. 09/176, 183 filed Oct. 21, 1998, hereby incorporated by reference in its entirety; Zylka et al., *Neuron* 21:1115 (1998) Koike et al., *FEBS Lett.* 441:427 (1998); Takumi et al., *Genes Cells* 4:67 (1999); Tischkau et al., *J. Neurosci.* 19:RC15 (1999)]. At the same time, another gene, BMAL1 [Ikeda and Nomura, *Biochem. Biophys. Res. Comm.* 233:258 (1997)], was found to encode the protein dimerization partner for CLOCK [Gekakis et al., *Science* 280:1564 (1998)], and together the CLOCK/BMAL complex was shown to transactivate mPer1 via conserved E-box elements found in the promoters of both Drosophila and mouse period genes [Gekakis et al., *Science* 280:1564 (1998); Hao et al., *Mol. Cell. Biol.* 17:3687 (1997); Darlington et al., *Science* 280:1599 (1998)]. Finally, in both Drosophila and mammals, the negative feedback effects of PER and TIM were shown to act at the level of the CLOCK/BMAL complex [Sangoram et al., *Neuron* 21:1101 (1998); Darlington et al., *Science* 280:1599 (1998)] in a surprisingly direct manner [Lee et al., *Mol. Cell. Biol.* 19:5316 (1999); Bae et al., *J. Neurosci.* 20:1746 (2000)].

In Drosophila, the core elements of the circadian oscillator consist of four proteins: two stimulatory components made up by dCLOCK and its partner, dBMAL (CYCLE); and two inhibitory components made up by PERIOD and TIMELESS [Hardin et al., *Nature* 343:536 (1990); Darlington et al., *Science* 280:1599 (1998); Allada et al., *Cell* 93: 791 (1998); Rutila et al., *Cell* 93:805 (1998); Sehgal et al., *Science* 270:808 (1995); Myers et al., *Science* 271: 1736 (1996)]. The cycle begins with dCLOCK/dBMAL activation of transcription from the period and timeless genes via E-box motifs in their respective promoters [Hao et al., *Mol. Cell. Biol.* 17:3687 (1997); Darlington et al., *Science* 280:599 (1998); So and Rosbash, *EMBO J.* 16:7146 (1997)]. For several hours, the protein products of the per and tim genes, PER and TIM, are synthesized in the cytoplasm, accumulate to a critical level, heterodimerize and then translocate to the nucleus [Sehgal et al., *Science* 270: 808 (1995); Myers et al., *Science* 271:1736 (1996); Edery et al., *Proc. Natl. Acad. Sci. U.S.A.* 91:2260 (1994); Saez and Young, *Neuron* 17:911 (1996)]. Once in the nucleus, the PER-TIM complex interacts negatively with the dCLOCK/ dBMAL complex to inhibit transcription from per and tim [Darlington et al., *Science* 280:1599 (1998); Lee et al., *Mol. Cell. Biol.* 19:5316 (1999); Bae et al., *J. Neurosci.* 20:1746 (2000)]. This inhibition stops the accumulation of PERIOD and TIMELESS, and the two proteins gradually disappear over the next 12 hours. This then allows the cycle to start again with the activation of period and timeless by dCLOCK and dBMAL. In addition to the circadian transcriptional cycle, there are a number of points of post-transcriptional control [Young, *Annu. Rev. Biochem.* 67:135 (1998)]. The cytoplasmic accumulation of PER and TIM, their heterodimerization, and their subsequent nuclear translocation are critical points for progression through the circadian cycle. PER is gradually phosphorylated over time [Edery et al., *Proc. Natl. Acad. Sci. U.S.A.* 91:2260 (1994)] and this occurs at least in part as a consequence of the product of the double-time (dbi) gene which is a casein kinase I epsilon (CK1ε) homolog [Price et al., *Cell* 94:83 (1998); B. Kloss et al., *Cell* 94:97 (1998), Examples 1 and 2, above]. DBT interacts with, and phosphorylates PER, which is thought to be critical for PER turnover.

In mammals, a transcription-translation autoregulatory feedback loop also appears to form the core mechanism of the circadian clock system [King and Takahashi, *Annu. Rev. Neurosci.* 23:713 (2000)]. Similar to that seen in Drosophila, CLOCK and BMAL are positive elements that act upstream of the mPer1 gene to activate its transcription [Gekakis et al., *Science* 280:1564 (1998)]. While the core set of four elements (PER, TIM, CLOCK and BMAL) are conserved, there are a number of differences. As described above, there are three Period genes in mammals, and all three express circadian rhythms of gene expression in the SCN, but are differentially regulated by light [Takumi et al., *Genes Cells* 3:167 (1998); Zylka et al., *Neuron* 20:1103 (1998); Takumi et al., *EMBO J.* 17:4753 (1998); Shigeyoshi et al., *Cell* 91:1043 (1997)]. Regulation of mammalian Timeless also differs from that seen in Drosophila [Zylka et al., *Neuron* 21:1115 (1998); Koike et al., *FEBS Lett.* 441:427 (1998); Hastings et al., *J. Neurosci.* 19:RC11 (1999)]. Perhaps the most interesting difference is the role of the mammalian Cryptochrome genes, mCry1 and mCry2, which are essential for the expression of circadian behavioral rhythms [van der Horst et al., *Nature* 398: 627 (1999); Vitatema et al., *Proc. Natl. Acad. Sci. USA.* 96:12114 (1999)] and which play a major role in the negative feedback regulation of mPer1 and mPer2 [Vitatema et al., *Proc. Natl. Acad. Sci. U.S.A.* 96:12114 (1999); Griffin Jr. et al., *Science* 286:768 (1999); Kume et al., *Cell* 98:193 (1999); Okamura et al., *Science* 286:2531(1999)]. Thus, in mammals there are at least eight different genes that are thought to play a role in the circadian clock system of mice (Clock, Bmal1, mPer1, mPer2, mPer3, mTim, mCry1 and mCry2). The positive elements (CLOCK and BMAL) are highly conserved, yet the negative elements (PERs, TIM, CRYs) are more diverse leading to a more complex feedback loop than that seen in Drosophila. Despite this remarkable progress in the identification of molecular components of the mammalian circadian clock, our understanding of how these components interact and the nature of their kinetic and dynamic properties remain largely undefined.

The Hamster tau Mutation: In 1988, Ralph and Menaker [Vitatema et al., *Proc. Natl. Acad. Sci. U.S.A.* 96:12114 (1999)] discovered a circadian period mutation in a routine laboratory shipment of Syrian hamsters (*Mesocricetus auratus*). Genetic analysis revealed a semidominant mode of transmission for this spontaneous mutation, named tau. As assayed by wheel-running locomotor activity in constant darkness, the free-running rhythm is about 24 hours in wild-type animals, 22 hours in tau heterozygotes, and just 20 hours in homozygous mutant animals. The importance of tau to the understanding of the mammalian circadian system cannot be overstated. At a time when studies of circadian mutations in invertebrate organisms were laying the foundations for our current molecular genetic dissection of the circadian system, the tau mutation provided a much-needed resource for behavioral, physiological and cellular studies of mammalian rhythms. Over the next decade, critical experiments utilizing the tau mutation would: (i) establish that the suprachiasmatic nucleus (SCN) determines circadian period at the organismal level in mammals [Ralph et al., *Science* 247:975 (1990).]; (ii) demonstrate that a diffusable signal from the SCN can drive circadian rhythms in the animal [Silver et al., *Nature* 382:810 (1996)]; and (iii) demonstrate the existence of SCN-independent circadian oscillators in the retina [Tosini and Menaker, *Science* 272:419 (1996)].

Unfortunately, the paucity of genetic resources available in the Syrian hamster has presented a formidable barrier to the identification and molecular analysis of mutants in this organism. Thus, heretofore the gene(s) involved in the tau phenotype has not been identified.

Materials and Methods

Hamsters: Wild-type M70 outbred hamsters were obtained from the National Institutes of Health (National Center for Research Resources, Genetic Resource Section, Bethesda, Md.). Wild-type males of the outbred M70 strain were mated with outbred female Lak:LVG(Syr) hamsters homozygous for the tau mutation. Siblings of the $F_1$ generation were intercrossed to produce 237 $F_2$ progeny. These animals are derived from founders captured near Aleppo, Syria and returned to the U.S. in 1971 by Dr. Michael Murphy [Murphy, *Am. Zool.* 11: 632 (1971); *Suprachiasmatic Nucleus: The Mind's Clock*, Klein et al., eds., Oxford University Press, New York, (1991)]. Hamsters of the outbred strain Lak:LVG(Syr), homozygous for the tau mutation, were obtained from a colony maintained by Dr. Michael Menaker at the University of Virginia (Charlottesville, Va.). Animals were bred at Northwestern University (Evanston, Ill.) by crossing female homozygous tau Lak:LVG(Syr) hamsters with wild-type male M70 animals to produce the $F_1$ generation. Six pairs of parental animals gave rise to separate 3-generation pedigrees. $F_1$ siblings were intercrossed to produce the $F_2$ generation consisting of 237 progeny. All animal care and use was in accordance with Northwestern University guidelines.

Genetically Directed Representational Difference Analysis (GDRDA): To create genomic representations or amplicons, equal amounts of DNA from 15 $F_2$ homozygous wild-type and 15 $F_2$ homozygous tau animals from the same family were pooled into tester and driver samples, respectively. Pooled DNA was digested with BamHI, phenol/chloroform extracted and amplified as described [Lisitsyn et al., *Nature Genet.* 6: 57 (1994); Lisitsyn and Wigler, *Science* 259:946 (1993)]. Following three rounds of RDA, products from the third round were separated by agarose gel electrophoresis, excised from the gel and cloned into the BamHI site of a plasmid vector (pBluescript II KS-, Stratagene). Southern blotting was performed by digesting with BamHI, DNA samples of the individual animals comprising the tester and driver pools. DNA was separated on 0.7% agarose gels and transferred to nylon membranes (GeneScreen Plus, NEN Life Science Products). Hybridization of individual radiolabeled RDA products to blots was performed at 65° C. in aqueous hybridization solution using standard protocols [*Current Protocols in Molecular Biology*, Ausubel et al., eds., Wiley, New York, (1993)]. Blots were exposed to phosphor screens and to X-OMAT AR film at −80° C. DNA was digested with BamHI and separated on a 0.7% agarose gel. Following transfer to nylon membrane, the blot was hybridized with a $^{32}$P-labeled probe, e.g., the $^{32}$P-labeled RDA-750 probe identified below.

Determination of locomotor activity: At approximately 2–3 months of age, hamsters were individually housed in cages equipped with running wheels within ventilated, light-tight chambers with timer-controlled lighting. Locomotor activity was recorded continuously by a PC computer data acquisition system (Chronobiology Kit, Stanford Software Systems). Animals were maintained on a light-dark cycle for at least one week [14 hours light, 10 hours dark (LD 14:10)] to assess the phase of their locomotor activity with respect to the LD cycle. For transfer to constant darkness (DD), lights were discontinued for a period of at least 3 weeks during which the free-running period of locomotor activity was measured. Steady-state period estimates were determined using a 10-day interval in which circadian period was stable during exposure to DD. Period estimates were calculated with a PC-based analysis program (Chronobiology Kit, Stanford Software Systems) using a $\chi^2$ periodogram [Sokolove and Bushell, *J. Theoret. Biol.* 72:131 (1978)].

Large-insert Lambda Clones: Large-insert lambda clones of approximately 12 kb and 20 kb containing the RDA-650 and RDA-750 products, respectively, were obtained by screening a commercially-available Syrian hamster genomic library (lambda DASH II genomic library, Stratagene #945900). Standard library screening protocols were used [Ausubel et al., eds., *Current Protocols in Molecular Biology*, Wiley, New York, (1993)]. CsCl-purified clones were prepared and partially sequenced from both ends by primer walking from T7 and T3 bacteriophage promoter sites. A microsatellite sequence, termed SSR2, consisting of the mixed repeat, $(CA)_{19}(CG)_{10}$, was identified in the RDA-750 lambda genomic clone by sequencing. PCR primers flanking the microsatellite were designed to test for polymorphism:
F 5'-GTGCAGTTGAGGAAGATATCTG-3', (SEQ ID NO:20),
R 5'-CAGTACTAGCAGTTGAATCAAGG-3' (SEQ ID NO:21).
Analysis of products on 7% denaturing polyacrylamide gels using methods modified from Dietrich et al. [*Genetics* 131:423 (1992)] revealed a product of approximately 230 bp in tau homozygous animals and of about 225 bp in homozygous wild-type animals.

Search for polymorphisms in hamster orthologs of genes that map to the region of conserved synteny in mouse and human: Primers were designed to amplify products of 2 kb or less using a standard 50 µl PCR reaction as follows: 1×GeneAmp PCR buffer (Perkin Elmer), 1.5 mM MgCl$_2$, 50 pmol of each primer, 200 µM dNTPs, 100 ng genomic DNA (M70 and tau parental samples), 1 M betaine (Sigma #B-2629) and 2.5 units AmpliTaq DNA polymerase (Perkin Elmer). A "hot start" reaction profile of 30 cycles of 95° C. for 1 min, 53° C. for 1 min and 72° C. for 2.5 min was used followed by a final extension at 72° C. for 10 min. Products were resolved on 1% agarose gels. Those reactions resulting in products in the expected size range were analyzed further by agarose gel electrophoresis, temperature modulated heteroduplex HPLC (WAVE DNA Fragment Analysis System, Transgenomic) or denaturing polyacrylamide gel electrophoresis as described herein. Linkage analysis was performed with the program Map Manager QTb28 [Manly and Olson, *Mamm. Genome* 10:327 (1999)].

A single nucleotide polymorphism was identified in the Mb gene (myoglobin) by sequencing an intronic PCR product. New primers were designed to amplify a product of approximately 350 bp containing the polymorphism:
F 5'-CAGAGGGTGCCCTTGACTTCCACC-3', (SEQ ID NO:22),
R 5'-TGGAGGTAGGTGGCCGCCGCTAAA-3' (SEQ ID NO:23).
Products were analyzed by temperature modulated heteroduplex HPLC according to manufacturer's protocols (Transgenomic).

A polymorphism in the Cacng2 gene (calcium channel, voltage-dependent, gamma subunit 2, stargazer) was identified using the following primers:
F 5'-CCCTGGCGCGCTGTGGAAGCCATC-3', (SEQ ID NO:24),
R 5'-ATTCCACTACTAATATAATGGATATATGT-3',(SEQ ID NO:25).
An allele of about 310 bp was amplified in tau homozygous animals and an allele of about 320 bp was amplified in homozygous wild-type animals. These products were resolved on 7% denaturing PAGE gels using protocols modified from Dietrich et al. [*Genetics,* 131:423 (1992)].

A polymorphism in the gene Cyp11b2 (aldosterone synthase) was identified using the following primers:
F 5'-GCATGCATGCACCAGTGTACATTC-3', (SEQ ID NO:26),
R 5'-GACCACTTACAACATGTACAAACCACAGCC-3', (SEQ ID NO:27).
Agarose gel analysis revealed an allele of approximately 1 kb in tau homozygous animals and an allele of 1.7 kb in homozygous wild-type animals.

A polymorphism in the Ela1 gene (elastase) was identified using the following primers:
F 5'-GGAAAGTCCTGGGTACTGTGTC-3', (SEQ ID NO:28),
R 5'-GTTCGCTTCCCTGGTCCTGTAT-3', (SEQ ID NO:29).
Agarose gel analysis revealed an allele of approximately 730 bp in the tau homozygous animals and an allele of about 760 bp in the homozygous wild-type animals.

Amplification of the Hamster Sequence That Corresponds to the Human CK1ϵ: Total RNA was isolated from SCN tissue pooled by genotype (8 homozygous tau samples and 8 homozygous wild-type samples). RNA (~200 ng) was reverse transcribed using random hexamers according to manufacturer's protocols (SuperScript Preamplification System, Life Technologies). Following reverse transcription, cDNA was amplified by PCR using primers designed to the human CK1ϵ cDNA sequence (GenBank accession #L37043) containing the initiation and termination codons in the forward and reverse primers, respectively:
F 5'-TCACTTCCCGAGATGGTCAAATGGCACACT-3', (SEQ ID NO:30),
R 5'-GGGAGCGGGTCCTTCGGAGATATCTACCTG-3 ', (SEQ ID NO:31).
A single product of about 1.3 kb was observed in homozygous tau and wild-type samples. PCR products were purified on spin columns (S-400 HR columns, Amersham Pharmacia) and sequenced directly. To obtain the complete coding region of hamster CK1ϵ, all available human and mouse 5'- and 3'-read CK1ϵ EST sequence data from GenBank were aligned. Primers were designed upstream of the ATG start codon and downstream of the TGA stop codon to amplify the entire hamster coding region. The primers used were as follows:
F 5'-GCCCCGGCGAATCCTCTGGCATC-3', (SEQ ID NO:32),

R 5'-TGAAGACACTAAGCAAACACTGGTC-3', (SEQ ID NO:33)

PCR products were purified and sequenced as described herein.

The amplification by PCR of a smaller region around the mutation in all animals from the hamster cross was performed as follows: PCR primers were designed around the CK1εpoint mutation in tau homozygous animals such that a product of approximately 160 bp was amplified:

F 5'-GATAACTTTCTCATGGGCTTGG-3', (SEQ ID NO:34),

R 5'-GGGTGTTGATGGAGGCATAG-3', (SEQ ID NO:35).

PCR products were digested for 2 hours at 60° C. directly in PCR reaction buffer without purification, using the restriction enzyme BstAPI (New England Biolabs). The point mutation in tau animals results in the creation of a BstAPI restriction site. Agarose gel analysis revealed an undigested product of approximately 160 bp in wild-type homozygous animals and a digested product of about 137 bp in tau homozygous animals.

Automated DNA Sequencing: Automated DNA sequencing was performed using dyedeoxy sequencing reactions (Dye Terminator Sequencing Ready Reaction AmpliTaq kit, Applied Biosystems) resolved on an ABI 377XL DNA sequencer. Sequence data were analyzed using the SEQUENCHER software package (ver. 3.0, Gene Codes). Nucleotide and protein homology comparisons were performed using BLAST algorithm searches of NCBI databases.

Mapping CK1ε in Mouse: To map CK1ε in mouse, a 160 bp segment of the mouse ortholog was PCR-amplified in the strains, C57BL/6J and BALB/cJ, using the PCR primers that were designed around the CK1ε point mutation in tau homozygous animals such that a product of approximately 160 bp was amplified:

F 5'-GATAACTTTCTCATGGGCTTGG-3', (SEQ ID NO:36),

R 5'-GGGTGTTGATGGAGGCATAG-3', (SEQ ID NO:37).

PCR products were digested for 2 hours at 60° C. directly in PCR reaction buffer without purification, using the restriction enzyme BstAPI (New England Biolabs). The point mutation in tau animals results in the creation of a BstAPI restriction site. Agarose gel analysis revealed an undigested product of approximately 160 bp in wild-type homozygous animals and a digested product of about 137 bp in tau homozygous animals. By sequencing, a restriction fragment length polymorphism was identified for the enzyme, HpaII between the two mouse strains. The C57BL/6J PCR product contains two restriction sites for this enzyme resulting in fragments of 108, 32 and 20 bp upon digestion. The BALB/cJ product contains only one HpaII site and, following digestion, results in fragments of 108 and 52 bp. CK1ε relative to the following mouse SSLP markers was mapped using 46 animals from a (BALB/cJ×C57BL/6J)$F_2$ intercross: D15Mit28 (4/88), D15Mit146 (3/90), and D15Mit35 (14/78). The number of recombinations from CK1ε out of the total number of meioses tested is given in parentheses following the marker name. The linkage analysis was performed with the program Map Manager QTb28 [Manly, and Olson, *Mamm. Genome* 10:327 (1999)]. All reactions were separated on 7% PAGE gels using protocols modified from Dietrich et al.[*Genetics* 131:423 (1992)].

Southern Blots. Southern blotting was performed by digesting with BamHI, DNA samples of the individual animals comprising the tester and driver pools. DNA was separated on 0.7% agarose gels and transferred to nylon membranes (GeneScreen Plus, NEN Life Science Products).

Hybridization of individual radiolabeled RDA products to blots was performed at 65 ° C. in aqueous hybridization solution using standard protocols [*Current Protocols in Molecular Biology*, Ausubel et al., eds., Wiley, New York, (1993)]. Blots were exposed to phosphor screens and to X-OMAT AR film at −80° C.

Northern analysis of total RNA: Total RNA was extracted from hamster tissue that had previously been soaked in storage solution (RNAlater, Ambion) and frozen. The extraction was performed using TRIZOL reagent according to the manufacturer's instructions (Life Technologies). Approximately 15 μg of total RNA was loaded per lane and separated on 1% agarose denaturing formaldehyde gels. RNA was transferred to nylon membranes (GeneScreen Plus, NEN Life Science Products). As probe, a 1.35 kb BglII/SalI fragment from the pET-30 LIC wild-type hamster CK1ε construct was labeled with [$\alpha^{32}$P]dCTP, 6000 Ci/mmol, using a commercial kit (Ready-To-Go DNA Labelling Beads, Amersham Pharmacia). Homozygous tau and wild-type full-length cDNA products were cloned into the pET-30 LIC T7 expression vector according to the manufacturer's protocols (Novagen). Expression of recombinant hamster tau and wild-type CK1ε was achieved by growing 250 ml cultures of BL21 (DE3)pLysS *E. coli* hosts containing expression constructs for 16–18 hours at 23° C. in LB medium supplemented with 34 μg/ml chloramphenicol and 30 μg/ml kanamycin. During incubation, cultures were shaken at 150 rpm. Expression of recombinant protein in the soluble phase was higher in the absence of IPTG; the addition of IPTG decreased the yield of soluble recombinant protein. Expressed protein from the soluble phase was purified by means of a 15 amino acid N-terminal S•Tag fusion using S-protein agarose according to the manufacturer's protocols (Novagen). S-protein agarose bound with expressed protein was resuspended in 30 mM HEPES, pH 7.5 and stored at 4° C. for up to one week. Protein concentrations were determined by taking several 5 μl aliquots of bound S-protein agarose, boiling each for 3 minutes to release protein, cooling on ice, spinning briefly in a microcentrifuge and then removing supernatants for analysis using a colorimetric protein assay according to the manufacturer's instructions (DC Protein Assay, Bio-Rad). Hybridization was performed at 42° C. for 16 hours according to manufacturer's protocols (NEN Life Science Products). Blots were normalized by probing with a 905 bp mouse GAPDH probe (DECAtemplate-GAPDH-mouse, Ambion) using the same hybridization conditions described above. Following hybridization, blots were exposed to phosphor screens overnight.

Immunoblots: Western analysis of CK1ε protein expressed in hamster brain tissue was performed as follows. Approximately 2 mg each of wild-type and tau mutant hypothalamic tissue was homogenized separately in 50 μl aliquots of extraction buffer [100 mM KCl, 20 mM HEPES (pH 7.5), 5% glycerol, 2.5 mM EDTA, 2.5 mM NaF, 5 mM DTT, 0.1% Triton X-100, 0.5 mM PMSF, 10 μg/ml aprotinin, 10 μg/ml leupeptin, 2 μg/ml pepstatin A]. Homogenates were centrifuged at 12,000×g for 15 min a portion (~20 μg/lane) of the resulting supernatant was separated on 12% SDS-PAGE gels. Following electrophoresis, proteins were transferred to PVDF (Immobilon-P, Millipore) membranes. A human CK1ε-specific antibody (Transduction Laboratories, #C40520) was used to probe the tissue blots and signal was detected with a chemifluorescent system according to the manufacturer's protocols (ECF Western blotting reagent, Amersham Pharmacia). Tissues were collected at two zeitgeber (ZT) times (13.5 and 23.5). Blots were probed with antibody to human CK1ε.

Preparation, expression and isolation of recombinant hamster tau and wild-type CK1ε: Homozygous tau and wild-type full-length cDNA products were cloned into the pET-30 LIC T7 expression vector according to the manufacturer's protocols (Novagen). Expression of recombinant hamster tau and wild-type CK1ε was achieved by growing 250 ml cultures of BL21(DE3)pLysS *E. coli* hosts containing expression constructs for 16–18 hours at 23° C. in LB medium supplemented with 34 μg/ml chloramphenicol and 30 μg/ml kanamycin. During incubation, cultures were shaken at 150 rpm. Expression of recombinant protein in the soluble phase was higher in the absence of IPTG. The addition of IPTG decreased the yield of soluble recombinant protein. Expressed protein from the soluble phase was purified by means of a 15 amino acid N-terminal S•Tag fusion using S-protein agarose according to the manufacturer's protocols (Novagen). S-protein agarose bound with expressed protein was resuspended in 30 mM HEPES, pH 7.5 and stored at 4° C. for up to one week. Protein concentrations were determined by taking several 5 μl aliquots of bound S-protein agarose, boiling each for 3 min to release protein, cooling on ice, spinning briefly in a microcentrifuge and then removing supernatants for analysis using a colorimetric protein assay according to the manufacturer's instructions (DC Protein Assay, Bio-Rad).

Western blot analysis of homozygous wild-type and tau mutant recombinant CK1ε enzymes: The enzymes were separated on 10% SDS-PAGE gels and transferred to either nitrocellulose (Optitran BA-S 85, Schleicher and Schuell) or PVDF (Immobilon-P, Millipore) membranes by semidry electroblotting methods (Trans-Blot SD, Bio-Rad). Recombinant proteins immobilized on nitrocellulose were detected using an antibody directed against the 15 amino acid N-terminal S•Tag fusion according to manufacturer's instructions (S•Tag HRP LumiBlot kit, Novagen). Recombinant hamster proteins immobilized on PVDF were detected using a commercially-available human CK1ε-specific antibody (Santa Cruz Biotechnology #sc-6471) and a chemifluorescent detection system according to the manufacturer's protocols (ECF Western blotting reagent, Amersham Pharmacia).

Comparison of the kinase activity of the wild-type and tau mutant CK1ε: Kinase assays were performed for 5 min at 37° C. in 20 μl of reaction mix [30 mM HEPES (pH 7.5), 7 mM MgCl$_2$, 0.5 mM DTT, 200 μM ATP, 50 μg/ml BSA, i0.5 mg/ml protein substrate, 5 μCi of [γ-$^{32}$P]ATP, 3000 Ci/mmol (NEN Research Products)] with approximately 200–300 ng recombinant CK1ε as prepared above. As indicated above, the reactions were performed either without a protein substrate or alternatively using either dephosphorylated α-casein (Sigma #C-8032) or phosvitin (Sigma #P-1253) as the substrate. Initiation of the reaction occurred upon addition of the enzyme. Reactions were incubated at 37° C. for 5 min. and then terminated by the addition of 2×sample buffer [100 mM DTT, 2% SDS, 80 mM Tris-HCl (pH 6.8), 0.0006% bromophenol blue, 15% glycerol] followed by boiling for 2 minutes. Products were resolved on 12% SDS-polyacrylamide gels. $^{32}$P incorporation was detected in dried gels with a Storm Phosphorimager (Molecular Dynamics) and by exposure of X-OMAT AR (Kodak) film at –80° C.

Dephosphorylation of the mutant and wild-type enzyme: Protein phosphatase 2B (PP2B; calcineurin) treatment of recombinant enzyme was performed as follows. Approximately 160 ng of each of mutant and wild-type recombinant enzyme was added to a reaction mixture consisting of 30 mM HEPES (pH 7.5), 7 mM MgCl$_2$, 0.5 mM DTT, 200 μM ATP, 50 μg/ml BSA, 4 units calmodulin (Sigma #P-2277), 100 μM CaCl$_2$, 6 units PP2B (Sigma #C-1907). Control reactions without PP2B were also performed. Dephosphorylation reactions were incubated at 37° C. for 15 min. To stop the reactions, 500 μM cypermethrin (BIOMOL #PR-100) and 1 mM EGTA were added.

Kinetic Analysis: Kinase reactions for kinetic analyses were performed as described above except that substrate concentrations were varied in a total reaction volume of 50 μl with 80 ng of recombinant enzyme. Time course experiments showed that the kinase assay was linear for up to 20 min. A 5 min incubation time was used for the kinetic analyses. Phosvitin substrate concentrations were as follows: 0, 2.5, 10, 15, 20, 30, 50, and 100 μM. Duplicate reactions were performed for each concentration. Products were separated on 12% SDS-PAGE gels. Gels were dried before detecting signal with a Storm Phosphorimager (Molecular Dynamics) and by exposure of X-OMAT AR film at –80° C. $^{32}$P incorporation was quantified by excising the phosvitin phosphorylation bands from the dried gels and counting gel pieces using liquid scintillation methods. The apparent $K_m$ and $V_{max}$ values for both the wild-type and the tau mutant enzymes were determined by nonlinear least squares regression of the untransformed kinetic data. Kinetic analysis was performed using nonlinear least squares regression of the kinetic equation [y=($V_{max}$* X)/($K_m$+X)] directly onto the untransformed data via PC statistical software (NCSS 97, Number Cruncher Statistical Systems). Data were plotted graphically as a double-reciprocal plot.

Per binding studies: For binding assays, mPER1 and mPER2 were synthesized from cDNAs cloned in plasmids by coupled in vitro transcription/translation reactions using $^{35}$S-methionine in a total reaction volume of 50 μl (TNT T7 Coupled Reticulocyte Lysate System, Promega). Recombinant CK1ε was purified from *E. coli* by capture on S-agarose beads as described above. To reduce non-specific binding, 20 μl of in vitro-translated product was mixed with 50 μl of plain S-agarose beads in HND buffer (20 mM HEPES, pH 7.5, 100 mM KCl, 10% glycerol, 0.4% NP40, 1 mM DTT) with 5% BSA. This mixture was incubated at room temperature with shaking for 1 hour. Following incubation, the mixture was centrifuged at 2500 rpm for 5 minutes and the resulting supernatant was divided into two equal aliquots. Aliquots were mixed with either S-agarose beads bound with recombinant wild-type protein or tau recombinant protein and incubated for 30 minutes at room temperature with shaking. Mixtures were washed with the following: 1×HND buffer with 5% BSA, 1×HND buffer with 1% BSA, 3×HND buffer alone and 1×HND buffer with 200 mM KCl. After washes, proteins were mixed with 2×sample buffer, separated on 12% SDS-PAGE gels, and exposed first to phosphor screens and then to X-OMAT AR film at –80° C. Recombinant CK1ε was purified from *E. coli* by capture to S-agarose beads. Beads containing wild-type or tau mutant enzyme were then incubated with in vitro-translated, $^{35}$S-methionine-labeled substrate (mPER1 or mPER2) and washed extensively.

Affinity kinase assays: Affinity kinase assays were performed by mixing 20 μl of an in vitro translation reaction (TNT T7 Coupled Reticulocyte Lysate System, Promega) containing $^{35}$S-methionine-labeled mPER1 or mPER2 with 20 μl S-protein agarose-bound recombinant CK1ε (either the tau mutant or the wild-type CK1ε). Unlabeled amino acid concentrations were increased by using 1×solutions of both methionine and cysteine free amino acid solutions. This resulted in 1 mM methionine, 1 mM cysteine and 2 mM for all other amino acids in the TNT reaction. Affinity reactions were washed at least 4 times with 1×S-protein agarose bind/wash buffer (Novagen). Half of the bound beads were then added to a kinase reaction as described above, but without α-casein or phosvitin, and incubated at 37° C. for 5 minutes. 2×loading buffer was added to the affinity and kinase reactions which were then boiled for 2 minutes prior to gel loading. Reactions were separated on 12% SDS-PAGE gels, dried and exposed to phosphor screens. Following exposure to detect both the $^{35}$S and $^{32}$P signals, dried gels were covered with two layers of exposed X-OMAT AR film to block the $^{35}$S signal. Covered gels were exposed to phosphor screens for 36 hours.

In situ hybridization: Hamsters were sacrificed by decapitation following 8 cycles in DD. Brains were quickly removed, frozen on dry ice and stored at −80° C. until sectioning. Coronal sections of 20 μm in thickness were cut and mounted on gelatin-coated slides. Sections were air dried, fixed in 5% paraformaldehyde and hybridized for 18 hours at 47° C. in a solution of 50% formamide, 300 mM NaCl, 10 mM Tris-HCl (pH 8.0), 1 mM EDTA, 1×Denhardt's solution, 10% dextran sulfate, 10 mM DTT, 750 μg/ml yeast tRNA and 5×10$^7$ cpm/ml $^{33}$P-labeled riboprobe. A plasmid containing ~1 kb fragment of the hamster Per1 gene cloned in the ApaI and HindIII sites was used to synthesize antisense and sense riboprobe using an in vitro transcription kit (MaxiScript, Ambion). For riboprobe to hamster CK1ε, the following primers were used to amplify a 157 bp fragment by RT-PCR corresponding to the C-terminal region of CK1ε which diverges in sequence from other CK1 isoforms:
(SEQ ID NO:38):
F 5'-TAATACGACTCACTATAGGGAGACTTGTCTG TGAGGCTGAAATCC-3',
(SEQ ID NO:39):
R 5'-AATTACCCTCACTAAAGGGAGAATCCAGCA AGCTGGCAATACT-3'.

The above primers contain the T7 and T3 promoter sites to produce antisense and sense probes from the resulting PCR product using an in vitro trascription kit. Hybridization, washing and data analyses were performed as described elsewhere [Sangoram et al., Neuron 21:1101 (1998)].

Single-letter abbreviations for the amino acid residues are as follows: A, Ala; C, Cys; D, Asp; E, Glu; F, Phe; G, Gly; H, His; I, Ile; K, Lys; L, Leu; M, Met; N, Asn; P, Pro; Q, Gin; R, Arg; S, Ser; T, Thr; V, Val; W, Trp; and Y, Tyr.

Results

The development of new techniques in genome analysis provided a possibility for the study of mutations in the map-poor hamster and suggested that a molecular genetic analysis of tau might be feasible [Lander, Nature Genet. 4:5 (1993); Okuizumi et al., Mamm. Genome 8:121 (1997)]. One technique, Genetically Directed Representational Difference Analysis (GDRDA), was chosen for the attempt [Lisitsyn et al., Nature Genet. 6:57 (1994); Lisitsyn, Trends Genet. 11:303 (1995)]. Through this method, polymorphic markers tightly linked to a monogenic trait can be identified without prior knowledge of the chromosomal location of that trait or the availability of genetic maps for the organism. GDRDA begins by separating progeny from an experimental cross into two groups based on phenotype such that the groups differ, on average, only at the locus under study. For example, homozygous wild-type and homozygous mutant animals could be identified and their DNA samples pooled into "tester" and "driver" groups, respectively. Next, genomic representations or "amplicons" are prepared for both pools via a whole genome polymerase chain reaction (PCR) technique. By applying the subtractive hybridization and kinetic enrichment properties of representational difference analysis, of which GDRDA is a modification, it is possible to isolate small DNA fragments that are enriched in the pooled tester samples and absent in the driver pools. Thus, polymorphic DNA markers linked to the trait of interest can be identified directly. The hamster tau mutation presents an ideal case for GDRDA because it is a single-gene mutation with well-characterized phenotypic effects that can be assayed accurately in a large number of animals.

Genetic Mapping of the tau Mutation: The overall strategy in the molecular genetic analysis of the tau mutation was first to construct a genetic cross with which markers linked to the mutation could be identified by applying GDRDA. Because finding markers linked to a mutation is, by itself, of limited value in searching for a gene in an organism lacking a genetic map, regions of conserved synteny between hamster and both mouse and human were identified. Then the focus could be on any obvious positional candidate loci in the hamster by referring to the dense genetic maps available in mouse and human around the region of conserved synteny. Candidate genes could then be narrowed by meiotic mapping and identification of mutations.

Figure 15A:
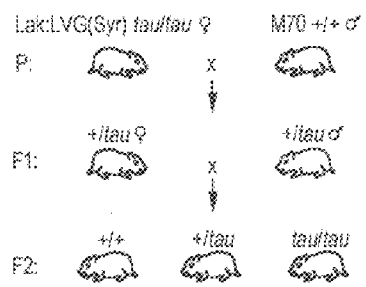
FIGS. 15A–15C show the cross-breeding of the tau/tau hamster with a wild type hamster and a tabulation of the results obtained.
Figure 15B:
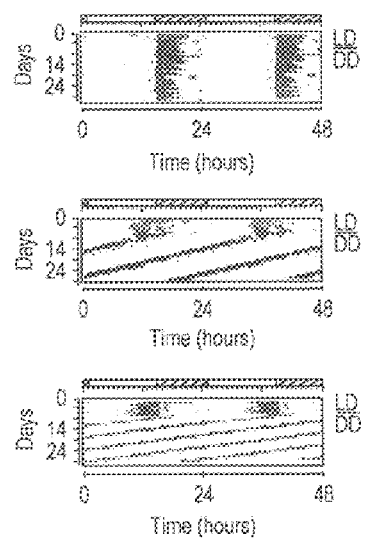
Figure 15C:
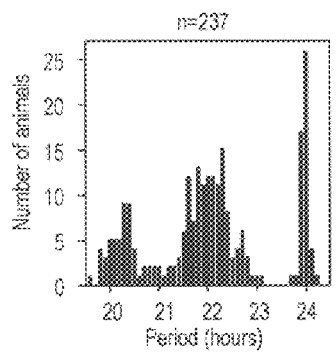

One initial problem was to create an appropriate Syrian hamster cross that would both segregate the tau mutation and provide the necessary heterozygosity for mapping purposes. The latter requirement was more problematic as all commonly available inbred and outbred hamster strains originate from just three littermates born to a female captured in the wild in 1930 [Adler, Nature 162:256 (1948); Suprachiasmatic Nucleus: The Mind's Clock, Klein, et al., Oxford University Press, New York, (1991)]. This includes the hamster which carries the tau mutation. Consequently, the level of heterozygosity in most strains of laboratory hamsters is quite low and, as such, a strain derived from a different founder population was sought. The M70 outbred strain maintained at the National Institutes of Health originates from a colony of wild-caught hamsters returned to the U.S. from Syria in 1971 by Dr. Michael Murphy [[Murphy, Am. Zool. 11: 632 (1971); Suprachiasmatic Nucleus: The Mind's Clock, Klein et al., eds., Oxford University Press, New York, (1991)]. M70 animals were obtained and wild-type males of this strain were crossed with Lak:LVG:(Syr) homozygous tau female animals to produce the $F_1$ generation. $F_1$ siblings were then interbred to produce an $F_2$ intercross consisting of 237 progeny (FIG. 15A) as described in the materials and methods above. Circadian phenotype of all animals was assessed by monitoring wheel-running locomotor activity in constant conditions (FIG. 15B) as described in the Materials and Methods above. As expected, the distribution of the period phenotype among the $F_2$ progeny exhibits the classical Mendelian ratio of 1:2:1 (+/+, n=50:+/tau, n=131:tau/tau, n=56) indicative of semi-dominance (FIG. 15C).

To identify markers linked to the tau mutation via GDRDA, 15 homozygous wild-type and 15 homozygous tau $F_2$ animals were selected from a single three-generation pedigree. DNA was extracted from each $F_2$ animal and an equal amount of genomic DNA from each was pooled into a tester (wild-type) fraction and a driver (homozygous tau) fraction. The animals were euthanized and internal organs were removed and frozen at −80° C. Genomic DNA was prepared from liver, spleen and kidney tissue using protocols adapted from standard methods [Current Protocols in Molecular Biology, Ausubel et al., eds., Wiley, New York, (1993)].

Figure 16B:
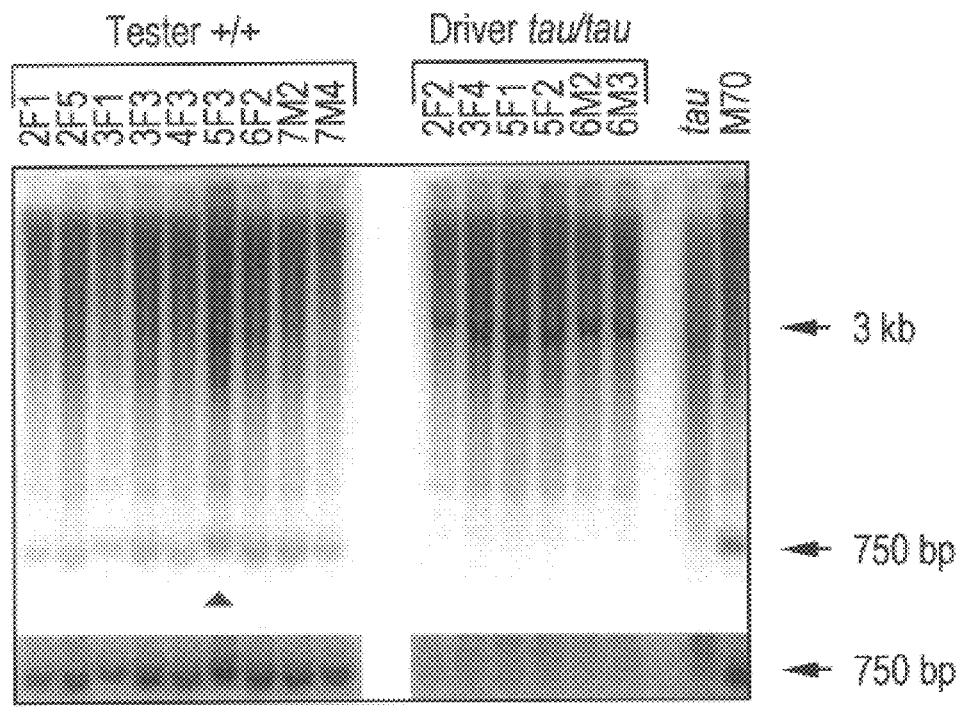
Figure 16C:
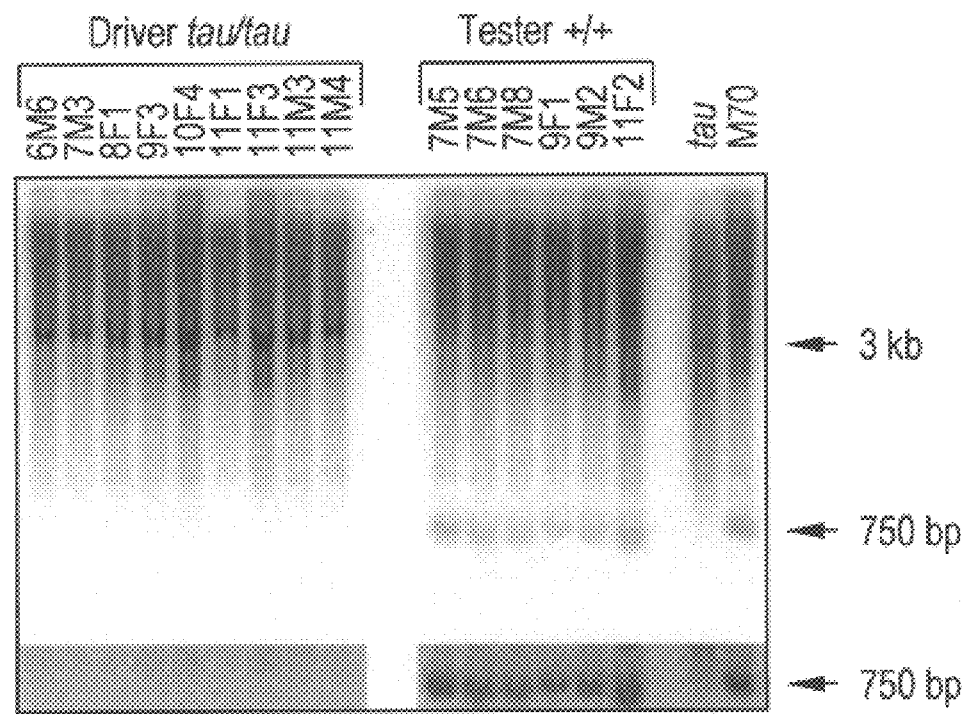

GDRDA was performed essentially as described [Lisitsyn et al., Nature Genet. 6:57 (1994); Lisitsyn and. Wigler, Science 259:946 (1993); Lisitsyn and Wigler, *Methods Enzymol.* 254:291 (1995) and see Materials and Methods above]. Results of three rounds of subtraction, extension and amplification yielded several distinct products by ethidium bromide staining (FIG. 16A). Five RDA products from the third round were cloned in a plasmid vector and tested for linkage to the mutation by hybridizing each to Southern blots of the individual $F_2$ DNA samples digested with BamHI as described above in the Materials and Methods. Two products, RDA-650 and RDA-750, were polymorphic for the hamster cross. The RDA-750 probe revealed a 750 base pair (bp) product in the tester DNA samples and ~3 kilobase (kb) fragment in the driver samples (FIGS. 16B–16C). Similarly, the RDA-650 probe detected a 650 bp product in the tester DNA samples and a ~7 kb fragment in the driver samples. The larger fragments present in the driver samples were not amplified in the original PCR reactions producing the genomic representations. Because the 15 tester and 15 driver animals are the progeny of an $F_2$ intercross, the 30 DNA samples represent a total of 60 meiotic events. Both probes revealed a recombination event in the same animal (FIG. 16B, triangle). As a result, the recombination fraction (θ) for both markers with respect to the tester and driver animals is 1/60 which is equivalent to a genetic distance of approximately 1.7 centimorgans (cM) from the tau mutation [Ott, *Analysis of Human Genetic Linkage,* Johns Hopkins Univ. Press, Baltimore, Md., revised edition, (1991)].

To obtain genomic clones containing the GDRDA products, a large-insert hamster lambda genomic DNA library was screened using the RDA-650 and 750 products as probes as described in the Materials and Methods above. The resulting clones were then scanned by direct DNA sequencing. In the course of sequencing the RDA-750 lambda genomic clone, two microsatellite repeats were found (see above in Material and Methods). PCR reactions using primers flanking the repeats were performed to test for polymorphism in our hamster cross. One of the microsatellites, termed SSR2, was polymorphic and thus simplified the genotyping of the RDA-750 product as it was no longer necessary to type the cross by Southern blotting. Typing of SSR2 in the entire $F_2$ cross placed this marker (SSR2=RDA-750) 5.6 cM from the tau locus. The hamster SSR2 primer pair was also tested for amplification of DNA from various mouse strains. The presence of a single amplification product was identified only in the SPRET/Ei strain. This facilitated the mapping of SSR2 in mouse using the Jackson Laboratory BSB [(C57BL/6J×*M. spreius*)×C57BL/6J)] panel [Rowe et al., *Mamm. Genome* 5:253 (1994); see Material and Methods, above]. In this way, SSR2 was mapped to a region of mouse chromosome 15. The locus amplified in mouse by the hamster SSR2 primers has been assigned the mouse locus symbol, D15Nwu1, in the Mouse Genome Database (MGD).

The sequence data from the RDA-650 lambda genomic clone were analyzed by BLAST and revealed a highly significant sequence similarity in the GenBank database to the mouse gene, Celsr1 which, like SSR2, maps to mouse chromosome 15. Two regions of SSR2 sequence aligned to Celsr1 cDNA for a total of 325 bp with a nucleotide identity of 92%. Given these findings, the tau locus appeared to reside in a region with conserved synteny to mouse chromosome 15. To test this hypothesis, a search was initiated for polymorphisms in hamster orthologs of genes that, in mouse, map to chromosome 15. After analyzing the mouse genetic map around the Celsr1 locus, several genes were chosen that were distal and proximal to Celsr1 for which mouse genomic sequence exists in the GenBank database.

This facilitated the design of primers to 5'- and 3'-untranslated sequences and to sequences flanking introns of PCR-amplifiable size (see Material and Methods, above).

The polymorphism search was limited to untranslated and intronic sequences as the likelihood of discovering differences in those regions is greater [Lyons et al., *Nature Genet.* 15:47 (1997); Andersson et al., *Mamm. Genoine* 7:717 (1996)]. Using this approach, polymorphisms were identified in a number of genes, all of which were found to be linked to tau in hamster and thus define a segment of conserved synteny between the two species. These genes are myoglobin (Mb), calcium channel, voltage-dependent, gamma subunit 2 (Cacng2, stargazer) [Letts et al., *Genomics* 43: 62 (1997); Letts et al., *Nature Genet.* 19:340 (1998)], aldosterone synthase (Cyp11b2) and elastase (Ela1). Several simple sequence length polymorphism (SSLP) mouse markers from chromosome 15 were also tested to determine if any would amplify hamster DNA. Mouse primer pairs that produced discrete products in hamster were then tested further for their ability to reveal polymorphisms and linkage to the tau locus. One SSLP marker, D15Mit146, out of more than 50 markers tested, was both polymorphic in the hamster cross and cosegregated with tau. The mouse SSLP marker, D15Mit146, was used to amplify a hamster polymorphism of approximately 200 bp in tau homozygous animals and approximately 205 bp in wild-type homozygotes. Products were separated on 7% denaturing PAGE gels using protocols modified from Dietrich et al. [*Genetics,* 131:423 (1992)]. Hence, using reciprocal mapping techniques between hamster and mouse genomes, a region of conserved synteny between the two species spanning a genetic distance of approximately 15 cM was established (FIG. 17A). Linkage analysis was performed with the program Map Manager QTb28 [Manly and Olson, *Mamm. Genome* 10:327 (1999)]. Based on mouse and human comparative maps, the region of conserved synteny spans segments of human chromosomes 8, 12 and 22 (FIG. 17A).

Identification of a Candidate Locus: Mapping to human chromosome 22 in the region of conserved synteny is the gene, casein kinase I epsilon (CK1ε) (FIG. 17A), a strong candidate for the tau locus given the degree of homology between it and the Drosophila circadian gene, dbt [Kloss et al., *Cell* 94: 97 (1998); Fish et al., *J. Biol. Chem.* 270:14875 (1995)]. While CK1ε had not yet been mapped in mouse, the human map position was known and the complete cDNA and genomic DNA sequences exist in the GenBank database [Fish et al., *J. Biol. Chem.* 270:14875 (1995)]. Consequently, primers were designed based on the human cDNA sequence to amplify the corresponding hamster sequence by RT-PCR (see Material and Methods, above). Separate reactions were performed using wild-type and tau total RNA samples isolated from pooled SCN tissue. A single product of approximately 1.3 kb was amplified from each pool, then sequenced and identified as the coding region of the hamster CK1ε ortholog.

Comparison of the sequence between wild-type and tau animals revealed a single base-pair substitution (FIGS. 17B–17C). This C→T transition results in the creation of a recognition sequence for the restriction enzyme BstAPI in the tau product only. This allowed the amplification by PCR of a smaller region around the mutation in all animals from the hamster cross and then the testing of each product for digestion with BstAPI (see Material and Methods, above). In doing so, no recombinants were found out of 474 meioses (FIGS. 17A–17C). Furthermore, conceptual translation of the tau CK1ε cDNA revealed that the mutation causes an amino acid substitution at residue #178 (FIG. 18). This arginine to cysteine mutation occurs at one of three residues forming an anion binding site as revealed by three-dimensional crystallographic analyses of *S. pombe* casein kinase-1 (Cki1) [Xu et al., *EMBO J*. 14:015 (1995)] and of mammalian casein kinase Iδ (CK1δ), a CK1 family member that is 97.5% similar to CK1ε throughout the kinase domain [Fish et al., *J. Biol. Chem.* 270:14875 (1995); Gross and Anderson, *Cell. Signal.* 10:699 (1998); Longenecker et al., *J. Mol. Biol.* 257:618 (1996); Longenecker et al., *Acta Crystallogr.* D54:473 (1998)]. Alignment of various CK1 isoforms from diverse species reveals that residue #178 is highly conserved (FIG. 18).

To confirm that CK1ε maps to chromosome 15 in mouse, a portion of the coding region of the mouse ortholog was amplified and a polymorphism between the C57BL/6J and BALB/cJ mouse strains was identified. As a result, CK1ε was mapped to chromosome 15 between SSLP markers D15Mit146 (proximal) and D15Mit35 (distal) using a (BALB/cJ×C57BL/6J)F$_2$ intercross. This finding validated the comparative mapping results and established that the ortholog of the hamster candidate locus mapped to chromosome 15 in mouse.

Northern analysis of CK1ε from total RNA of hamster brains collected at two circadian times (subjective day and subjective night; CT6 and CT18) reveals no obvious differences in size or abundance between the wild-type and tau transcripts (FIG. 19A). The tissue distribution of hamster CK1ε is similar to that reported in human with highest mRNA levels in brain, retina, skeletal muscle and lung (FIG. 19B) [Fish et al., *J. Biol. Chem.* 270:14875 (1995)]. As in human CK1ε, there is a major transcript of 2.7 kb, as well as minor transcripts at 1.6, 3.7 and 5.9 kb. Analysis of CK1ε protein expression in tissue extracts from brain shows a 48 kilodalton (kDa) protein expressed both in wild-type and tau mutant hamsters by Western analysis (FIG. 19C). Finally, experiments using in situ hybridization with probe to the C-terminal region of hamster CK1ε cDNA shows a low-level hybridization signal in the SCN of both genotypes at all circadian times examined when compared to controls using sense probe.

Taken together, the genetic linkage analysis and the amino acid substitution with attendant protein structural implications, indicate that tau represents a mutant allele of the hamster CK1ε gene. Given these results, wild-type and tau mutant CK1ε were expressed for functional studies.

Protein Expression and Functional Analysis: Hamster wild-type and tau full-length CK1ε cDNAs were cloned in a T7 bacterial expression vector containing sequence producing S•Tag and His-Tag fusions at the N-terminus of the recombinant protein as described in the Materials and Methods, above. As described for the human CK1ε protein product, the hamster recombinant protein has a molecular mass of approximately 48 kDa. To test the activity of the expressed proteins, in vitro casein kinase assays were first performed using two well-described exogenous CK1 substrates, phosvitin and α-casein. These assays revealed differences in phosphate transfer efficiency with the tau product exhibiting lower activity as compared to wild-type enzyme. Autophosphorylation of both the tau mutant and wild-type CK1ε occurred (FIG. 20A).

Immunoblot analysis of the recombinant tau and wild-type hamster CK1ε using an antibody to the S•Tag fusion sequence revealed a consistent difference in the mobility of the expressed proteins in denaturing gel electrophoresis suggesting a difference in autophosphorylation state (FIG. 20B). There are two major bands present for wild-type CK1ε which appear to reflect completely phosphorylated (~60 kDa) and unphosphorylated (~48 kDa) forms of the enzyme. In contrast, the tau mutant enzyme exhibits at least three phosphorylation states (the third form shows intermediate mobility). Following treatment with protein phosphatase 2B (PP2B; calcineurin), the mobility of the slower migrating species is changed and the wild-type and tau enzymes comigrate as a doublet of about 48 and 50 kDa. When probed with an antibody to part of the COOH-terminus of human CK1ε, only a single band is evident for both tau and wild-type products, identifying only the unphosphorylated species. PP2B treatment had no effect on the bands identified by the antibody. The recognition of only unphosphorylated CK1ε with this C-terminal antibody is consistent with the predominance of autophosphorylation sites in the C-terminal region of CK1ε as reported by Virshup and colleagues [ Gietzen and Virshup, *J. Biol. Chem.* 274:32063 (1999); see FIG. 18 for sites of autophosphorylation].

Because bacterially-expressed CK1ε is highly phosphorylated [Cegielska et al., *J. Biol. Chem.* 273:1357 (1998)], the recombinant wild-type and tau enzymes were treated with PP2B prior to the kinase reaction to determine if dephosphorylation enhances activity (FIG. 19C). Clearly, PP2B dephosphorylates wild-type and tau enzymes as judged by protein mobility shifts. Furthermore, phosphatase treatment enhances wild-type activity, and to a lesser degree, tau enzyme activity using either phosvitin or α-casein as substrate. Autophosphorylation is common among the various isoforms of CK1 and is implicated in the inhibition of CK1 activity [Gross and Anderson, *Cell. Signal.* 10:699 (1998); Gietzen and Virshup, *J. Biol. Chem.* 274:32063 (1999);Graves and Roach, *J. Biol. Chem.* 270:21689 (1995)]. Autoinhibition is presumably reversed by intracellular phosphatases [Rivers et al., *J. Biol. Chem.* 273:15980 (1998)]. The present PP2B results are consistent with an inhibitory role of autophosphorylation. While both the wild-type and tau hamster CK1ε enzymes exhibit autophosphorylation, this inhibitory mechanism does not account for the attenuated activity evident in the tau mutant. Following dephosphorylation by PP2B, the diminished activity of the tau enzyme relative to the wild-type enzyme persists.

To elucidate the mechanism of attenuation in kinase activity of the tau CK1ε enzyme, kinetic analyses of wild-type and tau enzyme using phosvitin as substrate were performed next. First, a time course experiment was performed to demonstrate that enzyme activity was linear under the conditions of the in vitro kinase assay. Next, using a range of substrate concentrations (0–100 μM) an initial estimate of the Michaelis constant ($K_m$) for both enzymes was obtained. Finally, two independent experiments were performed, each using duplicate reactions for each substrate concentration (FIG. 20D). The apparent $K_m$ and maximal velocity ($V_{max}$) values for the wild-type and tau CK1ε enzymes were determined by nonlinear least squares regression of the untransformed kinetic data. The data are represented graphically as a double-reciprocal plot (FIG. 20E). While there is a modest difference in the apparent $K_m$ between tau and wild-type enzymes, the most obvious difference is evident in the $V_{max}$ values. The lower $V_{max}$ value for the tau enzyme provides a kinetic validation of the SDS-PAGE analysis of the kinase results demonstrating diminished tau activity relative to the wild-type enzyme. That it binds substrate with a greater affinity than the wild-type enzyme is suggested by the slightly lower $K_m$ value obtained for the mutant. This is plausible considering that the tau mutation affects a site involved in substrate recognition. Should the mutant kinase be unable to release the substrate because of a conformational change in the substrate-binding region, both a lower enzyme velocity and $K_m$ might be expected.

Interaction of Hamster CK1ε with Mammalian PERIOD Proteins: To determine if there is a detectable interaction between the mutant and wild-type hamster CK1ε forms and the mammalian PERIOD proteins, in vitro binding assays were performed with the expressed proteins (FIG. 21A). CK1ε interacted with the PERIOD proteins; however, there was no consistent difference between mutant and wild-type CK1ε forms in this assay: both bound mPER1 and mPER2. This is similar to the finding that, in Drosophila, DBT interacts with PER [Kloss et al., Cell 94: 97 (1998), Examples 1 and 2 above].

To determine if the hamster CK1ε forms could phosphorylate mPER1 and mPER2, an affinity kinase assay was developed for in vitro-translated protein substrates (FIG. 21B; see Materials and Methods, above). Because both mutant and wild-type CK1ε could interact with PER1 and PER2, CK1ε was used as an affinity reagent to bind PER substrate. Kinase assays were then performed to determine if the bound substrate was phosphorylated by the recombinant enzymes. Indeed, this affinity kinase assay demonstrates that CK1ε phosphorylates mammalian PERIOD proteins. However, there is a clear attenuation in phosphorylation of mPER1 and mPER2 by the tau mutant enzyme as compared to wild type CK1ε. Thus, while tau and wild-type hamster CK1ε can both bind mPER1 and mPER2, the tau mutant enzyme phosphorylates PER less efficiently.

In vivo effects of the tau mutation: Given the in vitro results using mPER1 and mPER2 as substrates for hamster CK1ε, the corresponding in vivo effect was examined. More particularly, the effect of the tau mutation on the expression of Per1 mRNA in the SCN was examined (FIG. 22A). Antisense hamster Per1 riboprobe was hybridized to coronal sections of brains taken every three circadian hours for a total of eight timepoints in both tau and wild-type animals maintained in constant darkness. When normalized for circadian time, it is evident that there is a reduction in peak values of Per1 mRNA abundance in tau animals as compared to wild-type (FIGS. 22A–22B). Two-way analysis of variance reveals significant effects for circadian time, genotype and the interaction between time and genotype. Post-hoc analysis shows that tau mutant animals have lower Per1 mRNA levels at circadian times 0, 3, 6 and 12 (FIG. 22B). When these results are displayed in real time, it is clear that Per1 mRNA levels rise approximately 2 hours earlier and decline about 4 hours earlier in homozygous tau hamsters relative to wild-type hamsters (FIG. 22C). The decline of Per1 mRNA levels is an indicator of the negative feedback phase of the circadian cycle, and this phase of the cycle occurs about 4 hours earlier in tau mutants, largely accounting for the shortened circadian period expressed by these animals.

Discussion

The casein kinase I family is a unique group of serine/threonine protein kinases sharing more than 50% identity to one another through the catalytic domain [Gross and Anderson, Cell. Signal. 10:699 (1998)]. In mammals, seven different isoforms have been identified. Unlike most other protein kinases, CK1 members occur as bilobal monomeric proteins. The smaller amino-terminal lobe contains the nucleotide-binding domain, whereas the larger carboxyl-terminal lobe contains the phosphate transfer components. A cleft between the two lobes participates in substrate binding. The lobes are linked by a small hinge region that may determine the conformation of the cleft. All members share a near-consensus SV40 T antigen putative nuclear localization signal (NLS). Based on the three-dimensional crystallographic analyses of yeast CK11 and mammalian CK1δ, there exists in this family an anion binding site formed by three residues which are conserved throughout the CK1 family [Xu et al., EMBO J. 14:1015 (1995); Longenecker et al., J. Mol. Biol. 257:618 (1996)]. This motif resides in a region of the carboxyl-terminal lobe where it has ready substrate access and presumably recognizes the phosphate ester of the substrate. The CK1 family seems to have broad substrate specificity and an almost ubiquitous subcellular localization [Gross and Anderson, Cell. Signal. 10:699 (1998)]. The reported consensus phosphorylation sequence is S/T/Y(P)$X_{1-2}$S/T (SEQ ID NO:40), where S/T/Y(P) is any phosphorylated serine, threonine or tyrosine residue and X is any amino acid [Gross and Anderson, Cell. Signal. 10:699 (1998); Flotow et al., J. Biol. Chem. 265:14264 (1990); Flotow and Roach, J. Biol. Chem. 266;3724 (1991); Meggio et al., FEBS Lett. 283:303 (1991); Songyang et al., Mol. Cell. Biol. 16:6486 (1996)]. Given, however, the many isoforms of CK1, it is possible that substrate specificity differs among them. Indeed, even the reported consensus phosphorylation sequence is not always obeyed as CK1δ and CK1ε have been shown to autophosphorylate at non-consensus sites on their carboxyl-terminal tails [Gietzen and Virshup, J. Biol. Chem. 274:32063 (1999); Graves and Roach, J. Biol. Chem. 270:21689 (1995)]. Furthermore, CK1 seems not to require prior phosphorylation of some substrates [Marin et al., Eur. J. Biochem. 223:647 (1994)].

Although members of the casein kinase I family were among the first of the serine/threonine kinases to be identified, it has been difficult to demonstrate specific biological roles for the various isoforms [Gross and Anderson, Cell. Signal. 10:699 (1998)]. Recently, however, progress in understanding the roles of the CK1ε isoform in vivo has been made. The Drosophila gene, double-time (dbt) was identified in a chemical mutagenesis screen for aberrant circadian phenotype. It is regarded as the fly ortholog of mammalian CK1ε owing to its high degree of homology (92%) to this gene throughout the kinase domain [Kloss et al., Cell 94:97 (1998); Fish,et al., J. Biol. Chem. 270:4875 (1995); Examples 1 and 2, above]. In addition, studies of dbt provided the first in vivo demonstration of a specific CK1ε function in a biological system. In this case, DBT most likely functions to phosphorylate the Drosophila circadian clock component, PER. Evidence from the dbt null allele suggests that this phosphorylation event is essential for PER for turnover. PER levels are constitutively high in dbt null mutants and circadian rhythms of behavior and per/tim gene expression are abolished. Two additional missense mutations in dbt give rise to short and long circadian period phenotypes [Price et al., Cell 94:83 (1998); Kloss et al., Cell 94:97 (1998); Examples 1 and 2, above]. These two point mutations occur at conserved residues in the kinase domain (see FIG. 18).

Although eight different genes have been identified and proposed to be core components of the circadian clock in mammals [King and Takahashi, Annu. Rev. Neurosci. 23:713 (2000)], direct evidence for a role of CK1ε in the regulation of circadian rhythms in mammals has not previously been available. The results disclosed herein provide strong genetic evidence that CK1ε is a component of the mammalian circadian clock by demonstrating that the tau mutation is an allele of hamster CK1ε. Genetic linkage analysis reveals that CK1ε is tightly linked to the tau locus, with no recombinations occurring out of 474 meioses. Molecular analysis demonstrates that a single DNA base-pair substitution produces a missense mutation in an amino acid residue involved in the recognition of substrate by CK1ε. Arginine #178 of the wild-type enzyme is replaced by cysteine in the tau mutant, and kinetic analyses of wild-type and mutant enzymes demonstrate that the tau mutation causes an eight-fold reduction in the $V_{max}$ of CK1ε. In addition, a direct interaction between CK1ε and the mammalian PERIOD proteins in vitro are demonstrated. Using mPER1 and mPER2 as substrates, a striking reduction in kinase activity of the mutant form of CK1ε was found. Finally, the expression of Per1 mRNA levels in the SCN of tau mutant hamsters was found be lower and the decline in Per1 mRNA levels found to occur about four hours earlier in tau mutants. Both of these changes in Per1 gene expression are consistent with an enhanced negative feedback signal in tau mutants. Taken together, these results provide yet another example of the striking conservation of circadian mechanisms in Drosophila and mammals.

How might the Arg178Cys tau mutation exert it effects on CK1ε? The amino acid substitution occurs within a phosphate recognition site formed by three residues, Arg #178, Gly #215 and Lys #224. The corresponding amino acids (Arg #183, Gly #220, Lys #229) in the three-dimensional structure of S. pombe Cki1 are illustrated in FIG. 23A. In FIGS. 23A–23B the ribbon diagram and the catalytic surface model of CK1ε were created using coordinates from the published crystallographic data of Schizosaccharomyces pombe casein kinase-1 [Xu et al., EMBO J. 14:1015 (1995)]. The modeling program, MOLSCRIPT, was used to create the ribbon diagram [Kraulis, J. Appl. Cryst. 24:946 (1991)]. The catalytic surface model was created with the program, GRASP [Nicholls et al., Proteins 11:281 (1991)]. In yeast, residues forming the anion binding motif, Arg #183, Gly #220 and Lys #229, correspond to hamster CK1ε residues, Arg #178, Gly #215 and Lys #224, respectively (FIG. 18).

In the wild-type protein, the basic side groups of arginine and lysine, which are positively charged at physiological pH, are necessary for the formation of the anion binding characteristics of this site. Replacing Arg #178 with cysteine and its small hydrophobic sulfhydryl group could modify the ability of the site to bind the negatively charged phosphate ester of the substrate. This provides one possible explanation for our observation of attenuated kinase activity in the tau mutant protein.

In addition to a possible effect on substrate binding, Arg #178 is also located on the L-9D loop of the yeast Cki1 protein (FIG. 18) which is thought to be involved in activation of catalytic activity in other protein kinases [Xu et al., EMBO J. 14:1015 (1995); Morgan and Bondt, Curr. Opin. Cell Biol. 6:239 (1994); Taylor and Radzio-Andzelm, Structure 2: 345 (1994)]. FIG. 23B presents a close-up view of the catalytic region of the S. pombe yeast Cki1 enzyme. In this surface view, residues forming the catalytic loop are colored red (see FIG. 18 for the amino acids in CK1ε corresponding to the catalytic loop). To the left, Mg:ATP is shown bound in the cleft region and, to the right, Arg #183 can be seen adjacent to the catalytic loop. The proximity of Arg #183 to the catalytic region of CK11 and its location on the L-9D loop strongly suggest that the Arg178Cys tau mutation could disrupt catalytic activity.

Another possible effect of the tau mutation on CK1ε could be exerted on the process of nuclear localization. In addition to its role in the anion binding site, Lys #224 is one of six residues forming a putative nuclear localization signal (TKRQKY). Should a conformational change or interaction occur at this site as a consequence of the Arg178Cys mutation, nuclear localization of the protein could be modified. An alteration in the ability of CK1ε to translocate to the nucleus could affect its role in posttranslational modification of circadian system components such as PER.

How does the attenuation in hamster CK1ε activity observed in tau homozygotes give rise to a shortened circadian period? A model of the molecular components of the circadian clock in mammals is illustrated in FIG. 24. As described in the introduction, the basis of the circadian mechanism is a transcription-translation-based negative autoregulatory feedback loop [King and Takahashi, Annu. Rev. Neurosci. 23: 713 (2000)]. The shortened period likely arises as a result of the earlier repression of the CLOCK-BMAL1 complex in tau animals relative to wild-type animals. This is a unified explanation for both the observed reduction in, and earlier appearance of, Per1 message in tau homozygotes in vivo as revealed by in situ hybridization. If the mutant CK1ε in homozygous tau animals is less active, and if PER is one of its major substrates in circadian pacemaker cells, then it is reasonable to suggest that the reduced activity of mutant CK1ε results in hypophosphorylated PER. Evidence from Drosophila suggests that phosphorylation of PER by the casein kinase, DBT, is necessary for its turnover [Price et al., Cell 94: 83 (1998)]. Assuming this is also true of PER in mammalian cells, then hypophosphorylated PER would be expected to accumulate more rapidly in tau animals. This faster rate of PER accumulation in homozygous tau animals relative to wild-type animals could then lead to an earlier transport of PER into the nucleus causing repression of CLOCK-BMAL1.

It is important to note that although the negative feedback signal in tau mutants occurs earlier than that seen in wild type (FIG. 22C), the duration of this negative feedback is not prolonged as one might expect if PER turnover was slower. Indeed, it appears that the duration of negative feedback (as inferred from the trough of the Per1 mRNA in the SCN) is comparable in wild-type and tau mutant hamsters. This suggests that the turnover of the entire negative feedback complex (FIG. 24), which may be composed of six proteins (PER1, PER2, PER3, TIM, CRY1, CRY2), may be not be strongly influenced by the tau mutant CK1ε.

While the time course of the decline of the PER proteins is a major determinant of the derepression of CLOCK-BMAL1 transactivation, this might not be the case in tau homozygotes. A plausible scenario in tau mutants is that, because of the greater availability of PER, derepression of CLOCK-BMAL1 activity might now depend more on the time course of degradation of the PERs' dimerization partners. With the turnover of their partners, monomeric forms of PER would remain until they are eventually phosphorylated and targeted for degradation by the less active mutant CK1ε or some other mechanism, or until they could again dimerize with a partner. This would not be the case in wild-type animals where a significant delay is imposed by translation both of PER and its partners in addition to the time required for potential posttranslational modifications, such as phosphorylation of PER by CK1ε. In tau animals, the hypophosphorylated PER would be available for immediate nuclear translocation upon dimerization and would, therefore, result in an earlier inactivation of CLOCK-BMAL1 relative to wild-type animals. While it is clear from the results presented herein that some PER is phosphorylated by the mutant CK1ε, these levels should be lower with respect to wild-type animals. This limited amount of phosphorylated PER would be targeted for degradation, yet the synthesis of Per message during CLOCK-BMAL1-mediated transcription would make up for any loss and effectively maintain a pool of monomeric PER. Thus, a delicate balance must be achieved between the enhancement of the negative feedback signal leading to an earlier repression of CLOCK-BMAL1 on the one hand, and the maintenance of a normal turnover time of the inhibitory complex on the other hand, in order to shorten the period length of the circadian cycle in tau mutants. In contrast, if the turnover of the inhibitory complex was prolonged, perhaps by very strong hypomorphic CK1ε alleles, then one could explain the period lengthening effects of the dbt$^L$ allele in Drosophila. Finally, none of these interpretations considers the possibility of CK1ε acting as a regulator of nuclear entry of PER. Because CK1ε and the PER proteins strongly interact, CK1ε (or its mutant alleles) could exert an additional level of control by either retaining PER in the cytoplasm or promoting its nuclear localization. As already mentioned, because the tau mutation could influence Lys #224, which is located within the nuclear localization signal for CK1ε, such a mechanism is feasible.

In addition to the role of CK1ε in controlling circadian rhythms, recent work in both Drosophila and vertebrates has demonstrated significant effects of CK1ε on developmental pathways. The original dbt null allele causes pupal lethality [Price et al., *Cell* 94:83 (1998); Examples 1 and 2, above], and interestingly, shortly following the identification of dbt, the Drosophila gene, discs overgrown (dco), was cloned and shown to be identical to dbt [Zilian et al., *Development* 126:5409 (1999).] Several strong mutant alleles of dco give rise to aberrations in cell survival and growth control in imaginal discs. Specifically, it seems that dco is necessary for the inhibition of apoptosis during cell proliferation and for the arrest of growth when a disc has reached the proper size. Consequently, dco may be involved in two different signal transduction pathways. At this time, however, it is not known what substrates dco acts upon in these pathways. Similar to its role in Drosophila development, recent evidence suggests that CK1ε is a conserved component in the Wnt signaling cascade [Peters et al., *Nature* 401:345 (1999); Sakanaka et al., *Proc. Natl. Acad. Sci. U.S.A.* 96:12548 (1999)]. This pathway is crucial for the development of both invertebrates and vertebrates.

In *C. elegans,* Wnt signaling controls embryonic polarity, while in *X. laevis,* it controls the formation of the dorsal axis.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

It is further to be understood that all base sizes or amino acid sizes, and all molecular weight or molecular mass values, given for nucleic acids or polypeptides are approximate, and are provided for description.

Various publications are cited herein, the disclosures of which are incorporated by reference in their entireties.

What is claimed is:

1. A DOUBLETIME protein comprising an amino acid sequence selected from the group consisting of:
   (a) SEQ ID NO:2;
   (b) SEQ ID NO:2 comprising a conservative substitution;
   (c) amino acid residues 1–292 of SEQ ID NO:2; and
   (d) amino acid residues 1–292 of SEQ ID NO:2 comprising a conservative substitution.

2. The protein of claim 1 obtained from Drosophila.

3. A DOUBLETIME protein comprising an amino acid sequence selected from the group consisting of:
   (a) a fragment of SEQ ID NO:2 exhibiting protein kinase activity; and
   (b) a fragment of SEQ ID NO:2 capable of binding a period (PER) protein.

4. The protein of claim 3 obtained from Drosophila.

5. A fusion protein comprising a polypeptide of interest fused to a polypeptide selected form the group consisting of:
   (a) an amino acid sequence comprising SEQ ID NO:2;
   (b) a fragment of the sequence of (a) exhibiting protein kinase activity; and
   (c) a proteolytic fragment of the sequence of (a) comprising six or more amino acid residues.

6. The fusion protein of claim 5, wherein SEQ ID NO:2 is obtained from Drosophila.

* * * * *

SEQUENCE LISTING

<160> NUMBER OF SEQ ID NOS: 42

<210> SEQ ID NO 1
<211> LENGTH: 1520
<212> TYPE: DNA
<213> ORGANISM: Drosophila melanogaster

<400> SEQUENCE: 1

```
aaatccgagg aaccgaggag tccgaactct accacacaga aacccacaga aacagacgta      60
acaaaatgga gctgcgcgtg ggtaacaaat atcgcctggg ccgcaagata ggatcgggat     120
cgttcggcga catctacctg ggcaccacga tcaacactgg cgaggaggtg gccatcaagc     180
tggagtgcat ccgcaccaaa cacccccagc tgcacatcga gtcaaagttc tacaagacga     240
tgcagggtgg cataggcata ccccgcataa tctggtgcgg cagcgagggc gactacaatg     300
tgatggtgat ggagctactc ggaccctcgc tggaggacct cttcaacttt tgttcacgcc     360
gcttttcgtt gaagacggtt ctgctgctgg cggaccagat gatctcccgc atcgattaca     420
tacactcgcg ggacttcatc catcgcgaca tcaagccgga taacttcctc atgggtcttg     480
gcaagaaggg caacctggtg tacatcattg actttggcct ggccaagaaa ttccgcgatg     540
cccggtcgct gaagcacatt ccctatcggg aaaacaagaa cctcacgggc actgcccgct     600
atgcctccat caacacacat ttgggcattg agcaatcgcg tcgtgacgac ctggagtccc     660
tgggttacgt cctaatgtac ttcaatctgg gcgccttgcc ctggcagggc ttaaaggcag     720
ccaacaagag gcaaaagtac gagaggatct cggagaagaa gctgtccacc tcgattgtgg     780
tgctgtgcaa gggcttcccc agcgagttcg tcaactatct gaacttctgt cgccagatgc     840
```

-continued

```
atttcgacca gcgtcccgat tactgccacc tgcgcaaact cttccgcaac ttgttccacc    900
gtttgggctt cacttacgac tatgtgtttg actggaacct gcttaagttt ggcggacctc    960
gcaatcccca ggcgattcag caggcgcagg acggagcgga cggccaggcg ggtcatgatg   1020
cggtggccgc agcagcggcg gtggcagcag cggcagccgc ctcctcgcat caacagcagc   1080
agcacaaggt caatgcggcg ctgggtggcg aggaggcag tcgtgcgcaa cagcaactcc    1140
agggcggcca aacgctggcg atgctgggcg gcaatggagg cggtaacggc agccaactga   1200
tcggcggcaa cggactcaac atggacgatt cgatggcggc caccaactcg tcgagaccgc   1260
cgtacgacac gccggagcgt cggccctcga tacggatgcg gcagggaggc ggtggtggcg   1320
gcggtggagt gggcgtaggc ggtatgcaga gcggcggagg gggcggtggc gtggggaacg   1380
ccaaataata ttttatcgtt taggttgcga cgctggacac gacacagtag acaaacaaca   1440
acagaactca acaaactata catgtagtat atatagttat atatacctaa tatatataat   1500
acttgcttta tatatgcggt                                                1520
```

<210> SEQ ID NO 2
<211> LENGTH: 440
<212> TYPE: PRT
<213> ORGANISM: Drosophila melanogaster

<400> SEQUENCE: 2

```
Met Glu Leu Arg Val Gly Asn Lys Tyr Arg Leu Gly Arg Lys Ile Gly
  1               5                  10                  15

Ser Gly Ser Phe Gly Asp Ile Tyr Leu Gly Thr Thr Ile Asn Thr Gly
                 20                  25                  30

Glu Glu Val Ala Ile Lys Leu Glu Cys Ile Arg Thr Lys His Pro Gln
             35                  40                  45

Leu His Ile Glu Ser Lys Phe Tyr Lys Thr Met Gln Gly Gly Ile Gly
         50                  55                  60

Ile Pro Arg Ile Ile Trp Cys Gly Ser Glu Gly Asp Tyr Asn Val Met
 65                  70                  75                  80

Val Met Glu Leu Leu Gly Pro Ser Leu Glu Asp Leu Phe Asn Phe Cys
                 85                  90                  95

Ser Arg Arg Phe Ser Leu Lys Thr Val Leu Leu Leu Ala Asp Gln Met
            100                 105                 110

Ile Ser Arg Ile Asp Tyr Ile His Ser Arg Asp Phe Ile His Arg Asp
        115                 120                 125

Ile Lys Pro Asp Asn Phe Leu Met Gly Leu Gly Lys Lys Gly Asn Leu
    130                 135                 140

Val Tyr Ile Ile Asp Phe Gly Leu Ala Lys Lys Phe Arg Asp Ala Arg
145                 150                 155                 160

Ser Leu Lys His Ile Pro Tyr Arg Glu Asn Lys Asn Leu Thr Gly Thr
                165                 170                 175

Ala Arg Tyr Ala Ser Ile Asn Thr His Leu Gly Ile Glu Gln Ser Arg
            180                 185                 190

Arg Asp Asp Leu Glu Ser Leu Gly Tyr Val Leu Met Tyr Phe Asn Leu
        195                 200                 205

Gly Ala Leu Pro Trp Gln Gly Leu Lys Ala Ala Asn Lys Arg Gln Lys
    210                 215                 220

Tyr Glu Arg Ile Ser Glu Lys Lys Leu Ser Thr Ser Ile Val Val Leu
225                 230                 235                 240

Cys Lys Gly Phe Pro Ser Glu Phe Val Asn Tyr Leu Asn Phe Cys Arg
                245                 250                 255
```

```
Gln Met His Phe Asp Gln Arg Pro Asp Tyr Cys His Leu Arg Lys Leu
            260                 265                 270

Phe Arg Asn Leu Phe His Arg Leu Gly Phe Thr Tyr Asp Tyr Val Phe
            275                 280                 285

Asp Trp Asn Leu Leu Lys Phe Gly Pro Arg Asn Pro Gln Ala Ile
            290                 295             300

Gln Gln Ala Gln Asp Ala Asp Gly Gln Ala Gly His Asp Ala Val
305                 310                 315                 320

Ala Ala Ala Ala Ala Val Ala Ala Ala Ala Ala Ser Ser His Gln
            325                 330                 335

Gln Gln Gln His Lys Val Asn Ala Ala Leu Gly Gly Gly Gly Ser
            340                 345                 350

Arg Ala Gln Gln Gln Leu Gln Gly Gly Gln Thr Leu Ala Met Leu Gly
            355                 360                 365

Gly Asn Gly Gly Gly Asn Gly Ser Gln Leu Ile Gly Asn Gly Leu
            370                 375                 380

Asn Met Asp Asp Ser Met Ala Ala Thr Asn Ser Ser Arg Pro Pro Tyr
385                 390                 395                 400

Asp Thr Pro Glu Arg Arg Pro Ser Ile Arg Met Arg Gln Gly Gly Gly
                405                 410                 415

Gly Gly Gly Gly Gly Val Gly Val Gly Gly Met Gln Ser Gly Gly Gly
            420                 425                 430

Gly Gly Gly Val Gly Asn Ala Lys
            435                 440

<210> SEQ ID NO 3
<211> LENGTH: 440
<212> TYPE: PRT
<213> ORGANISM: Drosophila melanogaster

<400> SEQUENCE: 3

Met Glu Leu Arg Val Gly Asn Lys Tyr Arg Leu Gly Arg Lys Ile Gly
1               5                   10                  15

Ser Gly Ser Phe Gly Asp Ile Tyr Leu Gly Thr Thr Ile Asn Thr Gly
                20                  25                  30

Glu Glu Val Ala Ile Lys Leu Glu Cys Ile Arg Thr Lys His Ser Gln
            35                  40                  45

Leu His Ile Glu Ser Lys Phe Tyr Lys Thr Met Gln Gly Gly Ile Gly
        50                  55                  60

Ile Pro Arg Ile Ile Trp Cys Gly Ser Glu Gly Asp Tyr Asn Val Met
65                  70                  75                  80

Val Met Glu Leu Leu Gly Pro Ser Leu Glu Asp Leu Phe Asn Phe Cys
                85                  90                  95

Ser Arg Arg Phe Ser Leu Lys Thr Val Leu Leu Leu Ala Asp Gln Met
            100                 105                 110

Ile Ser Arg Ile Asp Tyr Ile His Ser Arg Asp Phe Ile His Arg Asp
        115                 120                 125

Ile Lys Pro Asp Asn Phe Leu Met Gly Leu Gly Lys Lys Gly Asn Leu
130                 135                 140

Val Tyr Ile Ile Asp Phe Gly Leu Ala Lys Lys Phe Arg Asp Ala Arg
145                 150                 155                 160

Ser Leu Lys His Ile Pro Tyr Arg Glu Asn Lys Asn Leu Thr Gly Thr
                165                 170                 175

Ala Arg Tyr Ala Ser Ile Asn Thr His Leu Gly Ile Glu Gln Ser Arg
```

-continued

```
                180                 185                 190
Arg Asp Asp Leu Glu Ser Leu Gly Tyr Val Leu Met Tyr Phe Asn Leu
            195                 200                 205
Gly Ala Leu Pro Trp Gln Gly Leu Lys Ala Ala Asn Lys Arg Gln Lys
            210                 215                 220
Tyr Glu Arg Ile Ser Glu Lys Lys Leu Ser Thr Ser Ile Val Val Leu
225                 230                 235                 240
Cys Lys Gly Phe Pro Ser Glu Phe Val Asn Tyr Leu Asn Phe Cys Arg
                245                 250                 255
Gln Met His Phe Asp Gln Arg Pro Asp Tyr Cys His Leu Arg Lys Leu
            260                 265                 270
Phe Arg Asn Leu Phe His Arg Leu Gly Phe Thr Tyr Asp Tyr Val Phe
            275                 280                 285
Asp Trp Asn Leu Leu Lys Phe Gly Pro Arg Asn Pro Gln Ala Ile
            290                 295                 300
Gln Gln Ala Gln Asp Gly Ala Asp Gly Gln Ala Gly His Asp Ala Val
305                 310                 315                 320
Ala Ala Ala Ala Val Ala Ala Ala Ala Ser Ser His Gln
                325                 330                 335
Gln Gln Gln His Lys Val Asn Ala Ala Leu Gly Gly Gly Gly Ser
            340                 345                 350
Arg Ala Gln Gln Gln Leu Gln Gly Gln Thr Leu Ala Met Leu Gly
            355                 360                 365
Gly Asn Gly Gly Asn Gly Ser Gln Leu Ile Gly Gly Asn Gly Leu
            370                 375                 380
Asn Met Asp Asp Ser Met Ala Ala Thr Asn Ser Ser Arg Pro Pro Tyr
385                 390                 395                 400
Asp Thr Pro Glu Arg Arg Pro Ser Ile Arg Met Arg Gln Gly Gly Gly
                405                 410                 415
Gly Gly Gly Gly Gly Val Gly Val Gly Gly Met Gln Ser Gly Gly Gly
            420                 425                 430
Gly Gly Gly Val Gly Asn Ala Lys
            435                 440

<210> SEQ ID NO 4
<211> LENGTH: 440
<212> TYPE: PRT
<213> ORGANISM: Drosophila melanogaster

<400> SEQUENCE: 4

Met Glu Leu Arg Val Gly Asn Lys Tyr Arg Leu Gly Arg Lys Ile Gly
1               5                   10                  15
Ser Gly Ser Phe Gly Asp Ile Tyr Leu Gly Thr Thr Ile Asn Thr Gly
                20                  25                  30
Glu Glu Val Ala Ile Lys Leu Glu Cys Ile Arg Thr Lys His Pro Gln
            35                  40                  45
Leu His Ile Glu Ser Lys Phe Tyr Lys Thr Met Gln Gly Gly Ile Gly
        50                  55                  60
Ile Pro Arg Ile Ile Trp Cys Gly Ser Glu Gly Asp Tyr Asn Val Ile
65                  70                  75                  80
Val Met Glu Leu Leu Gly Pro Ser Leu Glu Asp Leu Phe Asn Phe Cys
                85                  90                  95
Ser Arg Arg Phe Ser Leu Lys Thr Val Leu Leu Leu Ala Asp Gln Met
            100                 105                 110
```

Ile Ser Arg Ile Asp Tyr Ile His Ser Arg Asp Phe Ile His Arg Asp
         115                 120                 125

Ile Lys Pro Asp Asn Phe Leu Met Gly Leu Gly Lys Lys Gly Asn Leu
130                 135                 140

Val Tyr Ile Ile Asp Phe Gly Leu Ala Lys Lys Phe Arg Asp Ala Arg
145                 150                 155                 160

Ser Leu Lys His Ile Pro Tyr Arg Glu Asn Lys Asn Leu Thr Gly Thr
                165                 170                 175

Ala Arg Tyr Ala Ser Ile Asn Thr His Leu Gly Ile Glu Gln Ser Arg
            180                 185                 190

Arg Asp Asp Leu Glu Ser Leu Gly Tyr Val Leu Met Tyr Phe Asn Leu
        195                 200                 205

Gly Ala Leu Pro Trp Gln Gly Leu Lys Ala Ala Asn Lys Arg Gln Lys
    210                 215                 220

Tyr Glu Arg Ile Ser Glu Lys Lys Leu Ser Thr Ser Ile Val Val Leu
225                 230                 235                 240

Cys Lys Gly Phe Pro Ser Glu Phe Val Asn Tyr Leu Asn Phe Cys Arg
                245                 250                 255

Gln Met His Phe Asp Gln Arg Pro Asp Tyr Cys His Leu Arg Lys Leu
            260                 265                 270

Phe Arg Asn Leu Phe His Arg Leu Gly Phe Thr Tyr Asp Tyr Val Phe
        275                 280                 285

Asp Trp Asn Leu Leu Lys Phe Gly Gly Pro Arg Asn Pro Gln Ala Ile
    290                 295                 300

Gln Gln Ala Gln Asp Gly Ala Asp Gly Gln Ala Gly His Asp Ala Val
305                 310                 315                 320

Ala Ala Ala Ala Val Ala Ala Ala Ala Ser Ser His Gln
                325                 330                 335

Gln Gln Gln His Lys Val Asn Ala Leu Gly Gly Gly Gly Ser
            340                 345                 350

Arg Ala Gln Gln Gln Leu Gln Gly Gln Thr Leu Ala Met Leu Gly
        355                 360                 365

Gly Asn Gly Gly Asn Gly Ser Gln Leu Ile Gly Asn Gly Leu
    370                 375                 380

Asn Met Asp Asp Ser Met Ala Thr Asn Ser Ser Arg Pro Pro Tyr
385                 390                 395                 400

Asp Thr Pro Glu Arg Arg Pro Ser Ile Arg Met Arg Gln Gly Gly Gly
                405                 410                 415

Gly Gly Gly Gly Val Gly Val Gly Gly Met Gln Ser Gly Gly Gly
            420                 425                 430

Gly Gly Gly Val Gly Asn Ala Lys
        435                 440

<210> SEQ ID NO 5
<211> LENGTH: 72
<212> TYPE: DNA
<213> ORGANISM: Drosophila melanogaster

<400> SEQUENCE: 5
ataggatcgg gatcgttcgg cgacatctac ctgggcacca cgatcaacac tggcgaggag    60
gtggccatca ag    72

<210> SEQ ID NO 6
<211> LENGTH: 24
<212> TYPE: PRT

```
<213> ORGANISM: Drosophila melanogaster

<400> SEQUENCE: 6

Ile Gly Ser Gly Ser Phe Gly Asp Ile Tyr Leu Gly Thr Thr Ile Asn
 1               5                  10                  15

Thr Gly Glu Glu Val Ala Ile Lys
            20

<210> SEQ ID NO 7
<211> LENGTH: 39
<212> TYPE: DNA
<213> ORGANISM: Drosophila melanogaster

<400> SEQUENCE: 7
ttcatccatc gcgacatcaa gccggataac ttcctcatg                        39

<210> SEQ ID NO 8
<211> LENGTH: 13
<212> TYPE: PRT
<213> ORGANISM: Drosophila melanogaster

<400> SEQUENCE: 8

Phe Ile His Arg Asp Ile Lys Pro Asp Asn Phe Leu Met
 1               5                  10

<210> SEQ ID NO 9
<211> LENGTH: 416
<212> TYPE: PRT
<213> ORGANISM: Homo sapiens

<400> SEQUENCE: 9

Met Glu Leu Arg Val Gly Asn Lys Tyr Arg Leu Gly Arg Lys Ile Gly
 1               5                  10                  15

Ser Gly Ser Phe Gly Asp Ile Tyr Leu Gly Ala Asn Ile Ala Ser Gly
            20                  25                  30

Glu Glu Val Ala Ile Lys Leu Glu Cys Val Lys Thr Lys His Pro Gln
        35                  40                  45

Leu His Ile Glu Ser Lys Phe Tyr Lys Met Met Gln Gly Gly Val Gly
    50                  55                  60

Ile Pro Ser Ile Lys Trp Cys Gly Ala Glu Gly Asp Tyr Asn Val Met
65                  70                  75                  80

Val Met Glu Leu Leu Gly Pro Ser Leu Glu Asp Leu Phe Asn Phe Cys
                85                  90                  95

Ser Arg Lys Phe Ser Leu Lys Thr Val Leu Leu Leu Ala Asp Gln Met
            100                 105                 110

Ile Ser Arg Ile Glu Tyr Ile His Ser Lys Asn Phe Ile His Arg Asp
        115                 120                 125

Val Lys Pro Asp Asn Phe Leu Met Gly Leu Gly Lys Lys Gly Asn Leu
    130                 135                 140

Val Tyr Ile Ile Asp Phe Gly Leu Ala Lys Lys Tyr Arg Asp Ala Arg
145                 150                 155                 160

Thr His Gln His Ile Pro Tyr Arg Glu Asn Lys Asn Leu Thr Gly Thr
                165                 170                 175

Ala Arg Tyr Ala Ser Ile Asn Thr His Leu Gly Ile Glu Gln Ser Arg
            180                 185                 190

Arg Asp Asp Leu Glu Ser Leu Gly Tyr Val Leu Met Tyr Phe Asn Leu
        195                 200                 205

Gly Ser Leu Pro Trp Gln Gly Leu Lys Ala Ala Thr Lys Arg Gln Lys
```

-continued

```
                210                 215                 220
Tyr Glu Arg Ile Ser Glu Lys Lys Met Ser Thr Pro Ile Glu Val Leu
225                 230                 235                 240

Cys Lys Gly Tyr Pro Ser Glu Phe Ser Thr Tyr Leu Asn Phe Cys Arg
                245                 250                 255

Ser Leu Arg Phe Asp Asp Lys Pro Asp Tyr Ser Tyr Leu Arg Gln Leu
                260                 265                 270

Phe Arg Asn Leu Phe His Arg Gln Gly Phe Ser Tyr Asp Tyr Val Phe
                275                 280                 285

Asp Trp Asn Met Leu Lys Phe Gly Ala Ala Arg Asn Pro Glu Asp Val
290                 295                 300

Asp Arg Glu Arg Glu His Glu Arg Glu Arg Met Gly Gln Leu
305                 310                 315                 320

Arg Gly Ser Ala Thr Arg Ala Leu Pro Pro Gly Pro Pro Thr Gly Ala
                325                 330                 335

Thr Ala Asn Arg Leu Arg Ser Ala Ala Glu Pro Val Ala Ser Thr Pro
                340                 345                 350

Ala Ser Arg Ile Gln Pro Ala Gly Asn Thr Ser Pro Arg Ala Ile Ser
                355                 360                 365

Arg Val Asp Arg Glu Arg Lys Val Ser Met Arg Leu His Arg Gly Ala
370                 375                 380

Pro Ala Asn Val Ser Ser Ser Asp Leu Thr Gly Arg Gln Glu Val Ser
385                 390                 395                 400

Arg Ile Pro Ala Ser Gln Thr Ser Val Pro Phe Asp His Leu Gly Lys
                405                 410                 415

<210> SEQ ID NO 10
<211> LENGTH: 319
<212> TYPE: PRT
<213> ORGANISM: Arabidopsis thaliana

<400> SEQUENCE: 10

Met Asp Leu Val Ile Gly Gly Lys Phe Lys Leu Gly Arg Lys Ile Gly
 1               5                  10                  15

Ser Gly Ser Phe Gly Glu Leu Tyr Leu Gly Ile Asn Val Gln Thr Gly
                20                  25                  30

Glu Glu Val Ala Val Lys Leu Glu Ser Val Lys Thr Lys His Pro Gln
                35                  40                  45

Leu His Tyr Glu Ser Lys Leu Tyr Met Leu Leu Gln Gly Gly Thr Gly
            50                  55                  60

Val Pro Asn Leu Lys Trp Tyr Gly Val Glu Gly Asp Tyr Asn Val Met
65                  70                  75                  80

Val Ile Asp Leu Leu Gly Pro Ser Leu Glu Asp Leu Phe Asn Tyr Cys
                85                  90                  95

Asn Arg Lys Leu Ser Leu Lys Thr Val Leu Met Leu Ala Asp Gln Leu
                100                 105                 110

Ile Asn Arg Val Glu Phe Met His Thr Arg Gly Phe Leu His Arg Asp
                115                 120                 125

Ile Lys Pro Asp Asn Phe Leu Met Gly Leu Gly Arg Lys Ala Asn Gln
                130                 135                 140

Val Tyr Ile Ile Asp Phe Gly Leu Gly Lys Lys Tyr Arg Asp Leu Gln
145                 150                 155                 160

Thr His Arg His Ile Pro Tyr Arg Glu Asn Lys Asn Leu Thr Gly Thr
                165                 170                 175
```

```
Ala Arg Tyr Ala Ser Val Asn Thr His Leu Gly Val Glu Gln Ser Arg
            180                 185                 190

Arg Asp Asp Leu Glu Ala Leu Gly Tyr Val Leu Met Tyr Phe Leu Lys
        195                 200                 205

Gly Ser Leu Pro Trp Gln Gly Leu Lys Ala Gly Thr Lys Lys Gln Lys
    210                 215                 220

Tyr Asp Arg Ile Ser Glu Lys Lys Val Ala Thr Pro Ile Glu Val Leu
225                 230                 235                 240

Cys Lys Asn Gln Pro Ser Glu Phe Val Ser Tyr Phe Arg Tyr Cys Arg
                245                 250                 255

Ser Leu Arg Phe Asp Asp Lys Pro Asp Tyr Ser Tyr Leu Lys Arg Leu
            260                 265                 270

Phe Arg Asp Leu Phe Ile Arg Glu Gly Tyr Gln Phe Asp Tyr Val Phe
        275                 280                 285

Asp Trp Thr Val Leu Lys Tyr Pro Gln Ile Gly Ser Ser Ser Gly Ser
    290                 295                 300

Ser Ser Arg Thr Arg Val Val Tyr Ala Ala Phe Ser Phe Gly Ser
305                 310                 315

<210> SEQ ID NO 11
<211> LENGTH: 337
<212> TYPE: PRT
<213> ORGANISM: Xenopus laevis

<400> SEQUENCE: 11

Met Ala Ser Ser Gly Ser Lys Ala Glu Phe Ile Val Gly Gly Lys
  1               5                  10                  15

Tyr Lys Leu Val Arg Lys Ile Gly Ser Gly Ser Phe Gly Asp Ile Tyr
                20                  25                  30

Leu Ala Ile Asn Ile Thr Asn Gly Glu Glu Val Ala Val Lys Leu Glu
            35                  40                  45

Ser Gln Lys Ala Arg His Pro Gln Leu Leu Tyr Glu Ser Lys Leu Tyr
        50                  55                  60

Lys Ile Leu Gln Gly Gly Val Gly Ile Pro His Ile Arg Trp Tyr Gly
 65                 70                  75                  80

Gln Glu Lys Asp Tyr Asn Val Leu Val Met Asp Leu Leu Gly Pro Ser
                85                  90                  95

Leu Glu Asp Leu Phe Asn Phe Cys Ser Arg Arg Phe Thr Met Lys Thr
            100                 105                 110

Val Leu Met Leu Ala Asp Gln Met Ile Ser Arg Ile Glu Tyr Val His
        115                 120                 125

Thr Lys Asn Phe Ile His Arg Asp Ile Lys Pro Asp Asn Phe Leu Met
    130                 135                 140

Gly Ile Gly Arg His Cys Asn Lys Leu Phe Leu Ile Asp Phe Gly Leu
145                 150                 155                 160

Ala Lys Lys Tyr Arg Asp Asn Arg Thr Arg Gln His Ile Pro Tyr Arg
                165                 170                 175

Glu Asp Lys Asn Leu Thr Gly Thr Ala Arg Tyr Ala Ser Ile Asn Ala
            180                 185                 190

His Leu Gly Ile Glu Gln Ser Arg Arg Asp Asp Met Glu Ser Leu Gly
        195                 200                 205

Tyr Val Leu Met Tyr Phe Asn Arg Thr Ser Leu Pro Trp Gln Gly Leu
    210                 215                 220

Lys Ala Ala Thr Lys Lys Gln Lys Tyr Glu Lys Ile Ser Glu Lys Lys
225                 230                 235                 240
```

-continued

```
Met Ser Thr Pro Val Glu Val Leu Cys Lys Gly Phe Pro Ala Glu Phe
            245                 250                 255

Ala Met Tyr Leu Asn Tyr Cys Arg Gly Leu Arg Phe Glu Glu Ala Pro
            260                 265                 270

Asp Tyr Met Tyr Leu Arg Gln Leu Phe Arg Ile Leu Phe Arg Thr Leu
            275                 280                 285

Asn His Gln Tyr Asp Tyr Thr Phe Asp Trp Thr Met Leu Lys Gln Lys
            290                 295                 300

Ala Ala Gln Gln Ala Ala Ser Ser Gly Gln Gly Gln Gln Ala Gln
305                 310                 315                 320

Thr Pro Thr Gly Lys Gln Thr Asp Lys Ser Lys Ser Asn Met Lys Gly
            325                 330                 335

Phe

<210> SEQ ID NO 12
<211> LENGTH: 337
<212> TYPE: PRT
<213> ORGANISM: Gallus gallus

<400> SEQUENCE: 12

Met Ala Ser Ser Gly Ser Lys Ala Glu Phe Ile Val Gly Gly Lys
1               5                   10                  15

Tyr Lys Leu Val Arg Lys Ile Gly Ser Gly Phe Gly Asp Ile Tyr
            20                  25                  30

Leu Ala Ile Asn Ile Thr Asn Gly Glu Glu Val Ala Val Lys Leu Glu
            35                  40                  45

Ser Gln Lys Ala Arg His Pro Gln Leu Leu Tyr Glu Ser Lys Leu Tyr
     50                  55                  60

Lys Ile Leu Gln Gly Gly Val Gly Ile Pro His Ile Arg Trp Tyr Gly
65                  70                  75                  80

Gln Glu Lys Asp Tyr Asn Val Leu Val Met Asp Leu Leu Gly Pro Ser
            85                  90                  95

Leu Glu Asp Leu Phe Asn Phe Cys Ser Arg Arg Phe Thr Met Lys Thr
            100                 105                 110

Val Leu Met Leu Ala Asp Gln Met Ile Ser Arg Ile Glu Tyr Val His
            115                 120                 125

Thr Lys Asn Phe Ile His Arg Asp Ile Lys Pro Asp Asn Phe Leu Met
    130                 135                 140

Gly Ile Gly Arg His Cys Asn Lys Leu Phe Leu Ile Asp Phe Gly Leu
145                 150                 155                 160

Ala Lys Lys Tyr Arg Asp Asn Arg Thr Arg Gln His Ile Pro Tyr Arg
            165                 170                 175

Glu Asp Lys Asn Leu Thr Gly Thr Ala Arg Tyr Ala Ser Ile Asn Ala
            180                 185                 190

His Leu Gly Ile Glu Gln Ser Arg Arg Asp Asp Met Glu Ser Leu Gly
            195                 200                 205

Tyr Val Leu Met Tyr Phe Asn Arg Thr Ser Leu Pro Trp Gln Gly Leu
            210                 215                 220

Lys Ala Ala Thr Lys Lys Gln Lys Tyr Glu Lys Ile Ser Glu Lys Lys
225                 230                 235                 240

Met Ser Thr Pro Val Glu Val Leu Cys Lys Gly Phe Pro Ala Glu Phe
            245                 250                 255

Ala Met Tyr Leu Asn Tyr Cys Arg Gly Leu Arg Phe Glu Glu Ala Pro
            260                 265                 270
```

```
Asp Tyr Met Tyr Leu Arg Gln Leu Phe Arg Ile Leu Phe Arg Thr Leu
            275                 280                 285

Asn His Gln Tyr Asp Tyr Thr Phe Asp Trp Thr Met Leu Lys Gln Lys
        290                 295                 300

Ala Ala Gln Gln Ala Ala Ser Ser Gly Gln Gly Gln Gln Ala Gln
305                 310                 315                 320

Thr Pro Thr Gly Lys Gln Thr Asp Lys Ser Lys Ser Asn Met Lys Gly
                325                 330                 335

Phe

<210> SEQ ID NO 13
<211> LENGTH: 365
<212> TYPE: PRT
<213> ORGANISM: Schizosaccharomyces pombe

<400> SEQUENCE: 13

Met Ala Leu Asp Leu Arg Ile Gly Asn Lys Tyr Arg Ile Gly Arg Lys
 1               5                  10                  15

Ile Gly Ser Gly Ser Phe Gly Asp Ile Tyr Leu Gly Thr Asn Val Val
                20                  25                  30

Ser Gly Glu Glu Val Ala Ile Lys Leu Glu Ser Thr Arg Ala Lys His
            35                  40                  45

Pro Gln Leu Glu Tyr Glu Tyr Arg Val Tyr Arg Ile Leu Ser Gly Gly
        50                  55                  60

Val Gly Ile Pro Phe Val Arg Trp Phe Gly Val Glu Cys Asp Tyr Asn
 65                  70                  75                  80

Ala Met Val Met Asp Leu Leu Gly Pro Ser Leu Glu Asp Leu Phe Asn
                85                  90                  95

Phe Cys Asn Arg Lys Phe Ser Leu Lys Thr Val Leu Leu Ala Asp
            100                 105                 110

Gln Leu Ile Ser Arg Ile Glu Phe Ile His Ser Lys Ser Phe Leu His
        115                 120                 125

Arg Asp Ile Lys Pro Asp Asn Phe Leu Met Gly Ile Gly Lys Arg Gly
    130                 135                 140

Asn Gln Val Asn Ile Ile Asp Phe Gly Leu Ala Lys Lys Tyr Arg Asp
145                 150                 155                 160

His Lys Thr His Leu His Ile Pro Tyr Arg Glu Asn Lys Asn Leu Thr
                165                 170                 175

Gly Thr Ala Arg Tyr Ala Ser Ile Asn Thr His Leu Gly Ile Glu Gln
            180                 185                 190

Ser Arg Arg Asp Asp Leu Glu Ser Leu Gly Tyr Val Leu Val Tyr Phe
        195                 200                 205

Cys Arg Gly Ser Leu Pro Trp Gln Gly Leu Lys Ala Thr Thr Lys Lys
    210                 215                 220

Gln Lys Tyr Glu Lys Ile Met Glu Lys Lys Ile Ser Thr Pro Thr Glu
225                 230                 235                 240

Val Leu Cys Arg Gly Phe Pro Gln Glu Phe Ser Ile Tyr Leu Asn Tyr
                245                 250                 255

Thr Arg Ser Leu Arg Phe Asp Asp Lys Pro Asp Tyr Ala Tyr Leu Arg
            260                 265                 270

Lys Leu Phe Arg Asp Leu Phe Cys Arg Gln Ser Tyr Glu Phe Asp Tyr
        275                 280                 285

Met Phe Asp Trp Thr Leu Lys Arg Lys Thr Gln Gln Asp Gln Gln His
    290                 295                 300
```

Gln Gln Gln Leu Gln Gln Gln Leu Ser Ala Thr Pro Gln Ala Ile Asn
305                 310                 315                 320

Pro Pro Pro Glu Arg Ser Ser Phe Arg Asn Tyr Gln Lys Gln Asn Phe
            325                 330                 335

Asp Glu Lys Gly Gly Asp Ile Asn Thr Thr Val Pro Val Ile Asn Asp
            340                 345                 350

Pro Ser Ala Thr Gly Ala Gln Tyr Ile Asn Arg Pro Asn
            355                 360                 365

<210> SEQ ID NO 14
<211> LENGTH: 1331
<212> TYPE: DNA
<213> ORGANISM: Homo sapiens

<400> SEQUENCE: 14

| | | | | | |
|---|---|---|---|---|---|
| gaattccggg | caagagtgag | ccatggagct | acgtgtgggg | aacaagtacc | gcctgggacg | 60 |
| gaagatcggg | agcgggtcct | tcggagatat | ctacctgggt | gccaacatcg | cctctggtga | 120 |
| ggaagtcgcc | atcaagctgg | agtgtgtgaa | gacaaagcac | ccccagctgc | acatcgagag | 180 |
| caagttctac | aagatgatgc | agggtggcgt | ggggatcccg | tccatcaagt | ggtgcggagc | 240 |
| tgagggcgac | tacaacgtga | tggtcatgga | gctgctgggg | cctagcctcg | aggacctgtt | 300 |
| caacttctgt | tcccgcaaat | tcagcctcaa | gacggtgctg | ctcttggccg | accagatgat | 360 |
| cagccgcatc | gagtatatcc | actccaagaa | cttcatccac | cgggacgtca | gcccgacaa | 420 |
| cttcctcatg | gggctgggga | gaagggcaa | cctggtctac | atcatcgact | tcggcctggc | 480 |
| caagaagtac | cgggacgccc | gcacccacca | gcacattccc | taccgggaaa | acaagaacct | 540 |
| gaccggcacg | gcccgctacg | cttccatcaa | cacgcacctg | ggcattgagc | aaagccgtcg | 600 |
| agatgacctg | gagagcctgg | gctacgtgct | catgtacttc | aacctgggct | ccctgccctg | 660 |
| gcagggctc | aaagcagcca | ccaagcgcca | gaagtatgaa | cggatcagcg | agaagaagat | 720 |
| gtcaacgccc | atcgaggtcc | tctgcaaagg | ctatccctcc | gaattctcaa | catacctcaa | 780 |
| cttctgccgc | tccctgcggt | tgacgacaa | gcccgactac | tcttacctac | gtcagctctt | 840 |
| ccgcaacctc | ttccaccggc | agggcttctc | ctatgactac | gtctttgact | ggaacatgct | 900 |
| gaaattcggt | gcagcccgga | atcccgagga | tgtggaccgg | gagcggcgag | aacacgaacg | 960 |
| cgaggagagg | atgggggcagc | tacggggtc | cgcgacccga | gccctgcccc | ctggcccacc | 1020 |
| cacggggggcc | actgccaacc | ggctccgcag | tgccgccgag | cccgtggctt | ccacgccagc | 1080 |
| ctcccgcatc | cagccggctg | gcaatacttc | tcccagagcg | atctcgcggg | tcgaccggga | 1140 |
| gaggaaggtg | agtatgaggc | tgcacagggg | tgcgcccgcc | aacgtctcct | cctcagacct | 1200 |
| cactgggcgg | caagaggtct | cccggatccc | agcctcacag | acaagtgtgc | catttgacca | 1260 |
| tctcgggaag | tgaggagagc | ccccattgga | ccagtgtttg | cttagtgtct | tcactgtatt | 1320 |
| ttctggaatt | c | | | | | 1331 |

<210> SEQ ID NO 15
<211> LENGTH: 1251
<212> TYPE: DNA
<213> ORGANISM: Mesocricetus auratus

<400> SEQUENCE: 15

| | | | | | |
|---|---|---|---|---|---|
| atggagctgc | gtgtggggaa | taagtaccgc | ctgggccgaa | agatcggcag | tgggtccttt | 60 |
| ggagacatct | acttgggtgc | caacattgcc | tctggtgagg | aagtagccat | caaactcgaa | 120 |

-continued

```
tgtgtgaaaa caaagcaccc gcagctccac atagagagca agttctacaa gatgatgcaa    180
ggaggagtgg ggatcccgtc catcaagtgg tgcggggctg agggtgacta caatgtgatg    240
gtcatggagc tgctggggcc cagtctcgag gacctcttca acttctgttc ccgaaagttc    300
agcctcaaga cagtgctgct gctggccgac cagatgatca gccgcatcga gtacatccac    360
tccaagaact tcatccaccg ggacgtgaaa ccggataact ttctcatggg cttggggaag    420
aaaggcaacc tggtctacat cattgacttc ggcctggcca agaagtaccg tgatgcccgc    480
acccaccagc atatcccta ccgggaaaac aagaacctga ctggcactgc cgctatgcc    540 tccatcaaca cccacctggg catcgagcaa agccgtcgag atgacctgga gagcttgggc    600
tatgtgctga tgtacttcaa cctgggctcc ctgccctggc agggtctcaa agccgccacc    660
aagcgtcaga agtacgagcg gatcagtgag aagaagatgt caacgcccat tgaggtcctc    720
tgcaaaggct acccctccga gttctcaaca tacctcaact tctgccgctc cctgcggttc    780
gatgacaagc ccgactactc ctacctgcgc cagctcttcc gcaacctctt tcaccggcag    840
ggtttctcct acgactacgt cttcgactgg aacatgctca aattcggtgc agcccggaat    900
cccgaggacg tagaccggga gcgacgagaa cacgaacggg aagagaggat ggggcagttg    960
cgggggtccg cgaccagagc cctgccccct ggcccaccca caggggctac tgccaatcga    1020
ctccgcagtg cagccgagcc tgtggcttcc acgcctgcct ctcgaatcca gcaagctggc    1080
aatacttctc ccagagcgat ctcacgggcc gaccgggaga ggaaggtgag catgcgactc    1140
cacagaggcg cacctgccaa cgtctcctcc tcagacctca ctgggcggca agaggtctcc    1200
cggatttcag cctcacagac aagcgtgcca tttgaccatc tcgggaaatg a             1251
```

<210> SEQ ID NO 16
<211> LENGTH: 416
<212> TYPE: PRT
<213> ORGANISM: Mesocricetus auratus

<400> SEQUENCE: 16

```
Met Glu Leu Arg Val Gly Asn Lys Tyr Arg Leu Gly Arg Lys Ile Gly
  1               5                  10                  15

Ser Gly Ser Phe Gly Asp Ile Tyr Leu Gly Ala Asn Ile Ala Ser Gly
             20                  25                  30

Glu Glu Val Ala Ile Lys Leu Glu Cys Val Lys Thr Lys His Pro Gln
         35                  40                  45

Leu His Ile Glu Ser Lys Phe Tyr Lys Met Met Gln Gly Gly Val Gly
     50                  55                  60

Ile Pro Ser Ile Lys Trp Cys Gly Ala Glu Gly Asp Tyr Asn Val Met
 65                  70                  75                  80

Val Met Glu Leu Leu Gly Pro Ser Leu Glu Asp Leu Phe Asn Phe Cys
                 85                  90                  95

Ser Arg Lys Phe Ser Leu Lys Thr Val Leu Leu Leu Ala Asp Gln Met
            100                 105                 110

Ile Ser Arg Ile Glu Tyr Ile His Ser Lys Asn Phe Ile His Arg Asp
        115                 120                 125

Val Lys Pro Asp Asn Phe Leu Met Gly Leu Gly Lys Lys Gly Asn Leu
    130                 135                 140

Val Tyr Ile Ile Asp Phe Gly Leu Ala Lys Lys Tyr Arg Asp Ala Arg
145                 150                 155                 160

Thr His Gln His Ile Pro Tyr Arg Glu Asn Lys Asn Leu Thr Gly Thr
                165                 170                 175
```

```
Ala Arg Tyr Ala Ser Ile Asn Thr His Leu Gly Ile Glu Gln Ser Arg
            180                 185                 190
Arg Asp Asp Leu Glu Ser Leu Gly Tyr Val Leu Met Tyr Phe Asn Leu
            195                 200                 205
Gly Ser Leu Pro Trp Gln Gly Leu Lys Ala Ala Thr Lys Arg Gln Lys
            210                 215                 220
Tyr Glu Arg Ile Ser Glu Lys Lys Met Ser Thr Pro Ile Glu Val Leu
225                 230                 235                 240
Cys Lys Gly Tyr Pro Ser Glu Phe Ser Thr Tyr Leu Asn Phe Cys Arg
                245                 250                 255
Ser Leu Arg Phe Asp Asp Lys Pro Asp Tyr Ser Tyr Leu Arg Gln Leu
            260                 265                 270
Phe Arg Asn Leu Phe His Arg Gln Gly Phe Ser Tyr Asp Tyr Val Phe
            275                 280                 285
Asp Trp Asn Met Leu Lys Phe Gly Ala Ala Arg Asn Pro Glu Asp Val
            290                 295                 300
Asp Arg Glu Arg Arg Glu His Glu Arg Glu Glu Arg Met Gly Gln Leu
305                 310                 315                 320
Arg Gly Ser Ala Thr Arg Ala Leu Pro Pro Gly Pro Pro Thr Gly Ala
                325                 330                 335
Thr Ala Asn Arg Leu Arg Ser Ala Ala Glu Pro Val Ala Ser Thr Pro
            340                 345                 350
Ala Ser Arg Ile Gln Gln Ala Gly Asn Thr Ser Pro Arg Ala Ile Ser
            355                 360                 365
Arg Ala Asp Arg Glu Arg Lys Val Ser Met Arg Leu His Arg Gly Ala
            370                 375                 380
Pro Ala Asn Val Ser Ser Ser Asp Leu Thr Gly Arg Gln Glu Val Ser
385                 390                 395                 400
Arg Ile Ser Ala Ser Gln Thr Ser Val Pro Phe Asp His Leu Gly Lys
                405                 410                 415

<210> SEQ ID NO 17
<211> LENGTH: 1251
<212> TYPE: DNA
<213> ORGANISM: Mesocricetus auratus tau mutation

<400> SEQUENCE: 17
atggagctgc gtgtgggaa taagtaccgc ctgggccgaa agatcggcag tgggtccttt      60
ggagacatct acttgggtgc caacattgcc tctggtgagg aagtagccat caaactcgaa    120
tgtgtgaaaa caaagcaccc gcagctccac atagagagca agttctacaa gatgatgcaa    180
ggaggagtgg ggatcccgtc catcaagtgg tgcggggctg agggtgacta caatgtgatg    240
gtcatggagc tgctggggcc cagtctcgag gacctcttca acttctgttc ccgaaagttc    300
agcctcaaga cagtgctgct gctggccgac cagatgatca gccgcatcga gtacatccac    360
tccaagaact tcatccaccg ggacgtgaaa ccggataact ttctcatggg cttggggaag    420
aaaggcaacc tggtctacat cattgacttc ggcctggcca gaagtaccg tgatgcccgc    480 acccaccagc atatccccta ccgggaaaac aagaacctga ctggcactgc tgctatgcc    540 tccatcaaca cccacctggg catcgagcaa agccgtcgag atgacctgga gagcttgggc    600
tatgtgctga tgtacttcaa cctgggctcc ctgccctggc agggtctcaa agccgccacc    660
aagcgtcaga gtacgagcg gatcagtgag aagaagatgt caacgcccat tgaggtcctc    720
tgcaaaggct accctccga gttctcaaca tacctcaact tctgccgctc cctgcggttc    780
```

```
gatgacaagc ccgactactc ctacctgcgc cagctcttcc gcaacctctt tcaccggcag    840
ggtttctcct acgactacgt cttcgactgg aacatgctca aattcggtgc agcccggaat    900
cccgaggacg tagaccggga gcgacgagaa cacgaacggg aagagaggat ggggcagttg    960
cgggggtccg cgaccagagc cctgcccct ggcccaccca caggggctac tgccaatcga   1020
ctccgcagtg cagccgagcc tgtggcttcc acgcctgcct ctcgaatcca gcaagctggc   1080
aatacttctc ccagagcgat ctcacgggcc gaccgggaga ggaaggtgag catgcgactc   1140
cacagaggcg cacctgccaa cgtctcctcc tcagacctca ctgggcggca agaggtctcc   1200
cggatttcag cctcacagac aagcgtgcca tttgaccatc tcgggaaatg a           1251
```

<210> SEQ ID NO 18
<211> LENGTH: 416
<212> TYPE: PRT
<213> ORGANISM: Mesocricetus auratus tau mutation

<400> SEQUENCE: 18

```
Met Glu Leu Arg Val Gly Asn Lys Tyr Arg Leu Gly Arg Lys Ile Gly
  1               5                  10                  15

Ser Gly Ser Phe Gly Asp Ile Tyr Leu Gly Ala Asn Ile Ala Ser Gly
             20                  25                  30

Glu Glu Val Ala Ile Lys Leu Glu Cys Val Lys Thr Lys His Pro Gln
         35                  40                  45

Leu His Ile Glu Ser Lys Phe Tyr Lys Met Met Gln Gly Gly Val Gly
     50                  55                  60

Ile Pro Ser Ile Lys Trp Cys Gly Ala Glu Gly Asp Tyr Asn Val Met
 65                  70                  75                  80

Val Met Glu Leu Leu Gly Pro Ser Leu Glu Asp Leu Phe Asn Phe Cys
                 85                  90                  95

Ser Arg Lys Phe Ser Leu Lys Thr Val Leu Leu Leu Ala Asp Gln Met
            100                 105                 110

Ile Ser Arg Ile Glu Tyr Ile His Ser Lys Asn Phe Ile His Arg Asp
        115                 120                 125

Val Lys Pro Asp Asn Phe Leu Met Gly Leu Gly Lys Lys Gly Asn Leu
    130                 135                 140

Val Tyr Ile Ile Asp Phe Gly Leu Ala Lys Lys Tyr Arg Asp Ala Arg
145                 150                 155                 160

Thr His Gln His Ile Pro Tyr Arg Glu Asn Lys Asn Leu Thr Gly Thr
                165                 170                 175

Ala Cys Tyr Ala Ser Ile Asn Thr His Leu Gly Ile Glu Gln Ser Arg
            180                 185                 190

Arg Asp Asp Leu Glu Ser Leu Gly Tyr Val Leu Met Tyr Phe Asn Leu
        195                 200                 205

Gly Ser Leu Pro Trp Gln Gly Leu Lys Ala Ala Thr Lys Arg Gln Lys
    210                 215                 220

Tyr Glu Arg Ile Ser Glu Lys Lys Met Ser Thr Pro Ile Glu Val Leu
225                 230                 235                 240

Cys Lys Gly Tyr Pro Ser Glu Phe Ser Thr Tyr Leu Asn Phe Cys Arg
                245                 250                 255

Ser Leu Arg Phe Asp Asp Lys Pro Asp Tyr Ser Tyr Leu Arg Gln Leu
            260                 265                 270

Phe Arg Asn Leu Phe His Arg Gln Gly Phe Ser Tyr Asp Tyr Val Phe
        275                 280                 285

Asp Trp Asn Met Leu Lys Phe Gly Ala Ala Arg Asn Pro Glu Asp Val
```

```
                290                 295                 300
Asp Arg Glu Arg Arg Glu His Glu Arg Glu Glu Arg Met Gly Gln Leu
305                 310                 315                 320

Arg Gly Ser Ala Thr Arg Ala Leu Pro Pro Gly Pro Pro Thr Gly Ala
                325                 330                 335

Thr Ala Asn Arg Leu Arg Ser Ala Ala Glu Pro Val Ala Ser Thr Pro
                340                 345                 350

Ala Ser Arg Ile Gln Gln Ala Gly Asn Thr Ser Pro Arg Ala Ile Ser
                355                 360                 365

Arg Ala Asp Arg Glu Arg Lys Val Ser Met Arg Leu His Arg Gly Ala
                370                 375                 380

Pro Ala Asn Val Ser Ser Ser Asp Leu Thr Gly Arg Gln Glu Val Ser
385                 390                 395                 400

Arg Ile Ser Ala Ser Gln Thr Ser Val Pro Phe Asp His Leu Gly Lys
                405                 410                 415

<210> SEQ ID NO 19
<211> LENGTH: 428
<212> TYPE: PRT
<213> ORGANISM: Rattus norvegicus

<400> SEQUENCE: 19

Met Glu Leu Arg Val Gly Asn Arg Tyr Arg Leu Gly Arg Lys Ile Gly
1               5                   10                  15

Ser Gly Ser Phe Gly Asp Ile Tyr Leu Gly Thr Asp Ile Ala Ala Gly
                20                  25                  30

Glu Glu Val Ala Ile Lys Leu Glu Cys Val Lys Thr Lys His Pro Gln
                35                  40                  45

Leu His Ile Glu Ser Lys Ile Tyr Lys Met Met Gln Gly Gly Val Gly
        50                  55                  60

Ile Pro Thr Ile Arg Trp Cys Gly Ala Glu Gly Asp Tyr Asn Val Met
65                  70                  75                  80

Val Met Glu Leu Leu Gly Pro Ser Leu Glu Asp Leu Phe Asn Phe Cys
                85                  90                  95

Ser Arg Lys Phe Ser Leu Lys Thr Val Leu Leu Leu Ala Asp Gln Met
                100                 105                 110

Ile Ser Arg Ile Glu Tyr Ile His Ser Lys Asn Phe Ile His Arg Asp
            115                 120                 125

Val Lys Pro Asp Asn Phe Leu Met Gly Leu Gly Lys Lys Gly Asn Leu
            130                 135                 140

Val Tyr Ile Ile Asp Phe Gly Leu Ala Lys Lys Tyr Arg Asp Ala Arg
145                 150                 155                 160

Thr His Gln His Ile Pro Tyr Arg Glu Asn Lys Asn Leu Thr Gly Thr
                165                 170                 175

Ala Arg Tyr Ala Ser Ile Asn Thr His Leu Gly Ile Glu Gln Ser Arg
                180                 185                 190

Arg Asp Asp Leu Glu Ser Leu Gly Tyr Val Leu Met Tyr Phe Asn Leu
            195                 200                 205

Gly Ser Leu Pro Trp Gln Gly Leu Lys Ala Ala Thr Lys Arg Gln Lys
        210                 215                 220

Tyr Glu Arg Ile Ser Glu Lys Lys Met Ser Thr Pro Ile Glu Val Leu
225                 230                 235                 240

Cys Lys Gly Tyr Pro Ser Glu Phe Ala Thr Tyr Leu Asn Phe Cys Arg
                245                 250                 255
```

-continued

```
Ser Leu Arg Phe Asp Asp Lys Pro Asp Tyr Ser Tyr Leu Arg Gln Leu
            260                 265                 270

Phe Arg Asn Leu Phe His Arg Gln Gly Phe Ser Tyr Asp Tyr Val Phe
            275                 280                 285

Asp Trp Asn Met Leu Lys Phe Gly Ala Ser Arg Ala Ala Asp Asp Ala
            290                 295             300

Glu Arg Glu Arg Asp Arg Glu Glu Arg Leu Arg His Ser Arg Asn
305                 310                 315                 320

Pro Ala Thr Arg Gly Leu Pro Ser Thr Ala Ser Gly Arg Leu Arg Gly
                325                 330                 335

Thr Gln Glu Val Ala Pro Pro Thr Pro Leu Thr Pro Thr Ser His Thr
                340                 345                 350

Ala Asn Thr Ser Pro Arg Pro Val Ser Gly Met Glu Arg Glu Arg Lys
                355                 360                 365

Val Ser Met Arg Leu His Arg Gly Ala Pro Val Asn Val Ser Ser Ser
370                 375                 380

Asp Leu Thr Gly Arg Gln Asp Thr Ser Arg Met Ser Thr Ser Gln Arg
385                 390                 395                 400

Ser Arg Asp Met Ala Ser Leu Arg Leu His Ala Ala Arg Gln Gly Ala
                405                 410                 415

Arg Cys Arg Pro Gln Arg Pro Arg Arg Thr Thr Tyr
                420                 425
```

```
<210> SEQ ID NO 20
<211> LENGTH: 22
<212> TYPE: DNA
<213> ORGANISM: Artificial Sequence
<220> FEATURE:
<223> OTHER INFORMATION: Description of Artificial Sequence: Primer.

<400> SEQUENCE: 20
gtgcagttga ggaagatatc tg                                              22

<210> SEQ ID NO 21
<211> LENGTH: 23
<212> TYPE: DNA
<213> ORGANISM: Artificial Sequence
<220> FEATURE:
<223> OTHER INFORMATION: Description of Artificial Sequence: Primer.

<400> SEQUENCE: 21
cagtactagc agttgaatca agg                                             23

<210> SEQ ID NO 22
<211> LENGTH: 24
<212> TYPE: DNA
<213> ORGANISM: Artificial Sequence
<220> FEATURE:
<223> OTHER INFORMATION: Description of Artificial Sequence: Primer.

<400> SEQUENCE: 22
cagagggtgc ccttgacttc cacc                                            24

<210> SEQ ID NO 23
<211> LENGTH: 24
<212> TYPE: DNA
<213> ORGANISM: Artificial Sequence
<220> FEATURE:
<223> OTHER INFORMATION: Description of Artificial Sequence: Primer.

<400> SEQUENCE: 23
```

-continued tggaggtagg tggccgccgc taaa                24

<210> SEQ ID NO 24
<211> LENGTH: 24
<212> TYPE: DNA
<213> ORGANISM: Artificial Sequence
<220> FEATURE:
<223> OTHER INFORMATION: Description of Artificial Sequence: Primer.

<400> SEQUENCE: 24
ccctggcgcg ctgtggaagc catc                24

<210> SEQ ID NO 25
<211> LENGTH: 29
<212> TYPE: DNA
<213> ORGANISM: Artificial Sequence
<220> FEATURE:
<223> OTHER INFORMATION: Description of Artificial Sequence: Primer.

<400> SEQUENCE: 25
attccactac taatataatg gatatatgt           29

<210> SEQ ID NO 26
<211> LENGTH: 24
<212> TYPE: DNA
<213> ORGANISM: Artificial Sequence
<220> FEATURE:
<223> OTHER INFORMATION: Description of Artificial Sequence: Primer.

<400> SEQUENCE: 26
gcatgcatgc accagtgtac attc                24

<210> SEQ ID NO 27
<211> LENGTH: 30
<212> TYPE: DNA
<213> ORGANISM: Artificial Sequence
<220> FEATURE:
<223> OTHER INFORMATION: Description of Artificial Sequence: Primer.

<400> SEQUENCE: 27
gaccacttac aacatgtaca aaccacagcc          30

<210> SEQ ID NO 28
<211> LENGTH: 22
<212> TYPE: DNA
<213> ORGANISM: Artificial Sequence
<220> FEATURE:
<223> OTHER INFORMATION: Description of Artificial Sequence: Primer.

<400> SEQUENCE: 28
ggaaagtcct gggtactgtg tc                  22

<210> SEQ ID NO 29
<211> LENGTH: 22
<212> TYPE: DNA
<213> ORGANISM: Artificial Sequence
<220> FEATURE:
<223> OTHER INFORMATION: Description of Artificial Sequence: Primer.

<400> SEQUENCE: 29
gttcgcttcc ctggtcctgt at                  22

<210> SEQ ID NO 30
<211> LENGTH: 30
<212> TYPE: DNA
<213> ORGANISM: Artificial Sequence

```
<220> FEATURE:
<223> OTHER INFORMATION: Description of Artificial Sequence: Primer.

<400> SEQUENCE: 30
tcacttcccg agatggtcaa atggcacact                                    30

<210> SEQ ID NO 31
<211> LENGTH: 30
<212> TYPE: DNA
<213> ORGANISM: Artificial Sequence
<220> FEATURE:
<223> OTHER INFORMATION: Description of Artificial Sequence: Primer.

<400> SEQUENCE: 31
gggagcgggt ccttcggaga tatctacctg                                    30

<210> SEQ ID NO 32
<211> LENGTH: 23
<212> TYPE: DNA
<213> ORGANISM: Artificial Sequence
<220> FEATURE:
<223> OTHER INFORMATION: Description of Artificial Sequence: Primer.

<400> SEQUENCE: 32
gccccggcga atcctctggc atc                                           23

<210> SEQ ID NO 33
<211> LENGTH: 25
<212> TYPE: DNA
<213> ORGANISM: Artificial Sequence
<220> FEATURE:
<223> OTHER INFORMATION: Description of Artificial Sequence: Primer.

<400> SEQUENCE: 33
tgaagacact aagcaaacac tggtc                                         25

<210> SEQ ID NO 34
<211> LENGTH: 22
<212> TYPE: DNA
<213> ORGANISM: Artificial Sequence
<220> FEATURE:
<223> OTHER INFORMATION: Description of Artificial Sequence: Primer.

<400> SEQUENCE: 34
gataactttc tcatgggctt gg                                            22

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Primer.

<400> SEQUENCE: 35
gggtgttgat ggaggcatag                                               20

<210> SEQ ID NO 36
<211> LENGTH: 22
<212> TYPE: DNA
<213> ORGANISM: Artificial Sequence
<220> FEATURE:
<223> OTHER INFORMATION: Description of Artificial Sequence: Primer.

<400> SEQUENCE: 36
gataactttc tcatgggctt gg                                            22
```

```
<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Primer.

<400> SEQUENCE: 37
gggtgttgat ggaggcatag                                              20

<210> SEQ ID NO 38
<211> LENGTH: 45
<212> TYPE: DNA
<213> ORGANISM: Artificial Sequence
<220> FEATURE:
<223> OTHER INFORMATION: Description of Artificial Sequence: Primer.

<400> SEQUENCE: 38
taatacgact cactataggg agacttgtct gtgaggctga aatcc                  45

<210> SEQ ID NO 39
<211> LENGTH: 43
<212> TYPE: DNA
<213> ORGANISM: Artificial Sequence
<220> FEATURE:
<223> OTHER INFORMATION: Description of Artificial Sequence: Primer.

<400> SEQUENCE: 39
aattaccctc actaaaggga gaatccagca agctggcaat act                   43

<210> SEQ ID NO 40
<211> LENGTH: 4
<212> TYPE: PRT
<213> ORGANISM: Artificial Sequence
<220> FEATURE:
<223> OTHER INFORMATION: Description of Artificial Sequence: Consensus
      phosphorylation sequence.
<221> NAME/KEY: VARIANT
<222> LOCATION: (1)
<223> OTHER INFORMATION: It is any phosphorylated serine, threonine or
      tyrosine residue.
<221> NAME/KEY: VARIANT
<222> LOCATION: (2)..(3)
<223> OTHER INFORMATION: They are any amino acids. One of them can be
      missing but not both.
<221> NAME/KEY: VARIANT
<222> LOCATION: (4)
<223> OTHER INFORMATION: It is either serine or threonine.

<400> SEQUENCE: 40

Xaa Xaa Xaa Xaa
  1

<210> SEQ ID NO 41
<211> LENGTH: 6
<212> TYPE: PRT
<213> ORGANISM: Artificial Sequence
<220> FEATURE:
<223> OTHER INFORMATION: Description of Artificial Sequence: A putative
      nuclear localization signal.

<400> SEQUENCE: 41

Thr Lys Arg Gln Lys Tyr
  1               5

<210> SEQ ID NO 42
<211> LENGTH: 1960
<212> TYPE: DNA
```

<213> ORGANISM: Rattus norvegicus
<220> FEATURE:
<223> OTHER INFORMATION: Description of Artificial Sequence: Primer.

<400> SEQUENCE: 42

```
ctttaggcag ctgaaggggg atttaggccc ggaagatccg agtccatccg cggcggggag      60
agggcgagcg gggccggcag gggccgaagc agcggcggcg gcgctcggac tgtcccatcc     120
gccccgtatt gaggcgctga gagcgacggg gcgaccagaa agcgatggtg aaagcggggc     180
cgtgaggggg gcggagtcgg accggacccg cagtagcggc agcagcggcg ccgcctcccg     240
gagcgcagac ccaggaagcg gccgggcggg cagtagcgag ccgcaccgct gccatggagc     300
tgagggtcgg aataggtac cgactgggcc gcaagatcgg cagcggctcc ttcgagaca      360
tctatctcgg tacggacatt gctgcaggag aagaagttgc catcaagctt gaatgtgtca     420
aaaccaaaca tcctcagctc cacattgaga gcaagatcta caaatgatg cagggaggag     480
tgggcatccc taccatcaga tggtgtgggg ctgaggggga ctacaatgtc atggtgatgg     540
agctactggg acccagcctg gaagacctat tcaacttctg ttcaaggaag tttagtctca     600
aaactgttct gttgcttgct gaccaaatga taagtcgtat tgagtacatt cattcgaaga     660
atttttatcca ccgagacgtg aaaccagata acttcctcat ggggctggga aagaaaggca     720
acctggtcta catcattgac tttgggctgg ccaagaagta tcgggatgcc cgcacccacc     780
agcatatccc ctatcgagag aacaagaacc tcacaggaca gcacgctat gcctccatca     840
acacacacct tggcattgaa caatctcgaa gggatgactt ggagtctctg gggtacgtgc     900
tgatgtactt caacctgggc tctctcccct ggcaggggct gaaggccgcc accaagaggc     960
agaagtatga gaggatcagt gagaagaaga tgtccactcc aattgaagtg ctgtgcaagg    1020
gctatccttc tgaatttgcc acatacctga atttctgccg ttccttacgt tttgatgaca    1080
aacctgacta ctcctacctg agacagctct tcagaaatct gttccatcgc cagggcttct    1140
cctacgacta tgtgttcgac tggaacatgc tcaaatttgg tgccagccgg gctgcagatg    1200
atgctgagcg ggaacgccgg gaccgagaag aacgattaag acactcccgg aatccagcca    1260
ctcgtggcct cccttctaca gcttccggcc gtctgcgggg aacccaggaa gtggctcccc    1320
caacgcccct tacccctacc tcacatacgg ccaacacctc tcctagaccc gtctctggca    1380
tggaacgaga acggaaagtg agtatgcggc tgcaccgtgg ggcccagtc aacgtctcct    1440
catctgatct cacgggccga caagatacct ctcgcatgtc cacctcacag aggagcaggg    1500
acatggcatc tctccggctg cacgcggccc gccaaggtgc ccgctgccgt ccccagcgcc    1560
cacgacgtac cacctactga ggcggcccca gcggcctctg accgggcttc cagccacgca    1620
ggccgccacc ggccacaggg cagatccact ttggaatgac gcggttccca ccccgccacc    1680
tctccccgca aaacactgac ccgctgacca ggcagccaag agctgagccg atggccccgc    1740
ctcagctggt cctgtttgtg aaataaatat gagcgttgcc agtcaaaaaa ggggctgctg    1800
ccgacgcctc tggaagtagg gacggtttcg tggacgctgg ggctcaggcc gggagccatc    1860
agtgggcct tggctgggct tggtctctcc atccccacct tctgtggtag gctgttgggg    1920
tggcctgggg cggaaaggcc ttcggtacct gggccggaag                          1960
```